(12) United States Patent
Astles et al.

(10) Patent No.: US 6,977,263 B2
(45) Date of Patent: *Dec. 20, 2005

(54) CHEMICAL COMPOUNDS

(75) Inventors: Peter C. Astles, Sevenoaks (GB); Paul R. Eastwood, Romford (GB); Olivier Houille, Paris (FR); Julian Levell, Summit, NJ (US); Heinz Pauls, Bridgewater, NJ (US); Mark Czekaj, Doylestown, PA (US); Guyan Liang, Woodbridge, NJ (US); Yong Gong, Bridgewater, NJ (US); James Pribish, Stewartsville, NJ (US); Kent Neuenschwander, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/843,126

(22) Filed: Apr. 26, 2001

(65) Prior Publication Data

US 2003/0187020 A1 Oct. 2, 2003

(30) Foreign Application Priority Data

May 22, 2000 (GB) .............................................. 0012362

(51) Int. Cl.$^7$ ..................... A61K 31/445; C07D 401/06
(52) U.S. Cl. ...................... 514/318; 514/320; 514/324; 514/326; 514/330; 546/193; 546/196; 546/202; 546/214; 546/226
(58) Field of Search ................................ 514/318, 320, 514/324, 326, 330; 546/193, 196, 202, 214, 226

(56) References Cited

U.S. PATENT DOCUMENTS

| 5,342,844 | A | * | 8/1994 | Laborde et al. ............. 514/300 |
| 5,442,064 | A | * | 8/1995 | Pieper et al. ................ 544/360 |
| 5,629,321 | A | * | 5/1997 | Okumura et al. ........... 514/307 |
| 6,812,236 | B2 | | 11/2004 | Gibson et al. |
| 2002/0045613 | A1 | * | 4/2002 | Pauls et al. ............ 514/210.18 |
| 2002/0055522 | A1 | * | 5/2002 | Liebeschuetz et al. ...... 514/330 |
| 2002/0099216 | A1 | | 7/2002 | Gibson et al. |
| 2005/0085456 | A1 | * | 4/2005 | Gibson et al. ........... 514/210.2 |

FOREIGN PATENT DOCUMENTS

| EP | 1 072 592 | 1/2001 |
| GB | 9912411 | 5/1999 |

OTHER PUBLICATIONS

Pieper et al. Preparation of diazine–containing . . . CA 122:290875 (1995).*

Barbachyn et al. "Preparation of isoxazolines as antimicrobials" CA 128:192646 (1998).*

CAS structure for US 5,442,064 (1995).*

* cited by examiner

Primary Examiner—Celia Chang
(74) Attorney, Agent, or Firm—Raymond S. Parker, III; William C. Coppola; Julie Anne Knight

(57) ABSTRACT

Provided herein are novel and useful compounds having a tryptase inhibition activity, pharmaceutical compositions comprising such compounds, and methods treating subjects suffering from a condition, disease, or disorder that can be ameliorated by the administration of an inhibitor of tryptase, e.g., asthma and inflammatory diseases, to name only a few.

59 Claims, No Drawings

CHEMICAL COMPOUNDS

This application claims priority under 35 U.S.C. § 119 of United Kingdom patent application number 0012362.0 filed May 22, 2000, which is hereby incorporated by reference herein in its entirety.

REFERENCE TO A TABLE SUBMITTED ON A COMPACT DISC

Pursuant to 37 CFR § 1.52, table 4 of the instant Specification is filed herewith in compliance with the American Standard for Information Interchange (ASCII) on a recordable compact disc (CD-R), submitted in duplicate, which was created on Apr. 23, 2001, has a size of 237 KB, and is hereby incorporated by reference herein in its entirety.

FIELD OF THE INVENTION

This invention is directed to substituted arylmethylamines, their preparation, pharmaceutical compositions containing these compounds, and their pharmaceutical use in the treatment of disease states capable of being modulated by the inhibition of tryptase.

BACKGROUND OF THE INVENTION

Tryptase is stored in mast cell secretory granules and is the major secretory protease of human mast cells. Tryptase has been implicated in a variety of biological processes, including degradation of vasodilating and bronchorelaxing neuropeptides (Caughey, et al., J. Pharmacol. Exp. Ther., 1988, 244, pages 133–137; Franconi, et al., J. Pharmacol. Exp. Ther., 1988, 248, pages 947–951; and Tam, et al., Am. J. Respir. Cell Mol. Biol., 1990, 3, pages 27–32) and modulation of bronchial responsiveness to histamine (Sekizawa, et al., J. Clin. Invest., 1989, 83, pages 175–179). As a result, tryptase inhibitors may be useful as anti-inflammatory agents (K Rice, P. A. Sprengler, Current Opinion in Drug Discovery and Development, 1999, 2(5), pages 463–474) particularly in the treatment of chronic asthma (M. Q. Zhang, H. Timmerman, Mediators Inflamm., 1997, 112, pages 311–317) and may also be useful in treating or preventing allergic rhinitis (S. J. Wilson et al, Clin. Exp. Allergy, 1998, 28, pages 220–227), inflammatory bowel disease (S. C. Bischoff et al, Histopathology, 1996, 28, pages 1–13), psoriasis (A. Naukkarinen et al, Arch. Dermatol. Res., 1993, 285, pages 341–346), conjunctivitis (A. A. Irani et al, J. Allergy Clin. Immunol., 1990, 86, pages 34–40), atopic dermatitis (A. Jarvikallio et al, Br. J. Dermatol., 1997, 136, pages 871–877), rheumatoid arthritis (L. C Tetlow et al, Ann. Rheum. Dis., 1998, 54, pages 549–555), osteoarthritis (M. G. Buckley et al, J. Pathol., 1998, 186, pages 67–74), gouty arthritis, rheumatoid spondylitis, and diseases of joint cartilage destruction.

In addition, tryptase has been shown to be a potent mitogen for fibroblasts, suggesting its involvement in the pulmonary fibrosis in asthma and interstitial lung diseases (Ruoss et al., J. Clin. Invest., 1991, 88, pages 493–499). Therefore, tryptase inhibitors may be useful in treating or preventing fibrotic conditions (J. A. Cairns and A. F. Walls, J. Clin. Invest., 1997, 99, pages 1313–1321) for example, fibrosis, scleroderma, pulmonary fibrosis, liver cirrhosis, myocardial fibrosis, neurofibromas and hypertrophic scars.

Additionally, tryptase inhibitors may be useful in treating or preventing myocardial infarction, stroke, angina and other consequences of atherosclerotic plaque rupture (M. Jeziorska et al, J. Pathol., 1997, 182, pages 115–122). Tryptase has also been discovered to activate prostromelysin that in turn activates collagenase, thereby initiating the destruction of cartilage and periodontal connective tissue, respectively. Therefore, tryptase inhibitors could be useful in the treatment or prevention of arthritis, periodontal disease, diabetic retinopathy, and tumor growth (W. J. Beil et al, Exp. Hematol., (1998) 26, pages 158–169). Also, tryptase inhibitors may be useful in the treatment of anaphylaxis (L. B. Schwarz et al, J. Clin. Invest., 1995, 96, pages 2702–2710), multiple sclerosis (M. Steinhoff et al, Nat. Med. (N. Y.), 2000, 6(2), pages 151–158), peptic ulcers and syncytial viral infections.

Mast cell mediated inflammatory conditions, in particular asthma, are a growing public health concern. Asthma is frequently characterized by progressive development of hyper-responsiveness of the trachea and bronchi to both immunospecific allergens and generalized chemical or physical stimuli, which lead to the onset of chronic inflammation. Leukocytes containing IgE receptors, notably mast cells and basophils, are present in the epithelium and underlying smooth muscle tissues of bronchi. These leukocytes initially become activated by binding of specific inhaled antigens to the IgE receptors and then release a number of chemical mediators. For example, degranulation of mast cells leads to the release of proteoglycans, peroxidase, arylsulfatase B, tryptase and chymase, which results in bronchiole constriction.

Accordingly, what is needed is a novel and useful group of compounds having valuable pharmaceutical properties, particularly, the ability to inhibit tryptase. Such compounds readily have utility in treating a patient suffering condition that can be ameliorated by the administration of an inhibitor of tryptase, e.g., mast cell mediated inflammatory conditions, inflammation, and diseases or disorders related to the degradation of vasodilating and bronchorelaxing neuropeptides. Particular examples of such conditions are described infra.

The citation of any reference herein should not be construed as an admission that such reference is available as "Prior Art" to the instant application.

SUMMARY OF THE INVENTION

Broadly, the present invention extends to a compound of formula (I):

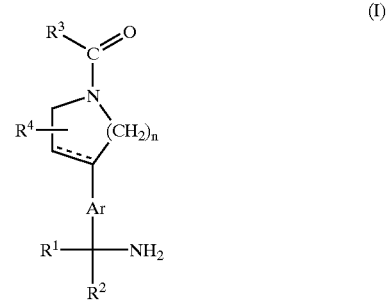

such that Ar is an aryl group or a heteroaryl group, and the

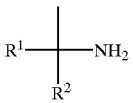

group is beta to the

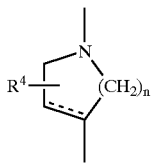

group on the aryl, wherein:—

----- is a single or a double bond;

$R^1$ and $R^2$ are each independently hydrogen or lower alkyl;

$R^3$ is aryl, arylalkenyl, cycloalkenyl, cycloalkyl, heteroaryl, heteroarylalkenyl, heterocycloalkenyl, a carbon linked heterocycloalkyl or alkyl optionally substituted by one or more groups selected from hydroxy, alkoxy, alkyloxycarbonylamino, cycloalkyl, heterocycloalkyl, $R^6$, —$OR^6$, —$S(O)_mR^6$ or —$C(=O)$—$R^6$;

$R^4$ is hydrogen, acyl, alkoxy, alkyloxycarbonyl, carboxy, cyano, halo, hydroxy, —$C(=O)$—$NY^1Y^2$ or alkyl optionally substituted with alkoxy, alkylcarbonylamino, alkylsulfonylamino, hydroxy, —$S(O)_m$-alkyl or —$NY^1Y^2$;

$R^5$ is hydrogen, acyl, alkoxy, alkyloxycarbonyl, aryl, carboxy, cyano, halo, heteroaryl, heteroaryloxy, heterocycloalkyl, heterocycloalkyloxy, heterocycloalkylalkyloxy, heteroarylalkyloxy, hydroxy, trifluoromethyl, —$C(=O)$—$NY^1Y^2$, —$NY^1Y^2$, —$Z^1$—$C_{2-6}$alkylene-$R^7$ or alkyl optionally substituted with alkoxy, alkylcarbonylamino, alkylsulfonylamino, aryl, heteroaryl, heterocycloalkyl, hydroxy, ureido, —$C(=O)$—$NY^1Y^2$, —$SO_2$—$NY^1Y^2$, —$S(O)_m$-alkyl or —$NY^1Y^2$;

$R^6$ is aryl or heteroaryl;

$R^7$ is hydroxy, alkoxy, ureido, —$C(=O)$—$NY^1Y^2$, —$SO_2$—$NY^1Y^2$, —$S(O)_m$-alkyl or —$NY^1Y^2$;

$R^8$ is hydrogen or lower alkyl;

$Y^1$ and $Y^2$ are independently hydrogen, alkenyl, alkyl, aryl, arylalkyl, cycloalkyl, heteroaryl, heteroarylalkyl or heterocycloalkyl; or the group —$NY^1Y^2$ may form a cyclic amine;

$Z^1$ is O, $S(O)_m$ or $NR^8$;

m is zero or an integer 1 to 2;

n is zero or an integer 1 to 4;

an N-oxide of said compound, a prodrug of said compound, a pharmaceutically acceptable salt of said compound, a solvate of said compound, and a hydrate of said compound.

Furthermore, the present invention extends to a compound of formula (Ia):—

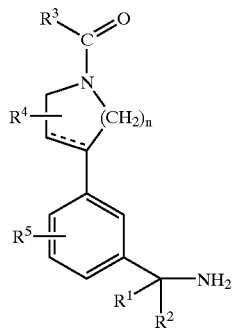

(Ia)

wherein:—

----- is a single or a double bond;

$R^1$ and $R^2$ are each independently hydrogen or lower alkyl;

$R^3$ is aryl, arylalkenyl, cycloalkenyl, cycloalkyl, heteroaryl, heteroarylalkenyl, heterocycloalkenyl, a carbon linked heterocycloalkyl or alkyl optionally substituted by one or more groups selected from hydroxy, alkoxy, alkyloxycarbonylamino, cycloalkyl, heterocycloalkyl, $R^6$, —$OR^6$, —$S(O)_mR^6$ or —$C(=O)$—$R^6$;

$R^4$ is hydrogen, acyl, alkoxy, alkyloxycarbonyl, carboxy, cyano, halo, hydroxy, —$C(=O)$—$NY^1Y^2$ or alkyl optionally substituted with alkoxy, alkylcarbonylamino, alkylsulfonylamino, hydroxy, —$S(O)_m$-alkyl or —$NY^1Y^2$;

$R^5$ is hydrogen, acyl, alkoxy, alkyloxycarbonyl, aryl, carboxy, cyano, halo, heteroaryl, heteroaryloxy, heterocycloalkyl, heterocycloalkyloxy, heterocycloalkylalkyloxy, heteroarylalkyloxy, hydroxy, trifluoromethyl, —$C(=O)$—$NY^1Y^2$, —$NY^1Y^2$, —$Z^1$—$C_{2-6}$alkylene-$R^7$ or alkyl optionally substituted with alkoxy, alkylcarbonylamino, alkylsulfonylamino, aryl, heteroaryl, heterocycloalkyl, hydroxy, ureido, —$C(=O)$—$NY^1Y^2$, —$SO_2$—$NY^1Y^2$, —$S(O)_m$-alkyl or —$NY^1Y^2$;

$R^6$ is aryl or heteroaryl;

$R^7$ is hydroxy, alkoxy, ureido, —$C(=O)$—$NY^1Y^2$, —$SO_2$—$NY^1Y^2$, —$S(O)_m$-alkyl or —$NY^1Y^2$;

$R^8$ is hydrogen or lower alkyl;

$Y^1$ and $Y^2$ are independently hydrogen, alkenyl, alkyl, aryl, arylalkyl, cycloalkyl, heteroaryl, heteroarylalkyl or heterocycloalkyl; or the group —$NY^1Y^2$ may form a cyclic amine;

$Z^1$ is O, $S(O)_m$ or $NR^8$;

m is zero or an integer 1 to 2;

n is zero or an integer 1 to 4;

and the corresponding N-oxides, and their prodrugs; and pharmaceutically acceptable salts and solvates (e.g. hydrates) of such compounds and their N-oxides and prodrugs.

2. In another embodiment, the present invention extends to a compound of formula (Ib):

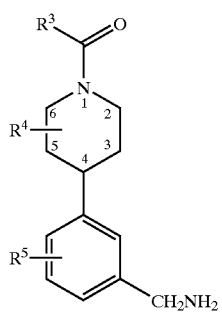

(Ib)

wherein
- R³ is aryl, arylalkenyl, cycloalkenyl, cycloalkyl, heteroaryl, heteroarylalkenyl, heterocycloalkenyl, a carbon linked heterocycloalkyl or alkyl optionally substituted by one or more groups selected from hydroxy, alkoxy, alkyloxycarbonylamino, cycloalkyl, heterocycloalkyl, $R^6$, —$OR^6$, —$S(O)_mR^6$ or —$C(=O)$—$R^6$;
- $R^4$ is hydrogen, acyl, alkoxy, alkyloxycarbonyl, carboxy, cyano, halo, hydroxy, —$C(=O)$—$NY^1Y^2$ or alkyl optionally substituted with alkoxy, alkylcarbonylamino, alkylsulfonylamino, hydroxy, —$S(O)_m$-alkyl or —$NY^1Y^2$; and
- $R^5$ is hydrogen, acyl, alkoxy, alkyloxycarbonyl, aryl, carboxy, cyano, halo, heteroaryl, heteroaryloxy, heterocycloalkyl, heterocycloalkyloxy, heterocycloalkylalkyloxy, heteroarylalkyloxy, hydroxy, trifluoromethyl, —$C(=O)$—$NY^1Y^2$, —$NY^1Y^2$, —$Z^1$—$C_{2-6}$alkylene-$R^7$ or alkyl optionally substituted with alkoxy, alkylcarbonylamino, alkylsulfonylamino, aryl, heteroaryl, heterocycloalkyl, hydroxy, ureido, —$C(=O)$—$NY^1Y^2$, —$SO_2$—$NY^1Y^2$, —$S(O)_m$-alkyl or —$NY^1Y^2$, and, a corresponding N-oxide of said compound, a prodrug of said compound, a pharmaceutically acceptable salt of said compound, a solvate of said compound, an N-oxides and prodrugs.

Particular examples of such compounds are described infra.

Furthermore, the present invention extends to a pharmaceutical composition comprising a compound of the present invention, as described above, and a pharmaceutically acceptable carrier thereof. Numerous examples of pharmaceutical carriers having applications in the present invention are described infra.

In addition, the present invention extends to a method for treating a patient suffering from a condition that can be ameliorated by the administration of an inhibitor of tryptase, comprising administering an effective amount of a compound of a compound of the present invention. An example of a condition that can be treated with a compound of the present invention includes, but certainly is not limited to inflammatory diseases, e.g., joint inflammation, arthritis, rheumatoid arthritis, rheumatoid spondylitis, gouty arthritis, traumatic arthritis, rubella arthritis, psoriatic arthritis, and other chronic inflammatory joint diseases. Other examples of conditions that can be treated with a method of the present invention include diseases of joint cartilage destruction, ocular conjunctivitis, vernal conjunctivitis, inflammatory bowel disease, asthma, allergic rhinitis, interstitial lung diseases, fibrosis, sceleroderma, pulmonary fibrosis, liver cirrhosis, myocardial fibrosis, neurofibromas, hypertrophic scars, various dermatological conditions, for example, atopic dermatitis and psoriasis, myocardial infarction, stroke, angina and other consequences of atherosclerotic plaque rupture, as well as periodontal disease, diabetic retinopathy, tumor growth, anaphylaxis, multiple sclerosis, peptic ulcers, and syncytial viral infections, to name only a few.

In a particular embodiment, the present invention extends to a method of treating a subject suffering from asthma, comprising administering to the subject an effective amount of a compound of the present invention.

In another embodiment, the present invention extends to a method for treating a patient suffering from joint inflammation, comprising administering to the patient an effective amount of a compound of the present invention.

In addition, the present invention extends to a pharmaceutical comprising a compound of the present invention, a second compound selected from the group consisting of a beta andrenergic agonist, an anticholinergic, an anti-inflammatory corticosteroid, and an anti-inflammatory agent, and a pharmaceutically acceptable carrier thereof. Particular inflammatory diseases or disorders that can be treated with such a pharmaceutical composition includes, but certainly is not limited to asthma.

Moreover, the present invention extends to a method for treating a patient suffering from an inflammatory disorder, comprising administering to the patient a compound of the present invention and a second compound selected from the group consisting of a beta andrenergic agonist, an anticholinergic, an anti-inflammatory corticosteroid, and an anti-inflammatory agent. In such a method of the present invention, a compound of the present invention can be administered to the patient before a second compound, a second compound can be administered to the patient before a compound of the present invention, or a compound of the present invention and a second compound can be administered concurrently. Particular examples of andrenergic agonists, anticholinergics, anti-inflammatory corticosteroids, and anti-inflammatory agents having applications in a method of the present invention are described infra.

Accordingly, it is a principal object to provide compounds having an anti-tryptase activity. Such compounds can readily be used to treat a condition that can be ameliorated by the administration of an inhibitor of tryptase.

It is another object of the present invention to provide pharmaceutical compositions for treating a condition that can be ameliorated by the administration of an inhibitor of tryptase.

It is yet another object of the present invention to provide pharmaceutical compositions comprising a compound of the present invention.

These and other aspects of the present invention will be better appreciated by reference to the following Detailed Description.

DETAILED DESCRIPTION

As used above, and throughout the instant specification and appending claims, the following terms, unless otherwise indicated, shall be understood to have the following meanings:

As used herein, the term "compounds of the present invention", and equivalent expressions, are meant to embrace compounds of formulae (I), (Ia), or (Ib) as hereinbefore described, which expression includes the prodrugs, the pharmaceutically acceptable salts and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used herein, the term "treatment" includes prophylactic therapy as well as treatment of an established condition.

"Patient" includes both human and other mammals.

"Effective amount" is meant to describe an amount of compound of the present invention effective in inhibiting tryptase and thus producing the desired therapeutic effect.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain that may be straight or branched. Exemplary alkenyl groups include ethenyl, propenyl, n-butenyl, i-butenyl, 3-methylbut-2-enyl, n-pentenyl, heptenyl, octenyl and decenyl.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkyloxycarbonyl" means an alkyl-O—C(=O)— group in which the alkyl group is as described herein. Exemplary alkyloxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylcarbonylamino" means an alkyl-C(=O)—NH— group in which the alkyl group is as described herein. Exemplary alkylcarbonylamino groups include acetamido and propionamido.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkyl—O— group in which the alkyl group is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-$SO_2$— group in which the alkyl group is as previously described. Preferred alkylsulfonyl groups are those in which the alkyl group is $C_{1-4}$alkyl.

"Alkylsulfonylamino" means an alkyl-$SO_2$—NH— group in which the alkyl group is as described herein. Exemplary alkylsulfonylamino groups include methanesulfonamido and ethanesulfonamido.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, 2-butynyl, 3-methylbut-2-ynyl, and n-pentynyl.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkyloxycarbonyl, alkylenedioxy, alkylsulfinyl, alkylsulfonyl, alkylthio, aroyl, aroylamino, aryl, arylalkenyl, arylalkynyl, arylalkyloxy, arylalkyloxycarbonyl, arylalkylthio, aryloxy, aryloxyalkyl, aryloxycarbonyl, arylsulfinyl, arylsulfonyl, arylthio, carboxy, cyano, halo, heteroaroyl, heteroaryl, heteroarylalkenyl, heteroarylalkynyl, heteroarylalkyloxy, heteroaroylamino, heteroaryloxy, heteroaryloxyalkyl, hydroxy, nitro, trifluoromethyl, —$NY^1Y^2$, —$CONY^1Y^2$, —$SO_2NY^1Y^2$, —$Z^2$—$C_{2-6}$alkylene-$NY^1Y^2$ {where $Z^2$ is O, $NR^8$ or $S(O)_m$}, —$NY^1$—(C=O)alkyl, —$NY^1$—$SO_2$alkyl or alkyl optionally substituted with alkoxy, aroyl, aryl, aryloxy, heteroaryl, hydroxy, or —$NY^1Y^2$.

"Arylalkenyl" means an aryl-alkenyl- group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl- group in which the aryl and alkynyl are as previously described. Exemplary arylalkynyl groups include phenylethynyl and 3-phenylbut-2-ynyl.

"Aryloxy" means an aryl-O— group in which the aryl group is as previously described. Exemplary aryloxy groups include optionally substituted phenoxy and naphthoxy.

"Aryloxyalkyl" means an aryl-O-alkyl- group in which the aryl and alkyl groups are as previously described. Exemplary aryloxyalkyl groups include phenoxymethyl and 1- or 2-naphthyloxymethyl.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-SO$_2$— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulfur, or nitrogen. Examples of azaheteroaryl groups include benzimidazolyl, imidazolyl, isoquinolinyl, isoxazolyl, pyrazolopyrimidinyl, pyridyl, pyrimidinyl, quinolinyl, quinazolinyl and thiazolyl.

"Cyclic amine" means a 3 to 8 membered monocyclic cycloalkyl ring system where one of the ring carbon atoms is replaced by nitrogen and which (i) may optionally contain an additional heteroatom selected from O, S or NY$^3$ (where Y$^3$ is hydrogen, alkyl, arylalkyl, and aryl) and (ii) may be fused to additional aryl or heteroaryl ring to form a bicyclic ring system. Exemplary cyclic amines include pyrrolidine, piperidine, morpholine, piperazine, indoline and pyrindoline.

"Cycloalkenyl" means a cycloalkyl group containing at least one carbon-carbon double bond. Exemplary monocyclic cycloalkenyl rings include cyclopentenyl, cyclohexenyl or cycloheptenyl.

"Cycloalkyl" means a saturated monocyclic or bicyclic ring system of about 3 to about 10 carbon atoms optionally substituted by oxo, alkyl, aryl or —C(=O)—NY$^1$Y$^2$. Exemplary monocyclic cycloalkyl rings include C$_{3-8}$cycloalkyl rings such as cyclopropyl, cyclopentyl, cyclohexyl and cycloheptyl.

"Cycloalkylalkyl" means a cycloalkyl-alkyl- group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Halo" or "halogen" means fluoro, chloro, bromo, or iodo. Preferred are fluoro or chloro.

"Heteroaroyl" means a heteroaryl—C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulfur (examples of such groups include benzimidazolyl, benzthiazolyl, benzthiophenyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above.

"Aryldiyl" means an optionally substituted bivalent radical derived from an aryl group as defined herein. Exemplary aryldiyl groups include optionally substituted phenylene, naphthylene and indanylene. Suitable substituents include one or more "aryl group substituents" as defined above, particularly halogen, methyl or methoxy.

"Heteroaryldiyl" means a bivalent radical derived from a heteroaryl group as defined below.

"Heteroarylalkenyl" means a heteroaryl-alkenyl- group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl- group in which the heteroaryl and alkyl moieties are as previously described. Preferred heteroarylalkyl groups contain a C$_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl- group in which the heteroaryl and alkynyl moieties are as previously described. Exemplary heteroarylalkenyl groups include pyridylethynyl and 3-pyridylbut-2-ynyl.

"Heteroaryloxy" means an heteroaryl-O— group in which the heteroaryl group is as previously described. Exemplary heteroaryloxy groups include optionally substituted pyridyloxy.

"Heteroaryloxyalkyl" means an heteroaryl-O-alkyl— group in which the heteroaryl and alkyl groups are as previously described. Exemplary heteroaryloxyalkyl groups include pyridyoxymethyl and 2-, 3- or 4-quinolinyloxymethyl.

"Heterocycloalkenyl" means a cycloalkenyl group of about 3 to 7 ring members which contains one or more heteroatoms selected from O, S or NY$^4$ (where Y$^4$ is hydrogen, alkyl, aryl, arylalkyl, and alkyloxycarbonyl). Exemplary heterocycloalkenyl groups include 1,2,3,6-tetrahydro-pyridine.

"Heterocycloalkyl" means: (i) a cycloalkyl group of about 3 to 7 ring members which contains one or more heteroatoms selected from O, S or NY$^4$ (where Y$^4$ is hydrogen, alkyl, aryl, arylalkyl, and alkyloxycarbonyl) and which may optionally be substituted by oxo (examples of such groups include piperidinyl, pyrrolidinyl, morpholinyl, tetrahydropyranyl and tetrahydrothiophenyl; (ii) an optionally substituted partially saturated multicyclic heterocarbocyclic moiety in which one or more aryl (or heteroaryl) rings and a cycloalkyl group of about 3 to 7 ring members, which contains one or more heteroatoms selected from O, S or NY$^4$ and which may optionally be substituted by oxo, are fused together to form a cyclic structure (examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Heterocycloalkylalkyloxy" means a heterocycloalkyl-alkyl-O— group in which the heterocycloalkyl and alkyl moieties are as previously described.

"Heterocycloalkyloxy" means a heterocycloalkyl-O— group in which the heterocycloalkyl is as previously described.

"Prodrug" means a compound which is suitable for administration to a patient without undue toxicity, irritation, allergic response, and the like, and is convertible in vivo by metabolic means (e.g. by hydrolysis) to a compound of the present invention, including N-oxides thereof. A thorough discussion is provided in T. Higuchi and V. Stella, *Pro-drugs as Novel Delivery Systems*, Vol. 14 of the A. C. S. Symposium Series, and in Edward B. Roche, ed., *Bioreversible Carriers in Drug Design*, American Pharmaceutical Association and Pergamon Press, 1987, both of which are incorporated herein by reference. For example an ester of a compound of the present invention containing a hydroxy group may be convertible by hydrolysis in vivo to the parent molecule. Alternatively an ester of a compound of the present invention containing a carboxy group may be convertible by hydrolysis in vivo to the parent molecule.

Suitable esters of compounds of present invention containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and quinates.

An especially useful class of esters of compounds of the present invention containing a hydroxy group, may be formed from acid moieties selected from those described by Bundgaard et al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Suitable esters of compounds of the present invention containing a carboxy group, are for example those described by F. J. Leinweber, Drug Metab. Res., 1987, 18, page 379.

The compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (Ia) above, the following are particular and preferred groupings:

$R^1$ may particularly represent hydrogen.

$R^2$ may particularly represent hydrogen.

$R^3$ may particularly represent aryl, such as optionally substituted phenyl or optionally substituted naphthyl, especially substituted phenyl. Exemplary optional substituents include one or more halo atoms or alkyl substituted by aryl, alkyl substituted by aryloxy, alkyl substituted by aroyl, alkyl substituted by heteroaryl, arylalkynyl, heteroarylalkynyl, aryl, heteroaryl, arylalkenyl or arylalkyloxy, in which the aryl or heteroaryl groups may be further substituted by one or more aryl group substituents.

$R^3$ may also particularly represent heteroaryl, such as optionally substituted pyridyl, optionally substituted quinolinyl, optionally substituted thienyl, optionally substituted furanyl or optionally substituted indolyl, especially substituted thienyl, substituted pyridyl or indolyl. Exemplary optional substituents include alkyl substituted by aryl, alkyl substituted by aryloxy, alkyl substituted by aroyl, alkyl substituted heteroaryl, arylalkynyl, heteroarylalkynyl, heteroaryl, arylalkenyl or arylalkyloxy, in which the aryl or heteroaryl groups are further substituted by one or more aryl group substituents.

$R^4$ may particularly represent hydrogen.

$R^4$ may also particularly represent cyano, especially when attached to the tertiary ring carbon atom.

$R^5$ may particularly represent hydrogen.

$R^5$ may also particularly represent lower alkyl (e.g. methyl) or halo (e.g. fluoro).

╌╌╌╌ may particularly represent a single bond.

n may particularly represent 2.

It is to be understood that this invention covers all appropriate combinations of the particular and preferred groupings referred to herein.

A particular group of compounds of the invention are compounds of formula (Ib):

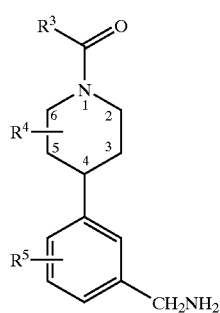

in which $R^3$, $R^4$ and $R^5$ are a herinbefore defined and the corresponding N-oxides, and their prodrugs; and pharmaceutically acceptable salts and solvates (e.g. hydrates) of such compounds and their N-oxides and prodrugs.

Compounds of formula (Ib) in which $R^3$ represents aryl, such as optionally substituted phenyl or optionally substituted naphthyl, especially substituted phenyl, are preferred. Preferred optional substituents include one or more halo atoms or alkyl substituted by aryl or alkyl substituted heteroaryl, in which the aryl or heteroaryl groups may be further substituted by one or more aryl group substituents. $R^3$ especially represents dichlorophenyl [e.g. 3,4-dichlorophenyl], phenyl$C_{1-3}$alkylphenyl [e.g. phenethyl], hydroxyphenyl$C_{1-3}$alkylphenyl [e.g. 4-hydroxyphenylethylphenyl] and aminopyridyl$C_{1-3}$alkylphenyl [e.g. (4-amino-pyrid-3-yl)ethylphenyl].

Compounds of formula (Ib) in which $R^3$ represents heteroaryl, such as optionally substituted pyridyl, optionally substituted quinolinyl, optionally substituted thienyl, optionally substituted furanyl or optionally substituted indolyl, especially substituted thienyl, substituted pyridyl or indolyl, are preferred. Preferred optional substituents include alkyl substituted by aryl and alkyl substituted heteroaryl in which the aryl or heteroaryl groups are further substituted by one or more aryl group substituents. $R^3$ especially represents phenyl$C_{1-3}$alkylpyridyl [e.g. 5-phenylethyl-pyrid-3-yl], phenyl$C_{1-3}$alkylthienyl [e.g. 5-phenylethyl-thien-2-yl] and indolyl [e.g. indol-6-yl].

Compounds of formula (Ib) in which $R^4$ represents hydrogen are preferred.

Compounds of formula (Ib) in which $R^4$ represents cyano are also preferred. $R^4$ is preferably attached at the 4 position of the piperidine ring.

Compounds of formula (Ib) in which $R^5$ represents hydrogen are preferred.

Compounds of formula (Ib) in which $R^5$ represents lower alkyl (e.g. methyl) or halo (e.g. fluoro), are also preferred. $R^5$ is preferably attached to the phenyl ring in the position para to the —$CH_2NH_2$ group.

A preferred group of compounds of the invention are compounds of formula (Ib) in which:—$R^3$ is substituted phenyl [especially 3,4-dichlorophenyl, phenethyl, 4-hydroxyphenylethylphenyl and (4-amino-pyrid-3-yl)ethylphenyl] or optionally substituted heteroaryl [especially 5-phenylethyl-pyrid-3-yl, 5-phenylethyl-thien-2-yl or indol-6-yl]; $R^4$ is hydrogen, or cyano attached at the 4 position of the piperidine ring; $R^5$ is hydrogen, or lower alkyl (e.g. methyl) or halo (e.g. fluoro) attached to the phenyl ring in the position para to the —$CH_2NH_2$ group; and the corresponding N-oxides, and their prodrugs; and pharmaceutically acceptable salts and solvates (e.g. hydrates) of such compounds and their N-oxides and prodrugs.

Particular compounds of the invention are selected from the compounds formed by joining the carbon atom (C*) of one of the fragments (A1 to A12) shown in Table 1 to the carbon atom (C*) of one of the fragments (B1 to B13) shown in Table 2, and joining the nitrogen atom (N*) of one of the fragments (B1 to B12) shown in Table 2 to the carbon atom (C*) of one of the acidic fragments (C1 to C140) depicted in Table 3.

TABLE 1

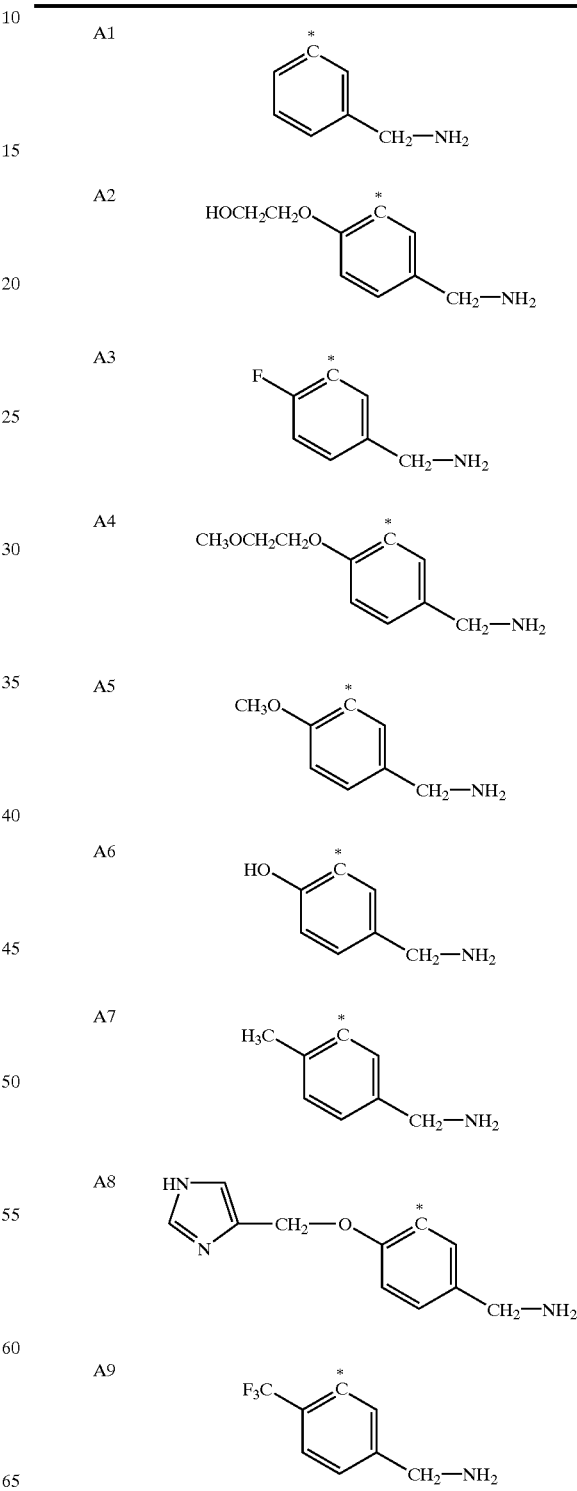

TABLE 1-continued
| | |
|---|---|
| A10 | 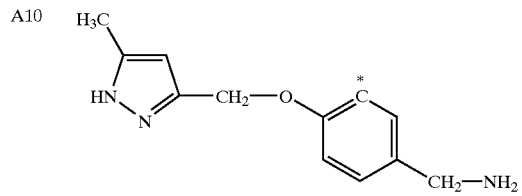 |
| A11 | 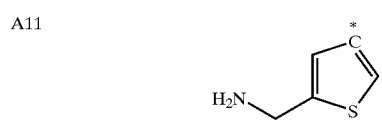 |
| A12 | 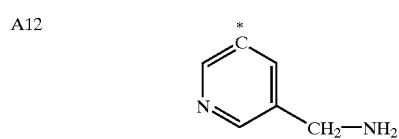 |
TABLE 2
| | |
|---|---|
| B1 |  |
| B2 | 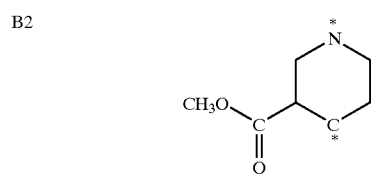 |
| B3 |  |
| B4 |  |
| B5 | 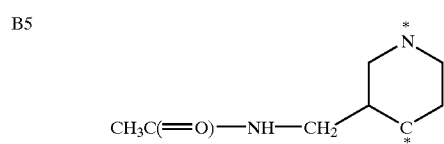 |
| B6 | 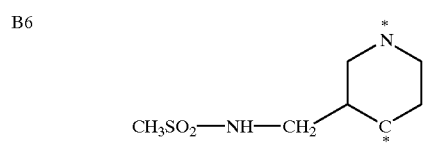 |
TABLE 2-continued
| | |
|---|---|
| B7 | 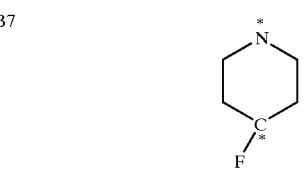 |
| B8 | 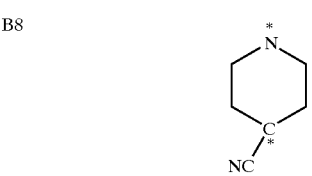 |
| B9 |  |
| B10 | 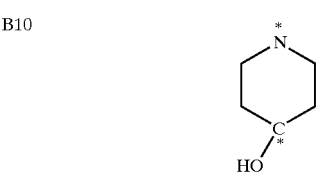 |
| B11 | 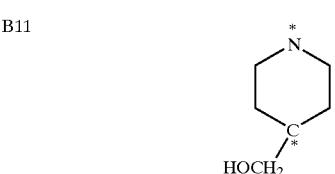 |
| B12 |  |
| B13 | 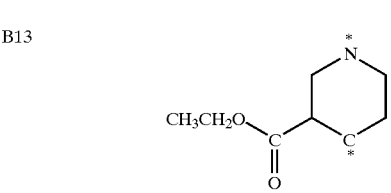 |
TABLE 3
| | |
|---|---|
| C1 | 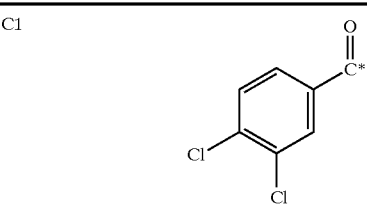 |

TABLE 3-continued
| | |
|---|---|
| C2 | 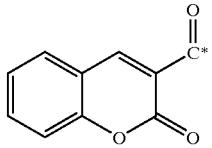 |
| C3 | 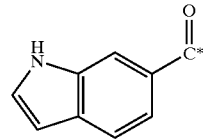 |
| C4 | 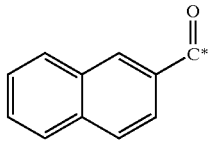 |
| C5 | 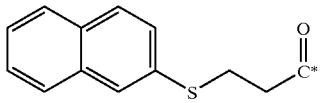 |
| C6 | 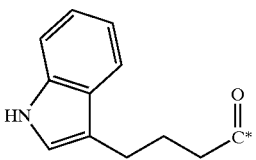 |
| C7 | 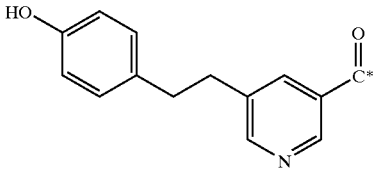 |
| C8 | 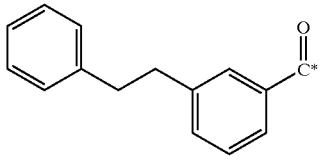 |
| C9 | 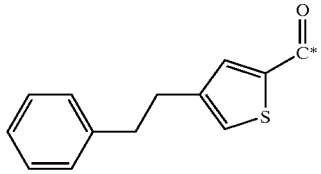 |
| C10 | 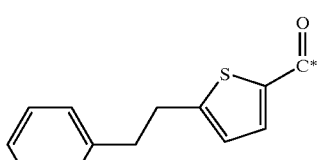 |
| C11 | 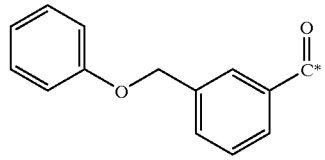 |
| C12 | 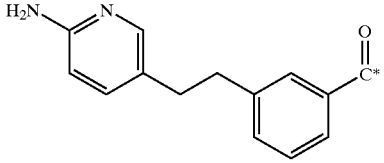 |
| C13 | 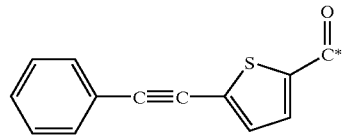 |
| C14 | 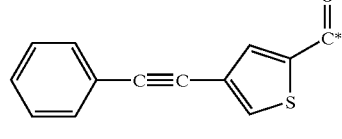 |
| C15 | 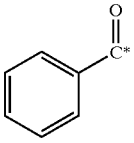 |
| C16 | 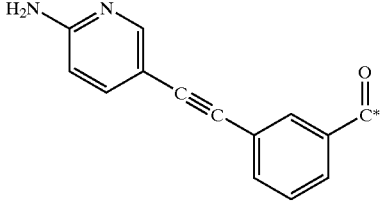 |
| C17 | 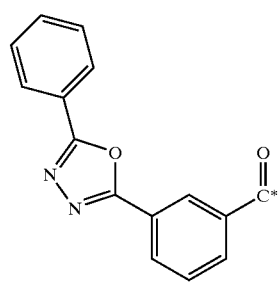 |
| C18 | 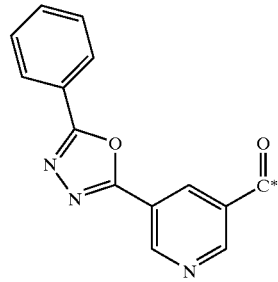 |

TABLE 3-continued
| | |
|---|---|
| C19 | 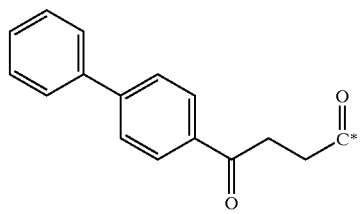 |
| C20 | 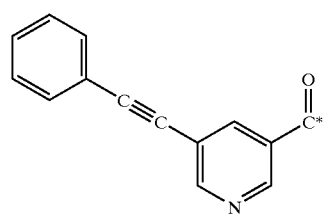 |
| C21 | 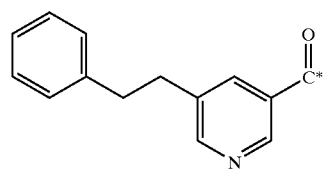 |
| C22 | 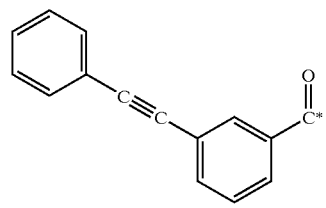 |
| C23 | 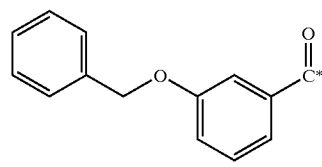 |
| C24 | 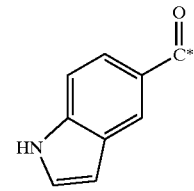 |
| C25 | 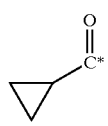 |
| C26 | 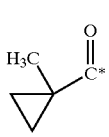 |
| C27 | 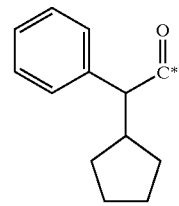 |
| C28 | 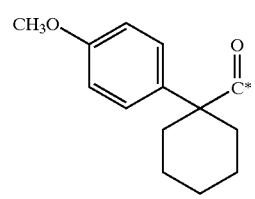 |
| C29 | 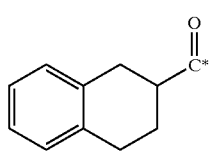 |
| C30 | 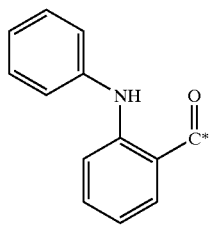 |
| C31 | 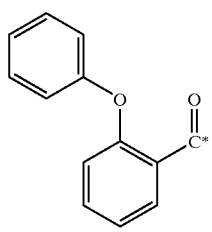 |
| C32 | 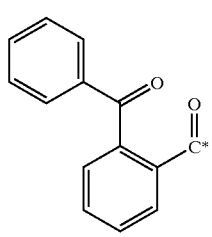 |
| C33 | 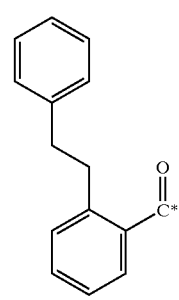 |

TABLE 3-continued
| | |
|---|---|
| C34 | 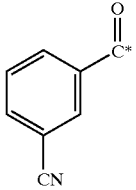 |
| C35 | 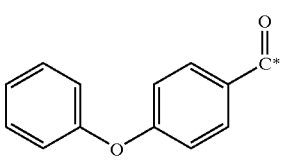 |
| C36 | 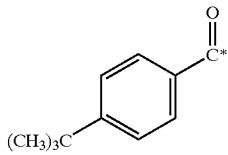 |
| C37 | 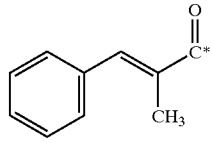 |
| C38 | 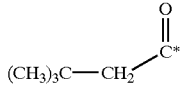 |
| C39 | 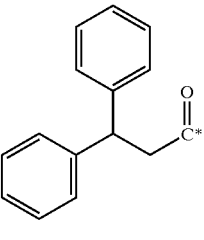 |
| C40 | 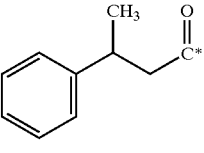 |
| C41 | 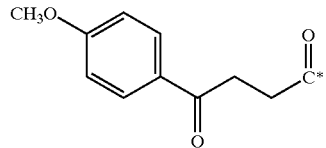 |
| C42 | 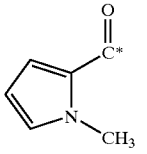 |
| C43 | 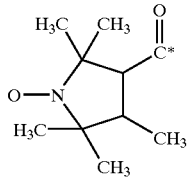 |
| C44 | 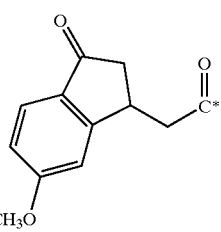 |
| C45 | 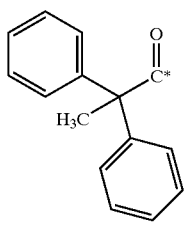 |
| C46 | 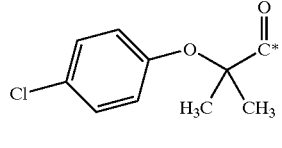 |
| C47 | 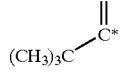 |
| C48 | 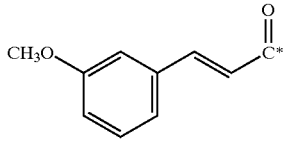 |
| C49 | 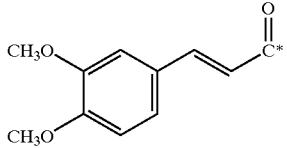 |
| C50 | 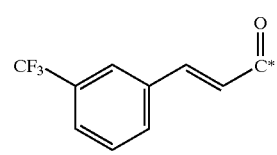 |
| C51 | 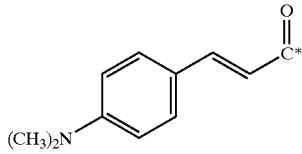 |

TABLE 3-continued

| | |
|---|---|
| C52 | (xanthene-9-carbonyl) |
| C53 | (lipoyl / 5-(1,2-dithiolan-3-yl)pentanoyl) |
| C54 | (3,4-methylenedioxycinnamoyl) |
| C55 | (quinoline-3-carbonyl) |
| C56 | (2-(methylthio)pyridine-3-carbonyl) |
| C57 | (3-chlorobenzo[b]thiophene-2-carbonyl) |
| C58 | (4-benzyloxybenzoyl) |
| C59 | ($(CH_3)_2CH$–CH(Ph)–C(=O)*) |
| C60 | (2-(methylthio)benzoyl) |
| C61 | (3-(pyridin-4-yl)acryloyl) |
| C62 | (4-tert-butylcyclohexanecarbonyl) |
| C63 | (3-methyl-1H-indene-2-carbonyl) |
| C64 | (quinoline-6-carbonyl) |
| C65 | (benzo[b]thiophene-2-carbonyl) |
| C66 | (2-(1H-pyrrol-1-yl)benzoyl) |
| C67 | (5-methyl-2-phenyl-2H-1,2,3-triazole-4-carbonyl) |
| C68 | (2-(1-oxo-1,3-dihydroisobenzofuran-3-yl)acetyl) |

TABLE 3-continued
| | |
|---|---|
| C69 |  |
| C70 |  |
| C71 |  |
| C72 |  |
| C73 |  |
| C74 |  |
| C75 |  |
TABLE 3-continued
| | |
|---|---|
| C76 | |
| C77 | |
| C78 | |
| C79 | |
| C80 | |
| C81 | |
| C82 | |
| C83 |  |

TABLE 3-continued

| ID | Structure |
|----|-----------|
| C84 | 2-(thiophen-2-ylvinyl)benzoyl group |
| C85 | thieno[3,2-b]thiophene-2-carbonyl |
| C86 | 1,3-dimethyl-1H-thieno[2,3-c]pyrazole-5-carbonyl |
| C87 | 4-(4-ethylphenyl)-4-oxobutanoyl |
| C88 | 1-(4-chlorophenyl)-2,5-dimethyl-1H-pyrrole-3-carbonyl |
| C89 | 1-carbamoylcyclopropane-1-carbonyl |
| C90 | 3-ethoxythiophene-2-carbonyl |
| C91 | 4-(2,3-dihydrobenzo[b][1,4]dioxin-6-yl)benzoyl |
| C92 | 2,6-dimethoxybenzoyl |
| C93 | 3-(3,4-dimethoxyphenyl)propanoyl |
| C94 | (R)-2-acetoxy-2-phenylacetyl |
| C95 | 3-((4-methoxyphenyl)thio)propanoyl |
| C96 | CH$_3$(CH$_2$)$_3$C*(=O)— |
| C97 | CH$_3$(CH$_2$)$_4$C*(=O)— |
| C98 | CH$_3$C*(=O)— |
| C99 | (CH$_3$)$_3$C—O—C(=O)—NH—(CH$_2$)$_3$—C*(=O)— |
| C100 | (CH$_3$)$_3$C—O—C(=O)—NH—(CH$_2$)$_2$—C*(=O)— |

TABLE 3-continued

| | |
|---|---|
| C101 | [structure: tert-butyl 4-(carbonyl)piperidine-1-carboxylate] |
| C102 | [structure: tert-butyl 2-(carbonyl)benzoate] |
| C103 | [structure: 5-oxo-5-phenylpentanoyl] |
| C104 | [structure: 1-(methylthio)-6,6-dimethyl-4-oxo-4,5,6,7-tetrahydrobenzo[c]thiophene-3-carbonyl] |
| C105 | [structure: 1-(propylthio)-4-oxo-4,5,6,7-tetrahydrobenzo[c]thiophene-3-carbonyl] |
| C106 | [structure: 1-ethyl-1H-indole-3-carbonyl] |
| C107 | [structure: 5-(phenylethynyl)furan-2-carbonyl] |
| C108 | [structure: 3-(2-fluorophenethyl)benzoyl] |
| C109 | [structure: 3-chlorobenzoyl] |
| C110 | [structure: 5,6-dichloropyridine-3-carbonyl] |
| C111 | [structure: 2,3-dihydrobenzofuran-5-carbonyl] |
| C112 | [structure: 3-(methylthio)-4,5-dihydrobenzo[c]thiophene-1-carbonyl] |
| C113 | [structure: 5-(2-(6-aminopyridin-3-yl)ethyl)pyridine-3-carbonyl] |
| C114 | [structure: 3-(4-fluorophenethyl)benzoyl] |
| C115 | [structure: 3-chlorothieno[3,2-b]thiophene-5-carbonyl] |
| C116 | [structure: 6-fluorothieno[3,2-b]thiophene-2-carbonyl] |

TABLE 3-continued
| | |
|---|---|
| C117 | 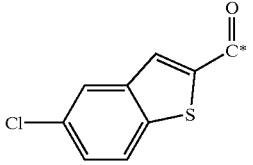 |
| C118 | 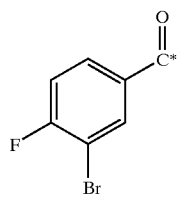 |
| C119 | 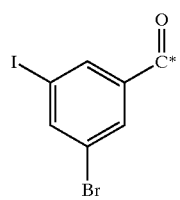 |
| C120 | 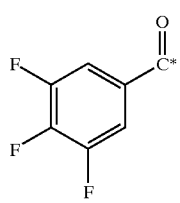 |
| C121 | 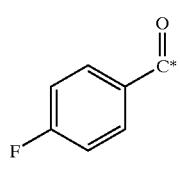 |
| C122 | 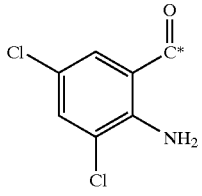 |
| C123 | 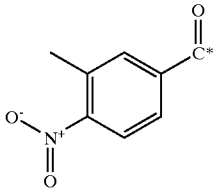 |
| C124 | 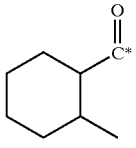 |
| C125 | 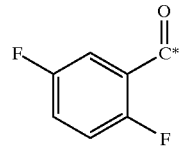 |
| C126 | 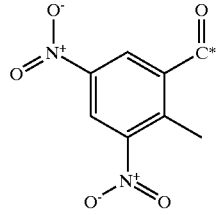 |
| C127 | 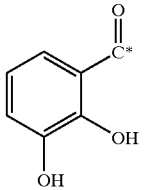 |
| C128 | 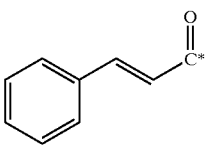 |
| C129 | 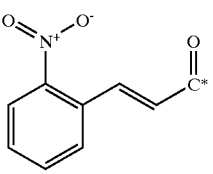 |
| C130 | 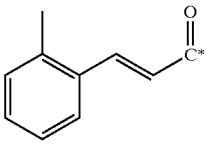 |
| C131 | 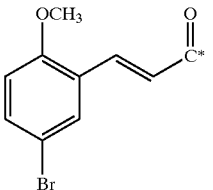 |
| C132 | 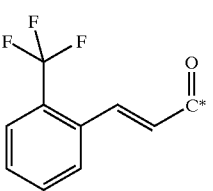 |

TABLE 3-continued

| | | | | |
|---|---|---|---|---|
| C133 | 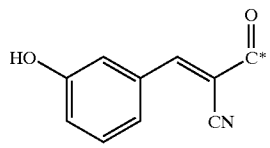 | | C137 | 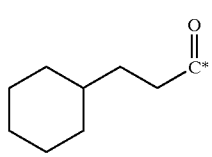 |
| C134 | 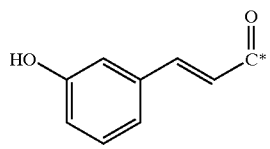 | | C138 | 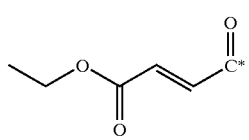 |
| C135 | 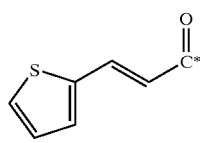 | | C139 | 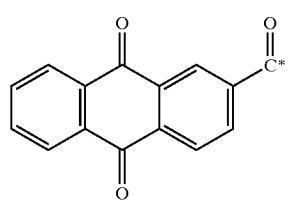 |
| C136 | 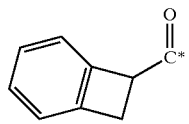 | | C140 | 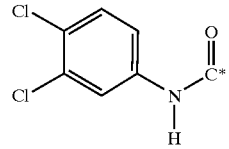 |

Particularly preferred examples of fragments "A", "B", and "C" are illustrated in Table 4 below:

TABLE 4

Pursuant to 37 CFR § 1.52, table 4 is filed herewith in compliance with the American Standard for Information Interchange (ASCII) on a recordable compact disc (CD-R), submitted in duplicate, created on April 23, 2001, having a size of 237 KB, and is hereby incorporated by reference herein in its entirety. Thus, for example, in the above list the compound denoted as A1–B1–C1 is the product of the combination of group A1 in Table 1 and B1 in Table 2 and C1 in Table 3, namely

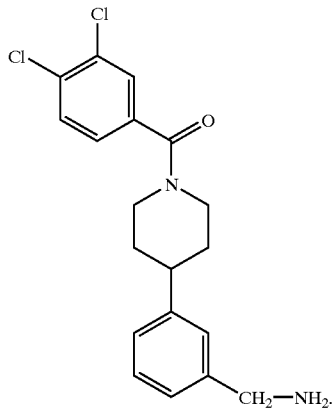

Preferred compounds of the invention are selected from:
3-[1-(5-phenylethynyl-pyridine-3-carbonyl)-piperidin-4-yl]-benzylamine
3-[1-(3-phenylethyl-benzoyl)-piperidin-4-yl]-benzylamine;
3-{1-[3-(4-hydroxyphenyl)ethyl-benzoyl]-piperidin-4-yl}-benzylamine;
3-{1-[3-(6-amino-pyridin-3-yl)ethyl-benzoyl]-piperidin-4-yl}-benzylamine;
3-[1-(5-phenylethyl-thiophene-2-carbonyl)-piperidin-4-yl]-benzylamine;
4-fluoro-3-[1-(5-phenylethyl-pyridine-3-carbonyl)-piperidin-4-yl]-benzylamine;
4-methyl-3-[1-(5-phenylethyl-pyridine-3-carbonyl)-piperidin-4-yl]-benzylamine;
3-[1-(indole-6-carbonyl)-piperidin-4-yl]-benzylamine;
4-(3-aminomethyl-phenyl)-1-(5-phenethyl-pyridine-3-carbonyl)-piperidine-4-carbonitrile

TABLE 4-continued

[4-(3-aminomethylphenyl)piperidin-1-yl]-(3,4-dichlorophenyl)methanone;
1-{1-[4-(3-Aminomethyl-phenyl)-piperidin-1-yl]-methanoyl}-3-methylsulfanyl-6,7-dihydro-5H-benzo[c]thiophen-4-one trifluoroacetate;
1-[4-(3-Aminomethyl-phenyl)-piperidin-1-yl]-1-(3-methylsulfanyl-6,7-dihydro-benzo[c]thiophen-1-yl)-methanone trifluoroacetate;
1-{1-[4-(3-Aminomethyl-phenyl)-piperidin-1-yl]-methanoyl}-3-ethylsulfanyl-6,6-dimethyl-6,7-dihydro-5H-benzo[c]thiophen-4-one trifluoroacetate;
1-{1-[4-(3-Aminomethyl-phenyl)-piperidin-1-yl]-methanoyl}-3-propylsulfanyl-6,7-dihydro-5H-benzo[c]thiophen-4-one trifluoroacetate;
1-{1-[4-(3-Aminomethyl-phenyl)-piperidin-1-yl]-methanoyl}-3-isopropylsulfanyl-6,7-dihydro-5H-benzo[c]thiophen-4-one trifluoroacetate;
1-[4-(3-Aminomethyl-phenyl)-piperidin-1-yl]-1-benzo[b]thiophen-2-yl-methanone-trifluoroacetate;
1-[4-(3-Aminomethyl-phenyl)-4-hydroxy-piperidin-1-yl]-1-(5-phenethyl-pyridin-3-yl)-methanone-ditrifluoroacetate;
1-[4-(3-Aminomethyl-phenyl)-piperidin-1-yl]-1-(1-methyl-1H-indol-3-yl)-methanone-trifluoroacetate;
1-[4-(3-Aminomethyl-phenyl)-piperidin-1-yl]-1-[3-(2-fluoro-phenylethynyl)-phenyl]-methanone trifluoroacetate;
1-[4-(3-Aminomethyl-phenyl)-piperidin-1-yl]-1-{3-[2-(2-fluoro-phenyl)-ethyl]-phenyl)}-methanone trifluoroacetate;
1-[4-(3-Aminomethyl-phenyl)-piperidin-1-yl]-1-{3-[2-(6-amino-pyridin-3-yl)-ethyl]-phenyl}-methanone tri-trifluoroacetate;
1-[4-(3-Aminomethyl-phenyl)-piperidin-1-yl]-1-(6-chloro-thieno[3,2-b]thiophen-2-yl)-methanone trifluoroacetate;
(3R,4S) and (3S, 4R)-4-(3-Aminomethyl-phenyl)-1-(5-phenethyl-pyridine-3-carbonyl)-piperidine-3-carboxylic acid ethyl ester dihydrochloride;
3-[1-(5-Phenylethynyl-furan-2-carbonyl)-piperidin-4-yl]-benzylamine trifluoroacetate;
4-(3-Aminomethyl-phenyl)-piperidine-1-carboxylic acid (3,4-dichloro-phenyl)-amide trifluoroacetate;
1-[4-(3-Aminomethyl-phenyl)-piperidin-1-yl]-1-(2,3-dihydro-benzofuran-5-yl)-methanone;
1-[4-(3-Aminomethyl-phenyl)-piperidin-1-yl]-1-(5,6-dichloro-pyridin-3-yl)-methanone;
1-[4-(3-Aminomethyl-phenyl)-piperidin-1-yl]-1-(3-bromo-4-fluoro-phenyl)-methanone;
(E)-1-[4-(3-Aminomethyl-phenyl)-piperidin-1-yl]-3-(2-nitro-phenyl)-propenone;
1-[4-(3-Aminomethyl-phenyl)-piperidin-1-yl]-1-(3-bromo-5-iodo-phenyl)-methanone;
(E)-1-[4-(3-Aminomethyl-phenyl)-piperidin-1-yl]-3-phenyl-propenone;
1-[4-(3-Aminomethyl-phenyl)-piperidin-1-yl]-3-cyclohexyl-propan-1-one;
and the corresponding N-oxides, and their prodrugs; and pharmaceutically acceptable salts and solvates (e.g. hydrates) of such compounds and their N-oxides and prodrugs.

Pharmaceutical Compositions

As explained above, compounds of the present invention exhibit useful pharmacological activity and accordingly are incorporated into pharmaceutical compositions and used in the treatment of patients suffering from certain medical disorders. The present invention thus provides, according to a further aspect, compounds of the invention and pharmaceutical compositions containing compounds of the invention for use in therapy, wherein a pharmaceutical composition of the present invention comprising a compound of the present invention, and a pharmaceutically acceptable carrier thereof. As used herein, the term "pharmaceutically acceptable" preferably means approved by a regulatory agency of a government, in particular the Federal government or a state government, or listed in the U.S. Pharmacopeia or another generally recognized pharmacopeia for use in animals, and more particularly in humans. Suitable pharmaceutical carriers are described in "Remington's Pharmaceutical Sciences" by E. W. Martin.

A pharmaceutical composition according to the present invention can be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used. Such pharmaceutically acceptable carriers can also be sterile water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include mannitol, human serum albumin (HSA), starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

Naturally, a pharmaceutical composition of the present invention compositions will contain an effective diagnostic or therapeutic amount of the active compound together with a suitable amount of carrier so as to provide the form for proper administration to the patient. While intravenous injection is a very effective form of administration, other modes can be employed, such as by injection, or by oral, nasal or parenteral administration, which are discussed infra.

Methods of Treatment

Compounds within the scope of the present invention possess tryptase inhibition activity according to tests described in the literature and described in vitro procedures hereinafter, and which test results are believed to correlate to pharmacological activity in humans and other mammals. Thus, in a further embodiment, the present invention provides compounds of the invention and compositions containing compounds of the invention for use in the treatment of a patient suffering from, or subject to, conditions that can be ameliorated by the administration of an inhibitor of tryptase. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis, osteoarthritis and other chronic inflammatory joint diseases, or diseases of joint cartilage destruction, ocular conjunctivitis, vernal conjunctivitis, inflammatory bowel disease, asthma, allergic rhinitis, interstitial lung diseases, fibrosis, sceleroderma, pulmonary fibrosis, liver cirrhosis, myocardial fibrosis, neurofibromas, hypertrophic scars, various dermatological conditions, for example, atopic dermatitis and psoriasis, myocardial infarction, stroke, angina and other consequences of atherosclerotic plaque rupture, as well as periodontal disease, diabetic retinopathy, tumor growth, anaphylaxis, multiple sclerosis, peptic ulcers, and syncytial viral infections.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of tryptase, for example conditions as hereinbefore described, which comprises the administration to the patient of an effective amount of compound of the invention or a composition containing a compound of the invention. "Effective amount" is meant to describe an amount of compound of the present invention effective in inhibiting tryptase and thus producing the desired therapeutic effect.

Combination Therapy

As explained above, other pharmaceutically active agents can be employed in combination with the compounds of the invention depending upon the disease being treated. For example, in the treatment of asthma, beta-adrenergic agonists such as albuterol, terbutaline, formoterol, fenoterol or prenaline can be included, as can anticholinergics such as ipratropium bromide, anti-inflammatory corticosteroids such as beclomethasone dipropionate, triamcinolone acetonide, flunisolide or dexamethasone, and anti-inflammatory agents such as sodium cromoglycate and nedocromil sodium. Thus, the present invention extends to a pharmaceutical composition comprising a compound of the present invention and a second compound selected from the group consisting of a beta andrenergic agonist, an anticholinergic, an anti-inflammatory corticosteroid, and an anti-inflammatory agent; and a pharmaceutically acceptable carrier thereof. Particular pharmaceutical carriers having applications in this pharmaceutical composition are described herein.

Furthermore, the present invention extends to a method for treating a patient suffering from asthma, comprising administering the patient a compound of the present invention, and a second compound selected from the group consisting of a beta andrenergic agonist, an anticholinergic, an anti-inflammatory corticosteroid, and an anti-inflammatory agent. In such a combination method, a compound of the present invention can be administered prior to the administration of the second compound, a compound of the present invention can be administered after administration of the second compound, or a compound of the present invention and the second compound can be administered concurrently.

Modes of Delivery

According to the invention, a compound of the present invention, or a pharmaceutical composition of the present invention, may be introduced parenterally, transmucosally, e.g., orally, nasally, pulmonarily, or rectally, or transdermally to a patient.

Oral Delivery

Contemplated for use herein are oral solid dosage forms, which are described generally in Remington's Pharmaceutical Sciences, 18th Ed. 1990 (Mack Publishing Co. Easton PA 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for a therapeutic is given by Marshall, K. In: *Modern Pharmaceutics* Edited by G. S. Banker and C. T. Rhodes Chapter 10, 1979, herein incorporated by reference. In general, the formulation will include a compound of the present invention, and inert ingredients which allow for protection against the stomach environment, and release of the biologically active material, i.e., a compound of the present invention, in the intestine.

Also specifically contemplated are oral dosage forms of a compound of the present invention. Such a compound may be chemically modified so that oral delivery is more efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the compound of the present invention, and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367–383; Newmark, et al., 1982, J. Appl. Biochem. 4:185–189. Other polymers that could be used are poly-1,3-dioxolane and poly-1,3,6-tioxocane. Preferred for pharmaceutical usage, as indicated above, are polyethylene glycol moieties.

For a compound of the present invention, the location of release may be the stomach, the small intestine (the duodenum, the jejunum, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the compound of the present invention, or by release of the compound beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the present invention may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of a compound of the present invention either alone or as a mixture in different ratios.

Additives which potentially enhance uptake of a compound of the present invention are, for instance, the fatty acids oleic acid, linoleic acid and linolenic acid.

Controlled release oral formulation may be desirable. The drug could be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Pulmonary Delivery

Also contemplated herein is pulmonary delivery of a compound of the present invention, either alone, or in a pharmaceutical composition. The compound is delivered to the lungs of a mammal while inhaling and traverses across the lung epithelial lining to the blood stream. Other reports of this include Adjei et al., 1990, Pharmaceutical Research, 7:565–569; Adjei et al., 1990, International Journal of Pharmaceutics, 63:135–144 (leuprolide acetate); Braquet et al., 1989, Journal of Cardiovascular Pharmacology, 13(suppl. 5):143–146 (endothelin-1); Hubbard et al., 1989, Annals of Internal Medicine, Vol. III, pp. 206–212 (a1-antitrypsin); Smith et al., 1989, J. Clin. Invest. 84:1145–1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482–3488 (interferon-γ and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass., to name only a few. All such devices require the use of formulations suitable for the dispensing a compound of the present invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compounds of the present invention may also be prepared in different formulations depending on the type of chemical modification or the type of device employed.

Formulations suitable for use with a nebulizer, either jet or ultrasonic, will typically comprise a compound of the present invention dissolved in water at a concentration of about 0.1 to 25 mg of compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing a compound of the invention suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing a compound of the invention, and may also include a bulking agent, such as lactose, sorbitol, sucrose, or mannitol in amounts which facilitate dispersal of the powder from the device, e.g., 50 to 90% by weight of the formulation. The compound of the present invention should most advantageously be prepared in particulate form with an average particle size of less than 10 mm (or microns), most preferably 0.5 to 5 mm, for most effective delivery to the distal lung.

Nasal Delivery

Nasal delivery of a compound of the present invention is also contemplated. Nasal delivery allows the passage of the compound to the blood stream directly after administering the therapeutic product to the nose, without the necessity for deposition of the product in the lung. Formulations for nasal delivery include those with dextran or cyclodextran.

Transdermal Delivery

Various and numerous methods are known in the art for transdermal administration of a drug, e.g., via a transdermal patch, have applications in the present invention. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Topical Administration

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

Rectal Administration

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

Furthermore, compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Naturally, a patient in whom administration of a compound of the present invention is an effective therapeutic regimen is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., ie., for veterinary medical use.

Preparation of Compounds of the Invention

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (Ia) wherein $R^3$, $R^4$, $R^5$ and n are as hereinbefore defined, $R^1$ and $R^2$ are both hydrogen and ------- is a single bond, represented by formula (IX), may be prepared as shown in Scheme 1

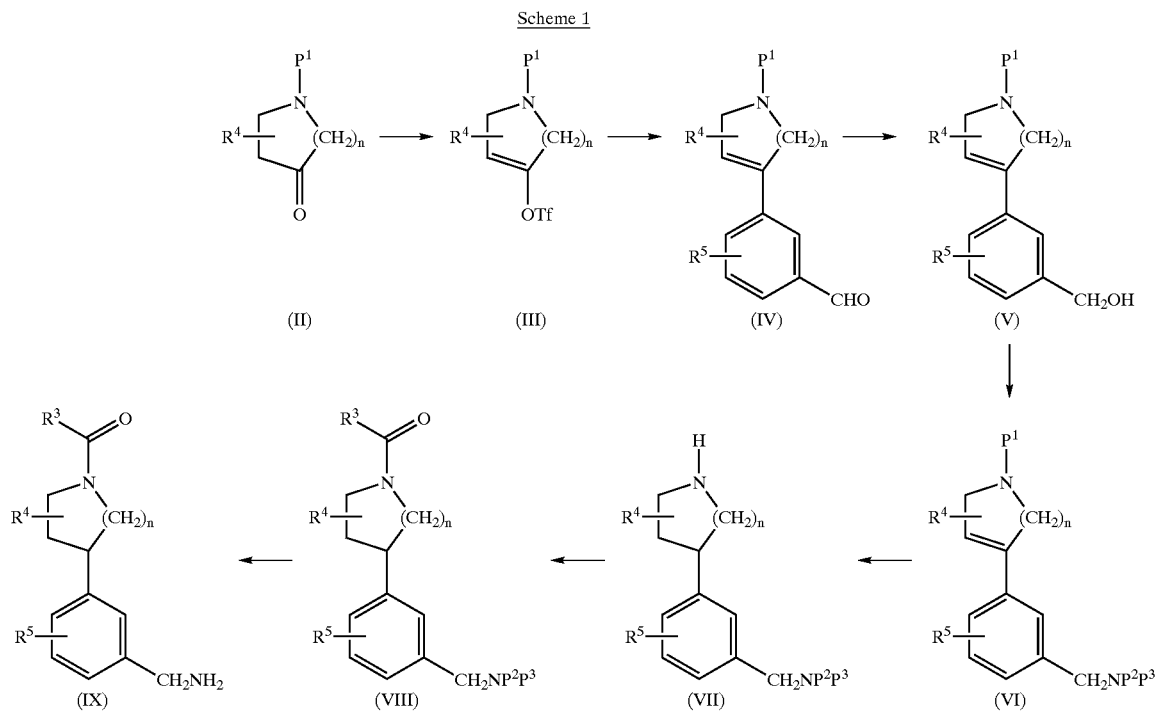

For example compounds of formula (IX) may be prepared by:—
(i) treating compounds of formula (II) wherein $R^4$ and n are as hereinbefore defined and $P^1$ is a suitable protecting group, such as benzyloxycarbonyl, with a suitable base, such as lithium hexamethyldisilazane, in an inert solvent, such as tetrahydrofuran, and at a temperature at about −78° C., followed by reaction with N-phenyltrifluoromethane-sulfonimide to give compounds of formula (III) wherein $R^4$, $P^1$ and n are as hereinbefore defined and Tf is —$SO_2CF_3$;
(ii) reaction of triflates of formula (III) with an aryl boronic acid of formula (X):—

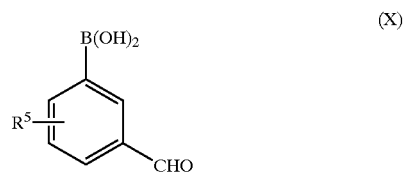

in the presence of an aqueous base such as sodium bicarbonate and a palladium catalyst such as palladium tetrakistriphenylphosphine, and at a temperature from about 80 to about 100° C., to give compounds of formula (IV) wherein $R^4$, $R^5$, $P^1$ and n are as hereinbefore defined;
(iii) reduction of compounds of formula (IV) with sodium borohydride in ethanol to give compounds of formula (V) wherein $R^4$, $R^5$, $P^1$ and are as hereinbefore defined;

(iv) conversion of the hydroxymethyl group in compounds of formula (V) to an aminomethyl group which is suitably protected to facilitate the further processes described hereinafter—for example reaction of compounds of formula (V) with phosphorus tribromide in pyridine followed by treatment of the resultant bromomethyl intermediate with di-tert-butyliminodicarboxylate to give compounds of formula (VI) wherein $R^4$, $R^5$, $P^1$ and n are as hereinbefore defined and $P^2$ and $P^3$ are each tertiary-butyloxycarbonyl (a suitable protecting group that is stable under conditions for the subsequent removal of protecting group $P^1$);

(v) removal of the protecting group $P^1$ in compounds of formula (VI), for example when $P^1$ is benzyloxycarbonyl and $P^2$ and $P^3$ are both tertiary-butyloxycarbonyl, the deprotection may conveniently be carried out by hydrogenation in the presence of a suitable metal catalyst, e.g. platinum or palladium optionally supported on an inert carrier such as carbon, preferably in a solvent such as methanol or ethanol to give compounds of formula (VII) wherein $R^4$, $R^5$ and n are as hereinbefore defined and $P^2$ and $P^3$ are as just defined;

(vi) reaction of compounds of formula (VII) with compounds of formula (XI):—

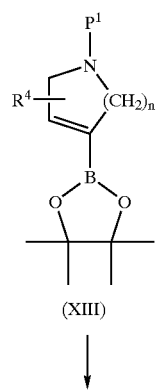

(XI)

wherein $R^3$ is as hereinbefore defined and $X^1$ is a hydroxy group, or a halogen, preferably chlorine, atom using standard coupling conditions [for example when $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide), at room temperature; and when $X^1$ is a halogen atom the acylation reaction may be carried out with the aid of a base, such pyridine, preferably in a solvent such as tetrahydrofuran and at a temperature at about room temperature] to give compounds of formula (VIII) wherein $R^3$, $R^4$, $R^5$, n, $P^2$ and $P^3$ are as defined above;

(vii) removal of the protecting groups $P^2$ and $P^3$ in compounds of formula (VIII), for example when $P^2$ and $P^3$ are both tertiary-butyloxycarbonyl the reaction may conveniently be carried out in the presence of an acid such as trifluoroacetic acid in an inert solvent, such as dichloromethane, or by treatment with hydrogen chloride in methanol.

Compounds of formula (Ia) wherein $R^1$, $R^2$, $R^3$, $R^4$, $R^5$ and n are as hereinbefore defined and ----- is a single bond, represented by formula (XVI), may be prepared as shown in scheme 2.

Scheme 2

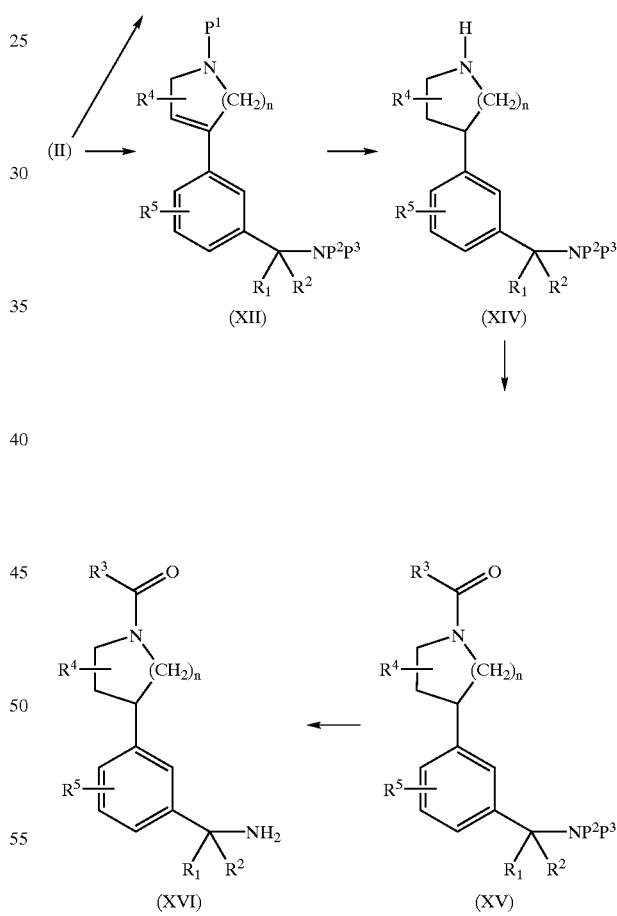

For example compounds of formula (XVI) may be prepared by:—

(i) reaction of compounds of formula (II) wherein $R^4$ and n are as hereinbefore defined and $P^1$ is a suitable protecting group, such as benzyloxycarbonyl, with an aryl boronate of formula (XVII):

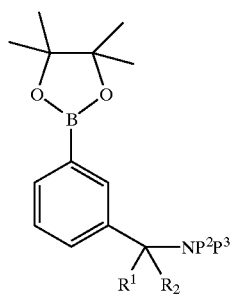

(XVII)

wherein $R^1$, $R^2$, $P^2$ and $P^3$ are as hereinbefore defined in the presence of potassium carbonate and a palladium catalyst such as [1,1'-bis-(diphenylphosphino) ferroceno]-dichloropalladium (II)-dichloromethane complex in an inert solvent, such as dimethylsulfoxide, and at a temperature at about 80° C. to give compounds of formula (XII) wherein $R^1$, $R^2$, $R^4$, $R^5$, n, $P^1$, $P^2$ and $P^3$ are as hereinbefore defined; alternatively compounds of formula (XII) may be prepared by reaction of compounds of formula (II) with bis(pinacolato)boron in the presence of potassium acetate, (diphenylphosphino)-ferrocene and [1,1'-bis-(diphenylphosphino)ferroceno]-dichloropalladium (II), in an inert solvent, such as dioxane, and at a temperature at about 80° C. followed by reaction of the intermediate boronate of formula (XIII) with compounds of formula (XVIII):—

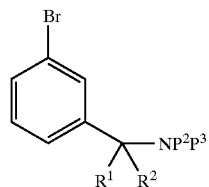

(XVIII)

wherein $R^1$, $R^2$, $P^1$ and $P^2$ are as hereinbefore defined in the presence of potassium carbonate and a palladium catalyst such as [1,1'-bis-(diphenylphosphino) ferroceno]-dichloropalladium (II)-dichloromethane complex in an inert solvent, such as dimethylsulfoxide, and at a temperature at about 80° C.];

(ii) removal of the protecting group $P^1$ in compounds of formula (XII), for example when $P^1$ is benzyloxycarbonyl and $P^2$ and $P^3$ are both tertiary-butyloxycarbonyl, the deprotection may conveniently be carried out by hydrogenation as described hereinabove to give compounds of formula (XIV) wherein $R^1$, $R^2$, $R^4$, $R^5$, n, $P^2$ and $P^3$ are as just defined;

(iii) reaction of compounds of formula (XIV) with compounds of formula (XI) wherein $R^1$ is as hereinbefore defined and $X^1$ is a hydroxy group, or a halogen, preferably chlorine, atom using standard coupling conditions [for example those described hereinabove] to give compounds of formula (XV) wherein $R^1$, $R^2$, $R^3$, $R^4$, $R^5$, n, $P^2$ and $P^3$ are as defined above;

(vii) removal of the protecting groups $P^2$ and $P^3$ in compounds of formula (XV), using standard coupling conditions [for example those described hereinabove].

Compounds of formula (Ia) wherein $R^1$, $R^2$, $R^3$, $R^4$, $R^5$ and n are as hereinbefore defined and ------ is a single bond, represented by formula (XVI), may also be prepared using resin technology as shown in scheme 3:—

Scheme 3

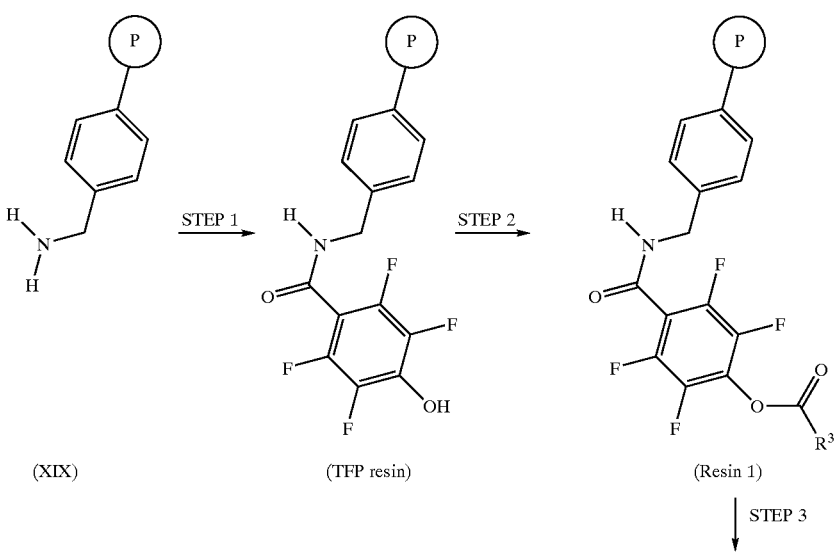

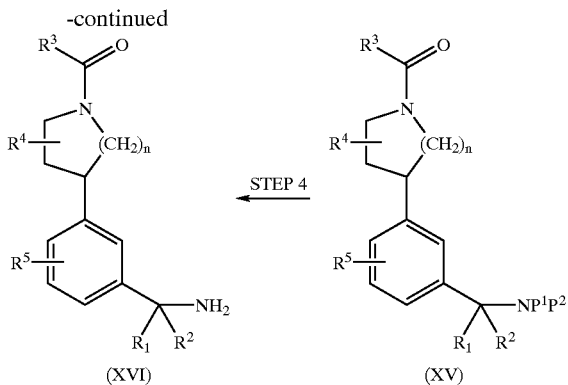

For example compounds of formula (XVI) may be prepared by:—
(i) Coupling of the resin (XIX, an aminomethylated styrene/divinylbenzene copolymer), where

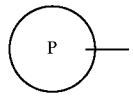

represents the polymeric core (comprising polystyrene crosslinked with 1% to 2% divinylbenzene), with 4-hydroxy-2,3,5,6-tetrafluorobenzoic acid, according to the procedure described by J. M. Salvino et. al. in International Patent Application Publication No. WO 99/67228, to give TFP resin wherein

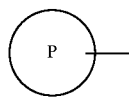

is as hereinbefore defined;
(ii) treatment of TFP resin with acids of formula (XI) wherein $R^3$ is as hereinbefore defined and $X^1$ is hydroxy, in the presence of diisopropyl carbodiimide and dimethylaminopyridine, in an inert solvent, such as dimethylformamide, and at a temperature at about room temperature, to give resin 1 wherein $R^3$ and

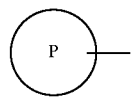

are hereinbefore defined;
(iii) treatment of resin 1 with compounds of formula (XIV) wherein $R^1$, $R^2$, $R^4$, $R^5$, n, $P^1$ and $P^2$ are as defined immediately hereinbefore, in an inert solvent, such as dichloromethane, and at a temperature at about room temperature, to give compounds of formula (XV);
(iv) removal of the protecting groups in compounds of formula (XV), for example when $P^2$ and $P^3$ are both tertiary-butyloxycarbonyl the reaction may conveniently be carried out in the presence of an acid such as trifluoracetic acid in an inert solvent, such as dichloromethane, or by treatment with hydrogen chloride in methanol.

Compounds of formula (Ib), wherein $R^3$ and $R^5$ are as hereinbefore defined and $R^4$ is cyano attached at the 4 position of the piperidine ring, represented by formula (XX), may be prepared as shown in scheme 4:—

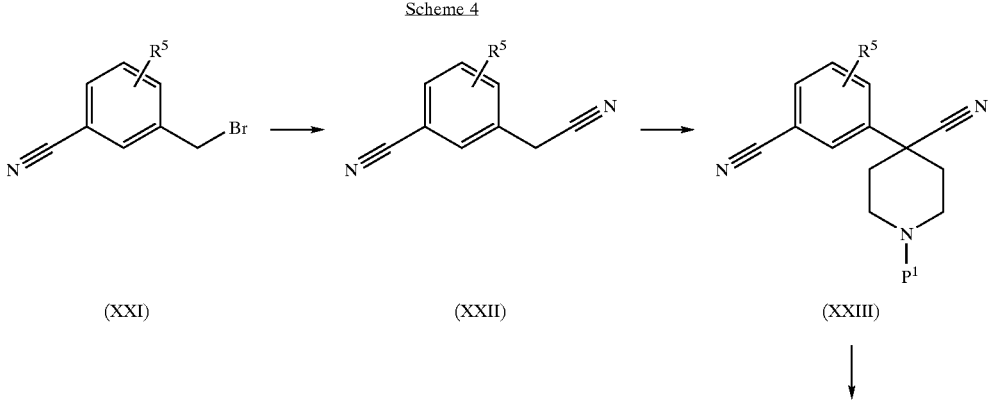

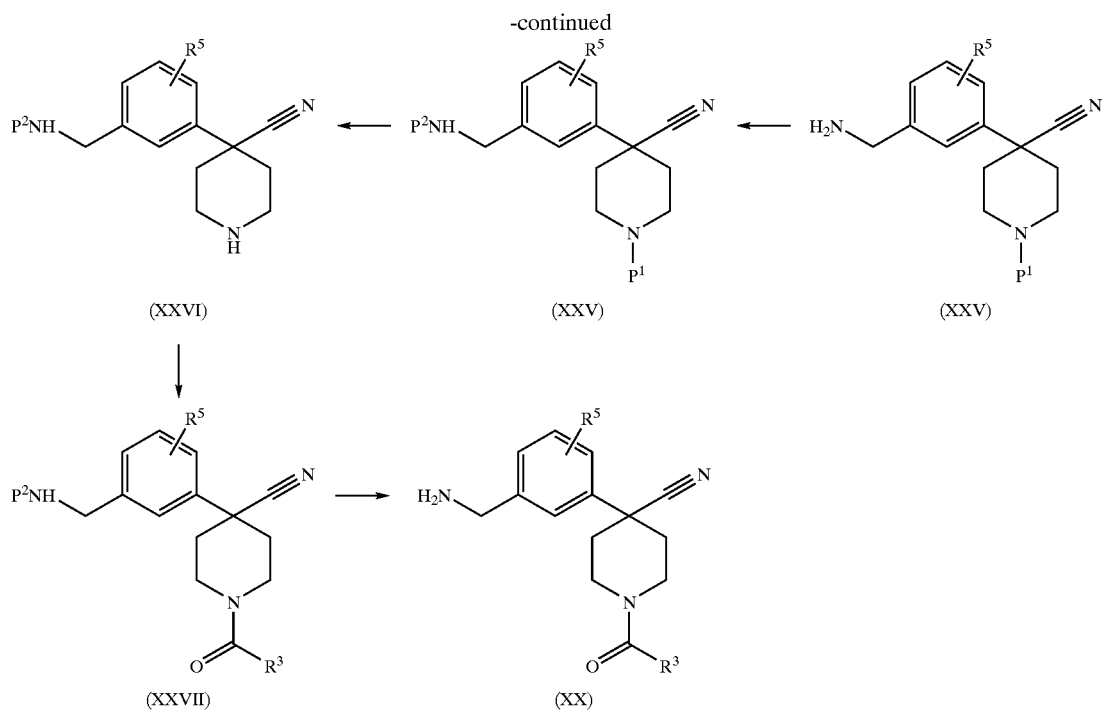

(XXVI)   (XXV)   (XXV)

(XXVII)   (XX)

For example compounds of formula (XX) may be prepared by:—

(i) Reacting a benzyl bromide of formula (XXI) wherein $R^5$ is as hereinbefore defined, with sodium cyanide, in the presence of a phase transfer catalyst, such as tetrabutylammonium bromide, in a mixture of water and an inert solvent, such as dichloromethane, and at a temperature at about room temperature to give compounds of formula (XXII) wherein $R^5$ is as hereinbefore defined;

(ii) treatment of the benzylcyanides of formula (XXII) with a suitably protected bis-(2-haloethyl)amine of formula (XXVIII):—

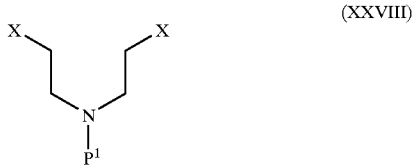

(XXVIII)

wherein X is halo, preferably chloro, and $P^1$ is a suitable protecting group, such as tertiary-butyloxycarbonyl, in the presence of sodium hydride and in an inert solvent, such as dimethylformamide, and at a temperature at about room temperature, to give compounds of formula (XXIII) wherein $R^5$ and $P^1$ are as hereinbefore defined;

(iii) hydrogenation of compounds of formula (XXIII) in the presence of hydrochloric acid in ethanol and under pressure to give compounds of formula (XXIV) wherein $R^5$ and $P^1$ are as hereinbefore defined;

(iv) protection of the amino group in compounds of formula (XXIV) with a suitable protecting group, for example with a benzyloxycarbonyl group, to give compounds of formula (XXV) wherein $R^5$, $P^1$ and $P^2$ are as hereinbefore defined;

(v) removal of the protecting group $P^1$ in compounds of formula (XXV) to give compounds of formula (XXVI) wherein $R^5$ and $P^2$ are as hereinbefore defined;

(vi) reaction of compounds of formula (XXVI) with compounds of formula (XI) wherein $R^1$ is as hereinbefore defined and $X^1$ is a hydroxy group, or a halogen, preferably chlorine, atom using standard coupling conditions [for example those described hereinabove] to give compounds of formula (XXVII) wherein $R^5$ and $P^2$ are as defined above;

(vii) removal of the protecting groups $P^2$ in compounds of formula (XXVII), using standard coupling conditions [for example those described hereinabove].

Compounds of formula (Ia) wherein $R^3$, $R^4$, $R^5$ and n are as hereinbefore defined, $R^1$ and $R^2$ are both hydrogen and ----- is a double bond, represented by formula (IX), may be prepared by removal of the $P^1$ protecting group in compounds of formula (VI) followed by acylation with compounds of formula (XI) and subsequent removal of the $P^2$ and $P^3$ protecting groups.

Compounds of formula (Ia) wherein $R^1$, $R^2$, $R^3$, $R^4$, $R^5$ and n are as hereinbefore defined and ----- is a double bond, represented by formula (XVI), may be prepared by removal of the $P^1$ protecting group in compounds of formula (XII) followed by acylation with compounds of formula (XI) and subsequent removal of the $P^2$ and $P^3$ protecting groups.

According to a further feature of the present invention, compounds of the invention may be prepared by interconversion of other compounds of the invention.

As an example of the interconversion process, compounds of formula (Ia) wherein $R^1$, $R^2$, $R^4$, $R^5$ and n are as hereinbefore defined and $R^3$ contains an optionally substituted alkylene linkage, may be prepared by hydrogenation of the corresponding compounds of formula (Ia) in which $R^3$ contains the corresponding optionally substituted alkenylene or alkynylene linkage. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of the invention containing a heterocyclic group wherein the heteroatom is a nitrogen atom may be oxidized to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

As another example of the interconversion process, compounds of formula (Ia) containing sulfone linkages may be prepared by the oxidation of corresponding compounds containing —S— or sulfoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

It will be appreciated that compounds of the present invention may contain asymmetric centers. These asymmetric centers may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds the present invention. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

The starting materials and intermediates may be prepared by the application or adaptation of known methods, for example methods as described in the Reference Examples or their obvious chemical equivalents.

Aryl boronates of formula (XVII) wherein $R^1$, $R^2$, $P^2$ and $P^3$ are as hereinbefore defined may be prepared by reaction of compounds of formula (XVIII) wherein $R^1$, $R^2$, $P^2$ and $P^3$ are as hereinbefore defined, with bis(pinacolato)boron in the presence of potassium acetate and [1,1'-bis-(diphenylphosphino)ferroceno]-dichloropalladium (II) in an inert solvent, such as dioxane, at and at a temperature at about 80° C.

Compounds of formula (XVIII) wherein $R^1$ and $R^2$ are as hereinbefore defined and $P^2$ and $P^3$ are both tertiary-butoxycarbonyl may be prepared by reaction of compounds of formula (XXIX):—

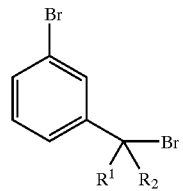

(XXIX)

wherein $R^1$ and $R^2$ are as hereinbefore defined with sodium hydride and di-tertiary-butyliminodicarboxylate, in an inert solvent, such as tetrahydrofuran, and at a temperature at about room temperature.

Intermediates of formulae (VIII) and (XV) are novel compounds and, as such, they and their processes described herein for their preparation constitute further features of the present invention.

The present invention is further Exemplified but not limited by the following illustrative Examples and Reference Examples.

In the nuclear magnetic resonance spectra (NMR) the chemical shifts are expressed in ppm relative to tetramethylsilane. Abbreviations have the following significances: br=broad, dd=double doublet, s=singlet; m=multiplet.

High Pressure Liquid Chromatography/Mass Spectrometry (LC-MS) conditions for determination of retention times ($R_T$) were as follows: 3 micron Luna C18 (2) HPLC column (30 mm×4.6 mm) eluting with (i) mixture of 0.05% trifluoroacetic acid in acetonitrile and 0.05% trifluoroacetic acid in water (1:19, v/v) for 2 minutes, (ii) mixture of 0.05% trifluoroacetic acid in acetonitrile and 0.05% trifluoroacetic acid in water (1:19 to 19:1, v/v) gradient elution over 10 minutes, (iii) mixture of 0.05% trifluoroacetic acid in acetonitrile and 0.05% trifluoroacetic acid in water (19:1, v/v) for 2 minutes, (iv) mixture of 0.05% trifluoroacetic acid in acetonitrile and 0.05% trifluoroacetic acid in water (1:19 to 1:19, v/v) gradient elution over 2 minutes; flow rate 2 ml/minute with approximately 200 µl/minute split to the Mass Spectrometer; injection volume 10–40 µl; in line Diode Array (220–450 nm), in line Evaporative light scattering (ELS) detection ELS—temperature 50° C., Gain 8–1.8 ml/minute; Source temperature 150° C.

The present invention may be better understood by reference to the following non-limiting Examples, which are provided as exemplary of the invention. The following examples are presented in order to more fully illustrate particular embodiments of the invention. They should in no way be construed, however, as limiting the broad scope of the invention.

In the nuclear magnetic resonance spectra (NMR), reported infra, the chemical shifts are expressed in ppm relative to tetramethylsilane. Abbreviations have the following significances: br=broad, dd=double doublet, s=singlet; m=multiplet.

Moreover, in the Examples, High Pressure Liquid Chromatography/Mass Spectrometry (LC-MS) conditions for determination of retention times ($R_T$) were as follows: 3 micron Luna C18 (2) HPLC column (30 mm×4.6 mm)

eluting with (i) mixture of 0.05% trifluoroacetic acid in acetonitrile and 0.05% trifluoroacetic acid in water (1:19, v/v) for 2 minutes, (ii) mixture of 0.05% trifluoroacetic acid in acetonitrile and 0.05% trifluoroacetic acid in water (1:19 to 19:1, v/v) gradient elution over 10 minutes, (iii) mixture of 0.05% trifluoroacetic acid in acetonitrile and 0.05% trifluoroacetic acid in water (19:1, v/v) for 2 minutes, (iv) mixture of 0.05% trifluoroacetic acid in acetonitrile and 0.05% trifluoroacetic acid in water (1:19 to 1:19, v/v) gradient elution over 2 minutes; flow rate 2 ml/minute with approximately 200 µl/minute split to the Mass Spectrometer; injection volume 10–40 µl; in line Diode Array (220–450 nm), in line Evaporative light scattering (ELS) detection ELS—temperature 50° C., Gain 8–1.8 ml/minute; Source temperature 150° C.

EXAMPLE 1

3-[1-(5-Phenylethynyl-pyridine-3-carbonyl)-piperidin-4-yl]-benzylamine di-hydrochloride (A.K.A. [4-(3-Aminomethyl-phenyl)-piperidin-1-yl]-(5-phenylethynyl-pyridin-3-yl)-methanone) di-hydrochloride A. B-{3-[N,N-bis-(tert-butoxycarbonyl)aminomethyl]-phenyl}-pinacolato-boron A solution of 3-bromobenzylbromide (7.5 g, 30 mmol) and di-tert-butyliminodicarboxylate (6.5 g, 30 mmol) in anhydrous tetrahydrofuran (80 ml) was treated portionwise with sodium hydride (1.2 g, 60% dispersion in mineral oil). After stirring at ambient temperature for 7 hours the reaction mixture was partitioned between saturated aqueous ammonium chloride solution (90 ml) and ethyl acetate (2 lots of 250 ml). The combined organic layers were washed with brine (75 ml), then dried over magnesium sulfate and then concentrated under vacuum. The residue was subjected to chromatography on silica gel eluting with a mixture of pentane and dichloromethane (2:1, v/v) to give 3-[N,N-bis-(tert-butoxycarbonyl)aminomethyl]-bromobenzene as a pale yellow oil (9.52 g). A sample of this material (2.0 g, 5.2 mmol) was dissolved in anhydrous dimethylsulfoxide (30 ml) and the solution was treated with potassium acetate (1.52 g, 15.5 mmol), bis(pinacolato)diboron (1.45 g, 5.7 mmol), and [1,1'-bis-(diphenylphosphino)ferroceno]-dichloropalladium (II)-dichloromethane complex (0.13 g, 0.16 mmol). This mixture was stirred at 80° C. under an atmosphere of nitrogen for 5 hours, then cooled and then partitioned between water (100 ml) and diethyl ether (4 lots of 75 ml). The combined organic layers were washed twice with brine (75 ml), then dried over magnesium sulfate and then concentrated under vacuum. The residue was subjected to chromatography on silica gel eluting with a mixture of pentane and dichloromethane (2:1, v/v) to give B-{3-[N,N-bis-(tert-butoxycarbonyl)-aminomethyl]-phenyl}-pinacolato-boron as a colorless oil (1.08 g). $^1$H NMR (CDCl$_3$, 500 MHz): δ 7.78 (s, 1H), 7.70 (m, 1H), 7.39 (m, 1H), 7.30 (m, 1H), 4.79 (s, 2H), 1.27 (s, 18H), 1.35 (s, 12H). MS(EI): 434(M$^+$+H).

B. 4-{3-[N,N-Bis-(tert-butoxycarbonyl)aminomethyl]-phenyl}-piperidine

A solution of lithium diisopropylamine (54 mmol) in anhydrous tetrahydrofuran (50 ml), at −78° C., was treated dropwise with a solution of benzyl 4-oxo-1-piperidinecarboxylate (11.4 g, 49 mmol) in anhydrous tetrahydrofuran (50 ml). This mixture was stirred at −78° C. for 20 minutes and then treated with a solution of N-phenyltrifluoromethanesulfonimide (19.26 g, 54 mmol) in anhydrous tetrahydrofuran (55 ml). The resultant orange suspension was warmed to 0° C., then stirred at 0° C. for 2 hours and then concentrated under vacuum. The residue was subjected to chromatography on silica gel eluting with dichloromethane to yield benzyl 1,2,3,6-tetrahydro-4-(trifluoromethylsulphonyloxy)-pyridine-1-carboxylate as a yellow oil (11.34 g). A portion of this material (0.84 g, 2.3 mmol) was dissolved in anhydrous dimethylformamide (20 ml) and the solution was treated with B-{3-[N,N-bis-(tert-butoxycarbonyl)aminomethyl]-phenyl-pinacolato-boron (1.0 g, 2.3 mmol), potassium carbonate (0.96 g, 6.7 mmol) and [1,1'-bis-(diphenylphosphino)ferroceno] dichloropalladium (II)-dichloromethane complex (0.1 g, 0.14 mmol). This mixture was heated at 80° C. under an atmosphere of nitrogen for 18 hours, then cooled and then concentrated under vacuum. The residue was partitioned between ethyl acetate (2 lots of 100 ml) and water (100 ml) containing concentrated ammonium hydroxide (6 ml). The combined organic extracts were dried over magnesium sulfate and then concentrated under vacuum. The resultant oil was subjected to chromatography on silica gel eluting with a mixture of ethyl acetate and pentane (1:4, v/v) to yield a yellow oil (0.9 g). This material was dissolved in ethanol (20 ml) and the solution was treated with 10% palladium on carbon (20 mg) then stirred at ambient temperature under an atmosphere of hydrogen for 5 hours. The reaction mixture was filtered through a short pad of hyflo and the filtrate was concentrated under vacuum to give 4-{3-[N,N-bis-(tert-butoxycarbonyl)aminomethyl]-phenyl}-piperidine as colorless oil (0.54 g). $^1$H NMR (CDCl$_3$, 500 MHz): δ 7.10 (m, 4H), 4.80 (s, 2H), 4.45 (br m, 1H), 3.20 (br m, 1H), 2.98 (br m, 1H), 2.75 (br m, 1H), 1.90 (m, 1H), 1.75–1.60 (m, 3H), 1.42 (s, 18H). MS(EI): 391(M$^+$+H).

C. N,N-Bis-(tert-butoxycarbonyl)-3-[1-(5-phenylethynyl-pyridine-3-carbonyl)-piperidin-4-yl]-benzylamine A solution of 5-phenylethynyl-pyridine-3-carboxylic acid (0.25 g, 1.1 mmol) in anhydrous dimethylformamide (5 ml) was treated with O-(7-azabenzotriazol-1-yl)-1,1,3,3-tetramethyluronium hexafluorophosphate (0.42 g, 1.1 mmol) and diisopropylethylamine (0.5 ml, 3 mmol). This mixture was stirred 15 minutes at ambient temperature and then treated with a solution of 4-{3-[N,N-Bis-(tert-butoxycarbonyl)aminomethyl]-phenyl}-piperidine (0.39 g, 1.0 mmol) in dimethylformamide (5 ml). After stirring at ambient temperature for 18 hours the reaction mixture was concentrated under vacuum. The residue was partitioned between ethyl acetate (50 ml) and saturated aqueous sodium bicarbonate (15 ml). The organic layer was dried over magnesium sulfate and then concentrated under vacuum. The residue was subjected to chromatography on silica gel eluting with a mixture of dichloromethane and methanol (49:1, v/v) to give N,N-bis-(tert-butoxycarbonyl)-3-[1-(5-phenylethynyl-pyridine-3-carbonyl)-piperidin-4-yl]-benzylamine as a yellow oil (0.25 g). $^1$H NMR [(CD$_3$)$_2$SO, 500 MHz]: δ 8.82 (s, 1H), 8.62 (s, 1H), 8.02 (s, 1H), 7.61 (m, 2H), 7.45 (m, 3H), 7.30 (m, 1H), 7.20 (m, 1H), 7.15 (m, 1H), 7.04 (m, 1H), 4.68 (s, 2H), 4.62 (br m, 1H), 3.60 (br m, 1H), 3.23 (br m, 1H), 2.85 (m, 2H), 1.83 (br m, 1H), 1.65 (m, 3H), 1.39 (s, 18H). MS(EI): 596(M$^+$+H).

D. 3-[1-(5-Phenylethynyl-pyridine-3-carbonyl)-piperidin-4-yl]-benzylamine di-hydrochloride A solution of 3-[1-(5-phenylethynyl-pyridine-3-carbonyl)-piperidin-4-yl]-benzonitrile (0.15 g, 0.25 mmol) in ethyl acetate (20 ml) was cooled to 0° C. and then saturated with hydrogen chloride gas. The reaction mixture was stirred at ambient temperature for 4 hours and then concentrated to dryness under vacuum. The residue was treated with ethyl acetate (10 ml) and the solvent removed under vacuum. This process was repeated twice to give 3-[1-(5-phenylethynyl-pyridine-3-carbonyl)-piperidin-4-yl]-benzylamine di-hydrochloride as a white solid (0.11 g).

¹H NMR [(CD₃)₂SO, 500 MHz]: δ 8.83 (s, 1H), 8.63 (s, 1H), 8.08 (s, 1H), 7.61 (m, 2H), 7.45 (m, 3H), 7.44 (s, 1H), 7.37 (m, 3H), 4.64 (br m, 1H), 4.00 (m, 2H), 3.62 (br m, 1H), 3.25 (br m, 1H), 2.90 (br m, 2H), 1.88 (br m, 1H), 1.70 (m, 3H). MS(EI): 396(M⁺+H).

EXAMPLE 2
3-[1-(5-Phenylethyl-pyridine-3-carbonyl)-piperidin-4-yl]-benzylamine di-hydrochloride (A.K.A. [4-(3-Aminomethyl-phenyl)-piperidin-1-yl]-(5-phenethyl-pyridin-3-yl)-methanone di-hydrochloride)

A. 5-Phenylethyl-pyridine-3-carboxylic acid

A solution of 5-phenylethynyl-pyridine-3-carboxylic acid (2 g, 8.9 mmol) in tetrahydrofuran (50 ml) was treated with 10% palladium on carbon (200 mg) and stirred at ambient temperature under an atmosphere of hydrogen for 5 hours. The reaction mixture was filtered through a short pad of hyflo and the filtrate was concentrated under vacuum to give 5-phenylethyl-pyridine-3-carboxylic acid as white solid (2 g). ¹H NMR [(CD₃)₂SO, 500 MHz]: δ 8.90 (m, 1H), 8.60 (m, 1H), 8.12 (m, 1H), 7.21 (m, 5H), 3.38 (br s, 1H), 2.95 (m, 4H).

B. N,N-Bis-(tert-butoxycarbonyl)-3-[1-(5-phenylethyl-pyridine-3-carbonyl)-piperidin-4-yl]-benzylamine By proceeding in a similar manner to the method described in EXAMPLE 1C, but using of 5-phenylethyl-pyridine-3-carboxylic acid in place of 5-phenylethynyl-pyridine-3-carboxylic acid, there was prepared N,N-bis-(tert-butoxycarbonyl)-3-[1-(5-phenylethyl-pyridine-3-carbonyl)-piperidin-4-yl]-benzylamine as a white amorphous solid. ¹H NMR [(CD₃)₂SO, 500 MHz]: δ 8.50 (s, 1H), 8.41 (s, 1H), 7.61 (m, 1H), 7.30–7.05 (m, 9H), 4.68 (s, 2H), 4.62 (br m, 1H), 3.48 (br m, 1H), 3.35 (s, 4H), 3.18 (br m, 1H), 2.85 (m, 2H), 1.82 (br m, 1H), 1.65 (br m, 1H), 1.58 (br m, 2H), 1.39 (s, 18H). MS(EI): 600(M⁺+H).

C. 3-[1-(5-Phenylethyl-pyridine-3-carbonyl)-piperidin-4-yl]-benzylamine di-hydrochloride By proceeding in a similar manner to the method described in EXAMPLE 1D, but using N,N-bis-(tert-butoxycarbonyl)-3-[1-(5-phenylethyl-pyridine-3-carbonyl)-piperidin-4-yl]-benzylamine in place of N,N-Bis-(tert-butoxycarbonyl)-3-[1-(5-phenylethynyl-pyridine-3-carbonyl)-piperidin-4-yl]-benzylamine, there was prepared 3-[1-(5-phenylethyl-pyridine-3-carbonyl)-piperidin-4-yl]-benzylamine di-hydrochloride as a white solid. ¹H NMR [(CD₃)₂SO, 500 MHz]: δ 8.90 (m, 2H), 8.42 (s, 1H), 7.58 (m, 1H), 7.38–7.20 (m, 8H), 4.62 (br m, 1H), 4.00 (m, 2H), 3.45 (br m, 1H), 3.20 (br m, 1H), 3.17 (m, 2H), 3.00 (m, 2H), 2.90 (br m, 2H), 1.88 (br m, 1H), 1.70 (br m, 3H). MS(EI): 400(M⁺+H).

EXAMPLE 3
3-[1-(1-oxy-5-phenylethyl-pyridine-3-carbonyl)-piperidin-4-yl]-benzylamine hydrochloride (A.K.A. [4-(3-Aminomethyl-phenyl)-piperidin-1-yl]-(1-oxy-5-phenethyl-pyridin-3-yl)-methanone hydrochloride)

A solution of N,N-Bis-(tert-butoxycarbonyl)-3-[1-(5-phenylethyl-pyridine-3-carbonyl)-piperidin-4-yl]-benzylamine (100 mg, 0.17 mmol, EXAMPLE 2B) in dichloromethane (10 ml) was treated with meta-chloroperbenzoic acid (80%, 80 mg, 0.37 mmol). After stirring for 18 hours at ambient temperature the reaction mixture was diluted with dichloromethane (40 ml) and then washed three times with saturated aqueous sodium bicarbonate solution (20 ml). The organic phase was dried over magnesium sulfate and then concentrated under vacuum. The residue was subjected to chromatography on silica gel eluting with a mixture of dichloromethane and methanol (98:2, v/v) to give N,N-bis-(tert-butoxycrbonyl)-3-[1-(1-oxy-5-phenylethyl-pyridine-3-carbonyl)-piperidin-4-yl]-benzylamine as a colorless oil (70 mg). This material was dissolved in ethyl acetate (10 ml) and the solution was cooled to 0° C., then saturated with hydrogen chloride gas, then stirred at ambient temperature for 4 hours and then concentrated to dryness under vacuum. This process was repreated twice to leave the title compound as a white solid (45 mg). ¹H NMR [(CD₃)₂SO, 500 MHz]: δ 8.39 (s, 1H), 8.30 (s, 1H, 7.45 (s, 1H), 7.40 (s, 1H), 7.38–7.18 (m, 8H), 4.59 (br m, 1H), 4.00 (m, 2H), 3.50 (br m, 1H), 3.20 (br m, 1H), 2.98 (s, 4H), 2.85 (br m, 2H), 1.84 (br m, 1H), 1.68 (br m, 3H). MS(EI): 416(M⁺+H).

EXAMPLE 4
3-[1-(Quinoline-3-carbonyl)-piperidin-4-yl]-benzylamine di-hydrochloride (A.K.A. [4-(3-Aminomethyl-phenyl)-piperidin-1-yl]-qunolin-3-yl-methanone di-hydrochloride)

By proceeding in a similar manner to the method described in Example 1, but using quinoine-3-carboxylic acid in place of 5-phenylethynyl-pyridine-3-carboxylic acid, there was prepared the title compound as a white amorphous solid. ¹H NMR [(CD₃)₂SO, 500 MHz]: δ 9.10 (s, 1H), 8.78 (s, 1H). 8.20 (m, 2H), 7.98 (m, 1H), 7.80 (m, 1H), 7.50 (s, 1H), 7.35 (m 3H), 4.72 (br m, 1H), 4.00 (m, 2H), 3.80 (br m, 1H), 3.30 (br m, 1H), 2.90 (br m, 2H), 1.90 (br m, 1H), 1.75 (br m, 3H). MS(EI): 346(M⁺+H).

EXAMPLE 5
3-[1-(3-Phenylethynyl-benzoyl)-piperidine-4-yl]-benzylamine hydrochloride (A.K.A. [4-(3-Aminomethyl-phenyl)-piperidin-1-yl]-(3-phenylethynyl-phenyl)-methanone hydrochloride)

A. N,N-Bis-(tert-butoxyaronyl)-3-[1-(3-ethynyl-benzoyl)-piperidin-4-yl]-benzylamine By proceeding in a similar manner to the method described in Example 1C, but using of 3-ethynyl-benzoic acid [prepared according to the procedure described by C. Eaborn et al., J. Chem. Soc. C, 1967, (15), pages 1364–1366] in place of 5-phenylethynyl-pyridine-3-carboxylic acid, there was prepared N,N-bis-(tert-butoxycarbonyl)-3-[1-(3-ethynyl-benzoyl)-piperidin-4-yl]-benzylamine as a white amorphous solid. ¹H NMR (CDCl₃, 500 MHz): δ 7.76 (m, 2H), 7.40 (m, 2H), 7.25 (m, 2H), 7.10 (m, 4H), 4.95 (br m, 1H), 4.79 (s, 2H), 3.80 (br m, 1H), 3.10 (br m, 1H), 2.84 (br m, 1H), 2.78 (br m, 1H), 1.90 (m, 1H), 1.75 (m, 3H), 1.42 (s, 18H). MS(EI): 541(M⁺+Na).

B. N,N-Bis-(tert-butoxycarbonyl)-3-[1-(3-phenylethynyl-benzoyl)-piperidin-4-yl]-benzylamine A mixture of N,N-bis-(tert-butoxycarbonyl)-3-[1-(3-ethynyl-benzoyl)-piperidin-4-yl]-benzylamine (0.24 g, 0.46 mmol), iodobenzene (95 mg, 0.46 mmol), dichlorobis (triphenylphosphine)palladium (II) (35 mg, 0.05 mmol), copper (I) iodide (26 mg, 0.14 mmol), triethylamine (0.57 ml, 4.1 mmol) and anhydrous dimethylformamide (8 ml) was stirred at ambient temperature under nitrogen for 18 hours. The solvent was removed under vacuum and the residue was partitioned between ethyl acetate (3 lots of 50 ml) and water (20 ml). The combined organic layers were washed with brine (50 ml), then dried over magnesium sulfate and then concentrated under vacuum. The residue was subjected to chromatography on silica gel eluting with a mixture of cyclohexane and ethyl acetate (3:2, v/v) to give N,N-bis-(tert-butoxycarbonyl)-3-[1-(3-phenylethynyl-benzoyl)-piperidin-4-yl]-benzylamine as a yellow oil (0.23 g). ¹H NMR (CDCl₃, 500 MHz): δ 7.58 (m, 4H), 7.40 (m, 5H), 7.25 (m, (m, 1H), 7.10 (m, 3H), 4.90 (br m, 1H), 4.79 (s, 2H), 3.80 (br m, 1H), 3.15 (br m, 1H), 2.84 (br, m, 1H), 2.78 (br m, 1H), 1.95 (m, 1H), 1.80 (m, 3H), 1.42 (s, 18H). MS(EI): 617(M$^+$+Na).

C. 3-[1-(3-Phenylethynyl-benzoyl)-piperidin-4-yl]-benzylamine hydrochloride

A solution of N,N-Bis-(tert-butoxycarbonyl)-3-[1-(3-phenylethynyl-benzoyl)-piperidin-4-yl]-benzylamine (100 mg, 0.17 mmol) in methanol (10 ml), cooled to 0° C., was saturated with hydrogen chloride gas. The mixture was stirred at ambient temperature for 4 hours then concentrated to dryness under vacuum. The residue was triturated with a mixture of dichloromethane and diethyl ether to give 3-[1-(3-phenylethynyl-benzoyl)-piperidin-4-yl]-benzylamine hydrochloride as a white amorphous solid (46 mg). $^1$H NMR [(CD$_3$)$_2$SO, 500 MHz]: δ 7.61–7.30 (m, 13H), 4.62 (br m, 1H), 4.00 (s, 2H), 3.62 (br m, 1H), 3.25 (br m, 1H), 2.85 (br m, 2H), 1.88 (br m, 1H), 1.70 (br m, 3H). MS(EI): 395(M$^+$+H).

EXAMPLE 6

2-{3-[4-(3-Aminomethyl-phenyl)-piperidine-1-carbonyl]-phenyl}-1-(4-hydroxyphenyl)-ethanone (A.K.A. 2-{3-[4-(3-Aminomethyl-phenyl)-piperidine-1-carbonyl]-phenyl}-1-(4-hydroxy-phenyl)-ethanone hydrochloride)

A. N,N-Bis-(tert-butoxycarbonyl)-3-{1-[3-(4-hydroxyphenyl)ethynyl-benzoyl]-piperidin-4-yl}-benzylamine By proceeding in a similar manner to the method described in EXAMPLE 5B, but using 4-iodophenol in place of iodobenzene, there was prepared N,N-bis-(tert-butoxycarbonyl)-3-{1-[3-(4-hydroxyphenyl)ethynyl-benzoyl]-piperidin-4-yl}-benzylamine as a yellow amorphous solid. $^1$H NMR (CDCl$_3$, 500 MHz): δ 7.58 (m, 2H), 7.40 (m, 4H), 7.25 (m, 1H), 7.15 (m, 3H), 6.80 (m, 2H), 4.90 (br m, 1H), 4.79 (s, 2H), 3.90 (br m, 1H), 3.15 (br m, 1H), 2.84 (br m, 1H), 2.78 (br m, 1H), 1.98 (m, 1H), 1.80 (m, 3H), 1.42 (s, 18H). MS(EI): 633(M$^+$+Na).

B. 2-{3-[4-(3-Aminomethyl-phenyl)-piperidine-1-carbonyl]-phenyl}-1-(4-hydroxyphenyl)-ethanone hydrochloride By proceeding in a similar manner to the method described in EXAMPLE 5C but using N,N-bis-(tert-butoxycarbonyl)-3-{1-[3-(4-hydroxyphenyl)ethynyl-benzoyl]-piperidin-4-yl}-benzylamine, there was prepared 2-{3-[4-(3-aminomethyl-phenyl)-piperidine-1-carbonyl]-phenyl}-1-(4-hydroxyphenyl)-ethanone hydrochloride as a white amorphous solid. $^1$H NMR [(CD$_3$)$_2$SO, 500 MHz]: δ 7.92 (m, 2H), 7.40–7.28 (m, 8H), 6.82 (m, 2H), 4.60 (br m, 1H), 4.38 (s, 2H), 4.00 s, 2H), 3.62 (br m, 1H), 3.18 (br m, 1H), 2.80 (br m,2H), 1.88 (br m, 1H), 1.70–1.60 (br m, 3H), MS(EI): 429(M$^{30}$ +H).

EXAMPLE 7

3-{1-[3-(6-Amino-pyridin-3-yl)ethynyl-benzoyl]-piperidin-4-yl}-benzylamine hydrochloride (A.K.A. [4-(3-Aminomethyl-phenyl)-piperidin-1-yl]-[3-(6-amino-pyridin-3-ylethynyl)-phenyl]-methanon hydrochloride)

A. 3-Iodo-6-(tert-butoxycarbonylamino)pyridine

A stirred solution of 6-amino-3-iodopyridine (0.44 g, 2.0 mmol) in anhydrous tetrahydrofuran (7 ml), under nitrogen, was treated dropwise with a solution of sodium bis(trimethylsilyl)amide (1M, 4.4 ml, 4.4 mmol). After stirring for a further 15 minutes the mixture was treated with a solution of di-tert-butyldicarboxylate (440 mg, 2 mmol) in anhydrous tetrahydrofuran (3 ml). The resulting thick slurry was stirred at ambient temperature for 18 hours then partitioned between ethyl acetate (3 lots of 50 ml) and water (50 ml). The combined organics were dried over sodium sulfate then concentrated under vacuum. The residue was subjected to chromatography on silica gel eluting with a mixture of cyclohexane and ethyl acetate (9:1, v/v) to give 3-iodo-6-(tert-butoxycarbonylamino)pyridine as a white solid (0.56 g). $^1$H NMR (CDCl$_3$, 500 MHz) δ 8.50 (s, 1H), 7.92 (m, 1H), 7.85 (m, 1H), 1.58 (s, 9H). MS(EI): 319(M$^+$–H).

B. N,N-Bis-(tert-butoxycarbonyl)-3-{1-[3-(6-tert-butoxycarbonylamino-pyridin-3-yl)ethynyl-benzoyl]-piperidin-4-yl}-benzylamine By proceeding in a similar manner to the method described in EXAMPLE 5B, but using 3-iodo-6-(tert-butoxycarbonylamino)pyridine in place of iodobenzene, there was prepared N,N-bis-(tert-butoxycarbonyl)-3-{1-[3-(6-tert-butoxycarbonylamino-pyridin-3-yl)ethynyl-benzoyl]-piperidin-4-yl}-benzylamine as a yellow amorphous solid. $^1$H NMR (CDCl$_3$, 500 MHz): δ 8.41 (s, 1H), 7.99 (m, 1H), 7.80 (m, 1H), 7.61 (s, 1H), 7.59 (m, 2H), 7.40 (m, 2H), 7.23 (m, 1H), 7.12 (m, 3H), 4.90 (br m, 1H), 4.79 (s, 2H), 3.84 (br m, 1H), 3.15 (br m, 1H), 2.84 (br m, 1H), 2.78 (br m, 1H), 1.95 (m, 1H), 1.80 (m, 3H), 1.55 (s, 9H), 1.42 (s, 18H). MS(EI): 710(M$^+$).

C. 3-{1-[3-(6-Amino-pyridin-3-yl)ethynyl-benzoyl]piperidin-4-yl}-benzylamine hydrochloride By proceeding in a similar manner to the method described in EXAMPLE 5C but using N,N-bis-(tert-butoxycarbonyl)-3-{1-[3-(6-tert-butoxycarbonylamino-pyridin-3-yl)ethynyl-benzoyl]-piperidin-4yl}-benzylamine, there was prepared 3-{1-[3-(6-Amino-pyridin-3-yl)ethynyl-benzoyl]-piperidin-4-yl}-benzylamine hydrochloride as a white amorphous solid.). $^1$H NMR [(CD$_3$)$_2$SO, 500 MHz]: δ 8.22 (s, 1H), 8.15 (br s, 2H), 7.90 (m, 1H), 7.60–7.41 (m, 5H), 7.30 (m, 3H), 6.93 (m, 1H), 4.60 (br m, 1H), 4.00 (m, 2H), 3.62 (br m, 1H), 3.25 (br m, 1H), 2.85 (br m, 2H), 1.84 (br m, 1H), 1.60 (br m, 3H). MS(EI): 411(M$^+$+H).

EXAMPLE 8

3-{1-[3-(4-hydroxymethylphenyl)ethynyl-benzoyl]-piperidin-4-yl}-benzylamine hydrochloride (A.K.A. [4-(3-Aminomethyl-phenyl)-piperidin-1-yl]-[3-(4-hydroxymethyl-phenylethynyl)-phenyl]-methanone hydrochloride)

By proceeding in a similar manner to the method described in EXAMPLE 5, but using 4-iodobenzylalcohol (prepared according to the procedure described by D. S. Tan et al., J. Am. Chem. Soc., 1998, 120(33), pages 8565–8566) in place of iodobenzene, there was prepared the title compound as a white amorphous solid. $^1$H NMR [(CD$_3$)$_2$SO, 500 MHz]: δ 7.61–7.25 (m, 12H), 5.33 (m, 1H), 4.62 (br m, 1H), 4.58 (m, 2H), 4.00 (s, 2H), 3.62 (br m, 1H), 3.20 (br m, 1H), 2.83 (br m, 2H), 1.84 (br m, 1H), 1.72–1.62 (br m, 3H). MS(EI): 425(M$^+$+H).

EXAMPLE 9

3-[1-(3-Phenylethyl-benzoyl)-piperidin-4-yl]-benzylamine hydrochloride (A.K.A. [4-(3-Aminomethyl-phenyl)-piperidin-1-yl]-(3-phenethyl-phenyl)-methanone hydrochloride)

A solution of N,N-bis-(tert-butoxycarbonyl)-3-[1-(3-phenylethynyl-benzoyl)-piperidin-4-yl]-benzylamine (110 mg, 0.18 mmol, EXAMPLE 5B) in ethanol (10 ml) was treated with 10% palladium on carbon (20 mg) and then stirred at ambient temperature under an atmosphere of hydrogen for 8 hours. The reaction mixture was filtered through a short pad of hyflo and then concentrated under vacuum to give a white amorphous solid (0.54 g). This material was treated with methanolic hydrogen chloride according to the procedure described in EXAMPLE 5C to give the title compound as white amorphous solid (25 mg). $^1$H NMR [(CD$_3$)$_2$SO, 500 MHz]: δ 7.40–7.15 (m, 13H), 4.62

(br m, 1H), 4.00 (s, 2H), 3.60 (br m, 1H), 3.10 (br m, 1H), 2.80 (br m, 2H), 1.85 (br m, 1H), 1.60 (br m, 3H), MS(EI): 399($M^+$+H).

EXAMPLE 10
3-{1-[3-(4-hydroxyphenyl)ethyl-benzoyl]-piperidin-4-yl}-benzylamine hydrochloride (A.K.A. [4-(3-Aminomethyl-phenyl)-piperidin-1-yl]-{3-[2-(4-hydroxy-phenyl)-ethyl]-phenyl}-methanone hydrochloride)

By proceeding in a similar manner to the method described in EXAMPLE 9, but using N,N-bis-(tert-butoxycarbonyl)-3-{1-[3-(4-hydroxyphenyl)ethynyl-benzoyl]-piperidin-4-yl}-benzylamine (EXAMPLE 6A), there was prepared the title compound as a white amorphous solid. $^1$H NMR [($CD_3$)$_2$SO, 500 MHz]: δ 9.18 (br s, 1H), 7.41 (s, 1H), 7.35 (m, 5H), 7.20 (m, 2H), 6.98 (m, 2H), 6.60 (m, 2H), 4.82 (br m, 1H), 4.00 (m, 2H), 3.80 (br m, 1H), 3.10 (br m, 1H), 2.80 (m, 6H), 1.82 (br m, 1H), 1.70 (br m, 1H), 1.60 (br m, 2H). MS(EI): 415($M^+$+H).

EXAMPLE 11
3-{1-[3-(6-amino-pyridin-3-yl)ethyl-benzoyl]-piperidin-4-yl}-benzylamine hydrochloride (A.K.A. [4-(3-Aminomethyl-phenyl)-piperidin-1-yl]-{3-[2-(6-amino-pyridin-3-yl)-ethyl]-phenyl}-methanone hydrochloride)

By proceeding in a similar manner to the method described in EXAMPLE 9, but using N,N-bis-(tert-butoxycarbonyl)-3-{1-[3-(6-tert-butoxycarbonylamino-pyridin-3-yl)ethynyl-benzoyl]-piperidin-4-yl}-benzylamine (EXAMPLE 7B), there was prepared the title compound as a white amorphous solid. 1H NMR [($CD_3$)$_2$SO, 500 MHz]: δ 7.90 (br s, 2H), 7.85 (m, 1H), 7.76 (s, 1H), 7.43 (s, 1H), 7.40–7.30 (m, 5H), 7.24 (m, 2H), 6.93 (m, 1H), 4.61 (br m, 1H), 4.00 (m, 2H), 3.60 (br m, 1H), 3.15 (br m, 1H), 2.92 (br m, 6H), 1.90 (br m, 1H), 1.70 (br m, 1H), 1.60 (br m, 2H). MS(EI): 415($M^+$+H).

EXAMPLE 12
3-[1-(4-Phenylethyl-thiophene-2-carbonyl)-piperidin-4-yl]-benzylamine hydrochloride (A.K.A. [4-(3-Aminomethyl-phenyl)-piperidin-1-yl]-(4-phenethyl-thiophen-2-yl)-methanone hydrochloride)

By proceeding in a similar manner to the method described in EXAMPLE 1, but using 4-phenylethyl-thiophene-2-carboxylic acid (prepared according the procedure described by S. Gronowitz et al., Heterocycles, 1981, 15(2), pages 947–959) in place of 5-phenylethynyl-pyridine-3-carboxylic acid, there was prepared the title compound as a white amorphous solid. $^1$H NMR [($CD_3$)$_2$SO, 500 MHz]: δ 7.41–7.18 (m, 11H), 4.37 (br m, 1H), 4.00 (m, 2H), 3.05 (br m, 2H), 2.98 (s, 4H), 2.85 (br m, 2H), 1.90 (br m, 2H), 1.60 (br m, 2H), MS(EI): 405($M^+$+H).

EXAMPLE 13
3-[1-(5-Phenylethyl-thiophene-2-carbonyl)-piperidin-4-yl]-benzylamine hydrochloride (A.K.A. [4-(3-Aminomethyl-phenyl)-piperidin-1-yl]-(5-phenethyl-thiophen-2-yl)-methanone hydrochloride)

By proceeding in a similar manner to the method described in EXAMPLE 2, but using 5-phenylethynyl-thiophene-2-carboxylic acid in place of 5-phenylethynyl-pyridine-3-carboxylic acid, there was prepared the title compound as a white amorphous solid. $^1$H NMR [($CD_3$)$_2$SO, 500 MHz]: δ 7.41 (s, 1H), 7.38–7.20 (m, 9H), 6.83 (s, 1H), 4.40 (br m, 1H), 4.00 (br s, 2H), 3.12 (m, 2H), 3.08 (br m, 2H), 2.98 (m, 2H), 2.85 (br m, 2H), 1.82 (br m, 2H), 1.60 (br m, 2H), MS(EI): 405($M^+$+H).

EXAMPLE 14
3-{1-[3-(Benzooxazo-2-yl)-benzoyl]-piperidin-4-yl}-benzylamine hydrochloride (A.K.A. [4-(3-Aminomethyl-phenyl)-piperidin-1-yl]-(3-benzoxazol-2-yl-phenyl)-methanone hydrochloride)

By proceeding in a similar manner to the method described in EXAMPLE 1, but using 3-(benzooxazo-2-yl)-benzoic acid (prepared according to the procedure described by V. F. Bystrov et al., Zh. Obshch. Khim., 1968, 38(5), pages 1001–1005) in place of 5-phenylethynyl-pyridine-3-carboxylic acid, there was prepared the title compound as a white amorphous solid. $^1$H NMR [($CD_3$)$_2$SO, 500 MHz]: δ 8.28 (m, 1H), 8.19 (s, 1H), 7.81 (m, 2H), 7.50 (m, 2H), 7.43 (m, 3H), 7.30 (m, 3H), 4.66 (br m, 1H), 4.00 (m, 2H), 3.70 (br m, 1), 3.25 (br m, 1H), 2.92 (br m, 1H), 2.82 (br m, 1H), 1.90 (br m, 1H), 1.70 (br m, 3H), MS(EI): 412($M^+$+H).

EXAMPLE 15
3-[1-(3-Phenoxymethyl-benzoyl)-piperidin-4-yl]-benzylamine hydrochloride (A.K.A. [4-(3-Aminomethyl-phenyl)-piperidin-1-yl]-(3-phenoxymethyl-phenyl)-methanone hydrochloride)

By proceeding in a similar manner to the method described in EXAMPLE 1, but using 3-phenoxymethyl-benzoic acid (prepared according to the procedure of H. Oelschlaeger et al., Arch. Pharm. (Weinheim, Ger.), 1978, 311(2), pages 81–97) in place of 5-phenylethynyl-pyridine-3-carboxylic acid, there was prepared the title compound as a white amorphous solid. $^1$H NMR [($CD_3$)$_2$SO, 500 MHz]: δ 7.58–7.25 (m, 10H), 7.00 (m, 2H), 6.96 (m, 2H), 5.18 (s, 2H), 4.62 (br m, 1H), 4.00 (m, 2H), 3.62 (br m, 1H), 3.18 (br m, 1H), 2.82 (br m, 2H), 1.88 (br m, 1H), 1.65 (br m, 3H), MS(EI): 401($M^+$+H).

EXAMPLE 16
3-{1-[3-(2-E-Phenylethenyl)-benzoyl]-piperidin-4-yl}-Benzylamine Hydrochloride (A.K.A. [4-(3-Aminomethyl-phenyl)-piperidin-1-yl]-[3-((E)-styryl)-phenyl]-methanone hydrochloride)

By proceeding in a similar manner to the method described in EXAMPLE 1, but using 3-(2-E-phenylethenyl)-benzoic acid (prepared according to the procedure of N. A. Bumagin et al., Zh. Org. Khim., 1995, 31(4), pages 481–487) in place of 5-phenylethynyl-pyridine-3-carboxylic acid, there was prepared the title compound as a white amorphous solid. $^1$H NMR [($CD_3$)$_2$SO, 500 MHz]: δ 7.71 (m, 1H), 7.63 (m, 3H), 7.50 (m, 2H), 7.40–7.25 (m, 9H), 4.63 (br m, 1H), 4.00 (s, 2H), 3.71 (br m, 1H), 3.10 (br m, 1H), 2.84 (br m, 2H), 1.88 (br m, 1H), 1.70 (br m, 3H), MS(EI): 397($M^+$+H).

EXAMPLE 17
4-Fluoro-3-[1-(5-phenylethyl-pyridine-3-carbonyl)-piperidin-4-yl]-benzylamine di-hydrochloride (A.K.A. [4-(5-Aminomethyl-2-fluoro-phenyl)-piperidin-1-yl]-(5-phenethyl-pyridin-3-yl)-methanone -hydrochloride)

A. 4-(Pinacolatoboronyl)-1,2,3,6-tetrahydro-pyridine trifluoroacetate

A solution of lithium diisopropylamine (59 mmol) in anhydrous tetrahydrofuran (50 ml) at −78° C. was treated dropwise with a solution of tert-butyl 4-oxo-1-piperidinecarboxylate (10.7 g, 54 mmol) in anhydrous tetrahydrofuran (70 ml). After stirring at −78° C. for a further 20 minutes the reaction mixture was treated with a solution of N-phenyltrifluoromethanesulfonimide (21.2 g, 59 mmol) in anhydrous tetrahydrofuran (90 ml). The resultant orange suspension was warmed to 0° C., then stirred at 0° C. for 3 hours and then concentrated under vacuum. The residue was subjected to chromatography on silica gel eluting with a mixture of pentane and dichloromethane (1:1, v/v) and then subjected to chromatography on alumina eluting with a mixture of pentane and ethyl acetate (9:1, v/v) to yield tert-butyl 1,2,3,6-tetrahydro-4-(trifluoromethylsulphonyloxy)-pyridine-1-carboxylate as a yellow oil (15 g). A portion of this material (1.72 g, 5.2 mmol) was dissolved in anhydrous dioxane (30 ml) and the solution was treated with bis(pinacolato)diboron (1.46 g, 5.75 mmol), potassium acetate (1.54 g, 15.7 mmol), (diphenylphosphino)-ferrocene (86 mg, 0.16 mmol) and [1,1'-bis-(diphenylphosphino)ferroceno](dichloropalladium (II) (114 mg, 0.16 mmol). The reaction mixture was heated at 80° C. under an atmosphere of nitrogen for 18 hours, then cooled and then concentrated under vacuum. The residue was partitioned between ethyl acetate (2 lots of 100 ml) and water (100 ml). The combined organic extracts were dried over magnesium sulfate then concentrated under vacuum. The resultant oil was subjected to chromatography on silica gel eluting with a mixture of ethyl acetate and pentane (1:8, v/v) to yield a yellow oil (1.4 g). A solution of this material in dichloromethane (10 ml), cooled to 0° C., was treated with trifluoracetic acid (3.9 ml). The mixture was stirred at ambient temperature for 2 hours then concentrated under vacuum to leave 4-(pinacolatoboronyl)-1,2,3,6-tetrahydro-pyridine trifluoroacetate as a brown oil. $^1$H NMR [(CD$_3$)$_2$SO, 500 MHz]: δ 8.76 (br s, 2H), 6.39 (br s, 1H), 3.61 (br m, 2H), 3.11 (br m, 2H), 2.23 (br m, 2H), 1.20 (s 12H). MS(EI): 210(M$^+$+H).

B. 1-(5-Phenylethyl-pyridine-3-carbonyl)-4-(pinacolatoboronyl)-1,2,3,6-tetrahydro-pyridine A solution of 5-phenylethyl-pyridine-3-carboxylic acid (0.46 g, 2.0 mmol, EXAMPLE 2A) in anhydrous dimethylformamide (9 ml) was treated with O-(7-azabenzotriazol-1-yl)-1,1,3,3-tetramethyluronium hexafluorophosphate (0.87 g, 2.2 mmol) and diisopropylethylamine (1.7 ml, 10 mmol). This mixture was stirred at ambient temperature for 10 minutes then treated with a solution of 4-(pinacolatoboronyl)-1,2,3,6-tetrahydro-pyridine trifluoroacetate (0.81 g, 2.5 mmol) in dimethylformamide (9 ml). The reaction mixture was stirred at ambient temperature for 18 hours and then concentrated under vacuum. The residue was partitioned between dichloromethane (2 lots of 50 ml) and saturated aqueous sodium bicarbonate (15 ml). The combined organic layers were dried over magnesium sulfate and then concentrated under vacuum. The residue was subjected to chromatography on silica gel eluting with ethyl acetate to give 1-(5-phenylethyl-pyridine-3-carbonyl)-4-(pinacolatoboronyl)-1,2,3,6-tetrahydro-pyridine as a brown amorphous solid (0.73 g). $^1$H NMR [(CD$_3$)$_2$SO, 500 MHz]: δ 8.49 (s, 1H), 8.40 (s, 1H), 7.61 (s, 1H), 7.20 (m, 5H), 6.48 (br s, 1H), 4.18 (br m, 1H), 3.83 (br m, 1H), 3.62 (br m, 1H), 3.23 (br m, 1H), 2.98 (m, 4H), 2.17 (br m, 2H), 1.20 (s, 12H). MS(EI): 441(M$^+$+Na).

C. N-(tert-Butoxycarbonyl)-3-bromo-4-fluoro-benzylamine

A mixture of 3-bromo-4 fluoro-benzylamine hydrochloride (2.41 g, 10 mmol), triethylamine (2.8 ml, 20 mmol), and di-tert-butoxycarbonate (1.8 g, 10.3 mmol) in dichloromethane (20 ml) was stirred at ambient temperature for 18 hours then washed with water (20 ml). The organic phase was dried over magnesium sulfate and then concentrated under vacuum. The residue was subjected to chromatography on silica gel eluting with a mixture of cyclohexane and ethyl acetate (3:1, v/v) to give N-(tert-butoxycarbonyl)-3-bromo-4-fluoro-benzylamine as a white solid (1.4 g). $^1$H NMR (CDCl$_3$, 500 MHz): δ 7.45 (m, 1H), 7.20 (m, 1H), 7.08 (m, 1H), 4.85 (br s, 1H), 4.21 (m, 2H), 1.42 (s, 9H).

D. N-(tert-Butoxycarbonyl)-4-fluoro-3-[1-(5-phenylethyl-pyridine-3-carbonyl)-1,2,3,6-tetrahydro-pyridin-4-yl]-benzylamine A mixture of N-(tert-butoxycarbonyl)-3-bromo-4-fluoro-benzylamine (0.28 g, 0.92 mmol), anhydrous dimethylformamide (10 ml), 1-(5-phenylethyl-pyridine-3-carbonyl)-4-(pinacolatoboronyl)-1,2,3,6-tetrahydro-pyridine (0.37 g, 0.88 mmol), potassium carbonate (0.36 g, 2.6 mmol) and [1,1'-bis-(diphenylphosphino)ferroceno]dichloropalladium (II)-dichloromethane complex (43 mg, 0.05 mmol) was heated at 80° C. under an atmosphere of nitrogen for 18 hours. The reaction mixture was cooled to room temperature and then concentrated under vacuum. The residue was partitioned between ethyl acetate (2 lots of 50 ml) and water (10 ml). The combined organic extracts were dried over magnesium sulfate and then concentrated under vacuum. The resultant oil was subjected to chromatography on silica gel eluting with ethyl acetate to yield N-(tert-butoxycarbonyl)-4-fluoro-3-[1-(5-phenylethyl-pyridine-3-carbonyl)-1,2,3,6-tetrahydro-pyridin-4-yl]-benzylamine as a pale yellow oil (0.18 g). $^1$H NMR (CDCl$_3$, 500 MHz): δ 8.58 (s, 1H), 8.50 (s, 1H), 7.51 (s, 1H), 7.25 (m, 2H), 7.18 (m, 5H), 7.00 (m, 1H), 6.01 (br s, 1H), 4.83 (br s, 1H), 4.38 (br m, 1H), 4.27 (m, 2H), 3.98 (br m, 2H), 3.50 (br m, 1H), 2.99 (m, 4H), 2.60 (br m, 1H), 2.50 (br m, 1H). MS(EI): 538 (M$^+$+Na).

E. 4-Fluoro-3-[1-(5-phenylethyl-pyridine-3-carbonyl)-piperidin-4-yl]-benzylamine di-hydrochloride A solution of N-(tert-butoxycarbonyl)-4-fluoro-3-[1-(5-phenylethyl-pyridine-3-carbonyl)-1,2,3,6-tetrahydro-pyridin-4-yl]-benzylamine in ethanol (12 ml) was treated with 10% palladium on carbon (75 mg) and the mixture was stirred at ambient temperature under an atmosphere of hydrogen for 72 hours. The reaction mixture was filtered through a short pad of hyflo and the filtrate was concentrated under vacuum to give N-(tert-butoxycarbonyl-4-fluoro-3-[1-(5-phenylethyl-pyridine-3-carbonyl)-piperidin-4-yl]-benzylamine as colorless oil (85 mg). This material was dissolved in methanol (10 ml) and the solution was cooled to 0° C. and then saturated with hydrogen chloride gas. This mixture was stirred at ambient temperature for 4 hours and then concentrated to dryness under vacuum. The residue was triturated with a mixture of dichloromethane and diethyl ether to give 4-fluoro-3-[1-(5-phenylethyl-pyridine-3-carbonyl)-piperidin-4-yl]-benzylamine di-hydrochloride as a white amorphous solid (50 mg). $^1$H NMR [(CD$_3$)$_2$SO, 500 MHz]: δ 8.60 (s, 1H), 8.58 (s, 1H), 7.83 (s, 1H), 7.60 (m, 1H), 7.38 (m, 1H), 7.20 (m, 6H), 4.61 (br m, 1H), 4.00 (m, 2H), 3.50 (br m, 1H), 3.20 (br m, 2H), 2.99 (m, 2H), 2.95 (m, 2H), 2.90 (br m, 1H), 1.82 (br m, 1H), 1.65 (br m, 3H). MS(EI): 418(M$^+$+H).

EXAMPLE 18

4-Methyl-3-[1-(5-phenylethyl-pyridine-3-carbonyl)-piperidin-4-yl]-benzylamine di-hydrochloride (A.K.A. [4-(5-Aminomethyl-2-methyl-phenyl)-piperidin-1-yl]-(5-phenethyl-pyridin-3-yl)-methanone di-hydrochloride)

A. 4-[N,N-Bis-(tert-butoxycarbonyl)aminomethyl]-2-bromo-toluene

A solution of 4-methyl-3-bromobenzylbromide (1.63 g, 6.2 mmol, prepared according to the procedure described in International Patent Application No. WO 0009475) and di-tert-butyliminodicarboxylate (1.48 g, 6.8 mmol) in anhydrous tetrahydrofuran (15 ml) was treated portionwise with sodium hydride (0.27 g of 60% dispersion in mineral oil, 6.8 mmol). The mixture was stirred at ambient temperature for 18 hours then partitioned between saturated aqueous ammonium chloride solution (20 ml) and ethyl acetate (3 lots of 80 ml). The combined organic layers were washed with brine (80 ml), then dried over magnesium sulfate and concentrated under vacuum. The residue was subjected to chromatography on silica gel eluting with a mixture of cyclohexane and diethyl ether (9:1, v/v) to give 4-[N,N-bis-(tert-butoxycarbonyl)aminomethyl]-2-bromo-toluene as a pale yellow oil (2.4 g). $^1$H NMR (CDCl$_3$, 500 MHz): δ 7.45 (s, 1H), 7.18 (m, 2H), 4.71 (s, 2H), 2.38 (s, 3H), 1.43 (s, 18H).

B. 4-Methyl-3-[1-(5-phenylethyl-pyridine-3-carbonyl)-piperidin-4-yl]-benzylamine di-hydrochloride By proceeding in a similar manner to the method described in EXAMPLE 17, but using 4-[N,N-bis-(tert-butoxycarbonyl)aminomethyl]-2-bromo-toluene in place of N-(tert-butoxycarbonyl)-3-bromo-4-fluoro-benzylamine, there was prepared 4-methyl-3-[1-(5-phenylethyl-pyridine-3-carbonyl)-piperidin-4-yl]-benzylamine di-hydrochloride as a white amorphous solid. $^1$H NMR [(CD$_3$)$_2$SO, 500 MHz]: δ 8.60 (m, 2H), 7.83 (s, 1H), 7.41 (s, 1H), 7.20 (m, 7H), 4.62 (br m, 1H), 3.98 (m, 2H), 3.45 (br m, 1H), 3.20 (br m, 1H), 3.07 (m, 2H), 3.00 (m, 2H), 2.95 (m, 2H), 2.32 (s, 3H), 1.80 (br m, 1H), 1.70 (br m, 3H). MS(EI): 414(M$^+$+H).

EXAMPLE 19

3-{1-[3-(5-Phenyl-1,3,4-oxadiazol-2-yl)-phenylcarbonyl]-piperidin-4-yl}-benzylamine hydrochloride) (A.K.A. [4-(3-Aminomethyl-phenyl)-piperidin-1-yl]-[3-(5-phenyl-1,3,4-oxadiazol-2-yl)-phenyl]-methanone hydrochloride)

A. 3-(5-Phenyl-1,3,4-oxadiazol-2-yl)-benzoic acid

A mixture of methyl hydrogen isopthalalate (1.8 g, 10 mmol), benzoic hydrazide (1.4 g, 10 mmol) and phosphorous oxychloride (20 ml), under an atmosphere of nitrogen, was heated at 120° C. for 18 hours, then cooled to room temperature and then poured into ice water (500 ml). This mixture was treated with solid sodium carbonate until the aqueous layer was basic (pH 8–9) and the resultant pink solid was filtered. This material was treated with 100 ml methanol and the suspension was treated with sodium hydroxide solution (30 ml, 1M). The reaction mixture was heated at reflux for 4 hours, then cooled and then concentrated to dryness. The residue was dissolved in water (100 ml) and the solution was acidified to pH 3 by addition of concentrated hydrochloric acid. The resultant precipitate was filtered, then dried and then subjected to chromatography on silica gel eluting with a mixture of dichloromethane and methanol (98:2, v/v) to yield 3-(5-phenyl-1,3,4-oxadiazol-2-yl)-benzoic acid as a white solid (600 mg). $^1$H NMR [(CD$_3$)$_2$SO, 500 MHz]: δ 8.80 (s, 1H), 8.38 (m, 1H), 8.18 (m, 3H), 7.78 (m, 1H), 7.62 (m, 3H). MS(EI): 265 (M$^+$–H).

B. 3-{1-[3-(5-Phenyl-1,3,4-oxadiazol-2-yl)-phenylcarbonyl]-piperidin-4-yl}-benzylamine hydrochloride By proceeding in a similar manner to the method described in EXAMPLE 1, but using 3-(5-phenyl-1,3,4-oxadiazol-2-yl)-benzoic acid in place of 5-phenylethynyl-pyridine-3-carboxylic acid, there was prepared 3-{1-[3-(5-phenyl-1,3,4-oxadiazol-2-yl)-phenylcarbonyl]-piperidin-4-yl}-benzylamine hydrochloride as a pale yellow amorphous solid. $^1$H NMR [(CD$_3$)$_2$SO, 500 MHz]: δ 8.21 (m, 1H), 8.20 (m, 3H), 7.75 (m, 2H), 7.68 (m, 3H), 7.50 (s, 1H), 7.37 (m, 3H), 4.70 (br m, 1H), 4.00 (m, 2H), 3.70 (br m, 1H), 3.25 (br m, 1H), 2.90 (br m, 1H), 2.85 (br m, 1H), 1.88 (br m, 1H), 1.70 (m, 3H). MS(EI): 439(M$^+$+H).

EXAMPLE 20

3-[1-(Indole-6-carbonyl)-piperidin-4-yl]-benzylamine trifluoroacetate (A.K.A. [4-(3-Aminomethyl-phenyl)-piperidin-1-yl]-(1H-indol-6-yl)-methanone trifluoroacetate)

A solution of diisopropylamine in dimethylformamide (1 ml, 180 μM) in a glass vial was treated with a solution of O-(7-azabenzotriazol-1-yl)-1,1,3,3-tetramethyluronium hexafluorophosphate in dimethylformamide (1 ml, 60 μM) followed by a solution of indole-6-carboxylic acid in dimethylformamide (1 ml, 60 μM). After standing at ambient temperature for 15 minutes the mixture was treated with a solution of 4-{3-[N,N-bis-(tert-butoxycarbonyl) aminomethyl]-phenyl}-piperidine in dimethylformamide(1 ml, 60 μM, EXAMPLE 1B). The reaction mixture was allowed to stand at ambient temperature for 18 hours then evaporated. The residue was treated with chloroform (5 ml) and aqueous sodium carbonate solution (5%). This mixture was shaken gently for 30 minutes, poured into a fritted polypropylene tube and the organic layer which passes through the frit collected in a glass vial. The chloroform was evaporated under vacuum and the residue was treated with a mixture of trifluoroacetic acid, dichloromethane and water (4 ml, 55/40/5, v/v/v). This mixture was shaken gently for 2 hours and then evaporated to leave the title compound as a yellow oil. LC-MS: R$_T$=3.43 minutes (>96% by ELSD); MS (ES$^+$), 334 (MH$^+$).

EXAMPLE 21

3-[1-(Coumarin-3-carbonyl)-piperidin-4-yl]-benzylamine trifluoroacetate (A.K.A. 3-[4-(3-Aminomethyl-phenyl)-piperidine-1-carbonyl]-1-benzopyran-2-one trifluoroacetate)

By proceeding in a similar manner to the method described in EXAMPLE 20, but using coumarin-3-carboxylic acid in place of indole-6-carboxylic acid, there was prepared the title compound as a yellow oil. LC-MS: R$_T$=3.15 minutes (>86% by ELSD); MS (ES$^+$), 363 (MH$^+$).

EXAMPLE 22

3-[1-(Naphthyl-2-carbonyl)-piperidin-4-yl]-benzylamine trifluoroacetate (A.K.A. [4-(3-Aminomethyl-phenyl)-piperidin-1-yl]-naphthalen-2-yl-methanone trifluoroacetate)

By proceeding in a similar manner to the method described in EXAMPLE 20, but using 2-naphthoic acid in place of indole-6-carboxylic acid, there was prepared the title compound as a yellow oil. LC-MS: R$_T$=3.66 minutes (100% by ELSD); MS (ES$^+$), 345 (MH$^+$).

EXAMPLE 23

3-{1-[3-(2-Naphthylthio)propionyl]-piperidin-4-yl}-benzylamine trifluoroacetate (A.K.A. 1-[4-(3-Aminomethyl-phenyl)-piperidin-1-yl]-3-(naphthalen-2-ylsulfanyl)-propan-1-one trifluoroacetate)

By proceeding in a similar manner to the method described in EXAMPLE 20, but using 3-(2-naphthylthio) propionic acid in place of indole-6-carboxylic acid, there was prepared the title compound as a yellow oil. LC-MS: R$_T$=4.00 minutes (>95% by ELSD); MS (ES$^+$), 405(MH$^+$).

EXAMPLE 24

3-{1-[4-(Indol-3-yl)butanoyl]-piperidin-4-yl}-benzylamine trifluoroacetate (A.K.A. 1-[4-(3-Aminomethyl-phenyl)-piperidin-1-yl]-4-(1H-indol-3-yl)-butan-1-one trifluoroacetate)

By proceeding in a similar manner to the method described in EXAMPLE 20, but using 4-(indol-3-yl) butanoic acid in place of indole-6-carboxylic acid, there was prepared the title compound as a yellow oil. LC-MS: R$_T$=3.64 minutes (>90% by ELSD); MS (ES$^+$), 376(MH$^+$).

EXAMPLE 25

3-{1-[4-(4-Biphenyl)-4-ketobutanoyl]-piperidin-4-yl}-benzylamine trifluoroacetate (A.K.A. [4-(3-Aminomethyl-phenyl)-piperidin-1-yl]-biphenyl-4-yl-methanone trifluoroacetate)

By proceeding in a similar manner to the method described in EXAMPLE 20, but using 4-(4-biphenyl)-4-ketobutanoic acid in place of indole-6-carboxylic acid, there was prepared the title compound as a yellow oil. LC-MS: $R_T$=4.00 minutes (100% by ELSD); MS (ES$^+$), 427(MH$^+$).

EXAMPLE 26

3-[1-(3-Benzyloxybenzoyl)-piperidin-4-yl]-benzylamine trifluoroacetate (A.K.A. [4-(3-Aminomethyl-phenyl)-piperidin-1-yl]-(3-benzyloxy-phenyl)-methanone trifluoroacetate)

By proceeding in a similar manner to the method described in EXAMPLE 23, but using 3-benzyloxybenzoic acid in place of indole-6-carboxylic acid, there was prepared the title compound as a yellow oil. LC-MS: $R_T$=3.87 minutes (100% by ELSD); MS (ES$^+$), 401 (MH$^+$).

EXAMPLE 27

3-[1-(5-Phenylethynyl-thiophene-2-carbonyl)-piperidin-4-yl]-benzylamine trifluoroacetate (A.K.A. [4-(3-Aminomethyl-phenyl)-piperidin-1-yl]-(5-phenylethynyl-thiophen-2-yl)-methanone trifluoroacetate)

By proceeding in a similar manner to the method described in EXAMPLE 20, but using 5-phenylethynyl-thiophene-2-carboxylic acid in place of indole-6-carboxylic acid, there was prepared the title compound as a yellow oil. LC-MS: $R_T$=4.09 minutes (>97% by ELSD); MS(ES$^+$), 410(MH$^+$).

EXAMPLE 28

3-[1-(4-Phenylethynyl-thiophene-2-carbonyl)-piperidin-4-yl]-benzylamine trifluoroacetate (A.K.A. [4-(3-Aminomethyl-phenyl)-piperidin-1-yl]-(4-phenylethynyl-thiophen-2-yl)-methanone trifluoroacetate)

By proceeding in a similar manner to the method described in EXAMPLE 20, but using 4-phenylethynyl-thiophene-2-carboxylic acid in place of indole-6-carboxylic acid, there was prepared the title compound as a yellow oil. LC-MS: $R_T$=4.08 minutes (>96% by ELSD); MS(ES$^+$), 401(MH$^+$).

EXAMPLE 29

3-(1-Benzoyl-piperidin-4-yl)-benzylamine trifluoroacetate (A.K.A. [4-(3-Aminomethyl-phenyl)-piperidin-1-yl]-phenyl-methanone trifluoroacetate)

By proceeding in a similar manner to the method described in EXAMPLE 20, but using benzoic acid in place of indole-6-carboxylic acid, there was prepared the title compound as a yellow oil. LC-MS: $R_T$=3.39 minutes (>95% by ELSD); MS(ES$^+$) 295(MH$^+$).

EXAMPLE 30

3-[1-(4-N,N-Dimethylaminobenzoyl)-piperidin-4-yl]-benzylamine trifluoroacetate (A.K.A. [4-(3-Aminomethyl-phenyl)-piperidin-1-yl]-(4-dimethylamino-phenyl)-methanone trifluoroacetate)

By proceeding in a similar manner to the method described in EXAMPLE 20, but using 4-N,N-dimethylaminobenzoic acid in place of indole-6-carboxylic acid, there was prepared the title compound as a yellow oil. LC-MS: $R_T$=3.32 minutes (100% by ELSD); MS(ES$^+$) 338 (MH$^+$).

EXAMPLE 31

6-Fluoro-3-[1-(5-phenylethyl-pyridine-3-carbonyl)-piperidin-4-yl]-benzylamine di-hydrochloride (A.K.A. [4-(3-Aminomethyl-4-fluoro-phenyl)-piperidin-1-yl]-(5-phenethyl-pyridin-3-yl)-methanone di-hydrochloride)

By proceeding in a similar manner to the method described in EXAMPLE 17, but using 3-bromo-6-fluoro-benzylamine in place of 3-bromo-4-fluoro-benzylamine, there was prepared the title compound as a pale yellow oil. $^1$H NMR [(CD$_3$)$_2$SO, 500 MHz]: δ 8.44 (m, 2H), 7.61 (s, 1H), 7.40 (m, 1H), 7.20 (m, 6H), 7.05 (m, 1H), 4.62 (br m, 1H), 3.98 (m, 2H), 3.45 (br m, 1H), 3.20 (br m, 1H), 3.07 (m, 2H), 3.00 (m, 2H), 2.95 (m, 2H) 1.80 (br m, 1H), 1.70 (br m, 3H). MS(EI): 418(M$^+$+H).

EXAMPLE 32

1-{3-[1-(5-Phenylethyl-pyridine-3-carbonyl)-piperidin-4-yl]-phenyl}ethylamine di-hydrochloride (A.K.A. {4-[3-(1-Amino-ethyl)-phenyl]-piperidin-1-yl}-(5-phenethyl-pyridin-3-yl)-methanone di -hydrochloride)

By proceeding in a similar manner to the method described in EXAMPLE 17, but using 1-(3-bromophenyl) ethylamine (prepared according to the procedure of C. P.Chen et al., Tetrahedron Letters, 199, 32(49), pages 7175–7178) in place of 3-bromo-4-fluoro-benzylamine, there was prepared the title compound as a white solid. $^1$H NMR[(CD$_3$)$_2$SO, 500 MHz]: δ 8.62 (m, 2H), 7.95 (s, 1H), 7.50 (s, 1H), 7.20 (m, 8H), 4.62 (br m, 1H), 4.38 (t, J=6 Hz, 1H), 3.50 (m, 1H), 3.45 (br m, 1H), 3.20 (br m, 1H), 3.07 (m, 2H), 3.00 (m, 2H), 2.95 (m, 2H), 1.87 (br m, 1H), 1.65 (br m, 3H), 1.50 (d, J=6 Hz, 3H). MS(EI): 414(M$^+$+H).

EXAMPLE 33

3-[1-(4-Hydroxy-quinoline-3-carbonyl)-piperidin-4-yl]-benzylamine (A.K.A. [4-(3-Aminomethyl-phenyl)-piperidin-1-yl]-(4-hydroxy-quinolin-3-yl)-methanone)

By proceeding in a similar manner to the method described in EXAMPLE 1, but using 4-hydroxy-quinoline-3-carboxylic acid (prepared according to the procedure of K. J. Shah, and E. A. Coats, J. Med. Chem., 1977, 20(8), pages 1001–1006) in place of 5-phenylethynyl-pyridine-3-carboxylic acid, there was prepared the title compound as a white amorphous solid. $^1$H NMR[(CD$_3$)$_2$SO, 500 MHz]: δ 8.10 (m, 2H), 7.68 (m, 1H), 7.59 (m, 1H), 7.36 (m, 3H), 7.22 (m, 2H), 4.65 (br m, 1H), 4.00 (m, 2H), 3.80 (br m, 1H), 3.35 (br m, 1H), 3.10 (br m, 1H), 3.00 (br m, 1H), 1.90–1.75 (br m, 4H). MS(EI): 362(M$^+$+H).

EXAMPLE 34

3-[1-(6-Phenyl-quinoline-3-carbonyl)-piperidin-4-yl]-benzylamine di-hydrochloride (A.K.A. [4-(3-Aminomethyl-phenyl)-piperidin-1-yl]-(6-phenyl-quinolin-3-yl)-methanone di-hydrochloride)

By proceeding in a similar manner to the method described in EXAMPLE 1, but using 6-phenyl-quinoline-3-carboxylic acid [prepared according to the procedure of J. Biwersi et al., Am. J. Physiol., 1992, 262(1, Pt. 1), C243–C250] in place of 5-phenylethynyl-pyridine-3-carboxylic acid, there was prepared the title compound as a white amorphous solid. $^1$H NMR[(CD$_3$)$_2$SO, 500 MHz]: δ 9.00 (s, 1H), 8.59 (s, 1H), 8.41 (s, 1H), 8.10 (m, 2H), 7.85 (m, 2H), 7.58 (m, 2H), 7.45 (m, 2H), 7.34 (m, 3H), 4.75 (br m, 1H), 4.00 (m, 2H), 3.80 (br m, 1H), 3.35 (br m, 1H), 3.00 (br m, 1H), 2.90 (br m, 1H), 1.90–1.75 (br m, 4H). MS(EI): 422(M$^+$+H).

EXAMPLE 35

4-(3-Aminomethyl-phenyl)-1-(5-phenethyl-pyridine-3-carbonyl)-piperidine-4-carbonitrile A. 3-Cyanobenzylcyanide To a solution of 9.8 g (200 mmole) of sodium cyanide and 1.61 g (5 mmole) of tetrabutylammonium bromide in 50 ml of water was added a solution of 19.61 g (100 mmole) of α-bromo-m-tolunitrile in 150 ml of dichloromethane. The mixture was stirred at room temperature for 24 hours. To this mixture was added 6.2 ml (100 mmole) of iodomethane. The mixture was stirred at room temperature for 3 hours. The layers were separated and the organic layer was dried over magnesium sulfate and was filtered. The filtrate was evaporated and the residue was triturated with petroleum ether and the insoluble material was collected to give 14.5 g of a white solid, mp-66–9° C.; 100% yield: $^1$H-NMR (300 MHz, CDCl$_3$) δ (TMS) 3.80–3.90(s, 2H), 7.49–7.72(m, 4H).

B. N-tert-Butoxycarbonyl-bis(2-chloroethyl)amine

To a mixture of 17.85 g (100 mmole) of bis(2-chloroethyl) amine hydrochloride and 24.0 g (110 mmole) of di-tert-butyl dicarbonate in 100 ml of dichloromethane was added a solution of 15.3 ml (110 mmole) of trietylamine in 50 ml of dichloromethane dropwise over 30 minutes. The mixture was stirred at room temperature for 24 hours and was poured into water. The organic layer was dried over magnesium sulfate and was filtered. The filtrate was evaporated to give 24 g of an oil, 100% yield: $^1$H-NMR (300 MHz, CDCl$_3$)δ (TMS) 1.37–1.56 (m, 9H), 3.50–3.62 (m, 8H); MS (ESI) m/e 242 (M+H)$^+$.

C. 4-(3-Cyanophenyl)-1-tert-butoxycarbonyl-piperidine-4-carbonitrile

To a solution of 2.8 g (19.7 mmole) of 3-cyanobenzylnitrile and 4.77 g (19.7 mmole) of N-tert-butylcarbonyl-bis(2-chloroethyl)amine in 100 ml of anhydrous DMF was added 2.36 g (59.1 mmole) of 60% sodium hydride in portions over 10 minutes. The mixture was stirred at room temperature for 3 days and was poured into water and was extracted with ether. The ether layer was dried over magnesium sulfate and was filtered. The filtrate was evaporated and the residue was purified by flash chromatography using 4:1 hexane:ethyl acetate to give the product as a white solid: 1H-NMR (300 MHz, CDCl$_3$) δ (TMS) 1.45(s, 9H), 1.85–2.0(m, 2H), 2.0–2.28(m, 2H), 3.05–3.30(m, 2H), 4.12–4.4(m, 2H), 7.53–7.80(m, 4H).

D. 4-(3-Aminomethyl-phenyl)-1-tert-butoxycarbonyl-piperidine-4-carbonitrile

To a mixture of 0.31 g (1 mmole) of 4-(3-cyanophenyl)-1-tert-butoxycarbonyl-piperidine-4-carbonitrile in 30 ml of absolute ethanol was added 0.08 ml (1 mmole) of conc. hydrochloric acid followed by 30 mg of 5% Pd/C. The mixture was agitated in a Parr shaker for 3 hours at 30 lbs. of pressure of hydrogen. The mixture was filtered through celite and the filtrate was evaporated. The residue was treated with ether and was stirred for 30 minutes and was filtered. The filter cake was treated with aqueous sodium carbonate and was extracted with dichloromethane to give 0.2 g of product: $^1$H-NMR (300 MHz, CDCl$_3$) δ (TMS) 1.38–1.60(m, 9H), 1.88–2.18(m, 4H), 3.05–3.30(m, 4H), 3.79–4.0(m, 2H), 7.22–7.85(m, 4H); MS (ESI) m/e 316 (M+H)$^+$.

E. 4-(3-Benzyloxycarbonylaminomethyl-phenyl)-1-tert-butoxycarbonyl-piperidine-4-carbonitrile To a solution of 0.2 g of 4-(3-Aminomethyl-phenyl)-1-tert-butoxycarbonyl-piperidine-4-carbonitrile in 15 ml of dichloromethane was added a few drops of triethylamine followed by a few drops of benzyl chloroformate. The mixture was stirred for 1 hour at room temperature and was poured into aqueous sodium carbonate and was extracted with dichloromethane. The organic layer was dried over magnesium sulfate and was filtered. The filtrate was evaporated and the residue was used directly in the next step without further purification: $^1$H-NMR (300 MHz, CDCl$_3$)δ (TMS) 1.39–1.52 (m, 9H), 1.80–2.16(m, 4H), 3.08–3.42(m, 4H), 4.19–4.50(m, 2H), 5.08–5.13(d, 2H), 7.28–7.79(m, 9H), MS (ESI) m/e 450 (M+H)$^+$.

F. 4-(3-Benzyloxycarbonylaminomethyl-phenyl)-piperidine-4-carbonitrile

The residue from the previous step was dissolved in dichloromethane containing 1 ml of trifluoroacetic acid and the solution was stirred at room temperature for 45 minutes. The solution was poured into aqueous sodium carbonate and was extracted with dichloromethane. The organic layer was dried and evaporated and the residue was purified by flash chromatography using 7:3 hexane:ethyl acetate to give the product: $^1$H-NMR (300 MHz, CDCl$_3$)δ (TMS) 1.80–2.18 (m, 4H), 3.07–3.35(m, 4H), 4.28–4.50(m, 2H), 5.09–5.13(d, 2H), 7.10–7.77(m, 9H); MS (ESI) m/e 349 (M+H)$^+$.

G. 4-(3-Benzyloxycarbonylaminomethyl-phenyl)-1-(5-phenethyl-pyridine-3-carbonyl)-piperidine-4-carbonitrile To a solution of 0.15 g (0.33 mmole) of 4-(3-benzyloxycarbonylaminomethyl-phenyl)-piperidine-4-carbonitrile in 20 ml of acetonitrile was added 0.038 g (0.33 mmole) of N-ethylmopholine followed by 0.11 g (0.33 mmole) of TBTU. To this solution was added 0.075 g (0,33 mmole) of 5-phenethylpyridine-3-carboxylic acid in portions over 10 minutes. The mixture was stirred for 2 hours. The solution was concentrated and the residue was purified by flash chromatography using 95:5 dichloromethane:methanol to provide 0.2 g of product: $^1$H-NMR (300 MHz, CDCl$_3$)δ (TMS) 1.79–2.20 (m, 4H), 2.70–2.82 (m, 4H), 2.90–3.07 (m, 2H), 3.15–3.70 (m, 2H), 4.35–4.40 (d, 2H), 5.07–5.25 (d, 2H), 7.10–7.50 (m, 15H), 8.42–8.58 (m, 2H); MS (ESI) m/e 559 (M+H)$^+$.

H. 4-(3-Aminomethyl-phenyl)-1-(5-phenethyl-pyridine-3-carbonyl)-piperidine-4-carbonitrile To a solution of 0.15 g of 4-(3-benzyloxycarbonylaminomethyl-phenyl)-1-(5-phenethyl-pyridine-3-carbonyl)-piperidine-4-carbonitrile in 5 ml of glacial acetic acid was added 1 ml of 30% HBr in acetic acid. The solution was stirred at room temperature for 2 hours. The solution was poured into a saturated sodium carbonate solution and was extracted with dichloromethane. The organic layer was dried over magnesium sulfate and was filtered and evaporated. The residue was purified by Rainin HPLC using 10–100% (acetonitrile-0.1% aqueous TFA) to yield 16 mg of product isolated as the trifluoroacetic acid salt: $^1$H-NMR (300 MHz, DMSO-d$^6$) δ (TMS); 1.95–2.30 (m, 4H), 2.45–2.62(m, 2H), 2.88–3.12(m, 4H), 3.70–4.20 (m, 2H), 7.12–7.38(m, 4H), 7.45–7.82(m, 6H), 8.50–8.65 (m, 2H); MS (ESI) m/e 425 (M+H)$^+$.

EXAMPLE 36

[4-(3-Aminomethylphenyl)piperidin-1-yl]-(3,4-dichlorophenyl)methanone trifluoroacetate TFP resin (125 mg of 1.25 mmol/g resin, with 100% loading of acid, 156 mmol, prepared according to the procedure described by J. M. Salvino et. al. in International Patent Application Publication No. WO 99/67228) was swollen in dichloromethane (2.5 mL) for 15 minutes then treated with a solution of 4-(3-aminomethylphenyl) piperidine (40 mg, 100 mmol) in dichloromethane (2.5 mL). The mixture was sealed in the reaction vessel then left shaking for 8 hours. The resin was filtered, then washed with dichloromethane (2 mL) [TLC (5% MeOH/EtOAc) showed single product spot (no baseline amine)] and then treated with trifluoroacetic acid (0.5 mL). After shaking for 2 hours TLC showed no residual intermediate and the reaction mixture was evaporated. The residue [97% purity by HPLC: $R_T$=7.32 minutes; 10 micron $C_{18}$ reverse phase column (4.6 mm×10 cm) eluting with 10–100% acetonitrile and water containing 0.1% trifluoroacetic acid] was dissolved in water (50 mL) and the solution was lyophilized to give the title compound as an amorphous solid. $^1$H NMR [(CD$_3$)$_2$SO]: δ 8.15 (br s, 3H), 7.72–7.69 (m, 2H), 7.40 (dd, 1H), 7.36–7.25 (m, 4H), 4.66–4.51 (m, 1H), 4.05–3.96 (m, 2H), 3.69–3.48 (m, 1H), 3.30–3.11 (m, 1H), 2.91–2.73 (m, 2H), 1.90–1.54 (m, 4H). MS(Ion spray): 363 and 365(M$^+$+1).

EXAMPLE 37

1-[4-(3-Aminomethyl-phenyl)-piperidin-1-yl]-1-(2-phenoxy-phenyl)-methanone trifluoroacetate By proceeding in a similar manner to the method described in EXAMPLE 36, but using the 2-phenoxybenzoic acid derived TFP resin in place of the 3,4-dichlorobenzoic acid TFP resin, there was prepared the title compound as a white amorphous solid. $^1$H NMR [(CD$_3$)$_2$SO]: δ 8.11 (br s, 3H, NH$_3^+$); 7.43–7.04 (m, 10H); 7.02–6.85 (m, 3H); 4.65–4.52 (m, H); 4.05–3.90 (m, 2H); 3.62–3.49 (m, H); 3.21–3.05 (m, H); 2.86–2.66 (m, 2H); 1.87–1.30 (m, 4H). MS(Ion spray): 587 (M$^+$+1).

EXAMPLE 38

1-{1-[4-(3-Aminomethyl-phenyl)-piperidin-1-yl]-methanoyl}-3-methylsulfanyl-6,7-dihydro-5H-benzo[c]thiophen-4-one trifluoroacetate 2-(1H-Benzotriazol-1-yl)-1,1,3,3-tetramethyluronium tetrafluoroborate (TBTU) (120 mg, 0.38 mmol) was added to a room temperature solution of 3-methylsulfanyl-4-oxo-4,5,6,7-tetrahydro-benzo[c]thiophene-1-carboxylic acid (88 mg, 0.36 mmol) and diisopropylethylamine (140 mg, 1.08 mmol) in dimethylformamide (2 mL), under nitrogen. The reaction mixture was stirred for 10 minutes at room temperature before adding a solution of 4-[3-(N,N-di-tert-butoxycarbonylaminomethyl)phenyl]piperidine (140 mg, 0.36 mmol) and diisopropylethylamine (140 mg, 1.08 mmol) in dimethylformamide (2 mL). The reaction mixture was stirred at room temperature for 16 hours, concentrated to dryness in vacuo, and subjected to dry flash column chromatography on silica with 50:50, dichloromethane:ethyl acetate. 1-{1-[4-(3-(N,N-di-tert-butoxycarbonylaminomethyl)phenyl)-piperidin-1-yl]-methanoyl}-3-methylsulfanyl-6,7-dihydro-5H-benzo[c]thiophen-4-one was isolated as a colorless oil (177 mg). The intermediate was dissolved in dichloromethane (20 mL), cooled at 0° C., and treated with trifluoroacetic acid (2 mL). The reaction mixture was stirred at room temperature under nitrogen for 2 hours, and concentrated to dryness in vacuo. The residue was dissolved in 20% acetonitrile/water [containing 0.1% trifluoroacetic acid] (9 mL) and purified by preparative reverse-phase HPLC (C-18, 10 micron reverse-phase column), eluting with 10% to 100% acetonitrile/water (containing 0.1% trifluoroacetic acid). The product fractions were combined and the acetonitrile removed in vacuo. The aqueous residue was frozen and lyophilized to give the title compound as an amorphous white solid (122 mg, 64%). $^1$H NMR [(CD$_3$)$_2$SO]: δ 8.16 (br s, 3H, NH$_3^+$); 7.41–7.24 (m, 4H); 4.21 (br d, 2H); 4.03 (q, 2H); 3.18–3.02 (m, 2H); 2.91–2.72 (m, 3H); 2.59 (s, 3H); 2.53–2.41 (m, 2H); 1.98–1.90 (m, 2H); 1.90–1.79 (m, 2H); 1.68–1.50 (m, 2H). MS(Ion spray): 415 (M$^+$+1).

EXAMPLE 39

1-[4-(3-Aminomethyl-phenyl)-piperidin-1-yl]-1-(6-chloro-benzo[b]thiophen-2-yl)-methanone trifluoroacetate By proceeding in a similar manner to the method described in EXAMPLE 38, but using 6-chlorobenzo[c]thiophene-2-carboxylic acid (prepared according to the procedure described in International Patent Application No. WO 0107436) in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$)$_2$SO]: δ 8.17 (d, H); 8.14 (br s, 3H, NH$_3^+$); 7.91 (d, H); 7.73 (s, H); 7.45 (dd, H); 7.37 (s, H); 7.35–7.24 (m, 3H); 4.42 (br s, 2H); 4.00 (q, 2H); 3.12 (br s, 2H); 2.93–2.79 (m, H); 1.89–1.77 (m, 2H); 1.70–1.55 (m, 2H). MS(Ion spray): 385 and 387 (M$^+$+1).

EXAMPLE 40

1-[4-(3-Aminomethyl-phenyl)-piperidin-1-yl]-1-(5-chloro-1H-indol-2-yl)-methanone trifluoroacetate By proceeding in a similar manner to the method described in EXAMPLE 38, but using 5-chloro-1H-indole-2-carboxylic acid in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$)$_2$SO]: δ 11.78 (s, H); 8.14 (br s, 3H, NH$_3^+$); 7.63 (s, H); 7.43–7.22 (m, 5H), 7.16 (dd, H); 6.76 (s, H); 4.55 (br d, 2H); 4.00 (q, 2H); 3.14 (br s, 2H); 2.94–2.80 (m, H); 1.90–1.79 (m, 2H); 1.73–1.54 (m, 2H); MS(Ion spray): 368 and 370 (M$^+$+1).

EXAMPLE 41

1-[4-(3-Aminomethyl-phenyl)-piperidin-1-yl]-1-(8-chloro-4H-1,5-dithia-cyclopenta[a]naphthalen-2-yl)-methanone trifluoroacetate By proceeding in a similar manner to the method described in EXAMPLE 38, but using 8-chloro-4H-1,5-dithiacyclopenta[a]naphthalene-2-carboxylic acid in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$)$_2$SO]: δ 8.14 (br s, 3H, NH$_3^+$); 7.52 (d, H); 7.44–7.23 (m, 7H); 4.45 (s, 2H); 4.43 (br d, 2H); 4.00 (q, 2H); 3.12 (br s, 2H); 2.95–2.80 (m, H); 1.90–2.80 (m, 2H); 1.72–1.56 (m, 2H). MS(Ion spray): 453 and 455 (M$^+$+1).

EXAMPLE 42

1-[4-(3-Aminomethyl-phenyl)-piperidin-1-yl]-1-(2',4'-difluoro-4-hydroxy-biphenyl -3yl)-methanone trifluoroacetate By proceeding in a similar manner to the method described in EXAMPLE 38, but using diflunisal in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$)$_2$SO]: δ 10.15 (s, H, OH); 8.15 (br s, 3H, NH$_3^+$); 7.56–7.46 (m, H); 7.40–7.22 (m, 7H); 7.13 (td, H); 6.97 (d, H); 4.64 (br s, H); 3.98 (q, 2H); 3.51 (br s, H); 3.10 (br s, H); 2.88–2.71 (m, H); 1.90–1.46 (m, 4H). MS(Ion spray): 423 and 424 (M$^+$+1).

EXAMPLE 43

1-[4-(3-Aminomethyl-phenyl)-piperidin-1-yl]-1-(3-methylsulfanyl-6,7-dihydro-benzo[c]thiophen-1-yl)-methanone trifluoroacetate By proceeding in a similar manner to the method described in EXAMPLE 38, but using 3-methylsulfanyl-6,7-dihydro-benzo[c]thiophene-1-carboxylic acid in place of 3-methylsulfanyl-4-oxo-4,5,6,7-tetrahydro-benzo[c]

thiophene-1-carboxylic acid, there was prepared the title compound as an amorphous white solid. $^1$H NMR [CDCl$_3$]: δ 8.13 (br s, 3H, NH$_3^+$); 7.38–7.30 (m, H); 7.27–7.18 (m, 3H); 6.68 (d, H); 6.11–6.04 (m, H); 4.52–4.25 (br m, 2H); 4.01–3.93 (br m, 2H); 3.40–3.38 (m, H); 3.12–2.97 (m, H); 2.90–2.75 (m, H); 2.75 (t, 2H); 2.43 (s, 3H); 2.37–2.28 (m, 2H); 1.97–1.81(m, 2H); 1.89–1.60 (m, 2H). MS(Ion spray): 400 (M$^+$+1).

EXAMPLE 44

1-{1-[4-(3-Aminomethyl-phenyl)-piperidin-1-yl]-methanoyl}-6,6-dimethyl-3-methylsulfanyl-6,7-dihydro-5H-benzo[c]thiophen-4-one trifluoroacetate By proceeding in a similar manner to the method described in EXAMPLE 38, but using 6,6-dimethyl-3-methylsulfanyl-4-oxo-4,5,6,7-tetrahydro-benzo[c]thiophene-1-carboxylic acid in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$)$_2$SO]: δ 8.16 (br s, 3H, NH$_3^+$); 7.40–7.34 (m, 2H); 7.32–7.26 (m, 2H); 4.20 (br d, 2H); 4.01 (br s, 2H); 3.20–3.06 (m, 2H), 2.93–2.80 (m, H); 2.67 (m, 2H); 2.60 (s, 3H); 2.38 (3,2H); 1.89–1.78 (m, 2H); 1.67–1.50 (m, 2H); 0.98 (s, 6H). MS(Ion spray): 444 (M$^+$+1).

EXAMPLE 45

1-[4-(3-Aminomethyl-phenyl)-piperidin-1-yl]-1-(6-bromo-pyridin-3-yl)-methanone bistrifluoroacetate A. 6-Bromonicotinic acid hydrochloride n-Butyllithium (8.0 mL of 2.5M in hexanes, 20 mmol) was added dropwise to a stirring solution of 2,5-dibromopyridine (4.74 g, 20 mmol) in THF (100 mL) at −100° C., under nitrogen. The reaction mixture was left at this temperature for 30 minutes before bubbling anhydrous carbon dioxide gas through the reaction mixture (for 20 minutes), and leaving to warm to −20° C. Quenched with 1N HCl (20 mL) and brine (20 mL), and extracted into ethyl acetate, dried over magnesium sulfate, concentrated to dryness. 6-Bromonicotinic acid hydrochloride was isolated as a pale yellow powder (3.8 g, 16 mmol). $^1$H NMR [CDCl$_3$+CD$_3$OD]: δ 8.86 (d, 1H), 8.07 (dd, 1H), 7.52 (d, 1H). MS(Ion spray): 202 and 204 (M$^+$+1).

B. 1-[4-(3-Aminomethyl-phenyl)-piperidin-1-yl]-1-(6-bromo-pyridin-3-yl)-methanone bistrifluoroacetate By proceeding in a similar manner to the method described in EXAMPLE 38, but using 6-bromonicotinic acid hydrochloride in place of 3-methylsulfanyl-4-oxo-4,5,6,7-tetrahydro-benzo[c]thiophene-1-carboxylic acid, there was prepared the title compound as an amorphous white solid. $^1$H NMR [CD$_3$OD]: δ 8.48 (d, H); 7.89 (dd, H); 7.82 (d, H); 7.48–7.30 (m, 4H); 4.90–4.81 (m, H); 4.15 (s, 2H); 3.84 (br d, H); 3.46–3.36 (m, H); 3.11–2.91 (m, 2H); 2.13–1.68 (m, 4H). MS(Ion spray): 374 and 376 (M$^+$+1).

EXAMPLE 46

6-{1-[4-(3-Aminomethyl-phenyl)-piperidin-1-yl]-methanoyl}-2,3-dihydro-thiazolo[3,2-a]pyrimidin-5-one By proceeding in a similar manner to the method described in EXAMPLE 38, but using 5-oxo-2,3-dihydro-5H-thiazolo[3,2-a]pyrimidine-6-carboxylic acid in place of 3-methylsulfanyl-4-oxo-4,5,6,7-tetrahydro -benzo[c]thiophene-1-carboxylic acid, there was prepared the title compound as an amorphous white solid. $^1$H NMR [CD$_3$OD]: δ 7.97 (s, H); 7.44–7.29 (m, 4H); 4.76 (br d, H); 4.59–4.51 (m, 2H); 4.07 (s, 2H); 3.83 (br d, H); 3.69–3.57 (m, 2H); 3.41–3.21 (m, H); 3.02–2.85 (m, 2H); 2.05–1.67 (m, 4H). MS(Ion spray): 371 (M$^+$+1).

EXAMPLE 47

1-[4-(3-Aminomethyl-phenyl)-piperidin-1-yl]-1-(3-chloro-phenyl)-methanone trifluoroacetate By proceeding in a similar manner to the method described in EXAMPLE 38, but using 3-chlorobenzoic acid in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$)$_2$SO]: δ 8.14 (br s, 3H, NH$_3^+$); 7.57–7.43 (m, 3H); 7.40–7.22 (m, 5H); 4.70–4.56 (m, H); 401 (q, 2H); 3.64–3.56 (m, H); 3.23–3.10 (m, H); 2.91–2.79 (m, 2H); 1.92–1.52 (m, 4H). MS(Ion spray): 329 and 331 (M$^+$+1).

EXAMPLE 48

1-[4-(3-Aminomethyl-phenyl)-piperidin-1-yl]-1-(4-chloro-phenyl)-methanone trifluoroacetate By proceeding in a similar manner to the method described in EXAMPLE 38, but using 4-chlorobenzoic acid in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$)$_2$SO]: δ 8.15 (br s, 3H, NH$_3^+$); 7.53 (d, 2H); 7.44 (d, 2H); 7.40–7.23 (m, 4H); 4.64–4.56 (m, H); 4.02 (q, 2H); 3.72–3.58 (m, H); 3.24–3.10 (m, H); 2.95–2.89 (m, 2H); 1.90–1.50 (m, 4H). MS(Ion spray): 329 and 331 (M$^+$+1).

EXAMPLE 49

1-[4-(3-Aminomethyl-phenyl)-piperidin-1-yl]-1-{3-[5-(2-chloro-phenyl)-[1,3,4]oxadiazol-2-yl]-phenyl}-methanone trifluoroacetate A. 3-[5-(2-Chlorophenyl)-[1,3,4]oxadiazol-2-yl]-benzoic acid methyl ester 3-(2H-Tetrazol-5-yl)-benzoic acid methyl ester (204 mg, 1 mmol) (prepared by the method of Tanaka et al, J. Med. Chem., 1998, 41(13), 2406) and 2-chlorobenzoyl chloride (175 mg, 1 mmol) were combined in anisole (10 mL) at room temperature and 2,4,6-collidine (121 mg, 1 mmol) in anisole (1 mL) was added. The reaction mixture was heated at 100° C. for 1 hour followed by 120° C. for 15 minutes, monitoring the evolution of gas by balloon [volume of gas evolved was measured by positive displacement of water, total =22 mL]. Cooled reaction mixture to room temperature, and concentrated to dryness in vacuo. The residue was subjected to flash column chromatography on silica with gradient dilution 5% to 40% ethyl acetate/heptane. 3-[5-(2-Chlorophenyl)-[1,3,4]oxadiazol-2-yl]-benzoic acid methyl ester was isolated as a colorless powder (229 mg, 73%). $^1$H NMR [CDCl$_3$]: δ 8.79 (s, H); 8.36 (d, H); 8.25 (d, H); 8.14 (d, H); 7.72–7.57 (m, 2H); 7.57–7.41 (m, 2H); 4.00 (s, 3H). MS(Ion spray): 315 and 317 (M$^+$+1).

B. 1-[4-(3-Aminomethyl-phenyl)-piperidin-1-yl]-1-{3-[5-(2-chloro-phenyl)-[1,3,4]oxadiazole-2-yl]phhenyl}methanone trifluoroacetate 1N Sodium hydroxide (2 mL, 2 mmol) was added to a solution of 3-[5-(2-chlorophenyl)-[1,3,4]oxadiazole-2-yl]-benzoic acid methyl ester (113 mg, 0.36 mmol) in methanol (5 mL) and THF (2 mL), and the reaction mixture stirred at room temperature for 2 h, before neutralizing to pH 7 with 1N hydrochloric acid. The solution was concentrated to dryness in vacuo and placed under high vacuum overnight. Crude material was used directly without purification [MS (Ion spray): 301 and 303 (M$^+$+1); LC/MS purity>95%, only major impurity is sodium chloride]. 2-(1H-Benzotriazol-1-yl) -1,1,3,3-tetramethyluronium tetrafluoroborate (TBTU) (116 mg, 0.36 mmol) was added to a room temperature solution/suspension of crude 3-[5-(2-chlorophenyl)-[1,3,4]oxadiazol-2-yl]-benzoic acid and diisopropylethylamine (150 mg, 1.14 mmol) in dimethylfornamide (2 mL), under nitrogen. The reaction mixture was stirred for 10 minutes at room temperature before adding a solution of 4-[3-(N,N-di-tert -butoxycarbonylaminomethyl)phenyl]piperidine (78 mg, 0.2 mmol) and diisopropylethylamine (150 mg, 1.14 mmol) in dimethylformamide (2 mL). The reaction mixture was stirred at room temperature for 16 hours, concentrated to dryness in vacuo, and subjected to dry flash column chromatography on silica with 50:50, dichloromethane:ethyl acetate. 1-{4-[3-(N,N-di-tert -butoxycarbonylaminomethyl)phenyl]-piperidin-1-yl}-1-{3-[5-(2-chloro-phenyl)-[1,3,4]oxadiazole-2-yl]-phenyl}-methanone was isolated as a colorless oil, which was dissolved in dichloromethane (10 mL), cooled at 0° C., and treated with trifluoroacetic acid (1 mL). The reaction mixture was stirred at room temperature under nitrogen for 2 hours, and concentrated to dryness in vacuo. The residue was dissolved in 20% acetonitrile/water [containing 0.1% trifluoroacetic acid] (9 mL) and purified by preparative reverse-phase HPLC (C-18, 10 micron reverse-phase column), eluting with 20% to 60% acetonitrile/water (containing 0.1% trifluoroacetic acid). The product fractions were combined and concentrated to dryness in vacuo. The title compound was isolated as an amorphous white glass solid (98 mg, 83%). $^1$H NMR [(CD$_3$)$_2$SO]: δ 8.16 (br s, 3H, NH$_3^+$) overlapped with 8.22–8.16 (m, 2H) and 8.13 (s, H); 7.79–7.72 (m, 3H); 7.69 (td, H); 7.62 (td, H); 7.41 (s, H); 7.39–7.27 (m, 3H); 4.64 (br d, H); 4.03 (q, 2H); 3.79–3.63 (m, H); 3.28–3.20 (m, H); 3.03–2.80 (m, 2H); 1.96–1.57 (m, 4H). MS(Ion spray): 473 and 475 (M$^+$+1).

EXAMPLE 50

1-[4-(3-Aminomethyl-phenyl)-piperidin-1-yl]-1-[3-(5-pyridin-3-yl-[1,3,4]oxadiazol-2yl)-phenyl]-methanone bis-trifluoroacetate A. 3-(5-Pyridin-3-yl-[1,3,4]oxadiazol-2-yl)-benzoic acid methyl ester Prepared in a similar manner to the method described in EXAMPLE 49A, but using nicotinoyl chloride hydrochloride instead of 2-chlorobenzoyl chloride, 2 mmol of 2,4,6-collidine, and heating at 110° C. instead of 100° C. The residue was subjected to flash column chromatography on silica with ethyl acetate and 5% methanol/ethyl acetate. 3-(5-Pyridin-3-yl-[1,3,4]oxadiazol-2-yl)-benzoic acid methyl ester was isolated as a colorless powder (84 mg, 30%). $^1$H NMR [CDCl$_3$]: δ 9.40 (s, H); 8.84–8.80 (m, H); 8.80–8.78 (m, H); 8.47 (dt, H); 8.38 (dt, H); 8.26 (dt, H); 7.67 (t, H); 7.52 (dd, H); 4.00 (s, 3H). MS(Ion spray): 282 (M$^+$+1).

B. 1-[4-(3-Aminomethyl-phenyl)-piperidin-1-yl]-1-[3-(5-pyridin-3-yl-[1,3,4]oxadiazol-2-yl)-phenyl]-methanone bis-trifluoroacetate By proceeding in a similar manner to the method described in EXAMPLE 49B, but using 3-(5-pyridin-3-yl-[1,3,4]oxadiazol-2-yl)-benzoic acid methyl ester in place of 3-[5-(2-chlorophenyl)-[1,3,4]oxadiazol-2-yl]-benzoic acid methyl ester, there was prepared the title compound as an amorphous white glass solid. $^1$H NMR [(CD$_3$)$_2$SO]: δ 9.37 (br s, H); 8.86 (br s, H); 8.55 (d, H); 8.28–8.23 (m, H); 8.20 (s, H); 8.16 (br s, 3H, NH$_3^+$); 7.79–7.65 (m, 3H); 7.41 (s, H); 7.39–7.26 (m, 3H); 4.63 (br d, H); 4.09–4.00 (m, 2H); 3.80–3.62 (m, H); 3.37–3.16 (m, H); 3.02–2.80 (m, 2H); 1.98–1.55 (m, 4H). MS(Ion spray): 441 (M$^+$+1).

EXAMPLE 51

1-{1-[4-(3-Aminomethyl-phenyl)-piperidin-1-yl]-methanoyl}-3-ethylsulfanyl-6,6-dimethyl-6,7-dihydro-5H-benzo[c]thiophen-4-one trifluoroacetate By proceeding in a similar manner to the method described in EXAMPLE 49B, but using 3-ethylsulfanyl-6,6-dimethyl-4-oxo-4,5,6,7-tetrahydro-benzo[c]thiophene-1-carboxylic acid methyl ester in place of 3-[5-(2-chlorophenyl)-[1,3,4]oxadiazol-2-yl]-benzoic acid methyl ester, there was prepared the title compound as an amorphous white glass solid. $^1$H NMR [(CD$_3$)$_2$SO]: δ 8.16 (br s, 3H, NH$_3^+$); 7.40–7.33 (m, 2H); 7.32–7.26 (m, 2H); 4.30–4.00 (m, 4H); 3.21–3.10 (m, 2H); 3.06 (q, 2H); 2.92–2.80 (m, H); 2.66 (s, 2H); 2.38 (s, 2H); 1.90–1.78 (m, 2H); 1.68–1.50 (m, 2H); 0.98 (s, 6H). MS(Ion spray): 458 (M$^+$+1).

EXAMPLE 52

1-{1-[4-(3-Aminomethyl-phenyl)-piperidin-1-yl]-methanoyl}-3-propylsulfanyl-6,7-dihydro-5H-benzo[c]thiophen-4-one trifluoroacetate By proceeding in a similar manner to the method described in EXAMPLE 49B, but using 4-oxo-3-propylsulfanyl-4,5,6,7-tetrahydro-benzo[c]thiophene-1-carboxylic acid ethyl ester in place of 3-[5-(2-chlorophenyl)-[1,3,4]oxadiazol-2-yl]-benzoic acid methyl ester, there was prepared the title compound as an amorphous white glass solid. $^1$H NMR [(CD$_3$)$_2$SO]: δ 8.14 (br s, 3H, NH$_3^+$); 7.41–7.23 (m, 4H); 4.21 (br d, 2H); 4.08–3.99 (m, 2H); 3.39–2.99 (m, 4H); 2.94–2.71 (m, 3H); 2.54–2.49 (m, 2H); 202–1.90 (m, 2H); 1.90–1.70 (m, 4H); 1.70–1.51 (m, 2H); 1.03 (t, 3H). MS(Ion spray): 443 (M$^+$+1).

EXAMPLE 53

1-{1-[4-(3-Aminomethyl-phenyl)-piperidin-1-yl]-methanoyl}-3-isopropylsulfanyl-6,7-dihydro-5H -benzol[c]thiophen-4-one trifluoroacetate By proceeding in a similar manner to the method described in EXAMPLE 49B, but using 3-isopropylsulfanyl-4-oxo-4,5,6,7-tetrahydro-benzo[c]thiophene-1-carboxylic acid ethyl ester in place of 3-[5-(2-chlorophenyl)-[1,3,4]oxadiazol-2-yl]-benzoic acid methyl ester, there was prepared the title compound as an amorphous white glass solid. $^1$H NMR [(CD$_3$)$_2$SO]: δ 8.14 (br s, 3H, NH$_3^+$); 7.43–7.23 (m, 4H); 4.30–4.16 (m, 2H); 4.09–3.98 (m, 2H); 3.53 (septet, H); 3.22–3.03 (m, 2H); 2.93–2.72 (m, 3H); 2.54–2.47 (m, 2H); 2.02–1.86 (m, 4H); 1.70–1.51 (m, 2H); 1.42 (d, 6H). MS(Ion spray): 443 (M$^+$+1).

EXAMPLE 54

3-{1-[4-(3-Aminomethyl-phenyl)-piperidin-1-yl]-methanoyl}-5,5-dimethyl-7-oxo-4,5,6,7-tetrahydro-benzo[c]thiophene-1-carbonitrile trifluoroacetate By proceeding in a similar manner to the method described in EXAMPLE 49B, but using 3-cyano-6,6-dimethyl-4-oxo-4,5,6,7-tetrahydro-benzo[c]thiophene-1-carboxylic acid ethyl ester in place of 3-[5-(2-chlorophenyl)-[1,3,4]oxadiazol-2-yl]-benzoic acid methyl ester, there was prepared the title compound as an amorphous white glass solid. $^1$H NMR [(CD$_3$)$_2$SO]: δ 8.14 (br s, 3H, NH$_3^+$); 7.41–7.33 (m, 2H); 7.32–7.26 (m, 2H); 4.30–3.90 (br m, 2H); 4.04–3.98 (m, 2H); 3.30–3.01 (m, 2H); 2.93–2.80 (m, H); 2.71 (s, 2H); 2.54 (s, 2H); 1.89–1.76 (m, 2H); 1.73–1.51 (m, 2H); 1.01 (s, 6H). MS(Ion spray): 423 (M$^+$+1).

EXAMPLE 55

3-{1-[4-(3-Aminomethyl-phenyl)-piperidin-1-yl]-methanoyl}-5,5-dimethyl-7-oxo-4,5,6,7-teterahydro-benzo[c]thiophene-1-carboxylic acid trifluoroacetate The title compound was isolated as a by-product from the reaction carried out to synthesize 3-{1-[4-(3-aminomethyl-phenyl)-piperidin-1-yl]-methanoyl}-5,5-dimethyl-7-oxo-4,5,6,7-tetrahydro-benzo[c]thiophene-1-carbonitrile trifluoroacetate, in EXAMPLE 54. $^1$H NMR [(CD$_3$)$_2$SO]: δ 9.70 (s, H, OH); 8.11 (br s, 3H, NH$_3$$^+$); 7.42–7.26 (m, 4H); 4.28–3.96 (br m, 2H); 4.03–3.99 (m, 2H); 3.27–3.06 (m, 2H); 2.96–2.85 (m, H); 2.70 (s, 2H); 2.63 (s, 2H); 1.93–1.72 (m, 2H); 1.69–1.52 (m, 2H); 1.01 (s, 6H). MS(Ion spray): 442 (M$^+$+1).

EXAMPLE 56

3-{1-[4-(3-Aminomethyl-phenyl)-piperidin-1-yl]-methanoyl}-5,5-dimethyl-7-oxo-4,5,6,7-tetrahydro-benzo[c]thiophene-1-carboxylic acid methyl ester trifluoroacetate The title compound was isolated as a by-product from the reaction carried out to synthesize 3-{1-[4-(3-aminomethyl-phenyl)-piperidin-1-yl]-methanoyl}-5,5-dimethyl-7-oxo-4,5,6,7-tetrahydro-benzo[c]thiophene-1-carbonitrile trifluoroacetate, in EXAMPLE 54. $^1$H NMR [(CD$_3$)$_2$SO]: δ 8.16 (br s, 3H, NH$_3$$^+$); 7.41–7.34 (m, 2H); 7.33–7.27 (m, 2H); 4.30–3.95 (br m, 2H); 4.06–4.00 (m, 2H); 3.84 (s, 3H); 3.25–3.04 (m, 2H); 2.94–2.80 (m, H); 2.71 (s, 2H); 2.51 (s, 2H); 1.90–1.78 (m, 2H); 1.71–1.51 (m, 2H); 1.00 (s, 6H). MS(Ion spray): 456 (M$^+$+1).

EXAMPLE 57

1-{1-[4-(3-Aminomethyl-phenyl)-piperidin-1-yl]-methanoyl}-3-methoxy-6,6-dimethyl-6,7-dihydro-5H-benzo[c]thiophen-4-one.

By proceeding in a similar manner to the method described in EXAMPLE 38, but using 3-Methoxy-6,6-dimethyl-4-oxo-4,5,6,7-tetrahydro-benzo[c]thiophene-1-carboxylic acid, there was prepared the title compound as an amorphous white solid. $^1$H NMR [(CD$_3$)$_2$SO]: δ 8.22 (br s, 3H, NH$_3$$^+$), 7.54–7.27 (m, 4H), 4.29–4.22 (m, 2H), 4.14 (s, 3H), 4.13–4.02 (m, 2H), 3.26–3.08 (m, 2H), 3.04–2.86 (m, 1H), 2.71 (s, 2H), 2.37 (s, 2H), 2.02–1.84 (m, 2H), 1.79–1.54 (m, 2H), 1.04 (s, 6H). MS(Ion spray): 427.3 (M$^+$+1).

EXAMPLE 58

1-[4-(3-Aminomethyl-phenyl)-piperidin-1-yl]-1-(4-pyrrol-1-yl-phenyl)-methanone -trifluoroacetate.

By proceeding in a similar manner to the method described in EXAMPLE 38, but using 4-(1H-Pyrrol-1-yl) benzoic acid in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$OD]: δ 7.62–7.51 (m, 4H), 7.41–7.22 (m, 6H), 6.32–6.28 (m, 2H), 4.85–4.66 (m, 2H), 4.08 (s, 2H), 4.03–3.88 (m, 1H), 3.15–2.86 (m, 2H), 2.11–1.62 (m, 4H). MS(Ion spray): 360 (M$^+$+1).

EXAMPLE 59

1-[4-(3-Aminomethyl-phenyl)-piperidin-1-yl]-1-benzo[b]thiophen-2-yl-methanone -trifluoroacetate By proceeding in a similar manner to the method described in EXAMPLE 38, but using benzo(b)-thiophene-2-carboxylic acid in place of 3-methylsulfanyl-4-oxo-4,5,6,7-tetrahydro-benzo[c]thiophene-1-carboxylic acid, there was prepared the title compound as an amorphous white solid. $^1$H NMR [(CD$_3$OD]: δ 7.98–7.81 (m, 2H), 7.62 (s, 1H), 7.45–7.32 (m, 5H), 7.31–7.22 (m, 1H), 4.80–4.40 (m, 2H), 4.10 (s, 2H), 3.28–3.05 (m, 1H), 3.02–2.90 (m, 2H), 2.02–1.88 (m, 2H), 1.86–1.65 (m, 2H). MS(Ion spray): 351 (M$^+$+1).

EXAMPLE 60

(E)-1-[4-(3-Aminomethyl-phenyl)-piperidin-1-yl]-3-(3-methoxy-phenyl)-propenone-trifluoroacetate.

By proceeding in a similar manner to the method described in EXAMPLE 38, but using 3-methoxycinnamic acid, there was prepared the title compound as an amorphous white solid. $^1$H NMR [(CD$_3$OD]: δ 7.56 (d, H), 7.45–7.25 (m, 5H), 7.23–7.13 (m, 3H), 6.98–6.90 (m, 1H), 4.85–4.70 (m, 1H), 4.50–4.35 (m, 1H), 4.08 (s, 2H), 3.83 (s, 3H), 3.40–3.32 (m, 1H), 3.01–2.75 (m, 2H), 2.08–1.83 (m, 2H), 1.81–1.61 (m, 2H). MS(Ion spray): 351 (M$^+$+1).

EXAMPLE 61

1-[4-(3-Aminomethyl-phenyl)-piperidin-1-yl]-1-(3-ethoxy-thiophen-2-yl)-methanone -trifluoroacetate.

By proceeding in a similar manner to the method described in EXAMPLE 38, but using 3-ethoxythiophene-2-carboxylic acid, there was prepared the title compound as an amorphous white solid. $^1$H NMR [(CD$_3$OD]: δ 7.53 (d, 1H), 7.46–7.22 (m, 4H), 6.94 (d, 1H), 4.60–4.21 (br.m., 2H), 4.19 (q, 2H), 4.08 (s, 2H), 3.18–2.98 (m, 1H), 2.96–2.85 (m, 2H), 2.0–1.86 (m, 2H), 1.84–1.65 (m, 2H), 1.37 (t, 3H). MS(Ion spray): 345 (M$^+$+1).

EXAMPLE 62

1-[4-(3-Aminomethyl-phenyl)-piperidin-1-yl]-2-indan-2-yl-ethanone-trifluoroacetate.

By proceeding in a similar manner to the method described in EXAMPLE 38, but using 2-indanylacetic acid, there was prepared the title compound as an amorphous white solid. $^1$H NMR [(CD$_3$OD]: δ 7.45–7.25 (m, 4H), 7.18–7.15 (m, 2H), 7.14–7.04 (m, 2H), 4.78–4.65 (m, 1H), 4.18–4.11 (m, 1H), 4.08 (s, 2H), 3.28–3.08 (m, 2H), 2.95–2.76 (m, 2H), 2.74–2.58 (m, 6H), 2.01–1.85 (m, 2H), 1.75–1.51 (m, 2H). MS(Ion spray): 349 (M$^+$+1).

EXAMPLE 63

1-[4-(3-Aminomethyl-phenyl)-piperidin-1-yl]-1-[5-(3-chloro-phenyl)-pyridin-3-yl]-methanone-ditrifluoroacetate.

A. 5-(3-chlorophenyl)-nicotinic Acid

A three neck flask was charged with 5-bromonicotinic acid (2 g, 9.90 mmol), 3-chlorophenylboronic acid (1.55 g, 9.90 mmol), a 0.4 M solution of sodiumcarbonate in water (37 mL, 14.8 mmol) and Acetonitrile (37 mL). The solution was degassed under vacuum and tetrakistriphenylphoshine Pd(0) (0.57 g, 0.495 mmol) was added and the reaction refluxed overnight under nitrogen. The reaction was cooled to room temperature and filtered through a celite pad. The filtrate was partially evaporated under reduced pressure and the remaining solution acidified to pH=2 with 1N HCl. The resulting solid was collected by filtration and dried under vacuum. $^1$H NMR [(CD$_3$)$_2$SO]: δ 9.15–9.05 (m, 2H), 8.45 (s, 1H), 7.85 (s, 1H), 7.80–7.65 (m, 1H), 7.60–7.42 (m, 2H).

B. 1-[4-(3-Aminomethyl-phenyl)-piperidin-1-yl]-1-[5-(3-chloro-phenyl)-pyridin-3-yl]-methanone-ditrifluoroacetate By proceeding in a similar manner to the method described in EXAMPLE 38, but using 5-(3-chlorophenyl)-nicotinic acid, there was prepared the title compound as an amorphous white solid. $^1$H NMR [(CD$_3$)$_2$SO]: δ 8.99 (s, 1H), 8.65 (s, 1H), 8.18 (s, 1H), 8.13 (br.s., 3H, NH$_3$$^+$), 7.88 (s, 1H), 7.76 (d, 1H), 7.58–7.45 (m, 2H), 7.40–7.20 (m, 4H), 4.80–4.58 (m, 1H), 3.98 (q, 2H), 3.78–3.55 (m 1H), 3.33–3.18 (m, 1H), 2.98–2.71 (m, 2H), 1.95–1.52 (m, 4H). MS(Ion spray): 406 (M$^{30}$ +1).

EXAMPLE 64

1-[4-(3-Aminomethyl-phenyl)-piperidin-1-yl]-1-(5-chloro-benzo[b]thiophen-2-yl) -methanone-trifluoroacetate.

By proceeding in a similar manner to the method described in EXAMPLE 38, but using 5-chloro-benzo(b) thiophene-2-carboxylic acid, prepared as in WO 0107436, there was prepared the title compound as an amorphous white solid. $^1$H NMR [(CD$_3$)$_2$SO]: δ 8.08 (br.s., 3H, NH$_3$$^+$), 8.05 (d, 1H), 8.01 (s, 1H), 7.68 (s, 1H), 7.47 (d, 1H), 7.40–7.21 (m, 4H), 4.41 (br.s., 2H), 3.99, (q, 2H), 3.30–3.15 (m, 2H), 2.95–2.78 (m, 1H), 1.90–1.75 (m, 2H), 1.73–1.52 (m, 2H). MS(Ion spray): 385 (M$^+$+1).

EXAMPLE 65
1-[4-(3-Aminomethyl-phenyl)-piperidin-1-yl]-2-(3,4-dichloro-phenyl)-ethanone-trifluoroacetate.

By proceeding in a similar manner to the method described in EXAMPLE 38, but using 3,4-dichlorophenyl acetic acid, there was prepared the title compound as an amorphous white solid. $^1$H NMR [(CD$_3$)$_2$SO]: δ 8.08 (br.s., 3H, NH$_3^+$), 7.56 (d, 1H), 7.48 (s, 1H), 7.38–7.15 (m, 5H), 4.58–4.45 (m, 1H), 4.15–3.92 (m, 3H), 3.85–3.65 (m, 2H), 3.18–3.03 (m, 1H), 2.85–2.55 (m, 2H), 1.80–1.65 (m, 2H), 1.55–1.32 (m, 2H). MS(Ion spray): 376 (M$^+$+1).

EXAMPLE 66
1-[4-(3-Aminomethyl-phenyl)-piperidin-1-yl]-2-(5-chloro-pyridin-3-yloxy)-ethanone -ditrifluoroacetate.

By proceeding in a similar manner to the method described in EXAMPLE 38, but using (5-chloro-pyridin-3-yloxy)-acetic acid, prepared as in WO 0107436, there was prepared the title compound as an amorphous white solid. $^1$H NMR [(CD$_3$)$_2$SO]: δ 8.28–8.21 (m, 2H), 8.15 (br.s., 3H, NH$_3^+$), 7.58 (s, 1H), 7.40–7.20 (M, 4H), 5.01 (s, 2H), 4.52–4.38 (m, 1H), 3.98 (q, 2H), 3.93–3.80 (m, 1H), 3.22–3.05 (m, 1H), 2.88–2.58 (m, 2H), 1.88–1.35 (m, 4H). MS(Ion spray): 360 (M$^+$+1).

EXAMPLE 67
1-[4-(3-Aminomethyl-phenyl)-piperidin-1-yl]-2-(6-chloro-pyridin-2-yloxy)-ethanone -ditrifluoroacetate.

By proceeding in a similar manner to the method described in EXAMPLE 38, but using (6-chloro-pyridin-2-yloxy)-acetic acid, prepared as in WO 0107436, there was prepared the title compound as an amorphous white solid. $^1$H NMR [(CD$_3$)$_2$SO]: δ 8.10 (br.s., 3H, NH$_3^+$), 7.81–7.71 (m, 1H), 7.41–7.18 (m, 4H), 7.08 (d, 1H), 6.88 (d, 1H), 5.15–4.92 (m, 2H), 4.50–4.31 (m, 1H), 4.08–3.81 (m, 3H), 3.27–3.08 (m, 1H), 2.92–2.76 (m, 1H), 2.75–2.60 (m, 1H), 1.90–1.58 (m, 2H), 1.5–1.35 (m, 2H). MS(Ion spray): 360 (M$^+$+1).

EXAMPLE 68
(E)-1-[4-(3-Aminomethyl-phenyl)-piperidin-1-yl]-3-(5-chloro-thiophen-2-yl)-propenone -trifluoroacetate.

By proceeding in a similar manner to the method described in EXAMPLE 38, but using 3-(5-chloro-thiophen-2-yl)-acrylic acid, prepared as in WO 0107436, there was prepared the title compound as an amorphous white solid. $^1$H NMR [(CD$_3$)$_2$SO]: δ 8.08 (br.s., 3H, NH$_3^+$), 7.56 (d, 1H), 7.40–7.28 (m, 3H), 7.26–7.18 (m, 2H), 7.12 (d, 1H), 6.92 (d, 1H), 4.70–4.50 (m, 1H), 4.41–4.21 (m, 1H), 3.98 (q, 2H), 3.28–3.05 (m, 1H), 2.90–2.63 (m, 2H), 1.91–1.72 (m, 2H), 1.65–1.35 (m, 2H).). MS(Ion spray): 361 (M$^+$+1).

EXAMPLE 69
(E)-1-[4-(3-Aminomethyl-phenyl)-piperidin-1-yl]-3-(4-chloro-thiophen-2-yl)-propenone -trifluoroacetate.

By proceeding in a similar manner to the method described in EXAMPLE 38, but using 3-(4-chloro-thiophen-2-yl)-acrylic acid, prepared as in WO 0107436, there was prepared the title compound as an amorphous white solid. $^1$H NMR [(CD$_3$)$_2$SO]: δ 8.06 (br.s., 3H, NH$_3^+$), 7.65 (s, 1H), 7.60–7.48 (m, 2H), 7.40–7.20 (m, 4H), 7.08 (d, 1H), 4.70–4.51 (m, 1H), 4.42–4.25 (m, 1H), 4.05–3.93 (m, 2H), 3.28–3.08 (m, 1H), 2.90–2.63 (m, 2H), 1.90–1.65 (m, 2H), 1.63–1.40 (m, 2H). MS(Ion spray): 361 (M$^+$+1).

EXAMPLE 70
1-[4-(3-Aminomethyl-phenyl)-piperidin-1-yl]-1-(4,5,6,7-tetrahydro-benzo[c]thiophen-1-yl)-methanone-trifluoroacetate By proceeding in a similar manner to the method described in EXAMPLE 38, but using 4,5,6,7-tetrahydro-benzo(c)thiophene-1-carboxylic acid, prepared as in JOC V62#6 1997 p. 1599, there was prepared the title compound as an amorphous white solid.

$^1$H NMR [(CD$_3$)$_2$SO]: δ 8.13 (br.s., 3H, NH$_3^+$), 7.40–7.33 (m, 2H), 7.31–7.25 (m, 2H), 7.20 (s, 1H), 4.35–4.15 (m, 2H), 4.03 (q, 2H), 3.17–2.98 (m, 2H), 2.95–2.78 (m, 1H), 2.73–2.58 (m, 4H), 1.90–1.78 (m, 2H), 1.75–1.63 (m, 4H), 1.61–1.42 (m, 2H). MS(Ion spray): 355 (M$^+$+1).

EXAMPLE 71
1-[4-(3-Aminomethyl-phenyl)-piperidin-1-yl]-1-(5-chloro-4-methoxy-thiophen-3-yl) -methanone-trifluoroacetate.

By proceeding in a similar manner to the method described in EXAMPLE 38, but using 2-chloro-3-methoxy-thiophene-4-carboxylic acid, there was prepared the title compound as an amorphous white solid. $^1$H NMR [(CD$_3$)$_2$SO]: δ 8.13 (br.s., 3H, NH$_3^+$), 7.57 (s, 1H), 7.40–7.22 (m, 4H), 4.70–4.58 (m, 1H), 4.05 (q, 2H), 3.85 (s, 3H), 3.75–3.60 (m, 1H), 3.25 (m, 1H), 2.95–2.78 (m, 2H), 1.93–1.70 (m, 2H), 1.68–1.45 (m, 2H). MS(Ion spray): 365 (M$^+$+1).

EXAMPLE 72
1-[4-(3-Aminomethyl-phenyl)-piperidin-1-yl]-1-(1H-indol-3-yl)-methanone-trifluoroacetate.

By proceeding in a similar manner to the method described in EXAMPLE 38, but using Indole-3-carboxylic acid, there was prepared the title compound as an amorphous white solid. $^1$H NMR [(CD$_3$)$_2$SO]:δ 8.13 (br.s., 3H, NH$_3^+$), 7.78–7.63 (m, 2H), 7.52–7.20 (m, 6H), 7.20–7.03 (m, 2H), 4.57–4.38 (m, 1H), 4.03 (q, 2H), 3.17–3.02 (m, 2H), 2.95–2.75 (m, 1H), 1.90–1.78 (m, 2H), 1.75–1.57 (m, 2H). MS(Ion spray): 334 (M$^+$+1).

EXAMPLE 73
1-[4-(3-Aminomethyl-phenyl)-4-hydroxy-piperidin-1-yl]-1-(5-phenethyl-pyridin-3-yl) -methanone-ditrifluoroacetate.

A. 4-(3-Cyano-phenyl)-4-hydroxy-piperidine-1-carboxylic acid-tert-butyl ester.

A solution of 3-Bromobenzonitrile (0.48 g, 2.64 mmol) in THF (20 mL) was stirred under nitrogen at −78° C. To this was added dropwise a solution of 2.0M nBuLi in hexanes (1.38 mL, 2.72 mmol). The solution was allowed to warm to −15° C. over 1.5 hours. The solution was recooled to −78° C. and a solution of N-Boc-4-piperidone (0.53 g, 2.64 mmol) in THF (5 mL) was added dropwise. The reaction mixture was allowed to warm to −10° C. and stirred at this temperature for three hours. The reaction was quenched with ½ saturated ammonium chloride solution (30 mL) and stirred 15 minutes. The THF was removed by evaporation and the residue extracted with methylene chloride (3×50 mL). The organic extracts were combined, dried over sodium sulfate, evaporated to give an orange oil which was purified by flash chromatography 3:5:2 methylene chloride: heptane: ethyl acetate to give the title compound (0.30 g) as a clear oil. $^1$H NMR [(CDCl$_3$]: δ 7.82 (s, 1H), 7.72 (d, 1H), 7.58 (d, 1H), 7.55–7.42 (m, 1H), 4.20–3.95 (m, 2H), 3.35–3.10 (m, 2H), 2.08–1.83 (m, 2H), 1.80–1.66 (m, 2H), 1.51 (s, 9H).

B. 4-[3-(Benzyloxycarbonylamino-methyl)-phenyl]-4-hydroxy-piperidine-1-carboxylic acid-tert-butyl ester.

A solution of 4-(3-Cyano-phenyl)-4-hydroxy-piperidine-1-carboxylic acid-tert-butyl ester (0.30 g, 0.99 mmol) in 7N ammonia/methanol (25 mL) and 5%Rhodium on alumina (0.15 g) was hydrogenated overnight on a Parr apparatus (45 psi). The reaction was filtered through celite, evaporated, and azeotroped with MeOH:toluene 1:1 (2×30 mL) to give 4-(3-Aminomethyl-phenyl)-4-hydroxy-piperidine-1-carboxylic acid-tert-butyl ester as a foam. This compound was used directly in the next step.

To a stirred mixture of 4-(3-Aminomethyl-phenyl)-4-hydroxy-piperidine-1-carboxylic acid-tert-butyl ester (0.30 g, 0.99 mmol), methylene chloride (10 mL) and water (10 mL) was added potassium carbonate (0.28 g, 2.02 mmol) followed by benzylchloroformate (0.34 g, 2.02 mmol). The reaction stirred overnight at room temperature. The reaction was extracted with methylene chloride (3×30 mL). The organic extracts were combined, dried over sodium sulfate and evaporated to give a tan oil. Purification by flash chromatography 40% Ethyl acetate: Heptane yielded 4-[3-(Benzyloxycarbonylamino-methyl)-phenyl]-4-hydroxy-piperidine-1-carboxylic acid-tert-butyl ester (0.40 g). $^1$H NMR [(CDCl$_3$: δ 7.45–7.18 (m, 9H), 5.15 (s, 2H), 5.08 (br.s., 1H, NH), 4.40 (d, 2H), 4.15–3.93 (m, 2H), 3.35–3.15 (m, 2H), 2.08–1.90 (m, 2H), 1.75–1.62 (m, 2H), 1.50 (s, 9H).

C. 1-[4-(3-Aminomethyl-phenyl)-4-hydroxy-piperidin-1-yl]-1-(5-phenethyl-pyridin-3-yl) methanone-ditrifluoroacetate.

To a stirred solution of 4-[3-(Benzyloxycarbonylamino-methyl)-phenyl]-4-hydroxy-piperidine-1-carboxylic acid-tert-butyl ester (0.38 g, 0.86 mmol) and methylene chloride (15 mL) at 0° C. was added trifluoroacetic acid (5 mL). The reaction was allowed to warm to room temperature, stirred one hour and was evaporated to dryness to give [3-(4-(Hydroxy-piperidin-4-yl)-benzyl]-carbamic acid benzyl ester which was used directly in the next step.

To a stirred solution of 5-phenethyl-pyridin-3-carboxylic acid (0.027 g, 0.1 mmol) and DMF (10 mL) was added diisopropylethyl amine (0.014 g, 0.11 mmol) followed by TBTU (0.0353 g, 0.11 mmol). This stirred for five minutes before adding a solution of [3-(4-(Hydroxy-piperidin-4-yl)-benzyl]-carbamic acid benzyl ester (0.045 g, 0.1 mmol), DMF (2 mL) and Diisopropylethylamine (0.039 g, 0.3 mmol). The reaction stirred overnight at room temperature. The solvent was removed by evaporation and the remaining residue partitioned between ethylacetate (50 mL) and saturated sodium bicarbonate (10 mL). The organic phase was separated, washed again with saturated sodium bicarbonate (10 mL) and dried over magnesium sulfate. Evaporation followed by purification by flash chromatography (100% ethylacetate) gave (3-{4-Hydroxy-1-[-1-(5-phenethyl-pyridin-3-yl)-methanoyl]-piperidin-4-yl}-benzyl)-carbamic acid benzyl ester (0.030 g) as a clear oil. Hydrogenation with Methanol (10 mL), Acetic acid (1 mL) and a catalytic amount of 10% Palladium on Carbon overnight followed by filtration through celite gave the crude product which was purified by HPLC as in Example 38 to give the title compound as an amorphous solid (9.1 mg). $^1$H NMR [(CD$_3$)$_2$SO]: δ 8.58–8.42 (m, 2H), 8.15 (br.s., 3H, NH$_3^+$), 7.73 (s, 1H), 7.63–7.51 (m, 2H), 7.40 (t, 1H), 7.38–7.25 (m, 1H), 7.23–7.10 (m, 5H), 4.58–4.38 (m, 1H), 4.03 (q, 2H), 3.60–3.10 (m, 3H), 3.05–2.86 (m, 4H), 2.06–1.80 (m, 2H), 1.78–1.63 (m, 1H), 1.62–1.42 (m, 1H). MS(Ion spray): 416 (M$^+$+1).

EXAMPLE 74

1-[4-(3-Aminomethyl-phenyl)-piperidin-1-yl]-1-(1-methyl-1H-indol-3-yl)-methanone -trifluoroacetate.

By proceeding in a similar manner to the method described in EXAMPLE 38, but using 1-Methyl-1H-indole-3-carboxylic acid, there was prepared the title compound as an amorphous white solid. 1H NMR [CDCl$_3$]: δ8.63 (br.s., 3H, NH$_3^+$), 7.60 (d, 1H), 7.51 (s, 1H), 7.41–7.18 (m, 5H), 7.15–7.05 (m, 2H), 4.55–4.35 (m, 2H), 4.01 (br.s., 2H), 3.78 (s, 3H), 3.18–2.95 (m, 2H), 2.80–2.61 (m, 1H), 1.85–1.45 (m, 4H). MS(Ion spray): 348 (M$^+$+1).

EXAMPLE 75

1-(3-{1-[4-(3-Aminomethyl-phenyl)-piperidin-1-yl]-methanoyl}-indol-1-yl)-ethanone -trifluoroacetate.

By proceeding in a similar manner to the method described in EXAMPLE 38, but using 1-Acetyl-1H-indole-3-carboxylic acid, there was prepared the title compound as an amorphous white solid. 1H NMR [(CD$_3$)$_2$SO]: δ 8.39 (d, 1H), 8.21 (br.s., 3H, NH$_3^+$), 8.13 (s, 1H), 7.70 (d, 1H), 7.68–7.25 (m, 6H), 4.40 (br.s., 2H), 4.15–4.02 (m, 2H), 3.15–3.03 (m, 2H), 2.99–2.80 (m, 1H), 2.71 (s, 3H), 1.95–1.76 (m, 2H), 1.74–1.55 (m, 2H). MS(Ion spray): 376 (M$^+$+1).

EXAMPLE 76

1-[4-(3-Aminomethyl-phenyl)-piperidin-1-yl]-1-(5-methoxy-1-methyl-1H-indol-3-yl)-methanone-trifluoroacetate.

By proceeding in a similar manner to the method described in EXAMPLE 38, but using 5-Methoxy-1-methyl-1H-indole-3-carboxylic acid, prepared as in WO 9522524, there was prepared the title compound as an amorphous white solid.

$^1$H NMR [(CD$_3$)$_2$SO]: δ 8.13 (br.s., 3H, NH$_3^+$), 7.71 (s, 1H), 7.51–7.23 (m, 5H), 7.20 (s, 1H), 6.83 (dd, 1H), 4.53–4.40 (m, 2H), 4.13–3.95 (m, 2H), 3.80 (s, 3H), 3.76 (s, 3H), 3.18–3.01 (m, 2H), 2.95–2.75 (m, 1H), 1.95–1.76 (m, 2H), 1.75–1.52 (m, 2H). MS(Ion spray): 378 (M$^+$+1).

EXAMPLE 77

1-[4-(3-Aminomethyl-phenyl)-piperidin-1-yl]-1-[3-(2-trifluoromethyl-phenylethynyl) -phenyl]-methanone trifluoroacetate A. 4-{3-[N,N-bis-(tert-butoxycarbonyl)aminomethyl]-phenyl}-piperidine As an alternative route, a one-pot cross coupling process was applied to the preparation of the title compound. A solution of 3-[N,N-bis-(tert-butoxycarbonyl)aminomethyl]-bromobenzene (EXAMPLE 1A) (7.7 g, 20 mmol) in anhydrous DMF (60 ml) was treated with potassium acetate (5.9 g, 60 mmol), bis(pinacolato)diboron (5 g, 20 mmol), and [1,1'-bis-(diphenylphosphino)ferroceno]-dichloropalladium (II)-dichloromethane complex (0.49 g, 0.60 mmol). This mixture was stirred at 80° C. under an atmosphere of nitrogen for 4 hours, then benzyl 1,2,3,6-tetrahydro-4-(trifluoromethylsulphonyloxy)-pyridine-1-carboxylate (EXAMPLE 1B) (9.2 g, crude, <25 mmol) was added, followed by aq Na$_2$CO$_3$ (2M, 60 mL). The mixture was heated at 80° C. under an nitrogen for another 2 hours and then concentrated. The cross coupling product (2.2 g) was obtained after purification (as described in EXAMPLE 1B). Further reduction (as described in EXAMPLE 1B) yielded title compound.

B. 1-[4-(3-Aminomethyl-phenyl)-piperidin-1-yl]-1-[3-(2-trifluoromethyl-phenylethynyl) -phenyl]-methanone trifluoroacetate By proceeding in a similar manner to the coupling method described in EXAMPLE 5B, but using 2-iodobenzotrifluoride, and the deprotection method described in EXAMPLE 38, the title compound was prepared as an amorphous off-white solid. $^1$H NMR [CD$_3$OD]: δ 7.80–7.30 (m, 12H), 4.81 (br, 1H), 4.10 (s, 2H), 3.87 (br 1H), 3.30 (br, 1H), 2.97 (m, 21H), 2.05–1.60 (br, 4H). MS (Ion spray): 463 (M+1).

EXAMPLE 78
1-[4-(3-Aminomethyl-phenyl)-piperidin-1-yl]-1-[3-(2-methyl-phenylethynyl)-phenyl]-methanone trifluoroacetate By proceeding in a similar manner to the coupling method described in EXAMPLE 5b, but using 2-iodotoluene, and the deprotection method described in EXAMPLE 38, the title compound was prepared as an amorphous off-white solid. $^1$H NMR [CD$_3$OD]: δ 7.66–7.16 (m, 12H), 4.81 (br, 1H), 4.11 (s, 2H), 3.87 (br 1H), 3.30 (br, 1H), 2.97 (m, 2H), 2.51 (s, 3H), 2.05–1.60 (br, 4H). MS (Ion spray): 409 (M+1).

EXAMPLE 79
1-[4-(3-Aminomethyl-phenyl)-piperidin-1-yl]-1-[3-(4-chloro-phenylethynyl)-phenyl]-methanone trifluoroacetate By proceeding in a similar manner to the coupling method described in EXAMPLE 5b, but using 1-chloro-4-iodobenzene, and the deprotection method described in EXAMPLE 38, the title compound was prepared as an amorphous off-white solid. $^1$H NMR [CD$_3$OD]: δ 7.68–7.28 (m, 12H), 4.82 (br, 1H), 4.11 (s, 2H), 3.87 (br 1H), 3.30 (br, 1H), 2.97 (m, 2H), 2.05–1.60 (br, 4H). MS (Ion spray): 429 and 431 (M+1).

EXAMPLE 80
1-[4-(3-Aminomethyl-phenyl)-piperidin-1-yl]-1-[3-(2-chloro-phenylethynyl)-phenyl]-methanone trifluoroacetate By proceeding in a similar manner to the coupling method described in EXAMPLE 5b, but using 1-chloro-2-iodobenzene, and the deprotection method described in EXAMPLE 38, the title compound was prepared as an amorphous off-white solid. $^1$H NMR [CD$_3$OD]: δ 7.69–7.28 (m, 12H), 4.82 (br, 1H), 4.11 (s, 2H), 3.87 (br 1H), 3.30 (br, 1H), 2.97 (m, 2H), 2.05–1.60 (br, 4H). Ms (Ion spray): 429 and 431 (M+1).

EXAMPLE 81
1-[4-(3-Aminomethyl-phenyl)-piperidin-1-yl]-1-[3-(2-fluoro-phenylethynyl)-phenyl]-methanone trifluoroacetate By proceeding in a similar manner to the coupling method described in EXAMPLE 5b, but using 1-fluoro-2-iodobenzene, and the deprotection method described in EXAMPLE 38, the title compound was prepared as an amorphous off-white solid. $^1$H NMR [CD$_3$OD]: δ 7.69–7.16 (m, 12H), 4.80 (br, 1H), 4.10 (s, 2H), 3.84 (br, 1H), 3.30 (br, 1H), 2.96 (m, 2H), 2.05–1.60 (br, 4H). MS (Ion spray): 4.13 (M+1).

EXAMPLE 82
1-[4-(3-Aminomethyl-phenyl)-piperidin-1-yl]-1-[3-(3-fluoro-phenylethynyl)-phenyl]-methanone trifluoroacetate By proceeding in a similar manner to the coupling method described in EXAMPLE 5b, but using 1-fluoro-3-iodobenzene, and the deprotection method described in EXAMPLE 38, the title compound was prepared as an amorphous off-white solid. $^1$H NMR [CD$_3$OD]: δ 7.67–7.10 (m, 12H), 4.80 (br, 1H), 4.10 (s, 2H), 3.85 (br, 1H), 3.30 (br, 1H), 2.95 (m, 2H), 2.05–1.60 (br, 4H). MS (Ion spray): 413 (M+1).

EXAMPLE 83
1-[4-(3-Aminomethyl-phenyl)-piperidin-1-yl]-1-[3-(4-fluoro-phenylethynyl)-phenyl]-methanone trifluoroacetate By proceeding in a similar manner to the coupling method described in EXAMPLE 5b, but using 1-fluoro-4-iodobenzene, and the deprotection method described in EXAMPLE 38, the title compound was prepared as an amorphous off-white solid. $^1$H NMR [CD$_3$OD]: δ 7.64–7.10 (m, 12H), 4.80 (br, 1H), 4.10 (s, 2H), 3.85 (br, 1H), 3.30 (br, 1H), 2.97 (m, 2H), 2.05–1.60 (br, 4H). MS (Ion spray): 413 (M+1).

EXAMPLE 84
1-[4-(3-Aminomethyl-phenyl)-piperidin-1-yl]-1-{3-[2-(2-fluoro-phenyl)-ethyl]-phenyl}-methanone trifluoroacetate By proceeding in a similar manner to the reduction method described in EXAMPLE 9, and the deprotection method described in EXAMPLE 38, the title compound was prepared as an amorphous off-white solid. $^1$H NMR [CD$_3$OD]: δ 7.43–6.96 (m, 12H), 4.78 (br, 1H), 4.11 (s, 2H), 3.72 (br 1H), 3.18 (br, 1H), 3.02–2.86 (m, 6H), 2.05–1.50 (br, 4H). MS (Ion spray): 417 (M+1).

EXAMPLE 85
1-[4-(3-Aminomethyl-phenyl)-piperidin-1-yl]-1-{3-[2-(3-fluoro-phenyl)-ethyl]-phenyl}-methanone trifluoroacetate By proceeding in a similar manner to the reduction method described in EXAMPLE 9, and the deprotection method described in EXAMPLE 38, the title compound was prepared as an amorphous off-white solid. $^1$H NMR [CD$_3$OD]: δ 7.43–6.80 (m, 12H), 4.78 (br, 1H), 4.11 (s, 2H), 3.70 (br 1H), 3.18 (br, 1H), 3.02–2.85 (m, 6H), 2.05–1.50 (br, 4H). MS (Ion spray): 417 (M+1).

EXAMPLE 86
1-[4-(3-Aminomethyl-phenyl)-piperidin-1-yl]-1-{3-[2-(4-fluoro-phenyl)-ethyl]-phenyl}-methanone trifluoroacetate By proceeding in a similar manner to the reduction method described in EXAMPLE 9, and the deprotection method described in EXAMPLE 38, the title compound was prepared as an amorphous off-white solid. $^1$H NMR [CD$_3$OD]: δ 7.43–6.88 (m, 12H), 4.78 (br, 1H), 4.10 (s, 2H), 3.69 (br 1H), 3.18 (br, 1H), 3.00–2.85 (m, 6H), 2.05–1.50 (br, 4H). MS (Ion spray): 417 (M+1).

EXAMPLE 87
1-[4-(3-Aminomethyl-phenyl)-piperidin-1-yl]-1-{3-[2-(6-amino-pyridin-3-yl)ethynl]-phenyl}-methanone tri-trifluoroacetate By proceeding in a similar manner to the method described in EXAMPLE 38, but using (6-tert-butoxycarbonylamino-pyridin-3-yl)ethynyl-pyridine-3-carboxylic acid (prepared according to the method described in EXAMPLE 7), the title compound was prepared as an amorphous off-white solid. $^1$H NMR [CD$_3$OD]: δ 8.82 (s, 1H), 8,66 (s, 1H), 8.17 (s, 1H), 8.07 (s, 1H), 8.02 (d, 1H), 7.43–7.27 (m, 4H), 7.05 (d, 1H), 4.81 (br, 1H), 4.10 (s, 2H), 3.79 (br, 1H), 3.37 (br, 1H), 2.97 (m, 2H), 2.05–1.70 (br, 4H). MS (Ion spray): 412 (M+1).

EXAMPLE 88
1-[4-(3-Aminomethyl-phenyl)-piperidin-1-yl]-1-{3-[2-(6-amino-pyridin-3-yl)-ethyl]-phenyl}-methanone tri-trifluoroacetate By proceeding in a similar manner to the reduction method described in EXAMPLE 9, and the deprotection method described in EXAMPLE 38, the title compound was prepared as an amorphous off-white solid. $^1$H NMR

[CD$_3$OD]: δ 8.60 (m, 2H), 7.94 (s, 1H), 7.89 (d, 1H), 7.61 (s, 1H), 7.45–7.28 (m, 4H), 6.97 (d, 1H), 4.80 (br, 1H), 4.11 (s, 2H), 3.76 (br, 1H), 3.10–2.90 (m, 7H), 2.05–1.60 (br, 4H). MS (Ion spray): 416 (M+1).

EXAMPLE 89

1-[4-(3-Aminomethyl-phenyl)-piperidin-1-yl]-1-(6-chloro-thieno[3,2-b]thiophen-2-yl)-methanone trifluoroacetate By proceeding in a similar manner to the method described in EXAMPLE 38, but using 6-chloro-thieno[3,2-b]thiophene-2-carboxylic acid, the title compound was prepared as an amorphous off-white solid. $^1$H NMR [CD$_3$OD]: δ 7.60 (s, 1H), 7.47 (s, 1H), 7.33–7.18 (m, 4H), 4.50 (br, 2H), 3.98 (s, 2H), 3.12 (br, 2H), 2.86 (m, 1H), 1.85 (b, 2H), 1.67 (m, 2H). MS (Ion spray): 391 and 393 (M+1).

EXAMPLE 90

1-[4-(3-Aminomethyl-phenyl)-piperidin-1-yl]-1-(5-fluoro-thieno[3,2-b]thiophen-2-yl)-methanone trifluoroacetate By proceeding in a similar manner to the method described in EXAMPLE 38, but using 5-fluoro-thieno[3,2-b]thiophene-2-carboxylic acid, the title compound was prepared as an amorphous off-white solid. $^1$H NMR [CD$_3$OD]: δ 7.65 (s, 1H), 7.44–7.17 (m, 4H), 7.03 (s, 1H), 4.60 (br, 2H), 4.12 (s, 2H), 3.22 (br, 2H), 2.97 (m, H), 1.97 (b, 2H), 1.78 (m, 2H). MS (Ion spray): 375 (M+1).

EXAMPLE 91

1-[4-(3-Aminomethyl-phenyl)-piperidin-1-yl]-1-(5-methyl-thieno[3,2-b]thiophen-2-yl)-methanone trifluoroacetate By proceeding in a similar manner to the method described in EXAMPLE 38, but using 5-methyl-thieno[3,2-b]thiophene-2-carboxylic acid, the title compound was prepared as an amorphous off-white solid. $^1$H NMR [CD$_3$OD]: δ 7.60 (s, 1H), 7.42–7.30 (m, 4H), 7.07 (s, 1H), 4.63 (br, 2H), 4.11 (s, 2H), 3.21 (br, 2H), 2.97 (m, 1H), 2.60 (s, 3H), 1.96 (b, 2H), 1.78 (m, 2H). MS (Ion spray): 371 (M+1).

EXAMPLE 92

1-[4-(3-Aminomethyl-phenyl)-piperidin-1-yl]-1-(5-chloro-thieno[3,2-b]thiophen-2-yl)-methanone trifluoroacetate By proceeding in a similar manner to the method described in EXAMPLE 38, but using 5-chloro-thieno[3,2-b]thiophene-2-carboxylic acid, the title compound was prepared as an amorphous off-white solid. $^1$H NMR [CD$_3$OD]: δ 7.63 (s, 1H), 7.42–7.29 (m, 5H), 4.60 (br, 2H), 4.11 (s, 2H), 3.12 (br, 2H), 2.97 (m, 1H), 1.97 (b, 2H), 1.78 (m, 2H). MS (Ion spray): 391

In a similar manner to the methods described above, the following compounds are prepared:

EXAMPLE 93

1-{4-[3-(1-Aminoethyl)phenyl]-piperidin-1-yl}-1-(5-phenylethyl-pyridin-3-yl)-methanone di-hydrochloride A. [1-(3-Bromophenyl)ethyl]-carbamic acid tert-butyl ester 3-Bromoacetophenone oxime (23.4 mmol) was stirred in glacial acetic acid (150 mL) at room temperature under nitrogen, and zinc dust (94 mmol) added portionwise. The reaction mixture was stirred at room temperature for 24 hours, filtered off the solids and concentrated the filtrate to dryness. The residue was diluted with water, acidified to pH 5 with 1N HCl, and washed with ethyl acetate. The aqueous was basified with sodium hydrogen carbonate, extracted into ethyl acetate, dried over magnesium sulfate, and concentrated to dryness. The residue was dissolved in dimethylformamide (30 mL) and triethylamine (36.9 mmol) added. To this solution was added, dropwise, a solution of di-tert-butyldicarbonate (32.4 mmol) in DMF (10 mL). The reaction mixture was stirred at room temperature for 6 hours, and left standing for 24 hours before concentrating to dryness. The residue was partitioned between water and ethyl acetate, and the aqueous phase extracted with ethyl acetate. The combined organic phase was washed with brine, dried over magnesium sulfate, and concentrated to dryness. The residue was purified by column chromatography on silica gel with dichloromethane as eluent, to give [1-(3-bromophenyl)ethyl]-carbamic acid tert-butyl ester as a pale yellow oil which crystallized upon standing. MS(EI): 300 and 302 (M$^+$+H).

B. 1-{4-[3-(1-Aminoethyl)phenyl]-piperidin-1-yl}-1-(5-phenylethyl-pyridin-3-yl)-methanone di-hydrochloride By proceeding in a manner similar to the method described in EXAMPLE 17D, but using [1-(3-bromophenyl)ethyl]-carbamic acid tert-butyl ester in place of N-(tert-butoxycarbonyl)-3-bromo-4-fluorobenzylamine, there was prepared [1-(3-{1-[1-(3-phenethyl-phenyl)-methanoyl]-1,2,3,6-tetrahydro-pyridin-4-yl}-phenyl)-ethyl]-carbamic acid tert-butyl ester. This material was subjected to the same conditions as described in EXAMPLE 2A, but using [1-(3-{1-[1-(3-phenethyl-phenyl)-methanoyl]-1,2,3,6-tetrahydro-pyridin-4-yl}-phenyl)-ethyl]-carbamic acid tert-butyl ester in place of 5-phenylethynylpyridine-3-carboxylic acid. The crude product from this reaction was purified by column chromatography on silica gel, before being subjected to the same conditions as described in EXAMPLE 1D, but using [1-(3-{1-[1-(3-phenethylphenyl)-methanoyl]-piperidin-4-yl}phenyl)ethyl]carbamic acid tert-butyl ester in place of 3-[1-(5-phenylethynylpyridine-3-carbonyl)piperidin-4-yl] benzonitrile. 1-{4-[3-(1-Aminoethyl)phenyl]-piperidin-1-yl}-1(5-phenylethyl-pyridin-3-yl)-methanone di-hydrochloride was isolated as a pale yellow solid. MS(EI): 414 (M$^+$+H).

EXAMPLE 94

1-[4-(5-Aminomethyl-3-hydroxyphenyl)-piperidin-1-yl]-1-(5-phenylethyl-pyridin-3-yl)-methanone dihydrochloride A. 3-Bromo-N,N-(bis-tert-butoxycarbonyl)-5-(tert-butyldimethylsilyloxy)benzylamine (3-Bromo-5-methyl-phenoxy)-tert-butyldimethylsilane (3.32 mmol) [prepared according to the procedure of J. E. Baldwin et al, Tetrahedron, 1991, 47(29), 5603], N-bromosuccinimide (3.65 mmol), and benzoyl peroxide (0.332 mmol) were dissolved in dichloromethane (10 mL) and the reaction mixture irradiated for 4 hours. Diluted with dichloromethane and washed with water, dried over magnesium sulfate and concentrated to dryness. The crude material was purified by column chromatography on silica gel with 10% ethyl acetate/cyclohexane to give (3-bromo-5-bromomethyl-phenoxy)-tert-butyldimethylsilane as a colorless oil. This material was subjected to the conditions described in the first part of EXAMPLE 1A, but using (3-bromo-5-bromomethyl-phenoxy)-tert-butyldimethylsilane in place of 3-bromobenzylbromide, to give 3-bromo-N,N-(bis-tert-butoxycarbonyl)-5-(tert-butyldimethylsilyloxy)benzylamine as a colorless oil. MS (EI) 516 and 518 (M$^+$+H).

B. 1-(5-Phenylethynylpyridine-3-carbonyl)-4-(pinacolatoboronyl)-1,2,3,6-tetrahydropyridine By proceeding in a manner similar to the method described in EXAMPLE 17B, but using 5-phenylethynylpyridine-3-carboxylic acid in place of 5-phenethylpyridine-3-carboxylic acid, there was prepared 1-(5-phenylethynylpyridine-3-carbonyl)-4-(pinacolatoboronyl)-1,2,3,6-tetrahydropyridine as a pale yellow solid. MS (EI) 415 (M$^+$+H).

C. 1-{4-[3-(N,N-bis-tert-Butoxycarbonyl)aminomethyl-5-hydroxyphenyl]-3,6-dihydro-2H-pyridin -1-yl}-1-(5-phenylethynylpyridin-3-yl)methanone By proceeding in a manner similar to the method described in EXAMPLE 17D, but using 3-bromo-N,N-(bis-tert-butoxycarbonyl) -5-(tert-butyldimethylsilyloxy) benzylamine in place of N-(tert-butoxycarbonyl)-3-bromo-4-fluorobenzylamine and 1-(5-phenylethynylpyridine-3-carbonyl)-4-(pinacolatoboronyl)-1,2,3,6-tetrahydropyridine in place of 1-(5-phenylethylpyridine-3-carbonyl)-4-(pinacolatoboronyl)-1,2,3,6-tetrahydropyridine, there was prepared 1-{4-[3-(N,N-bis-tert-Butoxycarbonyl) aminomethyl-5-hydroxyphenyl]-3,6-dihydro-2H-pyridin-1-yl}-1-(5-phenylethynylpyridin-3-yl)methanone as a pale brown solid. MS (EI) 610 ($M^++H$). The tert-butyl-dimethylsilyl moiety had unexpectedly been removed during this procedure.

D. 1-[4-(5-Aminomethyl-3-hydroxyphenyl)-piperidin-1-yl]-1-(5-phenylethyl-pyridin-3-yl)-methanone di-hydrochloride By proceeding in a manner similar to the method described in EXAMPLE 2A, but using 1-{4-[3-(N,N-bis-tert -butoxycarbonyl)aminomethyl-5-hydroxyphenyl]-3,6-dihydro-2H-pyridin-1-yl}-1-(5-phenylethynylpyridin-3-yl) methanone in place of 5-phenylethynylpyridine-3-carboxylic acid, there was prepared 1-{4-[3-(N,N-bis-tert-butoxycarbonyl)aminomethyl-5-hydroxy-phenyl]piperidin-1-yl}-1-(5-phenethylpyridin-3-yl)methanone. The crude product from this reaction was purified by column chromatography on silica gel, before being subjected to the same conditions as described in EXAMPLE 1D, but using 1-{4-[3-(N,N-bis-tert-butoxycarbonyl)aminomethyl-5-hydroxy-phenyl]piperidin-1-yl}-1-(5-phenethylpyridin-3-yl) methanone in place of 3-[1-(5-phenylethynylpyridine-3-carbonyl)piperidin-4-yl]benzonitrile. 1-[4-(5-Aminomethyl-3-hydroxyphenyl)-piperidin-1-yl]-1-(5-phenylethyl-pyridin-3-yl)-methanone di-hydrochloride was isolated as a pale yellow solid. MS(EI): 416 ($M^++H$).

EXAMPLE 95

1-[4-(5-Aminomethyl-2-hydroxyphenyl)-piperidin-1-yl]-1-(5-phenylethyl-pyridin-3-yl)-methanone dihydrochloride A. 4-Benzyloxy-3-bromobenzyl carbamic acid tert-butyl ester 3-Bromo-4-flurobenzonitrile (3.00 g, 15 mmol), benzyl alcohol (1.71 ml, 16.5 mmol) and THF (40 ml) are combined and treated with 60% sodium hydride in oil (0.66 g, 16.5 mmol). The reaction mixture is heated to reflux under nitrogen for 3 hours. Aqueous workup and chromatographic purification (cyclohexane:dichloromethane, 3:1) yields 4-benzyloxy-3-bromobenzonitrile as a white solid (3.88 g, 13.5 mmol). A portion of this material (2.64 g, 9.16 mmol) in THF (25 ml) is treated with a 1 M solution of borane in THF (18.3 ml, 18.3 mmol). After the exotherm subsides the reaction is refluxed a couple of days under nitrogen. The excess borane is destroyed by the addition of methanol and 4-benzyloxy-3-bromobenzylamine is precipitated as the hydrochloride salt (1.58 g, 4.8 mmol). This material is suspended in dichloromethane (30 ml) and treated successively with triethyl amine (1.68 ml, 12.02 mmol) and di-tert-butyl dicarbonate (1.26 g, 5.77 mmol). The reaction mixture is stirred under nitrogen four hours; aqueous workup and chromatographic purification (ethyl acetate:cyclohexane, 3:7) yields the title compound as a white solid (1.69 g, 4.3 mmol). MS(EI): 394($M^+$).

B. 4-Benzyloxy-3-{1-[1-(5-phenylethylpyridin-3-yl) methanoyl]-1,2,3,6-tetrahydropyridin-4-yl}-benzyl carbamic acid tert-butyl ester 1-(5-Phenylethylpyridine-3-carbonyl)-4-(pinacolatoboronyl)-1,2,3,6-tetrahyropyridine (0.628 g, 1.5 mmol) as prepared in EXAMPLE 17B, 4-benzyloxy-3-bromobenzyl carbamic acid tert-butyl ester (0.62 g, 1.58 mmol), dichlorobis(triphenylphosphine)palladium (II) (0.074, 0.08 mmol), potassium carbonate (0.622 g, 4.5 mmol) and DMF (15 mL) are heated to 80° C. under nitrogen for 3 hours. The DMF is removed in vacuo, the residue is subjected to an aqueous workup and the organic residue is purified by chromatography to give a gray foam (0.45 g, 0.75 mmol).

C. 3-Hydroxy-2-{1-[1-(5-phenylethylpyridin-3-yl) methanoyl]-piperidin-4-yl}-benzyl carbamic acid tert-butyl ester 4-Benzyloxy-3-{1-[1-(5-phenylethylpyridin-3-yl) methanoyl]-1,2,3,6-tetrahydropyridin-4-yl}-benzyl carbamic acid tert-butyl ester (0.34 g, 0.56 mmol) is hydrogenolyzed with hydrogen gas and 10% P/C to give the title compound as a white foam (0.27 g, 0.52 mmol). MS(EI): 515($M^+$).

D. 1-[4-1-(5-Aminomethyl-2-hydroxyphenyl)-piperidin-1-yl]-1-(5-phenylethyl-pyridin-3-yl)-methanone dihydrochloride 3-Hydroxy-2-{1-[1-(5-phenylethylpyridin-3-yl) methanoyl]-piperidin-4-yl}-benzyl carbamic acid tert-butyl ester (0.09 g, 0.175 mmol) is converted to the title compound (0.053 g, 0.11 mmol) by the procedure described in EXAMPLE 5C. MS(EI): 416($M^++H$).

EXAMPLE 96

1-[4-(5-Aminomethyl-2-benzyloxyphenyl)-3,6-dihydro-2H-pyridin-1-yl]-1-(5-phenylethyl-pyridin-3-yl)-methanone dihydrochloride 4-Benzyloxy-3-{1-[1-(5-phenylethylpyridin-3-yl) methanoyl]-1,2,3,6-tetrahydropyridin-4-yl}-benzyl carbamic acid tert-butyl ester (0.11 g, 0.184 mmol) is converted to the title compound (0.080 g, 0.15 mmol) by the procedure described in EXAMPLE 5C. MS(EI): 504($M^++H$).

EXAMPLE 97

1-[4-(3-Aminomethylphenyl)-piperidin-1-yl]-1-(4-phenylethyl-phenyl)-methanone hydrochloride A. 4-Phenylethynylbenzoic acid 4-Phenylethynylbenzaldehyde (1.01 g, 4.85 mmol) is added to a suspension of silver oxide (0.56 g, 2.43 mmol) in water (15 ml) and sodium hydroxide (0.97 g, 24.3 mmol). The reaction mixture is heated to 90° C. for 1.5 hours cooled and acidified. The aqueous mixture is extracted with ethyl acetate and the organic layer is concentrated. The resultant solid is partitioned between ether and 0.1 M sodium hydroxide solution. The aqueous layer is acidified and the precipitated title compound (0.55 g, 2.5 mmol) is collected. M.P. 224–225° C.; MS(EI): 222($M^+$).

B. 1-[4-(3-Aminomethylphenyl)-piperidin-1-yl]-1-(4-phenylethyl-phenyl)-methanone hydrochloride By proceeding in similar manner to the method described in EXAMPLE 1C but using 4-phenylethynyl benzoic acid, N,N-bis-(tert-butoxycarbonyl)-3-[1-(4-phenylethynyl-benzoyl)-piperidin-4-yl]-benzylamine was prepared. The title compound is subsequently prepared by applying in sequence the methods described in EXAMPLE 9. MS(EI): 399($M^++H$).

EXAMPLE 98

1-[4-(3-Aminomethyl-phenyl)-piperidin-1-yl]-1-{3-[2-(2-hydroxy-phenyl)-ethyl]-phenyl}-methanone hydrochloride By proceeding in a similar manner to the method described in EXAMPLE 10 but using N,N-bis-(tert-butoxycarbonyl)-3-{1-[3-(2-hydroxyphenyl)ethynyl-benzoyl]-piperidin-4-yl}-benzylamine, which was prepared in a similar manner to the method described in EXAMPLE 6a but using 2-iodophenol, there was prepared the title compound as a white amorphous solid. MS(EI): 415 (M+H).

EXAMPLE 99
1-[4-(5-Aminomethyl-2-hydroxymethylphenyl)-3,6-dihydro-2H-pyridin-1-yl]-1-(5-phenylethyl-pyridin-3-yl)-methanone A. Acetic acid 4-(N,N-bis-tert-butoxycarbonyl) aminomethyl-2-bromobenzyl ester 2-Bromo-4-(bromomethyl)benzylbromide (2.91 mmol) [prepared according to the procedure of Bridger et al, J. Med. Chem. 1995, 38(2), 366] and di-tert-butyliminodicarboxylate (2.91 mmol) were dissolved in tetrahydrofuran (10 mL), and sodium hydride (60% in mineral oil, 2.91 mmol) added at room temperature under argon. The reaction mixture was stirred at room temperature for 4 days, quenched with saturated aqueous ammonium chloride, extracted into ethyl acetate, washed with brine, dried over magnesium sulfate, and concentrated to dryness. The crude residue was purified by column chromatography on silica gel with cyclohexane:ethyl acetate=9:1. 3-bromo-4-bromomethyl-(N,N-bis-tert-butoxycarbonyl)benzylamine was isolated as a white solid. A portion of 3-bromo-4-bromomethyl-(N,N-bis-tert-butoxycarbonyl)benzylamine (1.88 mmol) was dissolved in acetonitrile (5 mL), and to this was added potassium acetate (3.7 mmol) and 18-crown-6 (0.095 mmol). The reaction mixture was stirred at room temperature for 16 hours, concentrated to dryness, extracted into ethyl acetate, washed with brine, dried over magnesium sulfate, and concentrated to dryness. Purification was carried out by column chromatography on silica gel with diethyl ether: cyclohexane=1:1. Acetic acid 4-(N,N-bis-tert-butoxycarbonyl)aminomethyl-2-bromobenzyl ester was isolated as a colorless solid. MS (EI) 458 and 460 (M$^+$+H).

B. 1-{4-[5-(N,N-bis-tert-Butoxycarbonyl)aminomethyl-2-acetoxymethylphenyl]-3,6-dihydro-2H-pyridin-1-yl}-1-(5-phenethylpyridin-3-yl)methanone By proceeding in a manner similar to the method described in EXAMPLE 17D, but using acetic acid 4-(N,N-bis-tert-butoxycarbonyl)aminomethyl-2-bromobenzyl ester in place of N-(tert-butoxycarbonyl)-3-bromo-4-fluorobenzylamine, there was prepared 1-{4-[5-(N,N-bis-tert-butoxycarbonyl)aminomethyl-2-acetoxymethylphenyl]-3,6-dihydro-2H-pyridin-1-yl}-1-(5-phenethylpyridin-3-yl)methanone. MS (EI) 670 (M$^+$+H).

C. 1-[4-(5-Aminomethyl-2-hydroxymethylphenyl)-3,6-dihydro-2H-pyridin-1-yl]-1-(5-phenylethyl-pyridin-3-yl)-methanone 1-{4-[5-(N,N-bis-tert-Butoxycarbonyl)aminomethyl-2-acetoxymethylphenyl]-3,6-dihydro-2H-pyridin-1-yl}-1-(5-phenethylpyridin-3-yl)methanone (0.3 mmol) was dissolved in methanol (10 mL) and cooled at 0° C. whilst adding potassium carbonate (0.1 mmol). Left at room temperature for 16 hours, concentrated to dryness and used crude residue directly in the next step. By proceeding in a manner similar to the method described in EXAMPLE 1D, but using 1-{4-[5-(N,N-bis-tert-butoxycarbonyl)aminomethyl-2-hydroxymethylphenyl]-3,6-dihydro-2H-pyridin-1-yl}-1-(5-phenethylpyridin-3-yl)methanone in place of 3-[1-(5-phenylethylpyridin-3-carbonyl)piperidin-4-yl]benzonitrile, there was prepared 1-[4-(5-aminomethyl-2-hydroxymethylphenyl)-3,6-dihydro-2H-pyridin-1-yl]-1-(5-phenylethyl-pyridin-3-yl)-methanone as a pale yellow solid. MS(EI): 428 (M$^+$+H).

EXAMPLE 100
1-[4-(5-Aminomethyl-thiophen-2-yl)-piperidin-1-yl]-(5-phenylethyl-pyridin-3-yl)-methanone dihydrochloride A. 2-[N,N-Bis-(tert-butoxycarbonyl)aminomethyl]-4-bromo-thiophene By proceeding in a similar manner to the method described in EXAMPLE 1A but using 4-bromo-2-bromomethyl-thiophene, which was simply prepared from reduction of 4-bromo-thiophene-2-carbaldehyde and subsequent bromonation of the alcohol, there was prepared the title compound.

B. 1-[4-(5-Aminomethyl-thiophen-2-yl)-piperidin-1-yl]-(5-phenylethyl-pyridin-3-yl)-methanone dihydrochloride By proceeding in a similar manner to the method described in EXAMPLE 93 but using 2-[N,N-bis-(tert-butoxycarbonyl)aminomethyl]-4-bromo-thiophene, there was prepared the title compound as a white amorphous solid. MS(EI): 406(M+H).

EXAMPLE 101
[4-(5-Aminomethyl-pyridin-3-yl)-piperidin-1-yl]-1-(5-phenylethyl-pyridin-3-yl)-methanone trihydrochloride A. 3-Bromo-5-(N,N-bis-tert-butoxycarbonyl) aminomethylpyridine 3-Bromo-5-hydroxymethylpyridine (16.1 mmol) [prepared according to the procedure of Ashimori et al, Chem. Pharm. Bull. 1990, 38(9), 2446] and pyridine (32.3 mmol) were dissolved in acetonitrile (32 mL) and cooled to 0° C. Dibromotriphenylphosphorane (20.9 mmol) added, and left reaction mixture to warm to room temperature in stoppered flask for 4 hours. The crude reaction mixture was purified by column chromatography directly on silica gel with diethyl ether:cyclohexane=1:1. 3-Bromo-5-bromomethylpyridine was isolated as a pale brown solid. 3-Bromo-5-bromomethylpyridine (7.7 mmol) and di-tert-butyliminodicarboxylate (10 mmol) were dissolved in tetrahydrofaran (20 mL), and sodium hydride (60% in mineral oil, 10 mmol) added at room temperature under argon. The reaction mixture was stirred at room temperature for 16 hours, quenched with saturated aqueous ammonium chloride, extracted into ethyl acetate, washed with brine, dried over magnesium sulfate, and concentrated to dryness. The crude residue was purified by column chromatography on silica gel with cyclohexane:diethyl ether=2:1. 3-bromo-5-(N,N-bis-tert-butoxycarbonyl)aminomethylpyridine was isolated as a pale yellow solid. MS (EI) 387 and 389 (M$^+$+H).

B. [4-(5-Aminomethyl-pyridin-3-yl)-piperidin-1-yl]-1-(5-phenylethyl-pyridin-3-yl)-methanone trihydrochloride By proceeding in a manner similar to the method described in EXAMPLE 17D, but using 3-bromo-5-(N,N-bis-tert-butoxycarbonyl)aminomethylpyridine in place of N-(tert-butoxycarbonyl)-3-bromo-4-fluorobenzylamine and 1-(5-phenylethynylpyridine-3-carbonyl)-4-(pinacolatoboronyl)-1,2,3,6-tetrahydropyridine in place of 1-(5-phenylethylpyridine-3-carbonyl)-4-(pinacolatoboronyl)-1,2,3,6-tetrahydropyridine, there was prepared 1-[5-(N,N-bis-tert-butoxycarbonyl)aminomethyl-3',6'-dihydro-2'H-[3,4']bipyridinyl-1'-yl]-1-(5-phenylethynylpyridin-3-yl)methanone. This material was subjected to the same conditions as described in EXAMPLE 2A, but using 1-[5-(N,N-bis-tert-butoxycarbonyl) aminomethyl-3',6'-dihydro-2'H-[3,4']bipyridinyl-1'-yl]-1-(5-phenylethynylpyridin-3-yl)methanone in place of 5-phenylethynylpyridine-3-carboxylic acid. The crude product from this reaction was purified by column chromatography on silica gel, before being subjected to the same conditions as described in EXAMPLE 1D, but using {4-[5-

(N,N-bis-tert-butoxycarbonyl)aminomethylpyridin-3-yl]-piperidin-1-yl}-1-(5-phenylethyl-pyridin-3-yl)-methanone in place of 3-[1-(5-phenylethynylpyridine-3-carbonyl)piperidin-4-yl]benzonitrile. [4-(5-Aminomethyl-pyridin-3-yl)-piperidin-1-yl]-1-(5-phenylethyl-pyridin-3-yl)-methanone tri-hydrochloride was isolated as a pale yellow solid. MS(EI): 401 (M$^+$+H).

EXAMPLE 102

1-[4-(3-Aminomethyl-phenyl)-piperidin-1-yl]-1-(1-ethyl-1-indol-3-yl)-methanone-trifluoroaceatate.

A. 1-Ethyl-1H-indole-3-carboxylic acid methyl ester

A flask was charged with 1H-indole-3-carboxylic acid methyl ester (2 g, 11.41 mmol) and iodoethane (4.4 g, 28.5 mmol) in dry THF (25 mL). The mixture was stirred in a water bath and a 60% dispersion of sodium hydride (0.68 g, 17.12 mmol) in mineral oil was added in portions over 5 minutes. The reaction stirred for 48 hours and was quenched by careful addition of water. The mixture was extracted with dichloromethane (2×100 mL), dried over sodium sulfate and evaporated under reduced pressure. The crude product was purified by silica flash chromatography (10% ethyl acetate/heptane) to give 1-ethyl-1H-indole-3-carboxylic acid methyl ester (1.8 g). $^1$H NMR [CDCl$_3$]: δ 8.22–8.15 (m, 1H), 7.87 (s, 1H), 7.42–7.33 (m, 1H), 7.31–7.25 (m, 2H), 4.22 (q, 2H), 3.92 (s, 3H), 1.52 (t, 3H).

B. 1-Ethyl-1H-indole-3-carboxylic acid.

A solution of 1-ethyl-1H-indole-3-carboxylic acid methyl ester (1.8 g, 8.8 mmol) was stirred in a 1:1 mixture of THF:MeOH (40 mL), and to this was added 2N NaOH (20 mL). The reaction was heated at reflux for 4 hours. The reaction mixture was partially evaporated to remove the THF, MeOH and the remaining material diluted with water (20 mL) and acidified to pH=2 with 1N HCl. The mixture was extracted with dichloromethane (100 mL), dried over sodium sulfate and evaporated under reduced pressure to give the title compound as a white solid, which was used directly in the next step.

C. 1-[4-(3-Aminomethyl-phenyl)-piperidin-1-yl]-1-(1-ethyl-1H-indol-3-yl)-methanone-trifluoroacetate.

By proceeding in a similar manner to the method described in EXAMPLE 38, but using 1-ethyl-1H-indole-3-carboxylic acid, there was prepared the title compound as an amorphous white solid. $^1$H NMR [CD$_3$OD]: δ 7.75–7.63 (m, 2H), 7.52 (d, 1H), 7.43–7.36 (m, 3H), 7.35–7.15 (m, 3H), 4.63–4.51 (m, 2H), 4.30 (q, 2H), 4.11 (s, 2H), 3.30–3.13 (m, 2H), 3.03–2.85 (m, 1H), (m, 1H), 2.00–1.86 (m, 2H), 1.85–1.68 (m, 2H), 1.49 (t, 3H). MS (ion spray): 362 (M$^+$+1).

A. 4-Hydroxy-5,6-dihydro-2H-pyridine-1,3-dicarboxylic acid 1-benzyl ester 3-ethyl ester To a solution of ethyl 4-piperidone-3-carboxylate hydrochloride (5 g, 24.05 mmol) in THF (70 mL) and water (35 mL) at 0° C., was added triethylamine (8.7 mL, 62.5 mmol), followed by N-(benzyloxycarbonyloxy)succinimide (7.79 g, 31.27 mmol). The reaction mixture was stirred and allowed to warm to room temperature. After 3 hours the reaction mixture was diluted with water (50 mL) and ethyl acetate (100 mL) added. The aqueous phase was extracted into ethyl acetate (2×100 mL). The organic phases were combined, washed with brine (50 mL), dried (MgSO$_4$), and the solvent removed in vacuo. The crude product was purified by column chromatography on silica gel (eluent, ethyl acetate:pentane=1:5) to give 4-hydroxy-5,6-dihydro-2H-pyridine-1,3-dicarboxylic acid 1-benzyl ester 3-ethyl ester as a colorless oil (7.26 g, 94%). MS (EI) 305 (M$^+$).

B. 4-Trifluoromethanesulfonyloxy-5,6-dihydro-2H-pyridine-1,3-dicarboxylic acid 1-benzyl ester 3-ethyl ester 4-Hydroxy-5,6-dihydro-2H-pyridine-1,3-dicarboxylic acid 1-benzyl ester 3-ethyl ester (15.94 g, 52.5 mmol) was dissolved in anhydrous THF (150 mL) under nitrogen and cooled at −78° C. during the addition of sodium bis(trimethylsilyl)amide (1M in THF; 68 mL, 68 mmol) via cannula. After stirring for 30 minutes at this temperature a solution of N-phenyltrifluoromethanesulfonimide (22.42 g, 62.8 mmol) in THF (230 mL) was added dropwise via cannula. The reaction mixture was stirred at this temperature for 10 minutes before warming to 0° C. and stirring for 2 hours. After 48 h the reaction mixture was quenched with water, extracted into DCM, dried (MgSO$_4$) and concentrated in vacuo. The crude product was purified by flash column chromatography on silica gel (eluent; ethyl acetate:pentane=4:1) to give 4-trifluoromethanesulfonyloxy-5,6-dihydro-2H-pyridine-1,3-dicarboxylic acid 1-benzyl ester 3-ethyl ester as colorless oil (18.59 g, 81%). This material decomposed to a deep red material upon standing so was stored under nitrogen at 0° C. in the dark. MS (EI) 437 (M$^+$).

C. 4-(4,4,5,5-Tetramethyl-1,3,2-dioxaborolan-2-yl)-5,6-dihydro-2H-pyridine-1,3-dicarboxylic acid 1-benzyl ester 3-ethyl ester 4-Trifluoromethanesulfonyloxy-5,6-dihydro-2H-pyridine-1,3-dicarboxylic acid 1-benzyl ester 3-ethyl ester (200 mg, 0.458 mmol) was dissolved in anhydrous dioxane (6 mL), and added dropwise, via cannula, to a mixture of potassium acetate (135 mg, 1.374 mmol), 1,1′-bis(diphenylphosphino)ferrocene (8 mg, 0.014 mmol), [1,1′-bis(diphenylphosphino)ferroceno]dichloropalladium-dichloromethane complex (10 mg, 0.014 mmol), and bis-pinnacolato diborane (116 mg, 0.458 mmol), under nitrogen. The mixture was heated at 80° C. overnight, cooled to room temperature and partitioned between DCM and water. The aqueous phase was extracted with DCM, and the organic phases combined and dried (MgSO$_4$). The crude product was purified by flash column chromatography on silica gel (eluent; pentane:ethyl acetate=5:1) to afford 4-(4,4,5,5-tetramethyl-1,3,2-dioxaborolan-2-yl)-5,6-dihydro-2H-pyridine-1,3-dicarboxylic acid 1-benzyl ester 3-ethyl ester as a colorless oil (94 mg, 50%). MS (EI) 415 (M$^+$).

D. 4-{3-[(N,N-Bis-tert-butoxycarbonyl)aminomethyl]phenyl}-5,6-dihydro-2H-pyridine-1,3-dicarboxylic acid 1-benzyl ester 3-ethyl ester A solution of 3-[N,N-bis-(tert-butoxycarbonyl)aminomethyl]bromobenzene (3.51 g, 9.1 mmol) [prepared by the method in Example 1A] and 4-(4,4,5,5-tetramethyl-1,3,2-dioxaborolan-2-yl)-5,6-dihydro-2H-pyridine-1,3-dicarboxylic acid 1-benzyl ester 3-ethyl ester (3.6 g, 8.67 mmol) in DMF (120 mL) were added, via cannula, to a mixture of [1,1′-bis(diphenylphosphino)ferroceno]dichloropalladium-dichloromethane complex (425 mg, 0.52 mmol) and potassium carbonate (3.59 g, 26 mmol) under nitrogen. The reaction mixture was heated at 80° C. overnight, concentrated to dryness in vacuo, and the residue partitioned between DCM and water. The aqueous phase was extracted with DCM, the organic phases combined, washed with brine, and dried (MgSO$_4$). The crude material was purified by column chromatography on silica gel (eluent; pentane:ethyl acetate=6:1) to give 4-{3-[(N,N-bis-tert-butoxycarbonyl)aminomethyl]phenyl}-5,6-dihydro-2H-pyridine-1,3-dicarboxylic acid 1-benzyl ester 3-ethyl ester as a colorless oil (2.27 g, 44%). MS (EI) 594 (M$^+$).

E. (3S,4S) and (3R,4R) 4-{3-[(N,N-Bis-tert-butoxycarbonyl)aminomethyl]phenyl}-piperidine-3-carboxylic acid ethyl ester Solid carbon dioxide (1 g) was added to a solution of 4-{3-[(N,N-bis-tert-butoxycarbonyl)aminomethyl]phenyl}-5,6-dihydro-2H-pyridine-1,3-dicarboxylic acid 1-benzyl ester 3-ethyl ester (2.07 g, 3.48 mmol) in IMS (20 mL). 10% palladium on carbon (200 mg) was added and the reaction mixture stirred at room temperature, under an atmosphere of hydrogen, for 4 hours. The palladium on carbon was filtered off through celite to give a 1:1 mixture of (3S,4S) and (3R,4R) 4-{3-[(N,N-Bis-tert-butoxycarbonyl)aminomethyl]phenyl}-piperidine-3-carboxylic acid ethyl ester as a pale grey/brown oil (1.35 g, 84%), which was pure enough for use in the subsequent reaction. MS (EI) 462 ($M^+$).

F. (3S,4S) and (3R,4R)-4-{3-[(Bis-tert-butoxycarbonyl)aminomethyl]phenyl}-1-(5-phenethylpyridine-3-carbonyl)piperidine-3-carboxylic acid ethyl ester By proceeding in a similar manner to the method described in EXAMPLE 2B, but using a 1:1 mixture of (3S,4S) and (3R,4R) 4-{3-[(N,N-Bis-tert-butoxycarbonyl)aminomethyl]phenyl}-piperidine-3-carboxylic acid ethyl ester instead of 4-{3-[N,N-bis(tert-butoxycarbonyl)aminomethyl]phenyl}piperidine, there was prepared a 1:1 mixture of (3S,4S) and (3R,4R)-4-{3-[(Bis-tert-butoxycarbonyl)aminomethyl]phenyl}-1-(5-phenethylpyridine-3-carbonyl)piperidine-3-carboxylic acid ethyl ester as a colorless glassy solid (414 mg, 0.62 mmol). MS (EI) 671 ($M^+$).

G. (3S,4S) and (3R, 4R)-4-(3-Aminomethyl-phenyl)-1-(5-phenethyl-pyridine-3-carbonyl)-piperidine-3-carboxylic acid ethyl ester dihydrochloride By proceeding in a similar manner to the method described in EXAMPLE 1D, but using a 1:1 mixture of (3S,4S) and (3R,4R)-4-{3-[(Bis-tert-butoxycarbonyl)aminomethyl]phenyl}-1-(5-phenethylpyridine-3-carbonyl)piperidine-3-carboxylic acid ethyl ester instead of N,N-bis-(tert-butoxycarbonyl)-3-[1-(5-phenylethynylpyridine-3-carbonyl)piperidin-4-yl]benzylamine, there was prepared a 1:1 mixture of (3S,4S) and (3R, 4R)-4-(3-Aminomethyl-phenyl)-1-(5-phenethyl-pyridine-3-carbonyl)-piperidine-3-carboxylic acid ethyl ester dihydrochloride as a white solid. MS (EI) 471 ($M^+$).

EXAMPLE 104

(3R,4S) and (3S,4R)-4-(3-Aminomethyl-phenyl)-1-(5-phenethyl-pyridine-3-carbonyl)-piperidine-3-carboxylic acid ethyl ester dihydrochloride A. (3R,4S) and (3S,4R)-4-{3-[(tert-Butoxycarbonyl)aminomethyl]phenyl}-1-(5-phenethylpyridine-3-carbonyl)-piperidine-3-carboxylic acid ethyl ester Sodium hydride (10 mg, 60% in mineral oil, 0.25 mmol) was added to ethanol (10 mL), and after the effervescence had subsided a 1:1 mixture of (3S,4S) and (3R,4R)-4-{3-[(bis-tert-butoxycarbonyl)aminomethyl]phenyl}-1-(5-phenethylpyridine-3-carbonyl)piperidine-3-carboxylic acid ethyl ester (100 mg) was added at room temperature. After 1 hour the solvent was removed in vacuo, and the residue partitioned between DCM and water. The aqueous phase was extracted with DCM, the combined organic phase washed with brine and dried ($MgSO_4$). The crude material was purified by column chromatography on silica gel (eluent; DCM:MeOH=10:1) to give a 1:1 mixture of (3R,4S) and (3S,4R)-4-{3-[(tert-butoxycarbonyl)aminomethyl]phenyl}-1-(5-phenethylpyridine-3-carbonyl)-piperidine-3-carboxylic acid ethyl ester as a pale yellow glassy solid (43 mg, 51%). MS (EI) 571 ($M^+$).

B. (3R,4S) and (3S,4R)-4-(3-Aminomethyl-phenyl)-1-(5-phenethyl-pyridine-3-carbonyl)-piperidine-3-carboxylic acid ethyl ester dihydrochloride By proceeding in a similar manner to the method described in EXAMPLE 1D, but using a 1:1 mixture of (3R,4S) and (3S,4R)-4-{3-[(tert-butoxycarbonyl)aminomethyl]phenyl}-1-(5-phenethylpyridine-3-carbonyl)-piperidine-3-carboxylic acid ethyl ester instead of N,N-bis-(tert-butoxycarbonyl)-3-[1-(5-phenylethynylpyridine-3-carbonyl)piperidin-4-yl]benzylamine, there was prepared a 1:1 mixture of (3R,4S) and (3S,4R)-4-(3-aminomethyl-phenyl)-1-(5-phenethyl-pyridine-3-carbonyl)-piperidine-3-carboxylic acid ethyl ester dihydrochloride as a white solid. MS (EI) 471 ($M^+$).

EXAMPLE 105

1-[4-(3-Aminomethyl-phenyl)-piperidin-1-yl]-1-[5-(4-bromo-2-fluoro-benzylamino)-pyridin-3-yl]-methanone trihydrochloride A. 5-tert-Butoxycarbonylamino-nicotinic acid To a solution of diethyl 3,5-pyridinedicarboxylate [prepared according to the procedure of J. C. Speelman and R. M. Kellogg, J. Org. Chem., 1990, 55 (2), pages 647–653; 64.19 g, 0.248 mol] in ethanol (650 mL) were added KOH pellets (14.56 g, 0.260 mol). The reaction mixture was stirred overnight at ambient temperature. Evaporation of solvent afforded a white solid that was rinsed with dichloromethane, and then dissolved in water. The aqueous solution was extracted with ether, and then acidified to pH 3. The resultant white precipitate was collected by filtration and dried to afford pyridine-3,5-dicarboxylic acid monomethyl ester (33.70 g). A portion of this material (10.00 g, 51.3 mmol) was dissolved in dry tert-butanol (300 mL) and treated sequentially with triethylamine (7.85 mL, 56.4 mmol) and diphenyl phosphoryl azide (11.5 mL, 53.4 mmol). The mixture was refluxed for 90 minutes, and then stirred at ambient temperature overnight. Solvent was removed under reduced pressure and the residue was partitioned between water and dichloromethane. The layers were separated and the aqueous phase was extracted twice with dichloromethane. The combined organic phases were dried and concentrated. Chromatography on silica gel eluting with a mixture of pentane and ethyl acetate (3:1, v/v) gave 5-tert-butoxycarbonylamino-nicotinic acid ethyl ester (4.79 g). This ester was dissolved in methanol (45 mL) and treated with 1 N NaOH (54 mL, 54 mmol). After stirring 2 hours, volatiles were evaporated under reduced pressure and the residue was treated with 1 N HCl until the resultant slurry reached pH 3. The precipitate was collected by filtration, washed with water, and dried to afford 5-tert-butoxycarbonylamino-nicotinic acid (4.21 g): $^1$H NMR (300 MHz, DMSO-$d_6$) δ 13.39 (br, s, 1H), 9.82 (s, 1H), 8.78 (d, J=2.5 Hz, 1H), 8.69 (d, J=1.9 Hz, 1H), 8.45–8.50 (m, 1H), 1.50 (s, 9H); $^{13}$C NMR (75 MHz, DMSO-$d_6$) δ 166.2, 152.7, 143.4, 143.2, 136.2, 126.3, 124.9, 80.0, 27.9; MS (ESI) m/z 239 (M+H).

B. {5-[1-(4-{3-[N,N-Bis-(tert-butoxycarbonyl)aminomethyl]-phenyl}-piperidin-1-yl)methanoyl]-pyridin-3-yl}carbamic acid tert-butyl ester To a 0° C. solution of 4-{3-[N,N-bis-(tert-butoxycarbonyl)aminomethyl]-phenyl}-piperidine (0.1545 g, 0.3956 mmol, EXAMPLE 1B), 5-tert-butoxycarbonylamino-nicotinic acid (0.0966 g, 0.4055 mmol), 1-hydroxy-7-azabenzotriazole (0.0290 g, 0.2131 mmol), and 1-(3-dimethylaminopropyl)-3-ethylcarbodiimide hydrochloride (0.1500 g, 0.7824 mmol) in dimethylformamide (5.0 mL) was added pyridine (0.065 mL, 0.8037 mmol). The reaction mixture was stirred 30 minutes at 0° C., then allowed to warm to room temperature under inert atmosphere. After 16 hours at ambient temperature the reaction solution was diluted with ethyl acetate (30 mL), washed with saturated ammonium chloride (2×15 mL), saturated sodium bicarbonate (15 mL), and brine (15 mL). The organic phase was dried over magnesium sulfate, filtered, and evaporated to dryness. The residue was purified by silica gel chromatography eluting with a mixture of ethyl acetate and methylene chloride (1:1, v/v) to give {5-[1-(4-{3-[N,N-bis-(tert-butoxycarbonyl)aminomethyl]-phenyl}-piperidin-1-yl)methanoyl]-pyridin-3-yl}carbamic acid tert-butyl ester as a colorless oil (0.1812 g): TLC, 50:50-methylene chloride:ethyl acetate, $R_f$=0.20. $^1$H NMR (300 MHz, CDCl$_3$) δ 8.67 (d, J=2.6 Hz, 1H), 8.34 (d, J=1.4 Hz, 1H), 8.09 (s, 1H), 7.93 (s, 1H), 7.21–7.35 (m, 1H), 7.08–7.18 (m, 3H), 4.81–4.93 (m, 1H), 4.78 (s, 2H), 3.81–3.93 (br m, 1H), 3.11–3.28 (br m, 1H), 2.70–2.96 (m, 2H), 1.51 (s, 9H), 1.45 (s, 18H), 1.40–2.02 (m partially obscured, 4H); $^{13}$C NMR (75 MHz, CDCl$_3$) δ 167.5, 152.6, 152.5, 144.8, 141.3, 141.0, 138.9, 135.7, 131.8, 128.5, 125.6, 125.3, 125.2, 124.1, 82.4, 81.0, 77.2, 49.3, 42.5, 28.1, 27.8; MS (CI) m/z 611 (M+H).

C. (4-Bromo-2-fluoro-benzyl)-{5-[1-(4-{3-[N,N-bis-(tert-butoxycarbonyl)aminomethyl]phenyl}-piperidin-1-yl)-methanoyl]-pyridin-3-yl}-carbamic acid dimethyl-ethyl ester To a solution of {5-[1-(4-{3-[N,N-bis-(tert-butoxycarbonyl)aminomethyl]-phenyl}-piperidin-1-yl)methanoyl]-pyridin-3-yl}carbamic acid tert-butyl ester (0.0745 g, 0.1220 mmol) in dimethylformamide (2.0 mL) was added sodium hydride (61% suspension in mineral oil, 0.0216 g, 0.5499 mmol). Deprotonation was allowed to occur over 3 minutes while stirring under inert atmosphere. 4-Bromo-2-fluorobenzyl bromide (0.1559 g, 0.5819 mmol) was added to the anion solution. The mixture was stirred an additional 10 minutes, then quenched with water (5.0 mL). The reaction solution was extracted with ethyl acetate (15 mL), and the organic phase was washed with brine (2×10 mL), dried over magnesium sulfate, filtered, and evaporated to dryness. Purification of the residue on silica gel eluting first with ethyl acetate/methylene chloride/hexane (1:1:2, v/v/v) and then with ethyl acetate and methylene chloride (1:1, v/v) afforded (4-bromo-2-fluoro-benzyl)-{5-[1-(4-{3-[N,N-bis-(tert-butoxycarbonyl)aminomethyl]-phenyl}-piperidin-1-yl)-methanoyl]-pyridin-3-yl}-carbamic acid dimethyl-ethyl ester as a colorless oil (0.0917 g): TLC, 50:50-methylene chloride:ethyl acetate, $R_f$=0.59. $^1$H NMR (300 MHz, CDCl$_3$) δ 8.47–8.51 (m, 2H), 7.61 (br s, 1H), 7.07–7.32 (m, 7H), 4.89 (s, 2H), 4.78 (s, 2H), 4.77–4.92 (m partially obscured, 1H), 3.68–3.83 (br m, 1H), 3.09–3.24 (br, m, 1H), 2.70–2.97 (m, 2H), 1.45 (s, 18H), 1.44 (s, 9H), 1.30–2.04 (m partially obscured, 4H); $^{13}$C NMR (75 MHz, CDCl$_3$) δ 167.0, 160.4 (d, 250.8), 154.0, 152.7, 148.5, 144.9, 139.0, 138.7, 132.2, 131.9, 130.7, 129.7, 127.9 (d, 3.4), 125.8, 125.7, 125.3, 123.8 (d, 14.5), 121.8 (d, 9.7), 119.3 (d, 24.8), 82.5, 82.2, 49.5, 46.9, 42.6, 32.8 (br), 28.4, 28.2, 28.0; $^{19}$F NMR (282 MHz, CDCl$_3$) δ-114.9; MS (CI) m/z 797 (M+H).

D. 1-[4-(3-Aminomethyl-phenyl)-piperidin-1-yl]-1-[5-(4-bromo-2-fluoro-benzylamino)-pyridin-3-yl]-methanone trihydrochloride (4-Bromo-2-fluoro-benzyl)-{5-[1-(4-{3-[N,N-bis-(tert-butoxycarbonyl)aminomethyl]-phenyl}-piperidin-1-yl)-methanoyl]-pyridin-3-yl}-carbamic acid dimethyl-ethyl ester (0.0806 g, 0.1010 mmol) was treated with 4 M HCl in 1,4-dioxane (2.0 mL, 8.0 mmol) and stirred at ambient temperature. After 25 minutes the reaction mixture was diluted with isopropyl alcohol (0.5 mL) and stirring was continued for an additional 2.5 hours. Dripping the reaction solution into ether (40 mL) with vigorous stirring afforded a white precipitate which was collected by filtration, washed with fresh ether (3.0 mL), and dried to afford 1-[4-(3-aminomethyl-phenyl)-piperidin-1-yl]-1-[5-(4-bromo-2-fluoro-benzylamino)-pyridin-3-yl]-methanone trihydrochloride (0.0563 g): $^1$H NMR (300 MHz, DMSO-d$_6$) δ 8.39 (br s, 2H), 8.16 (d, J=2.7 Hz, 1H), 8.08 (s, 1H), 7.16–7.70 (m, 8H), 4.49–4.64 (br m, 1H), 4.46 (s, 2H), 4.05–4.30 (m, 1H), 4.00 (AB q, J=5.7 Hz, 2H), 3.01–3.25 (m, 1H), 2.77–2.95 (m, 2H), 1.75–1.92 (m, 1H), 1.45–1.75 (br m, 3H); $^{19}$F NMR (282 MHz, DMSO-d$_6$) δ-114.1; MS (ESI) m/z 497 (M+H).

EXAMPLE 106

1-[4-(3-Aminomethyl-phenyl)-piperidin-1-yl]-1-(5-benzylamino-pyridin-3-yl)-methanone trihydrochloride A. Benzyl-{5-[1-(4-{3-[N,N-bis-(tert-butoxycarbonyl)aminomethyl]-phenyl}-piperidin-1-yl)-methanoyl]-pyridin-3-yl}-carbamic acid dimethyl-ethyl ester By proceeding in a similar manner to the method described in EXAMPLE 105C, but using benzyl bromide in place of 4-bromo-2-fluorobenzyl bromide, there was prepared benzyl-{5-[1-(4-{3-[N,N-bis-(tert-butoxycarbonyl)aminomethyl]-phenyl}-piperidin-1-yl)-methanoyl]-pyridin-3-yl}-carbamic acid dimethyl-ethyl ester as a yellow oil. TLC, 50:50-methylene chloride:ethyl acetate, $R_f$=0.48. $^1$H NMR (300 MHz, CDCl$_3$) δ 8.52 (d, J=2.2 Hz, 1H), 8.46 (d, J=1.2 Hz, 1H), 7.56 (s, 1H), 7.04–7.38 (m, 9H), 4.89 (s, 2H), 4.78 (s, 2H), 4.75–4.90 (m partially obscured, 1H), 3.63–3.88 (br m, 1H), 3.00–3.19 (br m, 1H), 2.68–2.90 (m, 2H), 1.45 (s, 18H), 1.44 (s, 9H), 1.37–2.04 (m, 4H); $^{13}$C NMR (75 MHz, CDCl$_3$) δ 167.0, 154.1, 152.6, 148.4, 144.8, 144.5, 138.9, 137.5, 132.0, 131.5, 128.6, 128.5, 127.5, 127.2, 125.7, 125.5, 125.2, 82.4, 81.6, 53.4, 49.4, 42.5, 33.8, 28.3, 28.1, 27.9; MS (CI) m/z 701 (M+H).

B. 1-[4-(3-Aminomethyl-phenyl)-piperidin-1-yl]-1-(5-benzylamino-pyridin-3-yl)-methanone trihydrochloride By proceeding in a similar manner to the method described in EXAMPLE 105D, but using benzyl-{5-[1-(4-{3-[N,N-bis-(tert-butoxycarbonyl)aminomethyl]-phenyl}-piperidin-1-yl)-methanoyl]-pyridin-3-yl}-carbamic acid dimethyl-ethyl ester, there was prepared 1-[4-(3-aminomethyl-phenyl)-piperidin-1-yl]-1-(5-benzylamino-pyridin-3-yl)-methanone trihydrochloride as a white solid. $^1$H NMR (300 MHz, DMSO-d$_6$) δ 8.45 (br s, 2H), 8.13 (d, J=2.5 Hz, 1H), 8.08 (d, J=1.0 Hz, 1H), 7.54 (s, 1H), 7.47 (s, 1H), 7.18–7.45 (m, 8H), 4.50–4.63 (br m, 1H), 4.45 (s, 2H), 4.02–4.12 (m, 1H), 3.99 (AB q, J=5.5 Hz, 2H), 3.05–3.25 (m, 1H), 2.70–2.95 (m, 2H), 1.75–1.90 (br m, 1H), 1.50–1.70 (br m, 3H); MS (ESI) m/z 401 (M+H).

EXAMPLE 107

1-[4-(3-Aminomethyl-phenyl)-piperidin-1-yl]-1-{5-[(naphthalen-2-ylmethyl)-amino]-pyridin-3-yl}-methanone trihydrochloride A. {5-[1-(4-{3-[N,N-Bis-(tert-butoxycarbonyl)aminomethyl]-phenyl}-piperidin-1-yl)-methanoyl]-pyridin-3-yl}-naphthalen-2-ylmethyl-carbamic acid dimethyl-ethyl ester By proceeding in a similar manner to the method described in EXAMPLE 105C, but using 2-(bromomethyl)naphthalene in place of 4-bromo-2-fluorobenzyl bromide, there was prepared {5-[1-(4-{3-[N,N-bis-(tert-butoxycarbonyl)aminomethyl]-phenyl}-piperidin-1-yl)-methanoyl]-pyridin-3-yl}-naphthalen-2-ylmethyl-carbamic acid dimethyl-ethyl ester as a colorless oil. TLC, 50:50-methylene chloride:ethyl acetate, $R_f$=0.42. $^1$H NMR (300

MHz, CDCl$_3$) δ 8.55 (d, J=1.8 Hz, 1H), 8.13 (d, J=187.5 Hz, 1H), 7.68–7.83 (m, 3H), 7.60 (s, 1H), 7.54 (br s, 1H), 7.35–7.49 (m, 3H)7.21–7.29 (m, partially obscured, 1H), 7.16 (d, J=7.7 Hz, 1H), 7.08 (s, 1H), 7.01 (d, J=7.7 Hz, 1H), 5.00–5.08 (m, 2H), 4.77 (s, 2H), 3.48–3.62 (br m, 1H), 2.59–3.03 (m, 3H), 1.45 (s, 27H), 1.27–1.95 (m, 4H); $^{13}$C NMR (75 MHz, CDCl$_3$) δ 166.9, 154.3, 152.6, 148.6, 144.8, 144.7, 138.9, 138.8, 134.9, 133.3, 132.8, 132.2, 131.6, 128.6, 127.7, 126.3, 126.2, 126.0, 125.8, 125.5, 125.3, 125.2, 82.4, 81.8, 53.6, 49.4, 42.5, 33.2, 28.4, 28.2, 28.0; MS (CI) m/z 752 (M+H).

B. 1-[4-(3-Aminomethyl-phenyl)-piperidin-1-yl]-1-{5-[(naphthalen-2-ylmethyl)-amino]-pyridin-3-yl}-methanone trihydrochloride By proceeding in a similar manner to the method described in EXAMPLE 105D, but using {5-[1-(4-{3-[N,N-bis-(tert-butoxycarbonyl)aminomethyl]-phenyl}-piperidin-1-yl)-methanoyl]-pyridin-3-yl}-naphthalen-2-ylmethyl-carbamic acid dimethyl-ethyl ester, there was prepared 1-[4-(3-aminomethyl-phenyl)-piperidin-1-yl]-1-{5-[(naphthalen-2-ylmethyl)-amino]-pyridin-3-yl}-methanone trihydrochloride as a as a white solid. $^1$H NMR (300 MHz, DMSO-d$_6$) δ 8.34 (br s, 2H), 8.17 (s, 1H), 8.03 (s, 1H), 7.75–7.97 (m, 4H), 5.58–7.77 (m, 1H), 7.25–7.57 (m, 6H), 7.22 (d, J=7.2 Hz, 1H), 4.61 (s, 2H), 4.50–4.68 (m partially obscured, 1H), 4.10–4.35 (m, 1H), 4.00 (AB q, J=5.7 Hz, 2H), 2.91–3.12 (m, 1H), 2.66–2.90 (m, 2H), 1.70–1.89 (m, 1H), 1.36–1.69 (m, 3H); MS (ESI) m/z 451 (M+H).

EXAMPLE 108

1-[4-(3-Aminomethyl-phenyl)-piperidin-1-yl]-1-[5-(4-bromo-benzylamino)-pyridin-3-yl]-methanone trihydrochloride A. (4-Bromobenzyl)-{5-[1-(4-{3-[N,N-bis-(tert-butoxycarbonyl)amino-methyl]-phenyl}-piperidin-1-yl)-methanoyl]-pyridin-3-yl}-carbamic acid dimethyl-ethyl ester By proceeding in a similar manner to the method described in EXAMPLE 105C, but using 4-bromobenzyl bromide in place of 4-bromo-2-fluorobenzyl bromide, there was prepared (4-bromobenzyl)-{5-[1-(4-{3-[N,N-bis-(tert-butoxycarbonyl)amino-methyl]-phenyl}-piperidin-1-yl)-methanoyl]-pyridin-3-yl}-carbamic acid dimethyl-ethyl ester as a colorless oil. TLC, 50:50-methylene chloride:ethyl acetate, R$_f$=0.41. $^1$H NMR (300 MHz, CDCl$_3$) δ 8.45–8.51 (m, 2H), 7.56 (br s, 1H), 7.43 (d, J=8.4 Hz, 2H), 7.24–7.30 (m partially obscured, 1H), 7.11 (d, J=8.4 Hz, 2H), 6.96–7.17 (m, partially obscured, 3H), 4.83 (s, 2H), 4.77 (s, 2H), 4.75–4.87 (m partially obscured, 1H), 3.65–3.80 (br m, 1H), 3.05–3.23 (br m, 1H), 2.69–2.91 (m, 2H), 1.45 (s, 18H), 1.43 (s, 9H), 1.30–2.00 (m, 4H); $^{13}$C NMR (75 MHz, CDCl$_3$) δ 166.8, 154.0, 152.5, 148.4, 144.7, 138.9, 138.7, 136.5, 132.1, 131.8, 131.7, 131.5, 129.0, 128.6, 125.7, 125.5, 125.2, 121.4, 82.4, 81.9, 52.8, 49.3, 42.5, 33.5, 28.3, 28.1, 27.9; MS (CI) m/z 781 (M+H).

B. 1-[4-(3-Aminomethyl-phenyl)-piperidin-1-yl]-1-[5-(4-bromo-benzylamino)-pyridin-3-yl]-methanone trihydrochloride By proceeding in a similar manner to the method described in EXAMPLE 105D, but using (4-bromobenzyl)-{5-[1-(4-{3-[N,N-bis-(tert-butoxycarbonyl)amino-methyl]-phenyl}-piperidin-1-yl)-methanoyl]-pyridin-3-yl}-carbamic acid dimethyl-ethyl ester, there was prepared 1-[4-(3-aminomethyl-phenyl)-piperidin-1-yl]-1-[5-(4-bromo-benzylamino)-pyridin-3-yl]-methanone trihydrochloride as a cream-colored solid. $^1$H NMR (300 MHz, DMSO-d$_6$) δ 8.34 (br s, 2H), 8.11 (d, J=2.5 Hz, 1H), 8.04 (s, 1H), 7.52 (d, J=8.5 Hz, 2H), 7.34 (d, J=8.5 Hz, 2H), 7.15–7.67 (m, 5H), 4.49–4.64 (br m, 1H), 4.42 (s, 2H), 4.05–4.15 (m, 1H), 4.01 (AB q, J=5.7 Hz, 2H), 3.00–3.20 (m, 1H), 2.70–2.90 (m, 2H), 1.72–1.88 (m, 1H), 1.45–1.70 (m, 3H); MS (ESI) m/z 479 (M+H).

EXAMPLE 109

3-[(5-{1-[4-(3-Aminomethyl-phenyl)piperidin-1-yl]-methanoyl}-pyridin-3-ylamino)-methyl]-benzonitrile trihydrochloride A. {5-[1-(4-{3-[N,N-Bis-(tert-butoxycarbonyl)aminomethyl]-phenyl}-piperidin-1-yl)-methanoyl]-pyridin-3-yl}-(3-cyano-benzyl)-carbamic acid dimethyl-ethyl ester By proceeding in a similar manner to the method described in EXAMPLE 105C, but using α-bromo-m-tolunitrile in place of 4-bromo-2-fluorobenzyl bromide, there was prepared {5-[1-(4-{3-[N,N-bis-butoxycarbonyl)aminomethyl]-phenyl}-piperidin-1-yl)-methanoyl]-pyridin-3-yl}-(3-cyano-benzyl)-carbamic acid dimethyl-ethyl ester as a yellow oil. TLC, 50:50-methylene chloride:ethyl acetate, R$_f$=0.44. $^1$H NMR (300 MHz, CDCl$_3$) δ 8.46–8.52 (m, 2H), 7.51–7.65 (m, 3H), 7.36–7.50 (m, 2H), 7.24–7.31 (m partially obscured, 1H), 7.03–7.18 (m, 3H), 4.92 (s, 2H), 4.79–4.92 (m partially obscured, 1H), 4.78 (s, 2H), 3.70–3.85 (br m, 1H), 3.10–3.28 (br m, 1H), 2.71–2.99 (m, 2H), 1.45 (s, 18H), 1.44 (s, 9H), 1.30–2.05 (m partially obscured, 4H); $^{13}$C NMR (75 MHz, CDCl$_3$) δ 166.7, 153.8, 152.5, 148.1, 145.2, 144.7, 139.2, 138.9, 138.7, 132.1, 131.9, 131.5, 131.2, 130.6, 129.6, 128.6, 125.6, 125.5, 125.2, 118.3, 112.9, 82.4, 80.6, 52.8, 49.3, 42.4, 33.5, 28.3, 28.0, 27.9; MS (CI) m/z 727 (M+H).

B. 3-[(5-{1-[4-(3-Aminomethyl-phenyl)piperidin-1-yl]-methanoyl}-pyridin-3-ylamino)-methyl]-benzonitrile trihydrochloride By proceeding in a similar manner to the method described in EXAMPLE 105D, but using {5-[1-(4-{3-[N,N-bis-(tert-butoxycarbonyl)amino-methyl]-phenyl}-piperidin-1-yl)-methanoyl]-pyridin-3-yl}-(3-cyano-benzyl)-carbamic acid dimethyl-ethyl ester, there was prepared 3-[(5-{1-[4-(3-aminomethyl-phenyl)piperidin-1-yl]-methanoyl}-pyridin-3-ylamino)-methyl]-benzonitrile trihydrochloride as a white solid. $^1$H NMR (300 MHz, DMSO-d$_6$) δ 8.33 (br s, 2H), 8.13 (d, J=2.5 Hz, 1H), 8.02 (s, 1H), 7.80–7.91 (m, 1H), 7.63–7.75 (m, 2H), 7.42–7.58 (m, 2H), 7.20–7.7.41 (m, 4H), 4.51 (s, 2H), 4.40–4.62 (m partially obscured, 1H), 4.10–4.25 (m, 1H), 4.00 (AB q, J=5.7 Hz, 2H), 2.90–3.20 (m, 1H), 2.72–2.93 (m, 2H), 1.75–1.90 (br m, 1H), 1.45–1.70 (br m, 3H); MS (ESI) m/z 426 (M+H).

EXAMPLE 110

1-[4-(3-Aminomethyl-phenyl)-piperidin-1-yl]-1-[5-(2-chloro-4-fluoro-benzylamino)-pyridin-3-yl]-methanone trihydrochloride A. {5-[1-(4-{3-[N,N-Bis-(tert-butoxycarbonyl) aminomethyl]-phenyl}-piperidin-1-yl)-methanoyl]-pyridin-3-yl}-(2-chloro-4-fluoro-benzyl)-carbamic acid dimethyl-ethyl ester By proceeding in a similar manner to the method described in EXAMPLE 105C, but using 2-chloro-4-fluorobenzyl bromide in place of 4-bromo-2-fluorobenzyl bromide, there was prepared {5-[1-(4-{3-[N,N-bis-(tert-butoxycarbonyl)aminomethyl]-phenyl}-piperidin-1-yl)-methanoyl]-pyridin-3-yl}-(2-chloro-4-fluoro-benzyl)-carbamic acid dimethyl-ethyl ester as a colorless oil. TLC, 50:50-methylene chloride:ethyl acetate, R$_f$=0.48. $^1$H NMR (300 MHz, CDCl$_3$) δ 8.51 (d, J=2.2 Hz, 1H), 8.46 (d, J=1.8 Hz, 1H), 7.62 (s, 1H), 7.24–7.34 (m, 2H), 7.04–7.19 (m, 4H), 6.97 (td, J=8.2, 2.5 Hz, 1H), 4.96 (s, 2H), 4.77 (s, 2H), 4.75–4.90 (m partially obscured, 1H), 3.70–3.85 (br m, 1H), 3.05–3.25 (br m, 1H), 2.70–2.90 (m, J=21.45, s Hz, 18H), 1.44 (s, 9H), 1.30–2.05 (m, 4H); $^{13}$C NMR (75 MHz, CDCl$_3$) δ 166.9, 161.8 (d, 250.1), 153.8, 152.6, 148.1, 144.7, 144.6, 138.9, 138.6, 133.6 (d, 9.7), 131.8, 131.7, 130.8 (d, 3.4), 129.8 (d, 7.6), 128.6, 125.7, 125.6, 125.2, 117.0 (d, 24.9), 114.3 (d, 21.4), 82.4, 82.1, 50.3, 49.4, 42.5, 33.8, 28.3, 28.1, 27.9; $^{19}$F NMR (282 MHz, CDCl$_3$) δ-112.0; MS (CI) m/z 754 (M+H).

B. 1-[4-(3-Aminomethyl-phenyl)-piperidin-1-yl]-1-[5-(2-chloro-4-fluoro-benzylamino)-pyridin-3-yl]-methanone trihydrochloride By proceeding in a similar manner to the method described in EXAMPLE 105D, but using {5-[1-(4-{3-[N,N-bis-(tert-butoxycarbonyl)aminomethyl]-phenyl}-piperidin-1-yl)-methanoyl]-pyridin-3-yl}-(2-chloro-4-fluoro-benzyl)-carbamic acid dimethyl-ethyl ester, there was prepared 1-[4-(3-aminomethyl-phenyl)-piperidin-1-yl]-1-[5-(2-chloro-4-fluoro-benzylamino)-pyridin-3-yl]-methanone trihydrochloride as a white solid. $^{1}$H NMR (300 MHz, DMSO-d$_6$) δ 8.34 (br s, 2H), 8.15 (d, J=2.5 Hz, 1H), 8.07 (s, 1H), 7.12–7.55 (m, 8H), 4.50–4.65 (br m, 1H), 4.46 (s, 2H), 4.12–4.24 (br m, 1H), 4.00 (AB q, J=5.8 Hz, 2H), 3.05–3.20 (br m, 1H), 2.70–2.90 (m, 2H), 1.72–1.90 (br m, 1H), 1.48–1.73 (br m, 3H); $^{19}$F NMR (282 MHz, DMSO-d$_6$) δ-112.6; MS (ESI) m/z 453 (M+H).

EXAMPLE 111

1-[4-(3-Aminomethyl-phenyl)-piperidin-1-yl]-1-[5-(4-trifluoromethoxy-benzylamino)-pyridin-3-yl]-methanone trihydrochloride A. {5-[1-(4-{3-[N,N-Bis-(tert-butoxycarbonyl)aminomethyl]-phenyl}-piperidin-1-yl)-methanoyl]-pyridin-3-yl}-(4-trifluoromethoxy-benzyl)-carbamic acid dimethyl-ethyl ester By proceeding in a similar manner to the method described in EXAMPLE 105C, but using 4-(trifluoromethoxy)benzyl bromide in place of 4-bromo-2-fluorobenzyl bromide, there was prepared {5-[1-(4-{3-[N,N-bis-(tert-butoxycarbonyl)amino-methyl]-phenyl}-piperidin-1-yl)-methanoyl]-pyridin-3-yl}-(4-trifluoromethoxy-benzyl)-carbamic acid dimethyl-ethyl ester as a colorless oil. TLC, 50:50-methylene chloride:ethyl acetate, R$_f$=0.48. $^{1}$H NMR (300 MHz, CDCl$_3$) δ 8.45–8.53 (m, 2H), 7.60 (s, 1H), 7.20–7.30 (m, 3H), 7.05–7.20 (m, 5H), 4.88 (s, 2H), 4.77 (s, 2H), 4.75–4.90 (m partially obscured, 1H), 3.70–3.84 (br m, 1H), 3.08–3.24 (br m, 1H), 2.70–2.93 (m, 2H), 1.45 (s, 18H), 1.44 (s, 9H), 1.35–2.05 (m, 4H); $^{13}$C NMR (75 MHz, CDCl$_3$) δ 166.9, 154.0, 152.6, 148.3, 144.7, 144.6, 138.9, 138.8, 136.3, 132.2, 131.9, 128.7, 128.6, 125.7, 125.6, 125.2, 121.2, 120.1 (q, 262), 82.4, 82.0, 52.7, 49.4, 42.5, 32.3, 28.3, 28.1, 27.9; $^{19}$F NMR (282 MHz, CDCl$_3$) δ-57.4; MS (CI) m/z 786 (M+H).

B. 1-[4-(3-Aminomethyl-phenyl)-piperidin-1-yl]-1-[5-(4-trifluoromethoxy-benzylamino)-pyridin-3-yl]-methanone trihydrochloride By proceeding in a similar manner to the method described in EXAMPLE 105D, but using {5-[1-(4-{3-[N,N-bis-(tert-butoxycarbonyl)amino-methyl]-phenyl}-piperidin-1-yl)-methanoyl]-pyridin-3-yl}-(4-trifluoromethoxy-benzyl)-carbamic acid dimethyl-ethyl ester, there was prepared 1-[4-(3-aminomethyl-phenyl)-piperidin-1-yl]-1-[5-(4-trifluoromethoxy-benzylamino)-pyridin-3-yl]-methanone trihydrochloride as a white solid. $^{1}$H NMR (300 MHz, DMSO-d$_6$) δ 8.35 (br s, 2H), 8.12 (d, J=2.8 Hz, 1H), 8.05 (s, 1H), 7.20–7.75 (m, 9H), 4.50–4.65 (m, 1H), 4.48 (s, 2H), 4.05–4.20 ) (m, 1H), 4.00 (AB q, J=5.9 Hz, 2H), 3.05–3.25 (m, 1H), 2.70–2.90 (m, 2H), 1.75–1.90 (m, 1H), (m, 1H), 1.50–1.70 (br m, 3H); $^{19}$F NMR (282 MHz, DMSO-d$_6$) δ-56.3; MS (ESI) m/z 485 (M+H).

EXAMPLE 112

1-[4-(3-Aminomethyl-phenyl)-piperidin-1-yl]-1-{5-[(pyridin-3-ylmethyl)-amino]-pyridin-3-yl}-methanone tetrahydrochloride A. {5-[1-(4-{3-[N,N-Bis-(tert-butoxycarbonyl)aminomethyl]-phenyl}-piperidin-1-yl)-methanoyl]-pyridin-3-yl}-pyridin-3-ylmethyl-carbamic acid dimethyl-ethyl ester By proceeding in a similar manner to the method described in EXAMPLE 105C, but using 3-(chloromethyl)pyridine hydrochloride in place of 4-bromo-2-fluorobenzyl bromide, there was prepared {5-[1-(4-{3-[N,N-bis-(tert-butoxycarbonyl)amino-methyl]-phenyl}-piperidin-1-yl)-methanoyl]-pyridin-3-yl}-pyridin-3-ylmethyl-carbamic acid dimethyl-ethyl ester as a colorless oil. TLC, 15:85-isopropyl alcohol:methylene chloride, R$_f$=0.54. $^{1}$H NMR (300 MHz, CDCl$_3$) δ 8.4–8.56 (m, 4H), 7.53–7.62 (m, 2H), 7.22–7.31 (m partially obscured, 2H), 7.05–7.18 (m, 3H), 4.90 (s, 2H), 4.77 (s, 2H), 4.75–4.99 (m partially obscured, 1H), 3.69–3.83 (br m, 1H), 3.05–3.25 (br m, 1H), 2.70–2.96 (m, 2H), 1.45 (s, 18H), 1.44 (s, 9H), 1.20–2.03 (m, 4H); $^{13}$C NMR (75 MHz, CDCl$_3$) δ 166.8, 154.0, 152.6, 149.1, 149.0, 148.6, 144.9, 144.7, 138.9, 138.7, 135.1, 133.1, 132.4, 131.9, 128.7, 125.7, 125.6, 125.3, 123.6, 82.5, 82.2, 51.2, 49.4, 42.6, 33.9, 28.4, 28.2, 28.0; MS (CI) m/z 702 (M+H).

B. 1-[4-(3-Aminomethyl-phenyl)-piperidin-1-yl]-1-{5-[(pyridin-3-ylmethyl)-amino]-pyridin-3-yl}-methanone tetrahydrochloride {5-[1-(4-{3-[N,N-Bis-(tert-butoxycarbonyl)aminomethyl]-phenyl}-piperidin-1-yl)-methanoyl]-pyridin-3-yl}-pyridin-3-ylmethyl-carbamic acid dimethyl-ethyl ester (0.0250 g, 0.0356 mmol) was treated with 5–6 M HCl in isopropanol (1.0 mL, 8.0 mmol) and stirred at ambient temperature. After 90 minutes the reaction mixture was diluted with methyl alcohol (0.5 mL) and stirring was continued for an additional 75 minutes. Dripping the reaction solution into ether (40 mL) with vigorous stirring afforded a white precipitate which was collected by filtration, washed with fresh ether (3.0 mL), and dried to afford 1-[4-(3-aminomethyl-phenyl)-piperidin-1-yl]-1-{5-[(pyridin-3-ylmethyl)-amino]-pyridin-3-yl}-methanone tetrahydrochloride (0.0160 g): $^{1}$H NMR (300 MHz, DMSO-d$_6$) δ 8.60–8.95 (m, 2H), 8.39 (br s, 2H), 8.29 (d, J=8.0 Hz, 1H), 7.97–8.25 (m, 2H), 7.65–7.85 (m, 2H), 7.47 (d, J=8.0 Hz, 2H), 7.20–7.38 (m, 3H), 4.63 (s, 2H), 4.43–4.61 (m partially obscured, 1H), 4.00 (AB q, J=5.8 Hz, 2H), 3.05–3.25 (m partially obscured, 1H), 2.72–2.95 (m, 2H), 1.80–1.88 (m, 1H), 1.47–1.77 (m, 3H); MS (CI) m/z 402 (M+H).

EXAMPLE 113

1-[4-(3-Aminomethyl-phenyl)-piperidin-1-yl]-1-{5-[(pyridin-2-ylmethyl)-amino]-pyridin-3-yl}-methanone tetrahydrochloride A. {5-[1-(4-{3-[N,N-Bis-(tert-butoxycarbonyl)aminomethyl]-phenyl}-piperidin-1-yl)-methanoyl]-pyridin-3-yl}-pyridin-2-ylmethyl-carbamic acid dimethyl-ethyl ester By proceeding in a similar manner to the method described in EXAMPLE 105C, but using 2-(chloromethyl)pyridine hydrochloride in place of 4-bromo-2-fluorobenzyl bromide, there was prepared {5-[1-(4-{3-[N,N-bis-(tert-butoxycarbonyl)amino-methyl]-phenyl}-piperidin-1-yl)-methanoyl]-pyridin-3-yl}-pyridin-2-ylmethyl-carbamic acid dimethyl-ethyl ester as a colorless oil. TLC, 50:50-methylene chloride:ethyl acetate, R$_f$=0.09. $^{1}$H NMR (300 MHz, CDCl$_3$) δ 8.67 (d, J=2.3 Hz, 1H), 8.52 (d, J=4.7 Hz, 1H), 8.44 (d, J=1.8 Hz, 1H), 7.81 (s, 1H), 7.59–7.72 (m, 1H), 7.22–7.31 (m partially obscured, 2H), 7.00–7.20 (m, 4H), 4.97 (s, 2H), 4.77 (s, 2H), 4.72–4.90 (m partially obscured, 1H), 3.74–3.89 (br m, 1H), 3.04–3.25 (br m, 1H), 2.69–2.94 (m, 2H), 1.45 (s, 18H), 1.41 (s, 9H), 1.23–2.03 (m partially obscured, 4H); MS (CI) m/z 702 (M+H).

B. 1-[4-(3-Aminomethyl-phenyl)-piperidin-1-yl]-1-{5-[(pyridin-2-ylmethyl)-amino]-pyridin-3-yl}-methanone tetrahydrochloride By proceeding in a similar manner to the method described in EXAMPLE 112B, but using {5-[1-(4-{3-[N,N-bis-(tert-butoxycarbonyl)amino-methyl]-phenyl}-piperidin-1-yl)-methanoyl]-pyridin-3-yl}-pyridin-2-ylmethyl-carbamic acid dimethyl-ethyl ester, there was prepared 1-[4-(3-aminomethyl-phenyl)-piperidin-1-yl]-1-{5-[(pyridin-2-ylmethyl)-amino]-pyridin-3-yl}-methanone tetrahydrochloride as a white solid. MS (ESI) m/z 402 (M+H).

In a similar manner to the methods described in EXAMPLES 105 and 112, the following compounds are prepared:

EXAMPLE 114
1-[4-(3-Aminomethyl-phenyl)-piperidin-1-yl]-1-{5-[(pyridin-4-ylmethyl)-amino]-pyridin-3-yl}-methanone tetrahydrochloride;

EXAMPLE 115
1-[4-(3-Aminomethyl-phenyl)-piperidin-1-yl]-1-(3-benzylamino-phenyl)-methanone dihydrochloride;

A. [3-(4-{3-[N,N-Bis-(tert-butoxycarbonyl)amino-methyl]-phenyl}-piperidine-1-carbonyl)-phenyl]-carbamic acid tert-butyl ester By proceeding in a similar manner to the method described in EXAMPLE 105B, but using 3-(Boc-amino) benzoic acid in place of 5-tert-butoxycarbonylamino-nicotinic acid, there was prepared [3-(4-{3-[N,N-bis-(tert-butoxycarbonyl)amino-methyl]-phenyl}-piperidine-1-carbonyl)-phenyl]-carbamic acid tert-butyl ester as a white solid. $^1$H NMR (300 MHz, CDCl$_3$) δ 7.40–7.50 (m, 2H), 7.22–7.37 (m, 2H), 7.04–7.15 (m, 4H), 4.77–4.90 (br m, 1H), 4.76 (s, 2H), 3.81–3.96 (br m, 1H), 3.05–3.20 (br m, 1H), 2.68–2.90 (m, 2H), 1.52 (s, 9H), 1.45 (s, 18H), 1.35–1.85 (m partially obscured, 4H)); MS (CI) m/z 610 (M+H).

B. Benzyl-[3-(4-{3-[N,N-Bis-(tert-butoxycarbonyl)amino-methyl]-phenyl}-piperidine-1-carbonyl)-phenyl]-carbamic acid tert-butyl ester By proceeding in a similar manner to the method described in EXAMPLE 105C, but using benzyl bromide in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared benzyl-[3-(4-{3-[N,N-Bis-(tert-butoxycarbonyl)amino-methyl]-phenyl}-piperidine-1-carbonyl)-phenyl]-carbamic acid tert-butyl ester as a white solid. $^1$H NMR (300 MHz, CDCl$_3$) δ 7.03–7.34 (m, 13H), 4.84 (br s, 2H), 4.78–4.90 (m partially obscured, 1H), 4.77 (s, 2H), 3.69–3.85 (br m, 1H), 2.90–3.10 (br m, 1H), 2.65–2.88 (m, 2H), 1.45 (s, 18H), 1.41 (s, 9H), 1.35–1.95 (m partially obscured, 4H)); MS (CI) m/z 700 (M+H).

C. 1-[4-(3-Aminomethyl-phenyl)-piperidin-1-yl]-1-(3-benzylamino-phenyl)-methanone dihydrochloride By proceeding in a similar manner to the method described in EXAMPLE 105D, but using prepared benzyl-[3-(4-{3-[N,N-Bis-(tert-butoxycarbonyl)amino-methyl]-phenyl}-piperidine-1-carbonyl)-phenyl]-carbamic acid tert-butyl ester, there was prepared 1-[4-(3-aminomethyl-phenyl)-piperidin-1-yl]-1-(3-benzylamino-phenyl)-methanone dihydrochloride as a white solid. MS (ESI) m/z 400 (M+H).

EXAMPLE 116
1-{4-(3-Aminomethyl-phenyl)-piperidin-1-yl]-1-{3-[(naphthalen-2-ylmethyl)-amino]-phenyl}-methanone dihydrochloride;

A. [3-(4-{3-[N,N-Bis-(tert-butoxycarbonyl)amino-methyl]-phenyl}-piperidine-1-carbonyl)-phenyl]-naphthalen-2-ylmethyl-carbamic acid tert-butyl ester By proceeding in a similar manner to the method described in EXAMPLE 105C, but using 2-(bromomethyl)naphthalene in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared [3-(4-{3-[N,N-bis-(tert-butoxycarbonyl)amino-methyl]-phenyl}-piperidine-1-carbonyl)-phenyl]-naphthalen-2-ylmethyl-carbamic acid tert-butyl ester as a white solid. MS (ESI) m/z 650 (M+H).

B. 1-{4-(3-Aminomethyl-phenyl)-piperidin-1-yl]-1-{3-[(naphthalen-2-ylmethyl)-amino]-phenyl}-methanone dihydrochloride By proceeding in a similar manner to the method described in EXAMPLE 105D, but using [3-(4-{3-[N,N-Bis-(tert-butoxycarbonyl)amino-methyl]-phenyl}-piperidine-1-carbonyl)-phenyl]-naphthalen-2-ylmethyl-carbamic acid tert-butyl ester, there was prepared 1-{4-(3-aminomethyl-phenyl)-piperidin-1-yl]-1-{3-[(naphthalen-2-ylmethyl)-amino]-phenyl}-methanone dihydrochloride as a white solid. MS (ESI) m/z 450 (M+H).

EXAMPLE 117
3-[(3-{1-[4-(3-Aminomethyl-phenyl)-piperidin-1-yl]-methanoyl}-phenylamino)-methyl]-benzonitrile dihydrochloride;

A. [3-(4-{3-[N,N-Bis-(tert-butoxycarbonyl)amino-methyl]-phenyl}-piperidine-1-carbonyl)-phenyl]-(3-cyano-benzyl)-carbamic acid tert-butyl ester By proceeding in a similar manner to the method described in EXAMPLE 105C, but using α-bromo-m-tolunitrile in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared [3-(4-{3-[N,N-bis-(tert-butoxycarbonyl)amino-methyl]-phenyl}-piperidine-1-carbonyl)-phenyl]-(3-cyano-benzyl)-carbamic acid tert-butyl ester as a white solid. MS (CI) m/z 725 (M+H).

B. 3-[(3-{1-[4-(3-Aminomethyl-phenyl)-piperidin-1-yl]-methanoyl}-phenylamino)-methyl]-benzonitrile dihydrochloride By proceeding in a similar manner to the method described in EXAMPLE 105D, but [3-(4-{3-[N,N-bis-(tert-butoxycarbonyl)amino-methyl]-phenyl}-piperidine-1-carbonyl)-phenyl]-(3-cyano-benzyl)-carbamic acid tert-butyl ester, there was prepared 3-[(3-{1-[4-(3-aminomethyl-phenyl)-piperidin-1-yl]-methanoyl}-phenylamino)-methyl]-benzonitrile dihydrochloride as a white solid. MS (ESI) m/z 425 (M+H).

EXAMPLE 118
1-[4-(3-Aminomethyl-phenyl)-piperidin-1-yl]-1-[3-(4-bromo-benzylamino)-phenyl]-methanone dihydrochloride;

A. (4-Bromo-benzyl)-[3-(4-{3-[N,N-bis-(tert-butoxycarbonyl)amino-methyl]-phenyl}-piperidine-1-carbonyl)-phenyl]-carbamic acid tert-butyl ester By proceeding in a similar manner to the method described in EXAMPLE 105C, but using 4-bromobenzyl bromide in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared (4-bromo-benzyl)-

[3-(4-{3-[N,N-bis-(tert-butoxycarbonyl)amino-methyl]-phenyl}-piperidine-1-carbonyl)-phenyl]-carbamic acid tert-butyl ester as a clear oil. MS (CI) m/z 778 (M+H).

B. 1-[4-(3-Aminomethyl-phenyl)-piperidin-1-yl]-1-[3-(4-bromo-benzylamino)-phenyl]-methanone dihydrochloride By proceeding in a similar manner to the method described in EXAMPLE 105D, but using (4-bromo-benzyl)-[3-(4-{3-[N,N-bis-(tert-butoxycarbonyl)amino-methyl]-phenyl}-piperidine-1-carbonyl)-phenyl]-carbamic acid tert-butyl ester, there was prepared 1-[4-(3-aminomethyl-phenyl)-piperidin-1-yl]-1-[3-(4-bromo-benzylamino)-phenyl]-methanone dihydrochloride as a white solid. MS (ESI) m/z 480 (M+H).

EXAMPLE 119

1-[4-(3-Aminomethyl-phenyl)-piperidin-1-yl]-1-{3-[(pyridin-2-ylmethyl)-amino]-phenyl}-methanone trihydrochloride;

A. [3-(4-{3-[N,N-Bis-(tert-butoxycarbonyl)amino-methyl]-phenyl}-piperidine-1-carbonyl)-phenyl]-pyridin-2-ylmethyl-carbamic acid tert-butyl ester By proceeding in a similar manner to the method described in EXAMPLE 105C, but using 2-picolyl chloride hydrochloride in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared [3-(4-{3-[N,N-bis-(tert-butoxycarbonyl)amino-methyl]-phenyl}-piperidine-1-carbonyl)-phenyl]-pyridin-2-ylmethyl-carbamic acid tert-butyl ester as a white solid. $^1$H NMR (300 MHz, CDCl$_3$): δ 8.53 (d, 1H), 7.60–7.70 (m, 2H), 7.29–7.37 (m, 4H), 7.08–7.24 (m, 5H), 4.97 (s, 2H), 4.70–4.90 (m partially obscured, 1H), 4.77 (s, 2H), 3.75–3.95 (br m, 1H), 2.65–3.20 (br m, 3H), 1.40–2.00 (m partially obscured, 4H), 1.45 (s, 18H), 1.39 (s, 9H). MS (ESI): m/z 701 (M+H).

B. 1-{4-(3-Aminomethyl-phenyl)-piperidin-1-yl]-1-{3-[(pyridin-2-ylmethyl)-amino]-phenyl}-methanone trihydrochloride By proceeding in a similar manner to the method described in EXAMPLE 105D, but using [3-(4-{3-[N,N-Bis-(tert-butoxycarbonyl)amino-methyl]-phenyl}-piperidine-1-carbonyl)-phenyl]-pyridin-2-ylmethyl-carbamic acid tert-butyl ester, there was prepared 1-{4-(3-aminomethyl-phenyl)-piperidin-1-yl]-1-{3-[(pyridin-2-ylmethyl)-amino]-phenyl}-methanone trihydrochloride as a light yellow solid. $^1$H NMR [300 MHz, (CD$_3$)$_2$SO]: δ 8.69 (d, 1H), 8.34 (br s, 3H), 8.19 (tr, 1H), 7.73 (d, 1H), 7.63 (tr, 1H), 7.25–7.42 (m, 4H), 7.14 (tr, 1H), 6.68 (d, 1H), 6.61 (m, 2H), 4.40–4.70 (br m partially obscured, 1H), 4.61 (s, 2H), 4.01 (q, 2H), 3.70–3.95 (br m partially obscured, 1H), 2.90–3.15 (br m, 1H), 2.65–2.90 (br m, 2H), 1.35–1.95 (br m, 4H). MS (ESI): m/z 401 (M+H).

EXAMPLE 120

1-[4-(3-Aminomethyl-phenyl)-piperidin-1-yl]-1-{3-[(pyridin-3-ylmethyl)-amino]-phenyl}-methanone trihydrochloride;

A. [3-(4-{3-[N,N-Bis-(tert-butoxycarbonyl)amino-methyl]-phenyl}-piperidine-1-carbonyl)-phenyl]-pyridin-3-ylmethyl-carbamic acid tert-butyl ester By proceeding in a similar manner to the method described in EXAMPLE 105C, but using 3-picolyl chloride hydrochloride in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared [3-(4-{3-[N,N-bis-(tert-butoxycarbonyl)amino-methyl]-phenyl}-piperidine-1-carbonyl)-phenyl]-pyridin-3-ylmethyl-carbamic acid tert-butyl ester as a cream oil. $^1$H NMR (300 MHz, CDCl$_3$): δ 8.49 (br s, 2H), 7.57 (d, 1H), 7.33 (m, 1H), 7.07–7.24 (m, 8H), 4.70–4.95 (m partially obscured, 1H), 4.85 (s, 2H), 4.77 (s, 2H), 3.65–3.90 (br m, 1H), 2.65–3.15 (br m, 3H), 1.40–2.00 (m partially obscured, 4H), 1.45 (s, 18H), 1.41 (s, 9H). MS (ESI): m/z 701 (M+H).

B. 1-{4-(3-Aminomethyl-phenyl)-piperidin-1-yl]-1-{3-[(pyridin-3-ylmethyl)-amino]-phenyl}-methanone trihydrochloride By proceeding in a similar manner to the method described in EXAMPLE 105D, but using [3-(4-{3-[N,N-Bis-(tert-butoxycarbonyl)amino-methyl]-phenyl}-piperidine-1-carbonyl)-phenyl]-pyridin-3-ylmethyl-carbamic acid tert-butyl ester, there was prepared 1-{4-(3-aminomethyl-phenyl)-piperidin-1-yl]-1-{3-[(pyridin-3-ylmethyl)-amino]-phenyl}-methanone trihydrochloride as a light yellow solid. $^1$H NMR [300 MHz, (CD$_3$)$_2$SO]: δ 8.81 (s, 1H), 8.70 (d, 1H), 8.34 (m, 4H), 7.86 (tr, 1H), 7.25–7.41 (m, 4H), 7.14 (tr, 1H), 6.67 (d, 1H), 6.59 (m, 2H), 4.40–4.70 (br m partially obscured, 1H), 4.50 (s, 2H), 4.01 (q, 2H), 3.70–3.90 (br m partially obscured, 1H), 2.90–3.15 (br m, 1H), 2.65–2.90 (br m, 2H), 1.35–1.95 (br m, 4H). MS (ESI): m/z 401 (M+H).

EXAMPLE 121

1-[4-(3-Aminomethyl-phenyl)-piperidin-1-yl]-1-{3-[(pyridin-4-ylmethyl)-amino]-phenyl}-methanone trihydrochloride.

A. [3-(4-{3-[N,N-Bis-(tert-butoxycarbonyl)amino-methyl]-phenyl}-piperidine-1--carbonyl)-phenyl]-pyridin-4-ylmethyl-carbamic acid tert-butyl ester By proceeding in a similar manner to the method described in EXAMPLE 105C, but using 4-picolyl chloride hydrochloride in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared [3-(4-{3-[N,N-bis-(tert-butoxycarbonyl)amino-methyl]-phenyl}-piperidine-1-carbonyl)-phenyl]-pyridin-4-ylmethyl-carbamic acid tert-butyl ester as a cream oil. $^1$H NMR (300 MHz, CDCl$_3$): δ 8.55 (br d, 2H), 7.33 (q, 2H), 7.06–7.26 (m, 8H), 4.70–4.90 (m partially obscured, 1H), 4.84 (s, 2H), 4.77 (s, 2H), 3.70–3.90 (br 1H), 268–3.15 (br m, 3H), 1.40–2.00 (m partially obscured, 4H), 1.45 (s, 18H), 1.41 (s, 9H). MS (ESI): m/z 701 (M+H).

B. 1-{4-(3-Aminomethyl-phenyl)-piperidin-1-yl]-1-{3-[(pyridin-4-ylmethyl)-amino]-phenyl}-methanone trihydrochloride By proceeding in a similar manner to the method described in EXAMPLE 105D, but using [3-(4-{3-[N,N-Bis-(tert-butoxycarbonyl)amino-methyl]-phenyl}-piperidine-1-carbonyl)-phenyl]-pyridin-4-ylmethyl-carbamic acid tert-butyl ester, there was prepared 1-{4-(3-aminomethyl-phenyl)-piperidin-1-yl]-1-{3-[(pyridin-4-ylmethyl)-amino]-phenyl}-methanone trihydrochloride as a cream solid. $^1$H NMR [300 MHz, (CD$_3$)$_2$SO]: δ 8.76 (br s, 2H), 8.33 (br s, 3H), 7.87 (d, 2H), 7.24–7.41 (m, 4H), 7.13 (tr, 1H), 6.65–7.00 (br 1H), 6.56–6.64 (m, 3H), 4.40–4.70 (br m partially obscured, 1H), 4.61 (s, 2H), 4.01 (q, 2H), 3.70–3.90 (br m partially obscured, 1H), 2.90–3.15 (br m, 1H), 2.65–2.90 (br m, 2H), 1.35–1.95 (br m, 4H). MS (ESI): m/z 401 (M+H).

EXAMPLE 122

3-[1-(5-Phenylethynyl-furan-2-carbonyl)-piperidin-4-yl]-benzylamine trifluoroacetate

A. 4-oxo-piperidine-1-carboxylic acid(trimethylsilyl)ethyl ester

A solution of 4-piperidone monohydrate. Hydrochloride (13.55 g, 88 mmol) 2-trimethylsilylethyl-p-nitrophenylcarbonate (25.00 g, 88 mmol) in acetonitrile (300 ml) was treated with triethylamine (50 ml, 359 mmol) and dimethyl-aminopyridine (10.78 g, 88 mmol) and heated to reflux for 2 hours. The solution was cooled and concentrated to an oil. The residue was dissolved in dichloromethane (300 ml) and washed twice with 1M hydrochloric acid and twice with 1M sodium hydroxide until all of the yellow color was removed from the organics. The organics were then washed with brine, dried over magnesium sulfate and concentrated under vacuum to give 4-oxo-piperidine-1-carboxylic acid (trimethylsilyl) ethyl ester as colorless oil. (19.35 g) $^1$H NMR (CDCl$_3$, 300 MHz): δ 4.24 (2H, t), 3.78 (4H, t), 2.45 (4H, t), 1.05 (2H, t), 0.05 (9H, s) MS (EI) 284(M+CH$_3$CN).

B. 4-(3-Cyano-phenyl)-3,6-dihydro-2H-pyridine-1-carboxylic acid 2-trimethylsilanyl-ethyl ester A solution of lithium hexamethyldisilazide (60 mmol) in anhydrous tetrahydrofuran (150 ml), at −78° C., was treated dropwise with a solution of 4-oxo-piperidine-1-carboxylic acid(trimethylsilyl) ethyl ester (13.30 g, 55 mmol) in anhydrous tetrahydrofuran (50 ml). The addition was over 20 minutes maintaining the internal temperature at −65 to −70° C. This solution was stirred at −78° C. for 45 minutes and then treated with a solution of N-phenyltrifluoromethanesulfonimide (19.65 g, 55 mmol) in anhydrous tetrahydrofuran (75 ml). The solution was warmed to 0° C., then stirred at 0° C. for 3 hours and then concentrated under vacuum. The residue was dissolved in dichloromethane and washed with water, dried over magnesium sulfate and concentrated to give 2-(trimethylsilyl) ethyl 1,2,3,6-tetrahydro-4-(trifluoromethylsulphonyloxy)-pyridine-1-carboxylate as a yellow oil (22.1 g). The material is used crude, as column chromatography on silica gel or alumina caused the material to deteriorate. A portion of this material (20.65 g, 55 mmol) was dissolved in acetonitrile (300 ml) and the solution was treated with 3-cyanoboronic acid (8.90 g, 60 mmol), 2M sodium carbonate (82.5 ml, 165 mmol) and lithium chloride (6.98 g, 165 mmol). The non-homogenous mixture was stirred vigorously and flushed with nitrogen for 5 minutes, then tetrakistriphenylphospine palladium (0) (3.10 g, 3 mmol). The mixture was heated to reflux (90° C. oil bath) for 90 minutes, then cooled and filtered. The red filtrate was concentrated and the residue was partitioned between dichloromethane (3 lots 100 ml) and 2M sodium carbonate (200 ml). The combined organic extracts were dried over magnesium sulfate and then concentrated under vacuum. The resultant oil was subjected to chromatography silica gel eluting with a mixture of ethyl acetate, heptane and dichloromethane (1:5:1, v/v) to yield 4-(3-cyano-phenyl)-3,6-dihydro-2H-pyridine-1-carboxylic acid 2-trimethylsilanyl-ethyl ester as a yellow oil (10.46 g). $^1$H NMR (CDCl$_3$, 300 MHz): δ 7.40–7.65 (m, 4H), 6.10 (m, 1H), 4.23 (t, 2H), 4.15 (d, 2H), 3.70 (t, 2H), 2.45 (m, 2H), 1.12 (t, 2H), 0.05 (s, 9H).

C. 4-(3-Aminomethyl-phenyl)-piperidine-1-carboxylic acid 2-trimethylsilanyl-ethyl ester hydrochloride 4-(3-Cyanophenyl)-3,6-dihydro-2H-pyridine-1-carboxylic acid 2-trimethylsilanyl-ethyl ester (10.40 g, 32 mmol) was dissolved in ethanol (250 ml), concentrated hydrochloric acid (3 ml, 35 mmol) and 10% palladium on carbon (50% wet, 5.0 g) was added. The mixture was hydrogenated at 50 psi for 4 hours then filtered through celite and concentrated. The oily solid obtained was triturated with ether/pentane and 4-(3-aminomethyl-phenyl)-piperidine-1-carboxylic acid 2-trimethylsilanyl-ethyl ester hydrochloride was obtained as a white solid (7.10 g). $^1$H NMR [(CD$_3$)$_2$SO, 300 MHz]: δ 8.38 (br s, 2H), 7.20–7.40 (m, 4H), 4.10 (t, 4H), 3.98 (s, 2H), 2.63–3.00 (m, 3H), 1.75 (m, 2H), 1.50 (m, 2H), 0.94 (t, 2H), 0.02 (s, 9H). LC-MS (ES) 335 (M$^+$+H), 93% TIC.

D. (3-Piperidin-4-yl-benzyl) carbamate Wang resin p-Nitrophenyl carbonate Wang resin (11.00 g, 15 mmol) and anhydrous dimethylformamide (100 ml) were placed in a peptide synthesis vessel and the resin was allowed to swell for 15 minutes. This was then treated with 4-(3-aminomethyl-phenyl)-piperidine-1-carboxylic acid 2-trimethylsilanyl-ethyl ester hydrochloride (7.50 g, 21 mmol) in 50 ml dimethylformamide, dimethylaminopyridine (0.72, 6 mmol) and diisopropylethyl-amine. The peptide vessel was shaken at room temperature for 24 hours, then washed thoroughly with dimethylformamide (×5), methanol (×2), dimethylformamide (×2), methanol (×2), dichloromethane (×3), methanol (×2), dichloromethane (×2), methanol (×3), and dried. The resin was then treated with tetrahydrofuran to swell the resin and then allowed to drain. Then anhydrous tetrahydrofuran (100 ml) and tetrabutylammonium fluoride (75 ml, 1M in tetrahydrofuran) were added and the resin shaken for 18 hours. The resin was drained and washed with tetrahydrofuran (×5), methanol (×3), dichloromethane (×3), methanol (×3), dichloromethane (×3), methanol (×3) and dried to give (3-piperidin-4-yl-benzyl) carbamate Wang resin (12.30 g).

E. 3-[-(5-Phenylethynyl-furan-2-carbonyl)-piperidin-4-yl]-benzylamine trifluoroacetate (3-Piperidin-4-yl-benzyl) carbamate Wang resin (60 mg, 0.075 mmol) suspended in dimethylformamide (3 ml) and 5-phenylethynyl-furan 2 carboxylic acid (80 mg, 0.38 mmol), diisopropylcarbodiimide (48 mg, 0.38 mmol) and 1-hydroxybenzotriazole (50 mg, 0.38 mmol) were added. The mixture was shaken at room temperature overnight and washed with dimethylformamide (×5), methanol (×5), dichloromethane then methanol (repeat 5 times). The resin was treated with trifluoroacetic acid and dichloromethane (1:1 v/v, 4 ml) for 45 minutes and filtered. The filtrate was concentrated to give 3-[1-(5-phenylethynyl-furan-2-carbonyl)-piperidin-4-yl]-benzylamine trifluoroacetate as a pale yellow oil (30 mg). LC-MS (ES) 385 (M$^+$+H) 100% TIC.

In a similar manner to the methods described in EXAMPLE 112, the following compounds set forth in Table 5 were prepared as the trifluoroacetate salts:

TABLE 5

| EG | Structure | M/Z | MS area % |
|---|---|---|---|
| 123 | 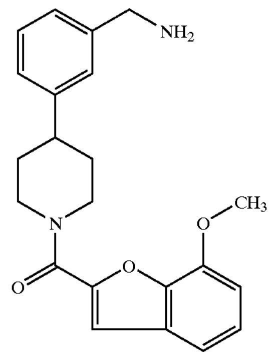 | 365.2 | 93 |
| 124 | 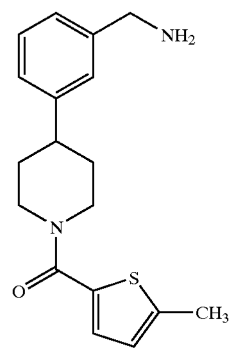 | 381.4 | 100 |
| 125 | 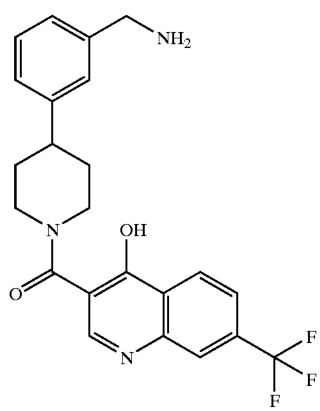 | 430.2 | 100 |
| 126 | 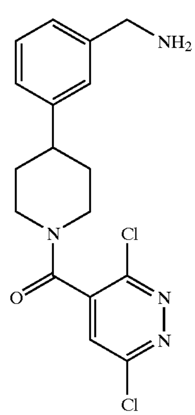 | 413.1 | 100 |

TABLE 5-continued
| EG | Structure | M/Z | MS area % |
|---|---|---|---|
| 127 | 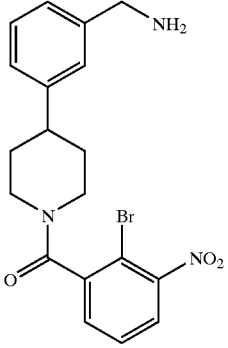 | 418.2 | 100 |
| 128 | 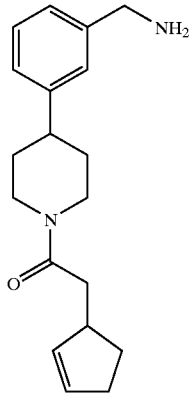 | 299.3 | 100 |
| 129 | 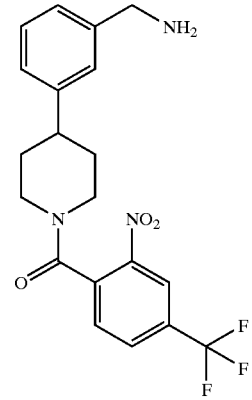 | 408.3 | 94 |
| 130 | 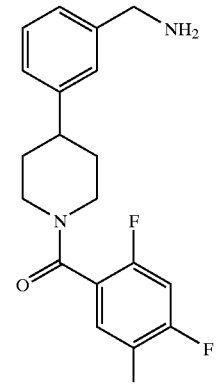 | 349.1 | 100 |

TABLE 5-continued
| EG | Structure | M/Z | MS area % |
|----|-----------|-----|-----------|
| 131 | 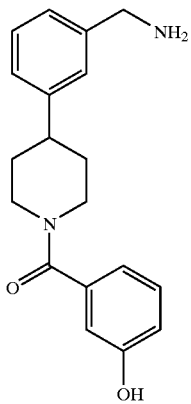 | 311.1 | 90 |
| 132 | 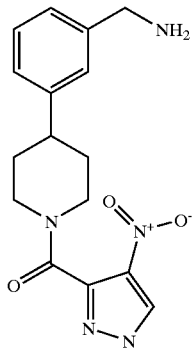 | 313.1 | 100 |
| 133 | 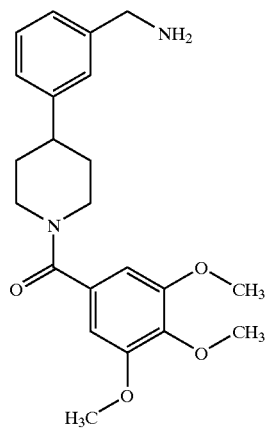 | 385.2 | 100 |

TABLE 5-continued

| EG | Structure | M/Z | MS area % |
|---|---|---|---|
| 134 | 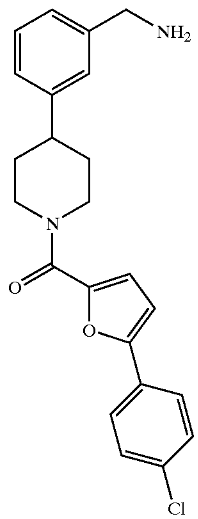 | 395.1 | 100 |
| 135 | 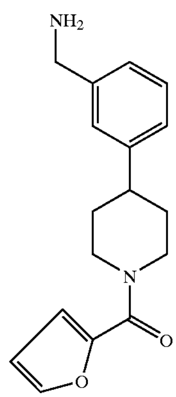 | 285.1 | 100 |
| 136 | 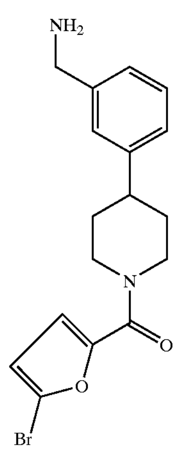 | 363 | 100 |

TABLE 5-continued

| EG | Structure | M/Z | MS area % |
|---|---|---|---|
| 137 | 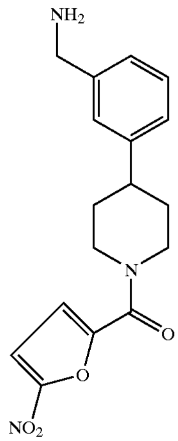 | 330.1 | 100 |
| 138 | 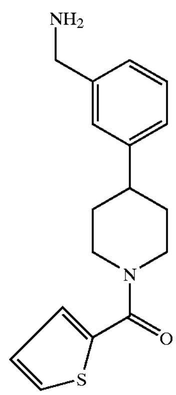 | 301.1 | 100 |
| 139 | 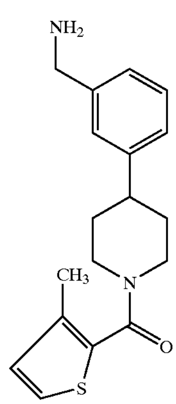 | 315.1 | 100 |

TABLE 5-continued
| EG | Structure | M/Z | MS area % |
|---|---|---|---|
| 140 | 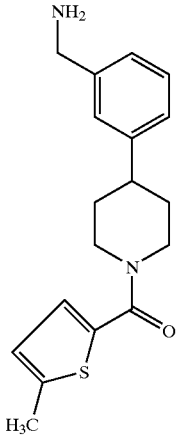 | 315.1 | 100 |
| 141 | 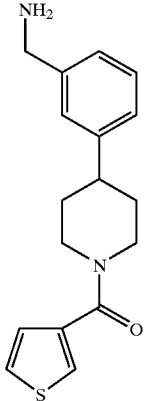 | 301.1 | 100 |
| 142 | 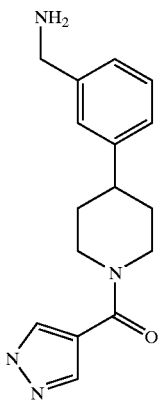 | 285.1 | 79 |

TABLE 5-continued
| EG | Structure | M/Z | MS area % |
|----|-----------|-----|-----------|
| 143 | 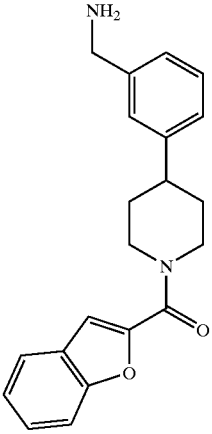 | 335.1 | 100 |
| 144 | 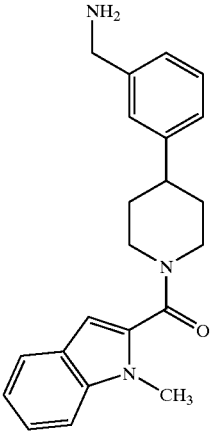 | 348.2 | 100 |
| 145 | 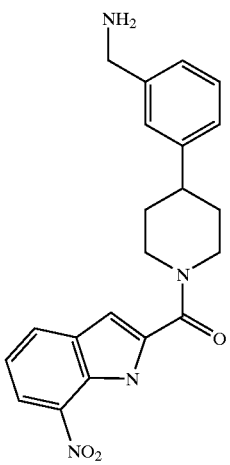 | 379.2 | 100 |

TABLE 5-continued

| EG | Structure | M/Z | MS area % |
|---|---|---|---|
| 146 | 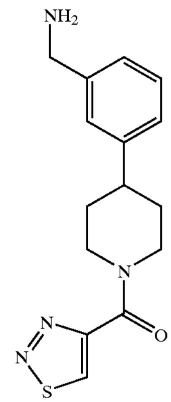 | 303.1 | 100 |
| 147 | 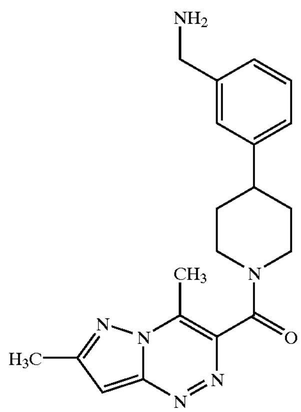 | 365.2 | 100 |
| 148 | 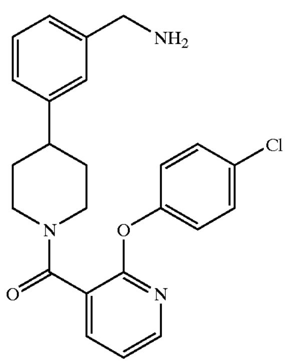 | 422.2 | 100 |
| 149 | 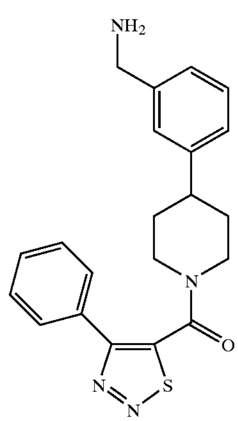 | 379.2 | 99 |

TABLE 5-continued
| EG | Structure | M/Z | MS area % |
|---|---|---|---|
| 150 | 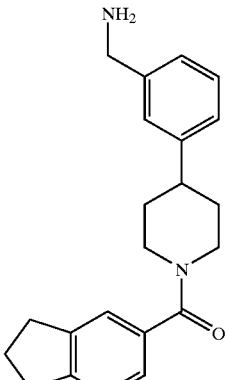 | 337.2 | 99 |
| 151 | 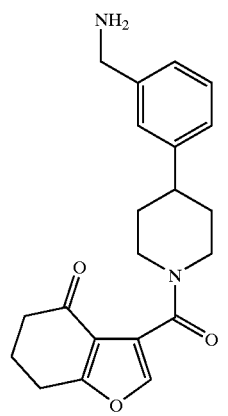 | 353.3 | 100 |
| 152 | 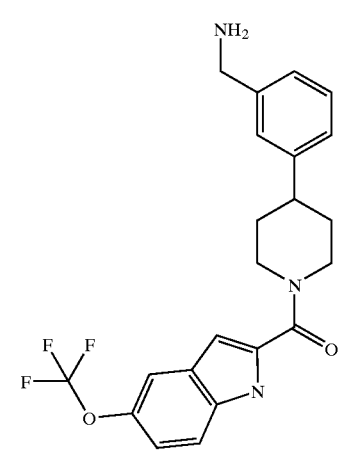 | 418.2 | 99 |

TABLE 5-continued

| EG | Structure | M/Z | MS area % |
|---|---|---|---|
| 153 | 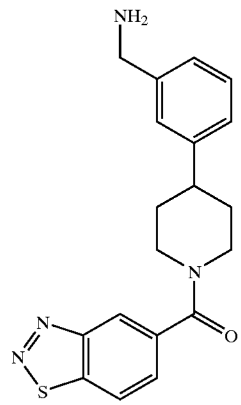 | 353.2 | 99 |
| 154 | 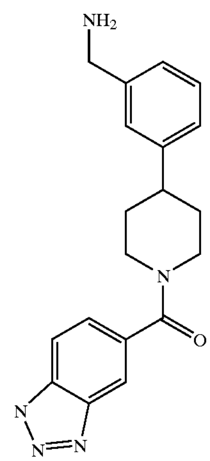 | 336.3 | 89 |
| 155 | 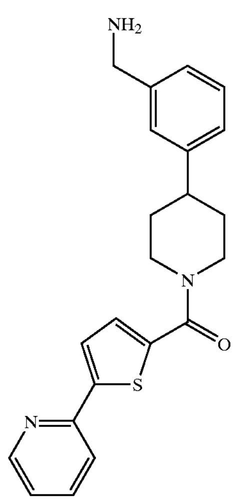 | 378.2 | 61 |

TABLE 5-continued
| EG | Structure | M/Z | MS area % |
|---|---|---|---|
| 156 | 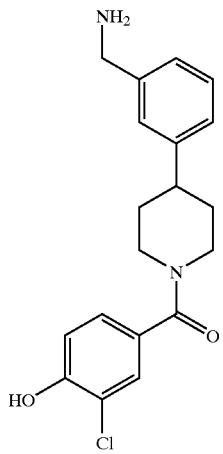 | 345.2 | 100 |
| 157 | 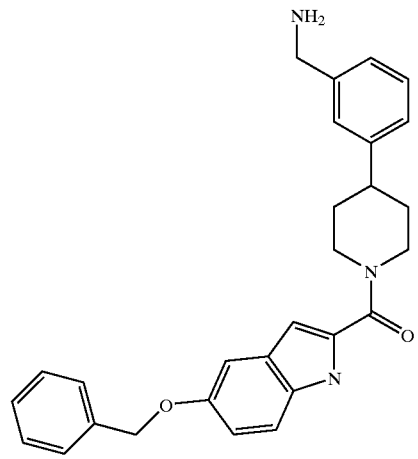 | 440.3 | 100 |
| 158 | 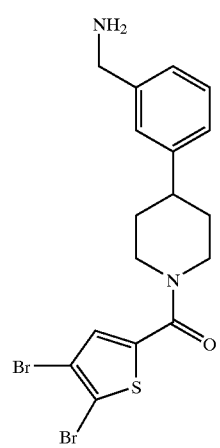 | 459 | 100 |

TABLE 5-continued
| EG | Structure | M/Z | MS area % |
|---|---|---|---|
| 159 | 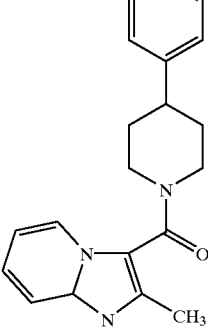 | 305.2 | 100 |
| 160 | 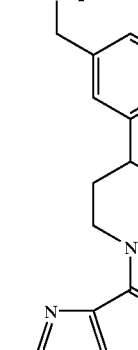 | 379.2 | 80 |
| 161 | 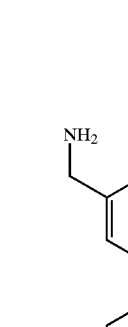 | 364.2 | 100 |

TABLE 5-continued

| EG | Structure | M/Z | MS area % |
|---|---|---|---|
| 162 | 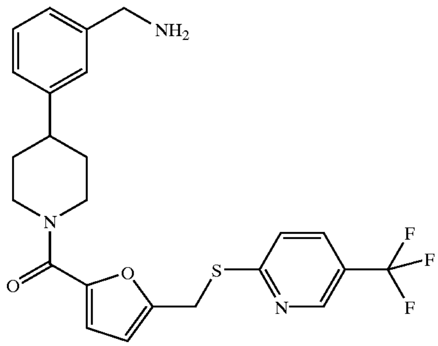 | 476.2 | 100 |
| 163 | 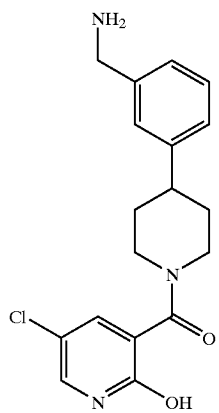 | 346.2 | 100 |
| 164 | 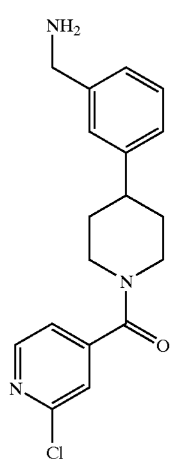 | 330.2 | 100 |

TABLE 5-continued

| EG | Structure | M/Z | MS area % |
|----|-----------|-----|-----------|
| 165 | 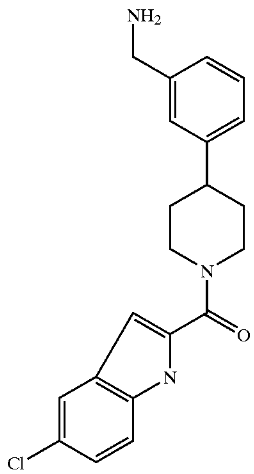 | 368.2 | 100 |
| 166 | 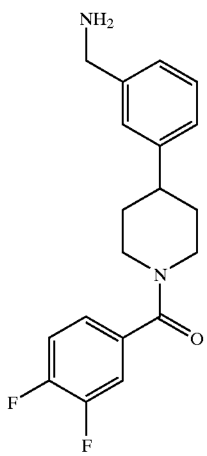 | 331.2 | 100 |
| 167 | 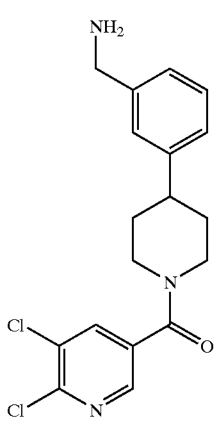 | 364.2 | 100 |

TABLE 5-continued
| EG | Structure | M/Z | MS area % |
|----|-----------|-----|-----------|
| 168 | 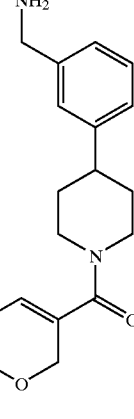 | 387.2 | 100 |
| 169 | 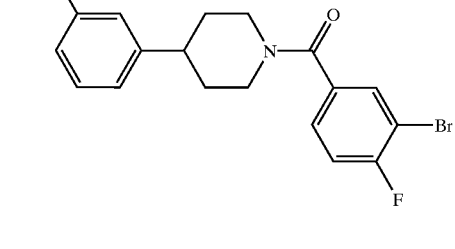 | 391 | 94 |
| 170 | 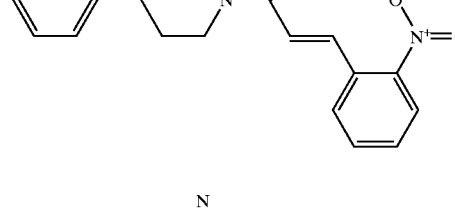 | 366.1 | 95 |
| 171 | 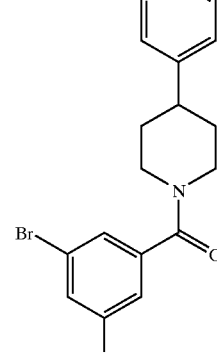 | 498.9 | 100 |

TABLE 5-continued
| EG | Structure | M/Z | MS area % |
|----|-----------|-----|-----------|
| 172 | 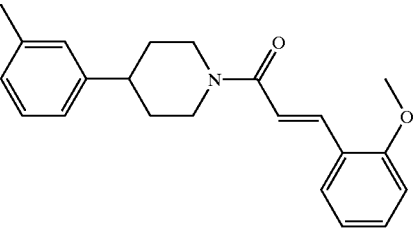 | 351.2 | 66 |
| 173 | 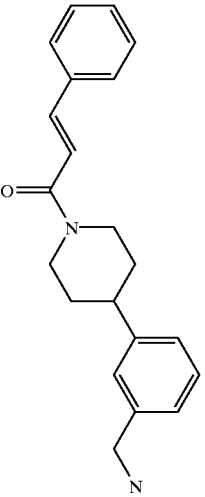 | 321.2 | 100 |
| 174 | 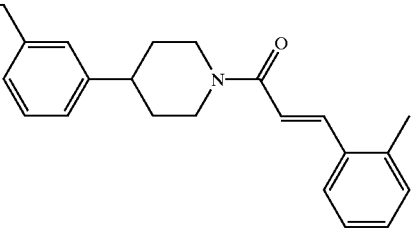 | 335.2 | 100 |
| 175 | 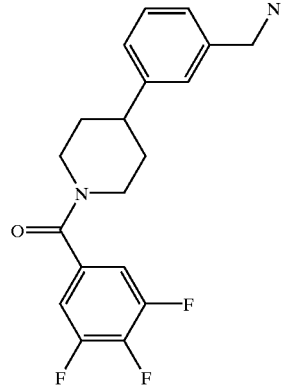 | 349.1 | 100 |

TABLE 5-continued
| EG | Structure | M/Z | MS area % |
|---|---|---|---|
| 176 | 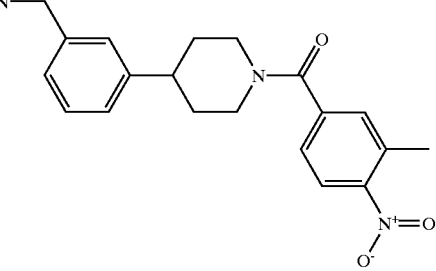 | 354.2 | 100 |
| 177 | 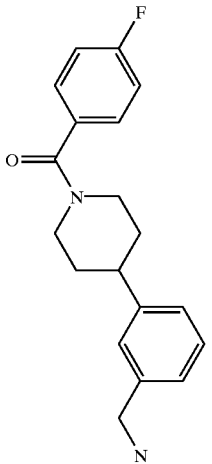 | 313.1 | 100 |
| 178 | 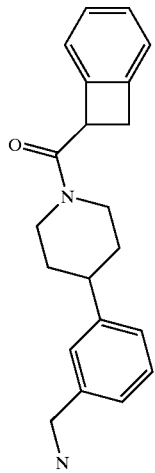 | 321.2 | 84 |
| 179 | 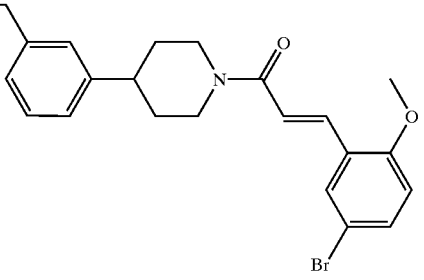 | 429.1 | 81 |

TABLE 5-continued

| EG | Structure | M/Z | MS area % |
|---|---|---|---|
| 180 | 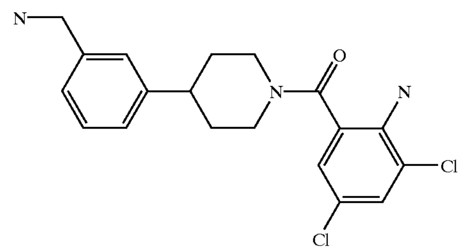 | 378.1 | 100 |
| 181 | 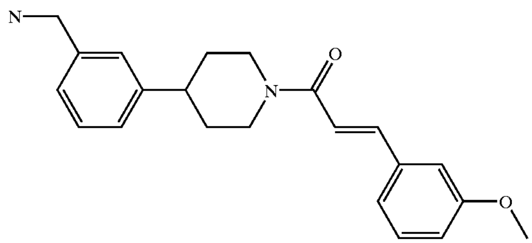 | 351.2 | 100 |
| 182 | 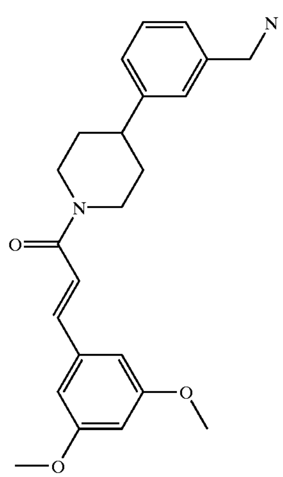 | 381.2 | 85 |
| 183 | 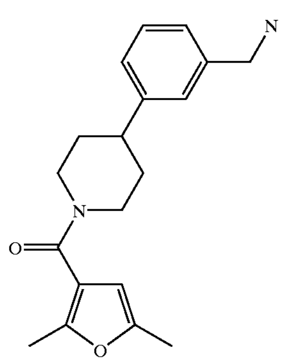 | 313.2 | 100 |

TABLE 5-continued
| EG | Structure | M/Z | MS area % |
|----|-----------|-----|-----------|
| 184 | 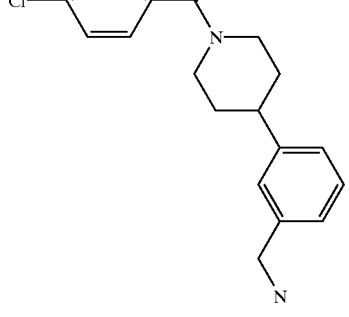 | 374.1 | 100 |
| 185 | 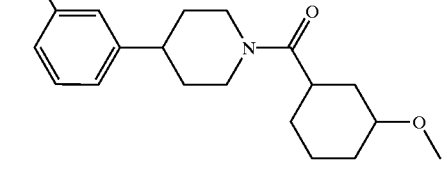 | 331.2 | 100 |
| 186 | 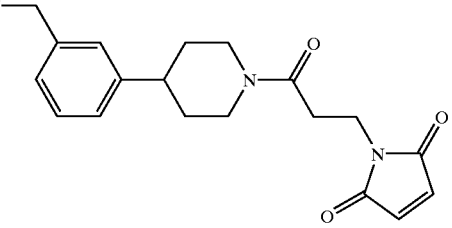 | 342 | 84 |
| 187 | 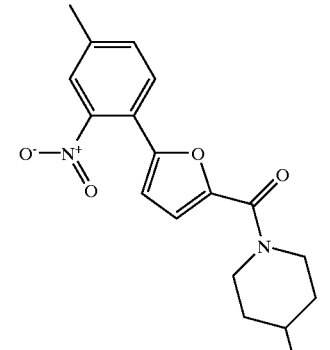 | 420.1 | 100 |

TABLE 5-continued

| EG | Structure | M/Z | MS area % |
|---|---|---|---|
| 188 | 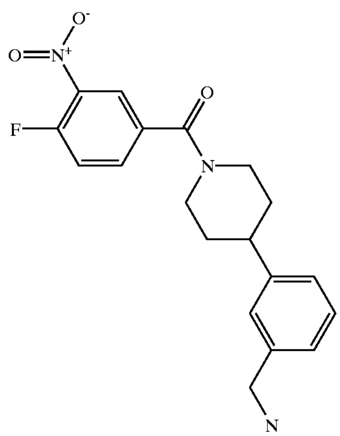 | 358.1 | 100 |
| 189 | 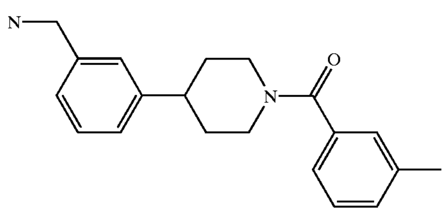 | 309.1 | 100 |
| 190 | 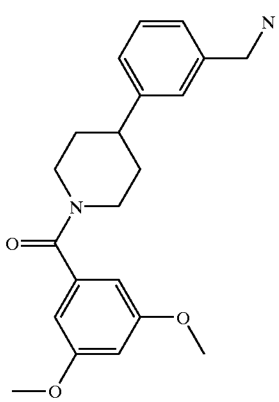 | 355.2 | 100 |
| 191 | 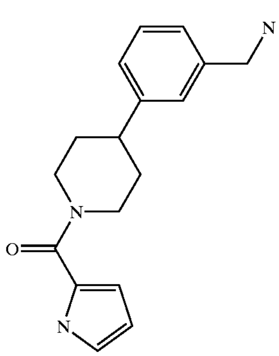 | 284.2 | 100 |

TABLE 5-continued
| EG | Structure | M/Z | MS area % |
|---|---|---|---|
| 192 | 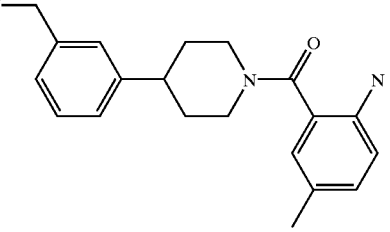 | 324.2 | 81 |
| 193 | 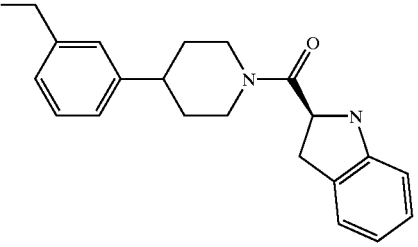 | 336.2 | 19 |
| 194 | 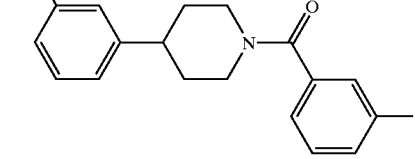 | 313.1 | 95 |
| 195 | 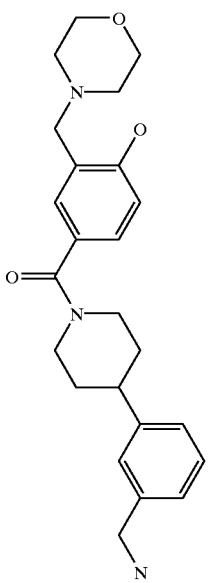 | 220.1 | 89 |

TABLE 5-continued

| EG | Structure | M/Z | MS area % |
|---|---|---|---|
| 196 | 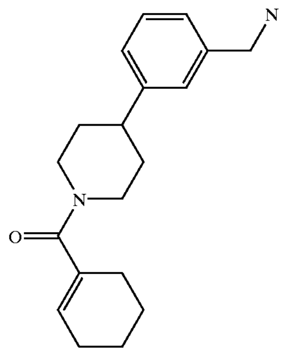 | 299.2 | 100 |
| 197 | 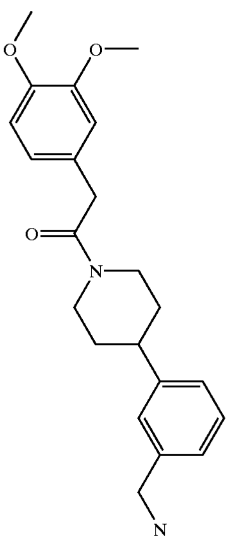 | 369.2 | 100 |
| 198 | 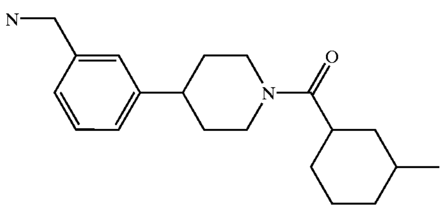 | 315.2 | 100 |
| 199 | 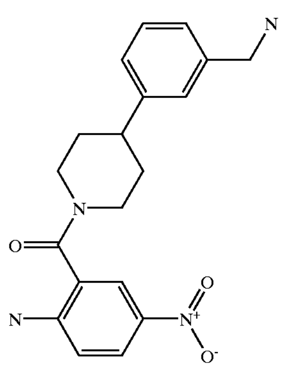 | 355.1 | 92 |

TABLE 5-continued
| EG | Structure | M/Z | MS area % |
|---|---|---|---|
| 200 | 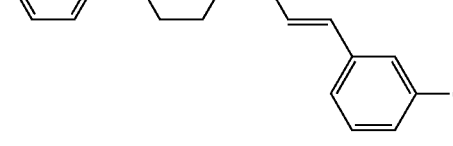 | 331.2 | 100 |
| 201 | 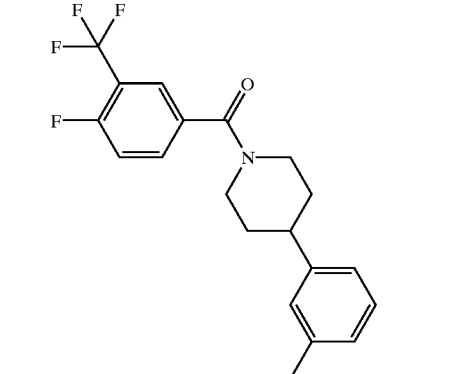 | 327.2 | 100 |
| 202 | 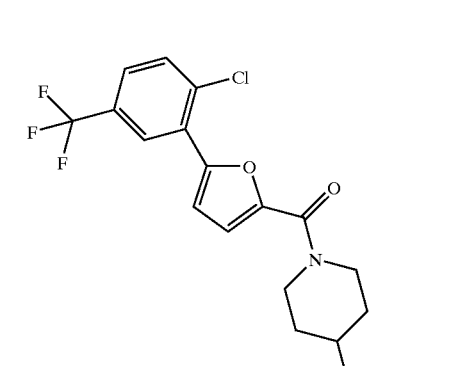 | 463.1 | 100 |

TABLE 5-continued

| EG | Structure | M/Z | MS area % |
|---|---|---|---|
| 203 | 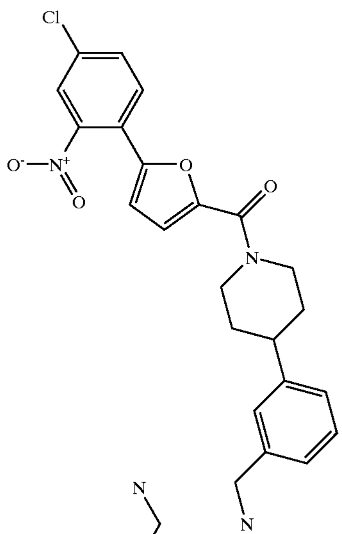 | 440.1 | 94 |
| 204 | 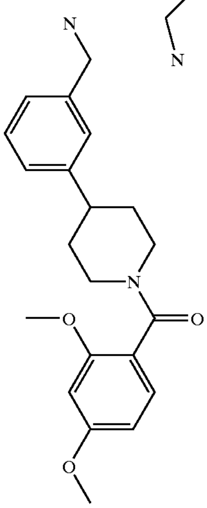 | 355.2 | 100 |
| 205 | 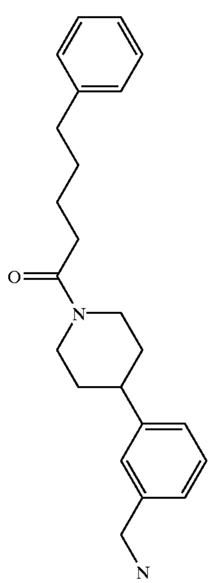 | 351.2 | 100 |

TABLE 5-continued

| EG | Structure | M/Z | MS area % |
|---|---|---|---|
| 206 | 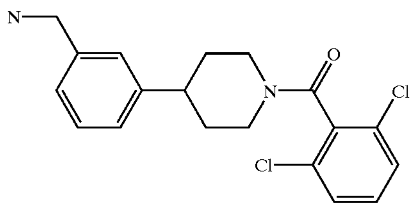 | 363.1 | 100 |
| 207 | 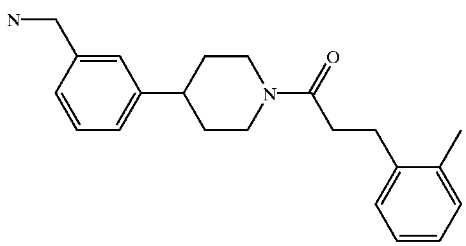 | 337.2 | 100 |
| 208 | 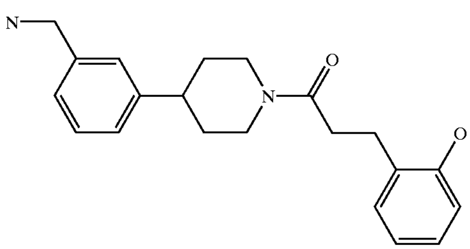 | 339.2 | 54 |
| 209 | 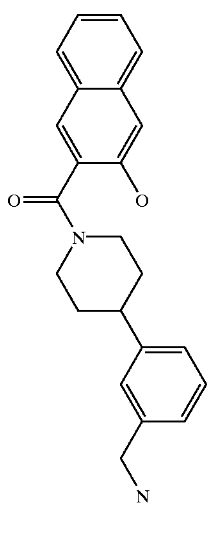 | 361.2 | 65 |
| 220 | 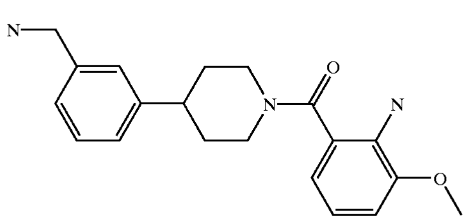 | 340.2 | 97 |

TABLE 5-continued
| EG | Structure | M/Z | MS area % |
|---|---|---|---|
| 211 | 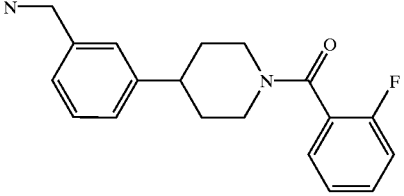 | 313.2 | 100 |
| 212 | 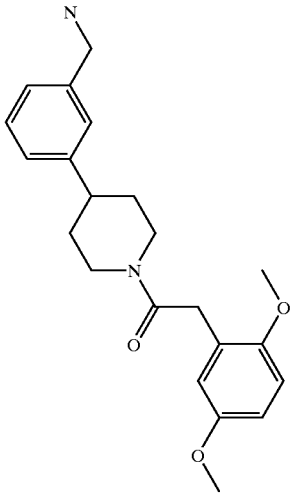 | 369.2 | 100 |
| 213 | 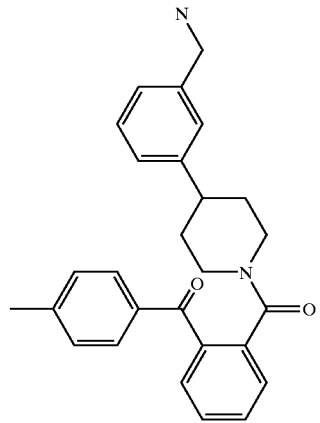 | 413.1 | 100 |

TABLE 5-continued
| EG | Structure | M/Z | MS area % |
|---|---|---|---|
| 214 | 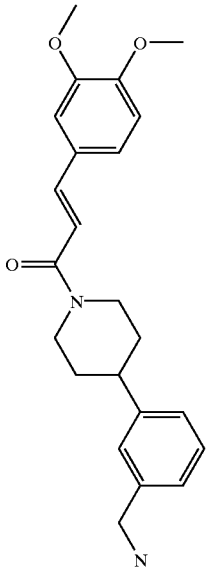 | 381.2 | 62 |
| 215 | 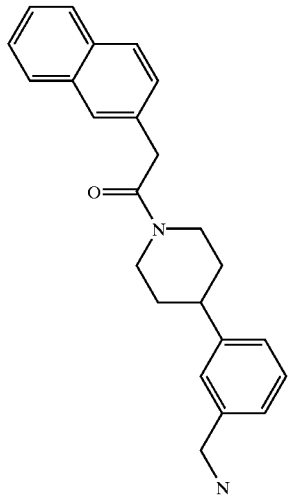 | 359.2 | 94 |
| 216 | 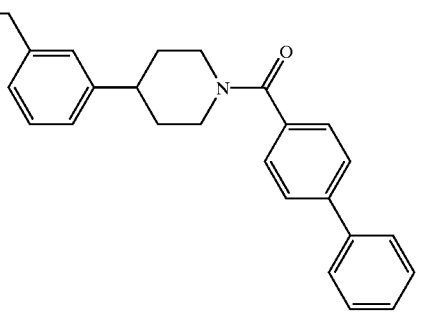 | 371.1 | 100 |

TABLE 5-continued

| EG | Structure | M/Z | MS area % |
|----|-----------|-----|-----------|
| 217 | 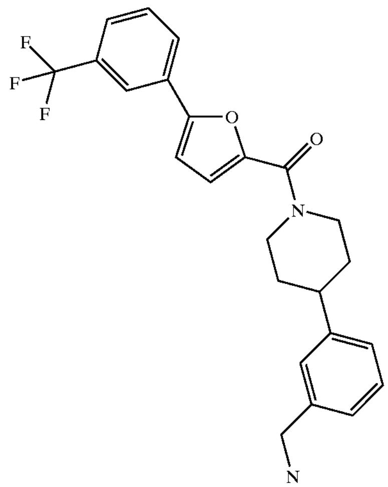 | 429.1 | 100 |
| 218 | 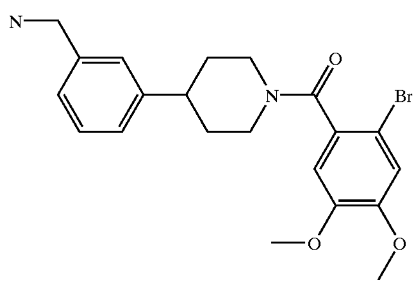 | 433.1 | 100 |
| 219 | 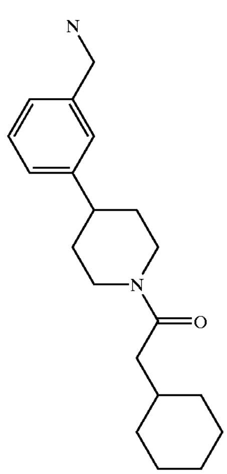 | 315.2 | 100 |

TABLE 5-continued
| EG | Structure | M/Z | MS area % |
|---|---|---|---|
| 220 | 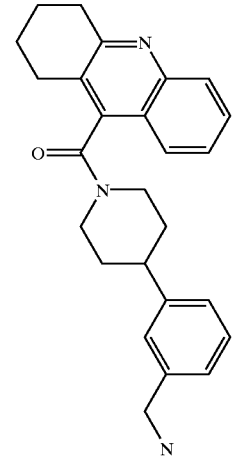 | 400.2 | 100 |
| 221 | 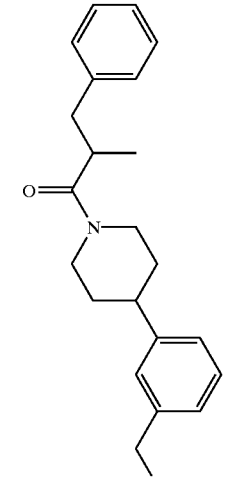 | 337.2 | 100 |
| 222 | 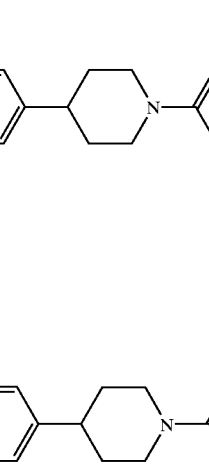 | 375.1 | 100 |
| 223 | 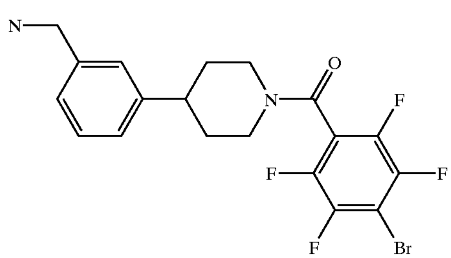 | 445 | 100 |

TABLE 5-continued
| EG | Structure | M/Z | MS area % |
|---|---|---|---|
| 224 | 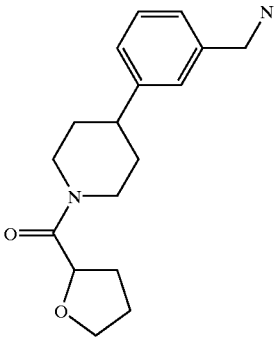 | 289.1 | 100 |
| 225 | 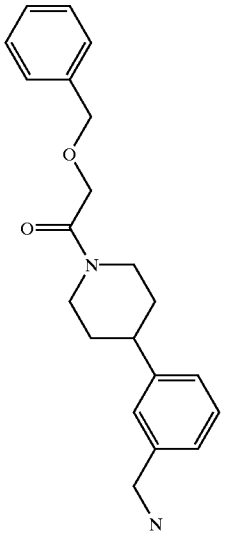 | 339.2 | 100 |
| 226 | 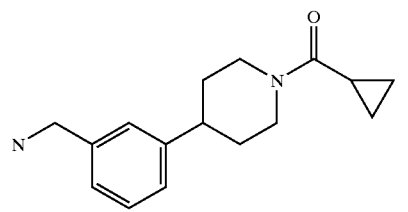 | 259.2 | 100 |
| 227 | 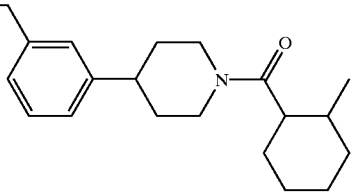 | 315.2 | 100 |

TABLE 5-continued

| EG | Structure | M/Z | MS area % |
|----|-----------|-----|-----------|
| 228 | 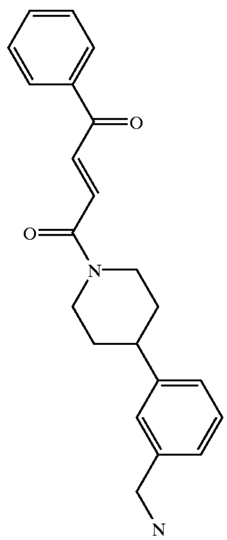 | 349.2 | 86 |
| 229 | 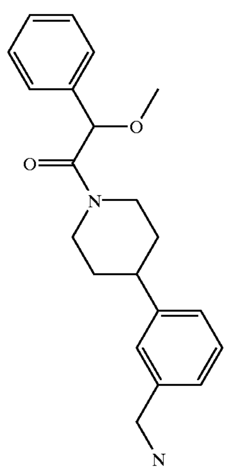 | 339.3 | 100 |
| 230 | 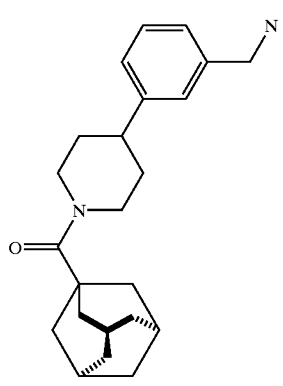 | 353.3 | 100 |

TABLE 5-continued
| EG | Structure | M/Z | MS area % |
|---|---|---|---|
| 231 | 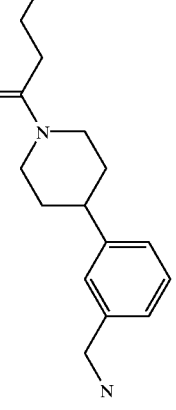 | 329.3 | 100 |
| 232 | 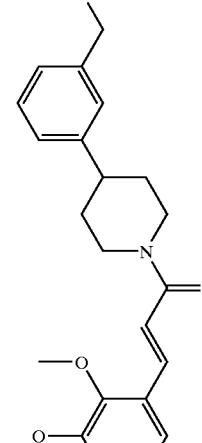 | 381.2 | 93 |
| 233 | 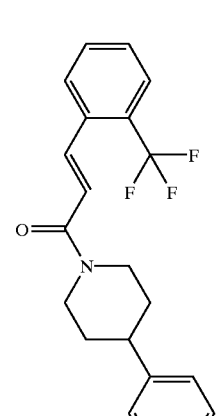 | 389.2 | 94 |

TABLE 5-continued

| EG | Structure | M/Z | MS area % |
|---|---|---|---|
| 234 | 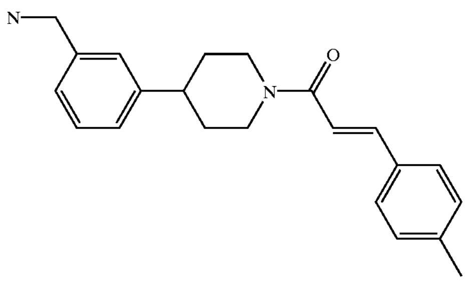 | 335.2 | 100 |
| 235 | 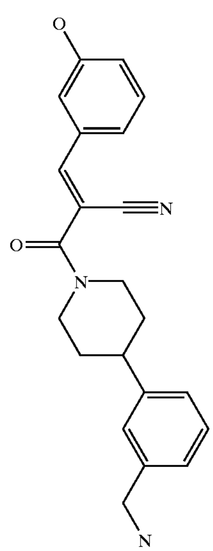 | 362.2 | 71 |
| 236 | 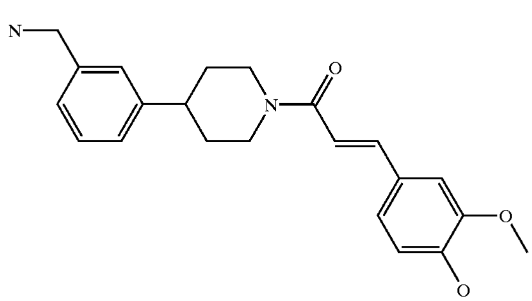 | 367.2 | 100 |

TABLE 5-continued

| EG | Structure | M/Z | MS area % |
|---|---|---|---|
| 237 | 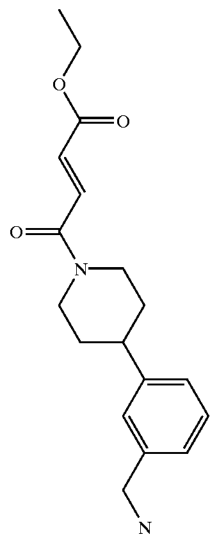 | 317.2 | 100 |
| 238 | 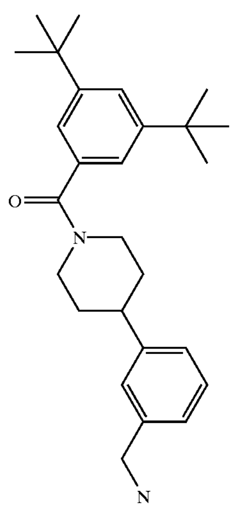 | 407.3 | 100 |
| 239 | 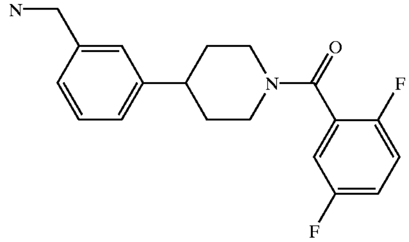 | 331.2 | 100 |

TABLE 5-continued

| EG | Structure | M/Z | MS area % |
|---|---|---|---|
| 240 | 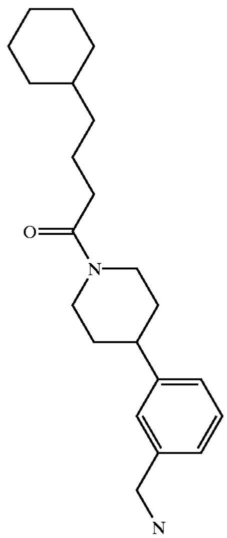 | 343.3 | 100 |
| 241 | 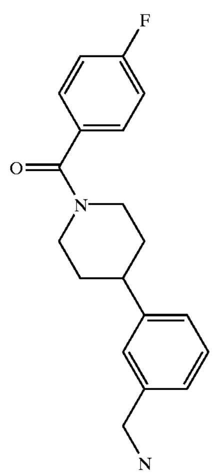 | 313.2 | 100 |
| 242 | 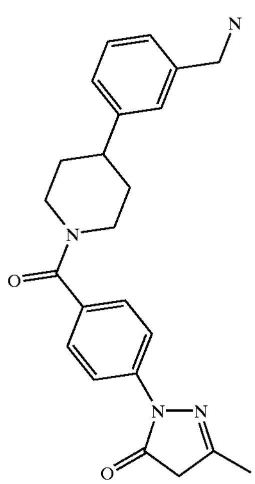 | 391.3 | 100 |

TABLE 5-continued
| EG | Structure | M/Z | MS area % |
|---|---|---|---|
| 243 | 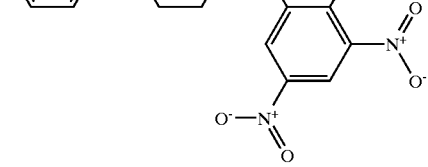 | 399.2 | 100 |
| 244 | 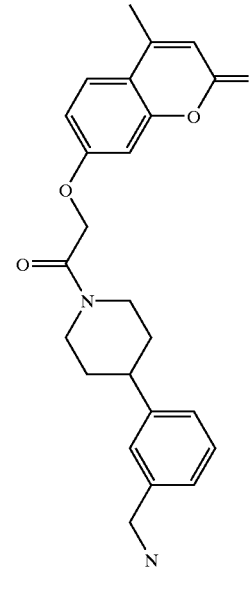 | 407.2 | 100 |
| 245 | 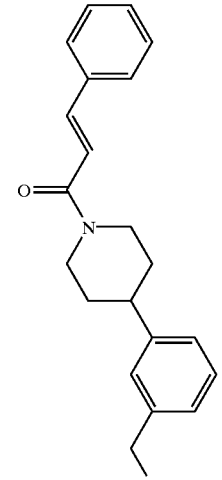 | 321.2 | 100 |

TABLE 5-continued
| EG | Structure | M/Z | MS area % |
|---|---|---|---|
| 246 | 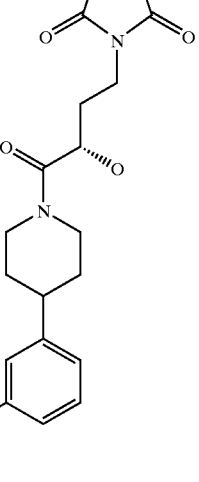 | 422.3 | 88 |
| 247 | 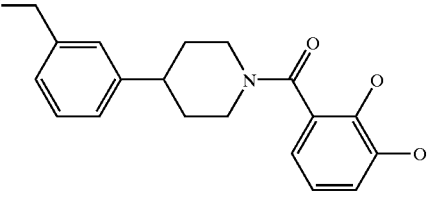 | 327.2 | 100 |
| 248 | 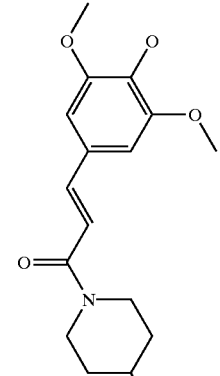 | 397.3 | 91 |

TABLE 5-continued

| EG | Structure | M/Z | MS area % |
|---|---|---|---|
| 249 | 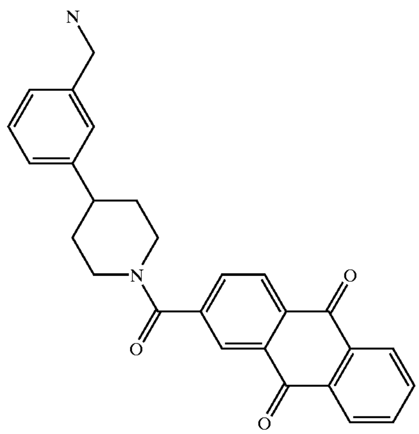 | 425.2 | 80 |
| 250 | 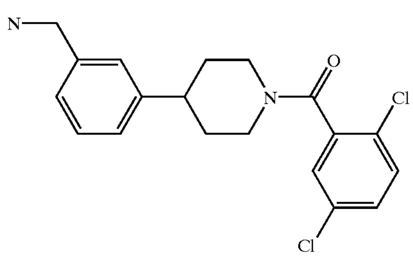 | 363.1 | 100 |
| 251 | 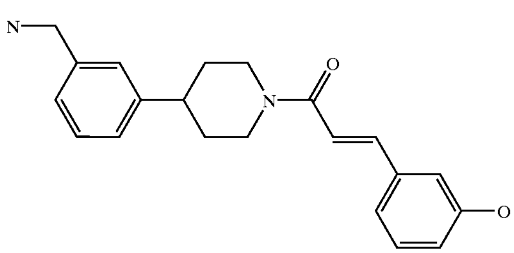 | 337.2 | 90 |
| 252 | 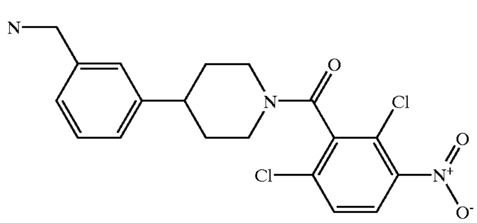 | 408.2 | 60 |

TABLE 5-continued
| EG | Structure | M/Z | MS area % |
|---|---|---|---|
| 253 | 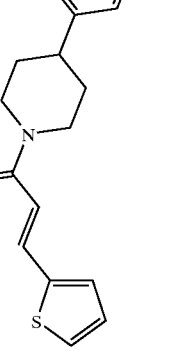 | 327.2 | 96 |
| 254 | 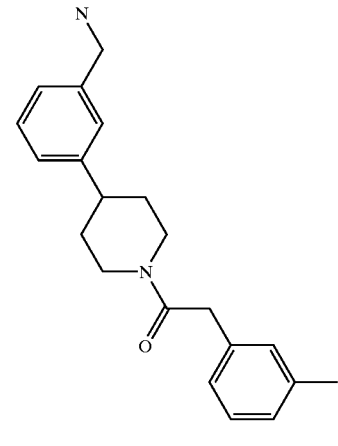 | 323.2 | 100 |
| 255 | 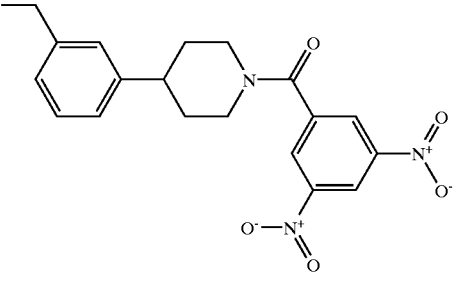 | 385.2 | 100 |
| 256 | 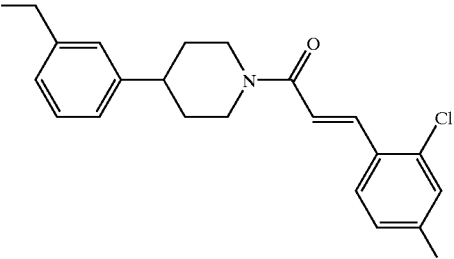 | 389.2 | 100 |

TABLE 5-continued

| EG | Structure | M/Z | MS area % |
|---|---|---|---|
| 257 | 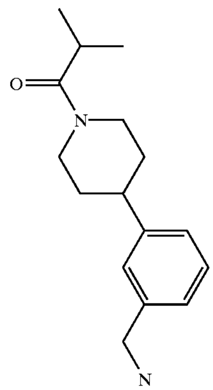 | 261.2 | 100 |
| 258 | 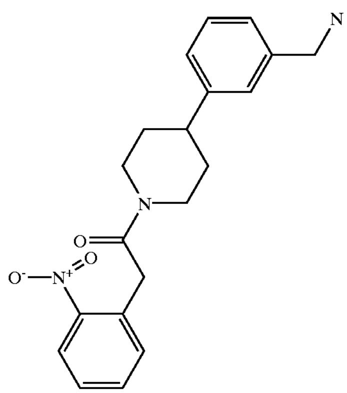 | 354.2 | 100 |
| 259 | 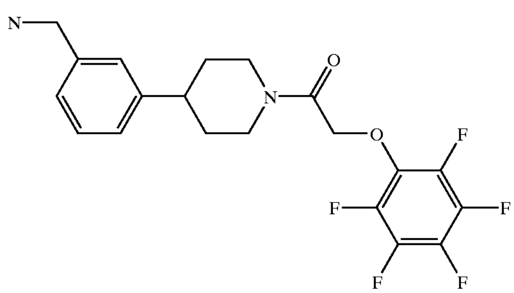 | 415.2 | 100 |
| 260 | 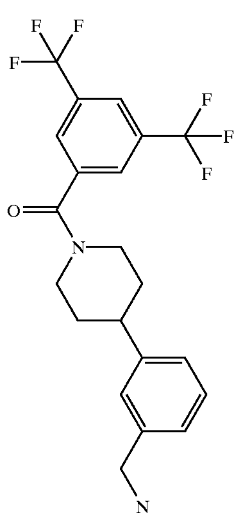 | 431.2 | 100 |

TABLE 5-continued
| EG | Structure | M/Z | MS area % |
|---|---|---|---|
| 261 | 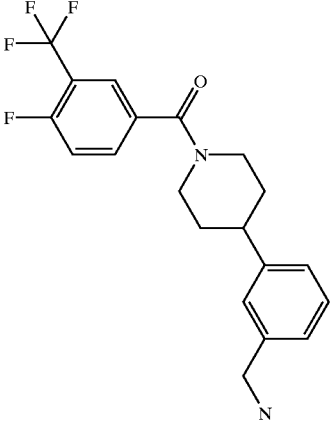 | 381.2 | 91 |
| 262 | 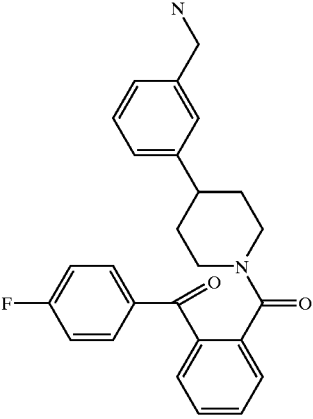 | 417.2 | 100 |
| 263 | 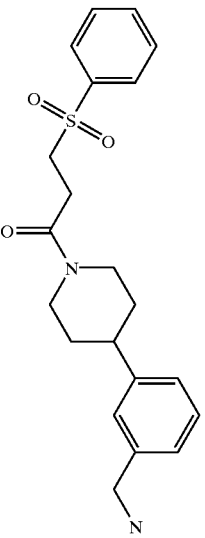 | 387.2 | 100 |

TABLE 5-continued

| EG | Structure | M/Z | MS area % |
|---|---|---|---|
| 264 | 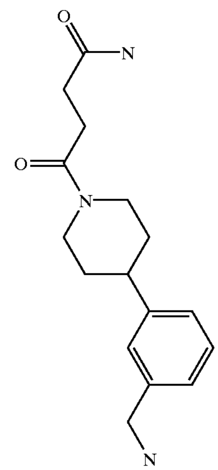 | 290.2 | 100 |
| 265 | 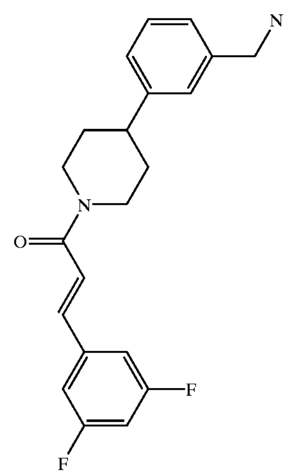 | 357.2 | 100 |
| 266 | 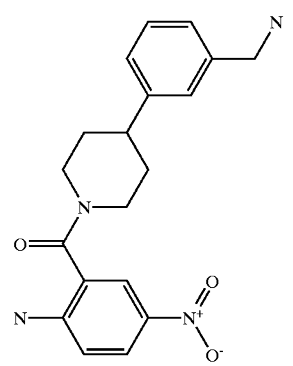 | 355.2 | 91 |
| 267 | 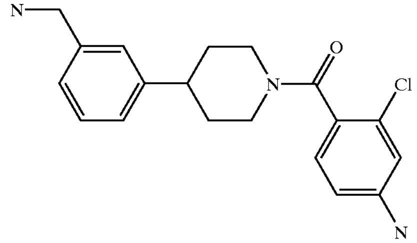 | 344.2 | 83 |

TABLE 5-continued
| EG | Structure | M/Z | MS area % |
|---|---|---|---|
| 268 | 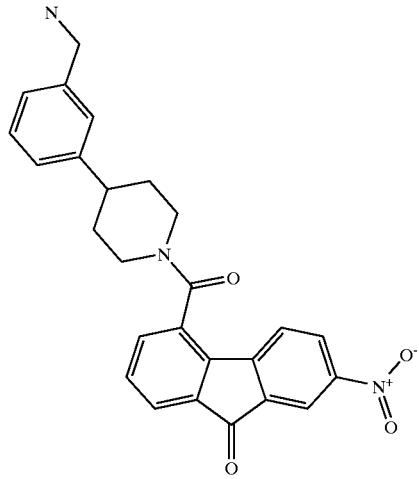 | 442.2 | 100 |
| 269 | 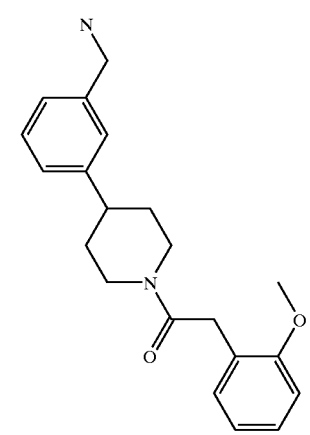 | 339.2 | 100 |
| 270 | 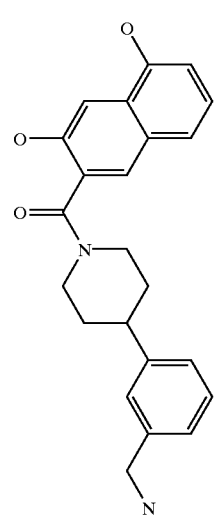 | 377.3 | 78 |

TABLE 5-continued

| EG | Structure | M/Z | MS area % |
|---|---|---|---|
| 271 | 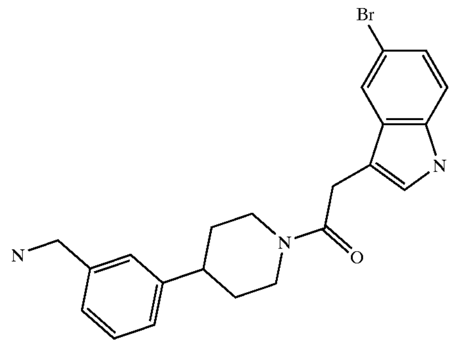 | 428.2 | 44 |
| 272 | 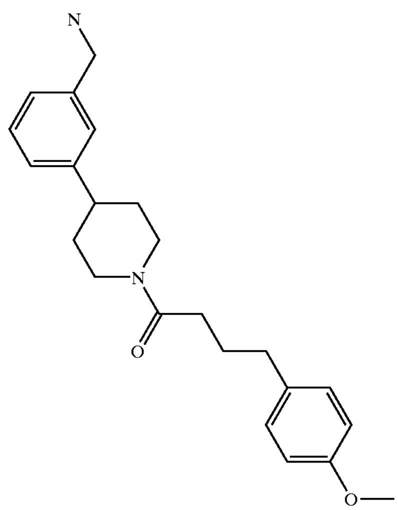 | 367.3 | 100 |
| 273 | 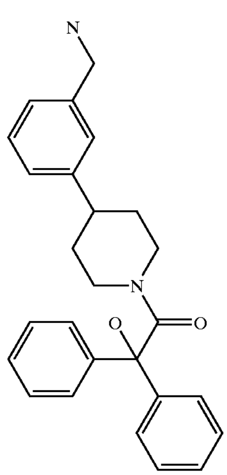 | 383.3 | 100 |

TABLE 5-continued

| EG | Structure | M/Z | MS area % |
|---|---|---|---|
| 274 | 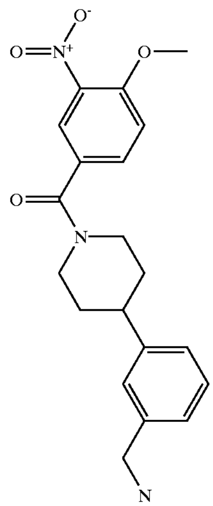 | 370.2 | 100 |
| 275 | 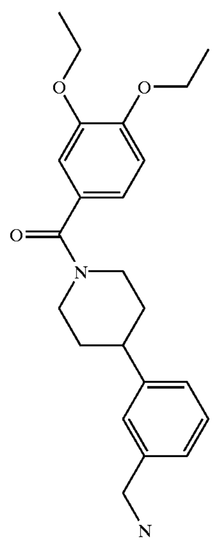 | 383.3 | 100 |
| 276 | 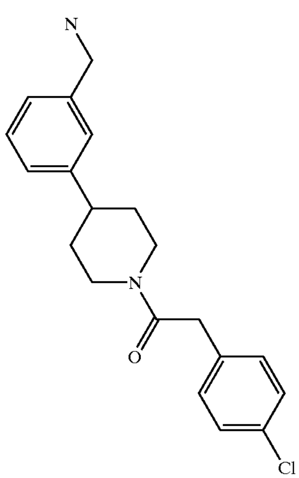 | 343.2 | 95 |

TABLE 5-continued

| EG | Structure | M/Z | MS area % |
|---|---|---|---|
| 277 | 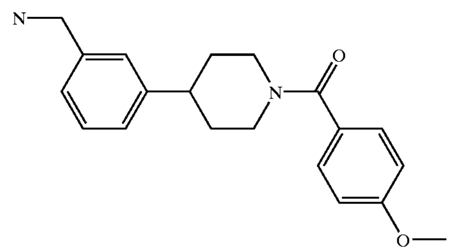 | 325.2 | 100 |
| 278 | 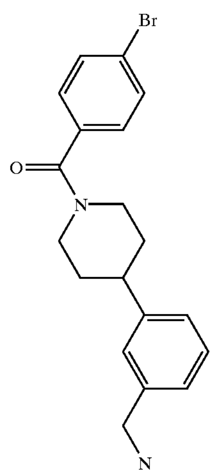 | 373.1 | 100 |
| 279 | 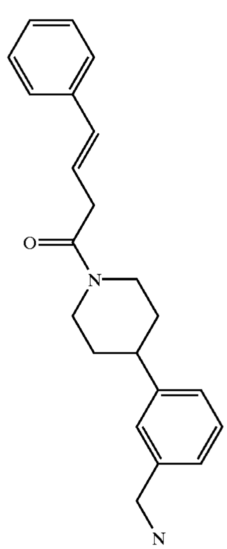 | 335.2 | 100 |

TABLE 5-continued

| EG | Structure | M/Z | MS area % |
|---|---|---|---|
| 280 | *(structure)* | 341.2 | 100 |
| 281 | *(structure)* | 375.2 | 100 |

By proceeding in a similar manner to the method described in EXAMPLE 36, but using the appropriate carboxylic acid derived TFP resin in place of the 3,4-dichlorobenzoic acid TFP resin, the following compounds set forth in Table 6 were prepared as the trifluoroacetate salts:

TABLE 6

| EG | Structure | M/Z | MS area % |
|---|---|---|---|
| 282 | *(structure)* | 273.3 | >95% |
| 283 | *(structure)* | 369.2 | >95% |

TABLE 6-continued

| EG | Structure | M/Z | MS area % |
|---|---|---|---|
| 284 | 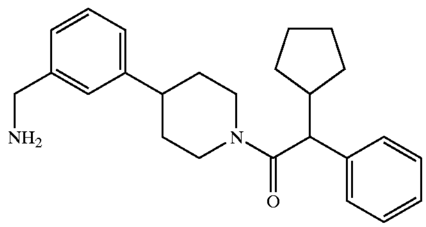 | 377.4 | >95% |
| 285 | 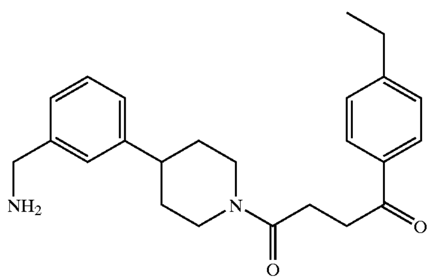 | 379.3 | >95% |
| 286 | 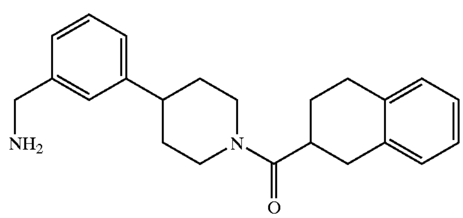 | 349.3 | >95% |
| 287 | 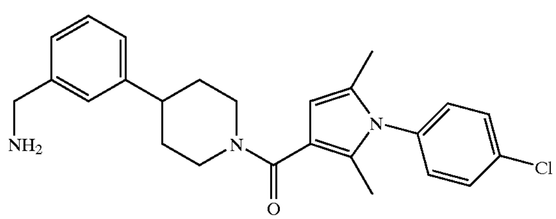 | 422.3, 424.3 | >95% |
| 288 | 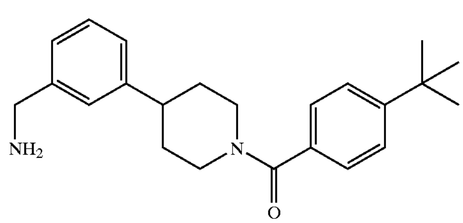 | 351.3 | >95% |
| 289 | 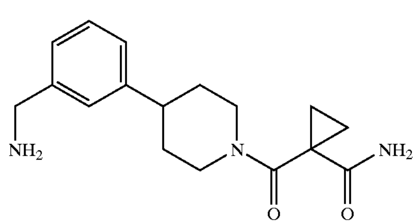 | 302.2 | >95% |

TABLE 6-continued

| EG | Structure | M/Z | MS area % |
|---|---|---|---|
| 290 | 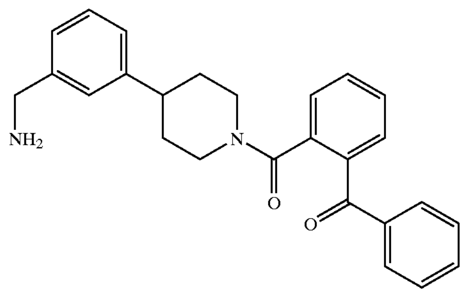 | 399.3 | >95% |
| 291 | 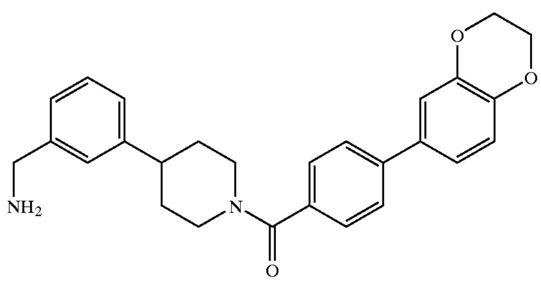 | 429.3 | >95% |
| 292 | 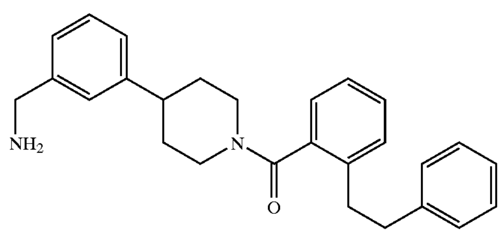 | 399.3 | >95% |
| 293 | 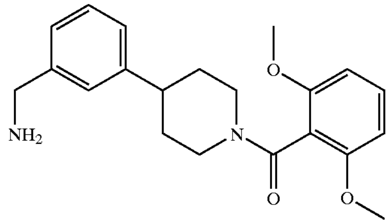 | 355.2 | >95% |
| 294 | 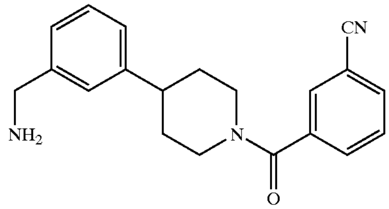 | 320.3 | >95% |
| 295 | 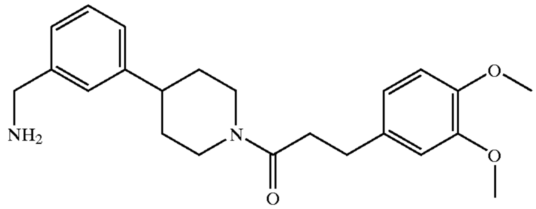 | 383.3 | >95% |

TABLE 6-continued

| EG | Structure | M/Z | MS area % |
|---|---|---|---|
| 296 | 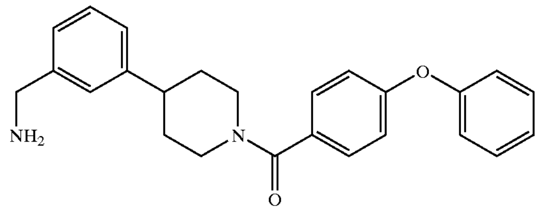 | 387.3 | >95% |
| 297 | 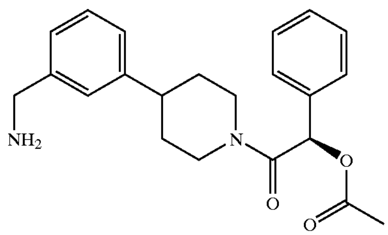 | 367.3 | 85% |
| 298 | 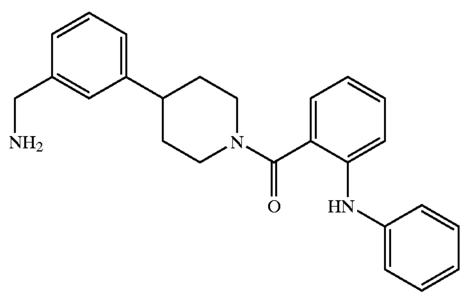 | 386.3 | >95% |
| 299 | 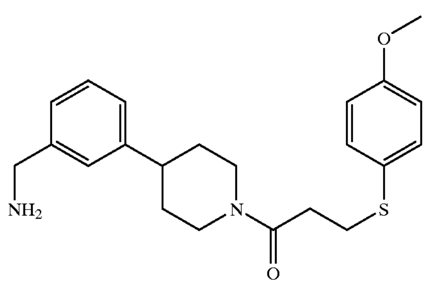 | 385.2 | >95% |
| 300 | 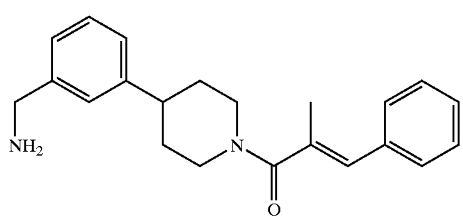 | 335.3 | >95% |
| 301 | 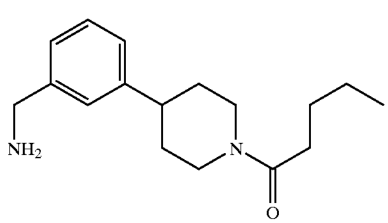 | 275.2 | >95% |

TABLE 6-continued

| EG | Structure | M/Z | MS area % |
|---|---|---|---|
| 302 | 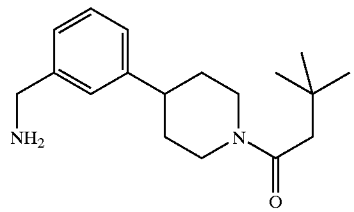 | 289.3 | >95% |
| 303 | 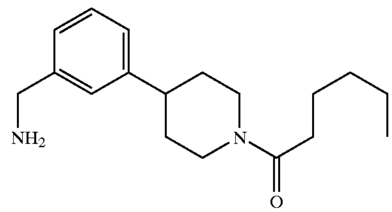 | 289.3 | >95% |
| 304 | 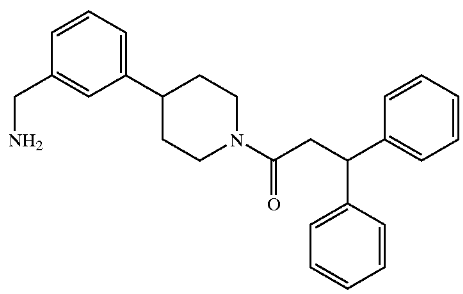 | 399.3 | 90% |
| 305 | 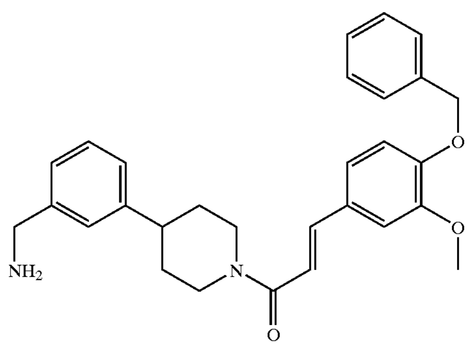 | 457.3 | 60% |
| 306 | 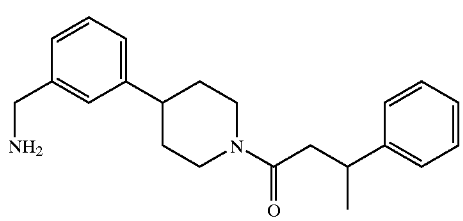 | 337.3 | >95% |
| 307 | 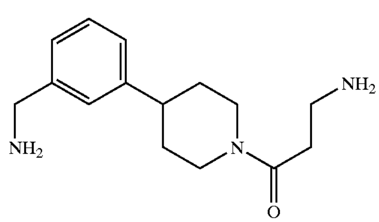 | 262.2 | >95% |

TABLE 6-continued

| EG | Structure | M/Z | MS area % |
|---|---|---|---|
| 308 | 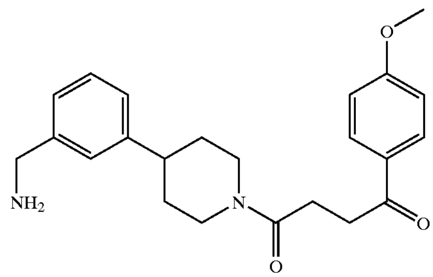 | 381.3 | >95% |
| 309 | 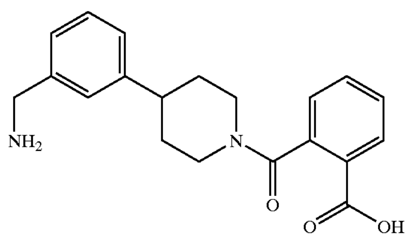 | 339.2 | 75% |
| 310 | 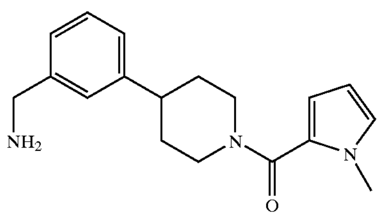 | 298.3 | >95% |
| 311 | 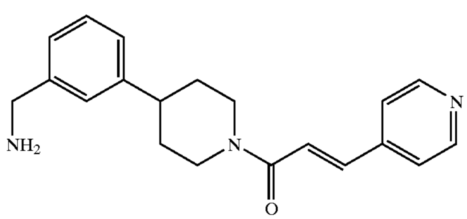 | 322.3 | >95% |
| 312 | 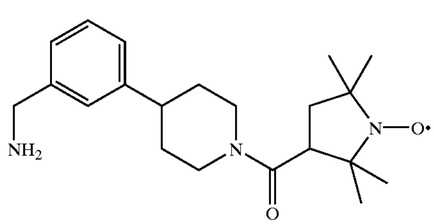 | 359.3, 360.3 | 75% |
| 313 | 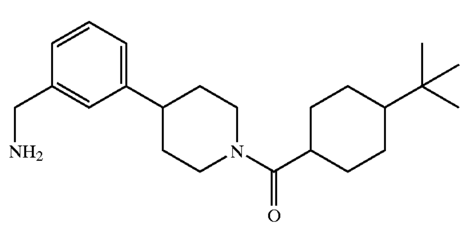 | 357.4 | >95% |

TABLE 6-continued

| EG | Structure | M/Z | MS area % |
|---|---|---|---|
| 314 | 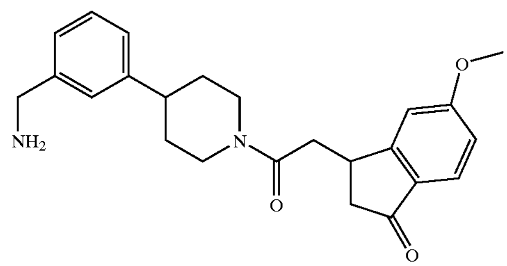 | 393.3 | >95% |
| 315 | 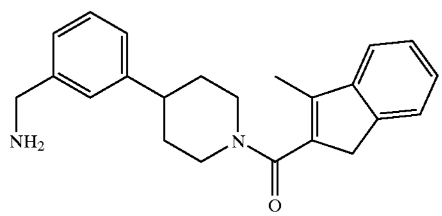 | 347.3 | >95% |
| 316 | 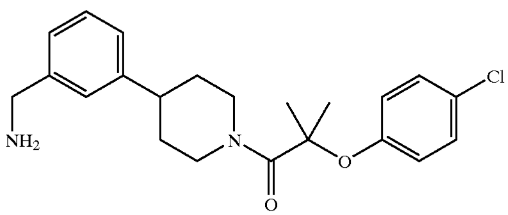 | 387.3, 389.3 | >95% |
| 317 | 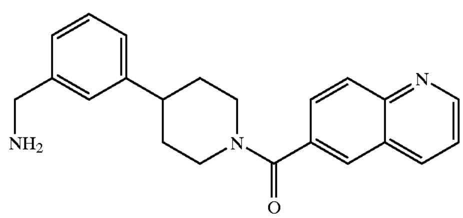 | 346.3 | >95% |
| 318 | 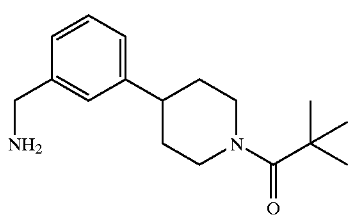 | 275.3 | >95% |
| 319 | 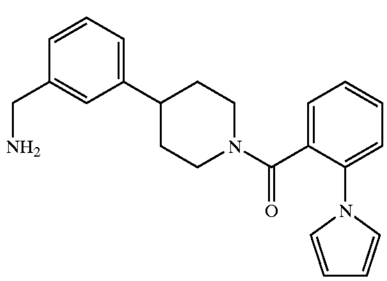 | 360.3 | 90% |

TABLE 6-continued

| EG | Structure | M/Z | MS area % |
|---|---|---|---|
| 320 | 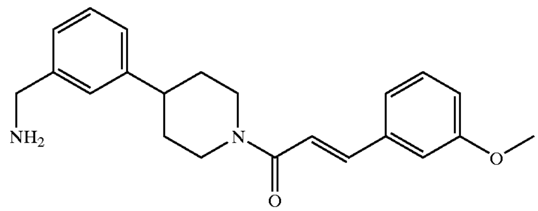 | 351.3 | >95% |
| 321 | 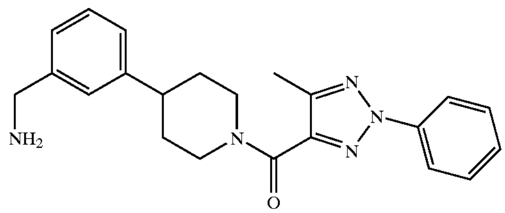 | 376.2 | >95% |
| 322 | 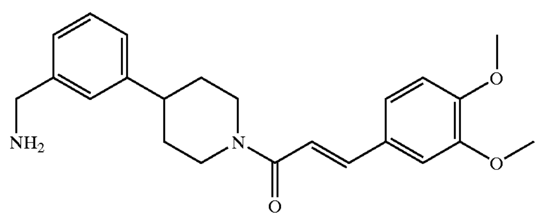 | 381.3 | 90% |
| 323 | 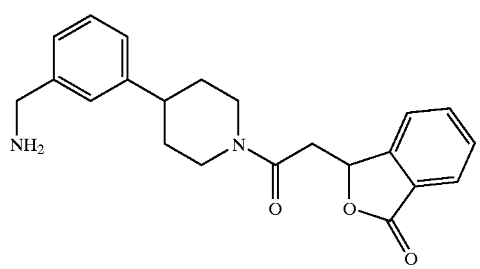 | 365.2 | 65% |
| 324 | 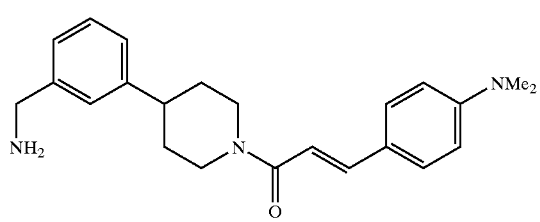 | 364.3 | >95% |
| 325 | 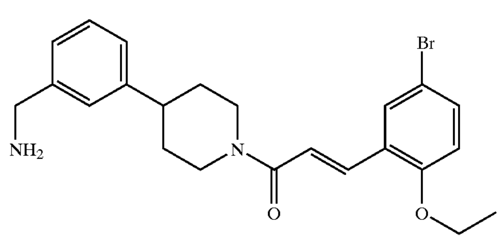 | 443.2, 445.2 | 75% |

TABLE 6-continued

| EG | Structure | M/Z | MS area % |
|---|---|---|---|
| 326 | 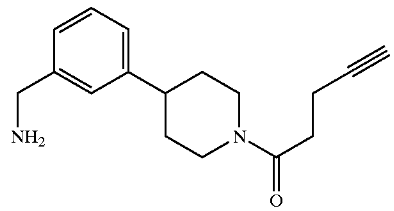 | 271.2 | >95% |
| 327 | 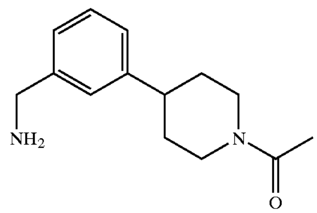 | 233.2 | >95% |
| 328 | 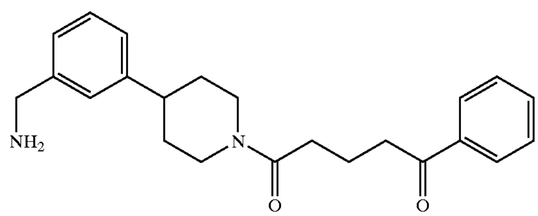 | 365.3 | >95% |
| 329 | 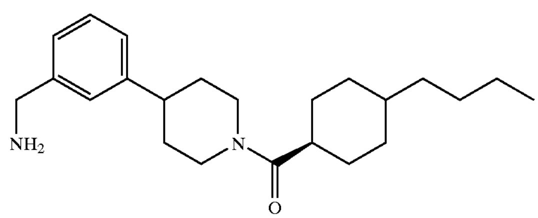 | 357.3 | >95% |
| 330 | 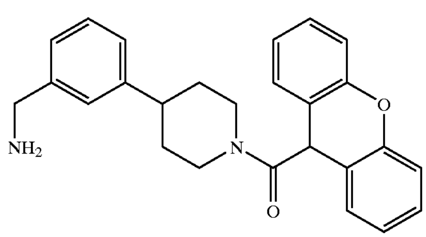 | 399.3 | 70% |
| 331 | 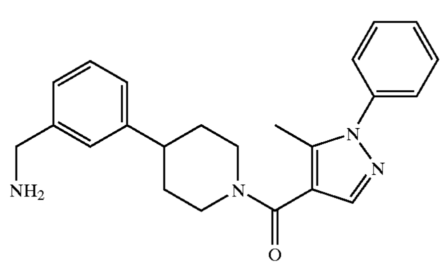 | 375.3 | >95% |

TABLE 6-continued

| EG | Structure | M/Z | MS area % |
|---|---|---|---|
| 332 | 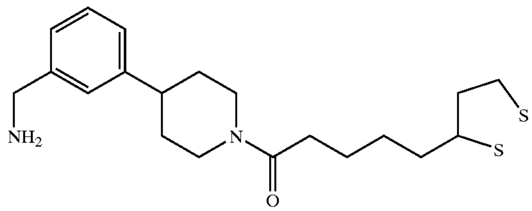 | 379.3 | 80% |
| 333 | 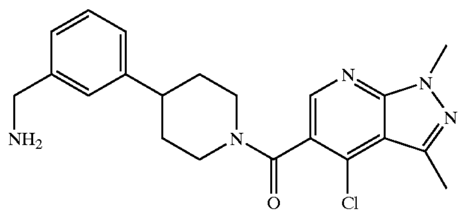 | 398.2, 400.2 | >95% |
| 334 | 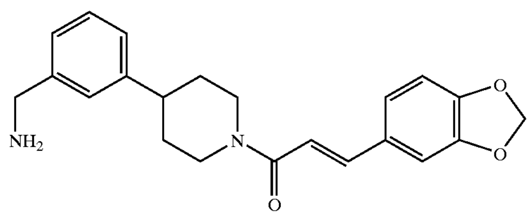 | 365.3 | >95% |
| 335 | 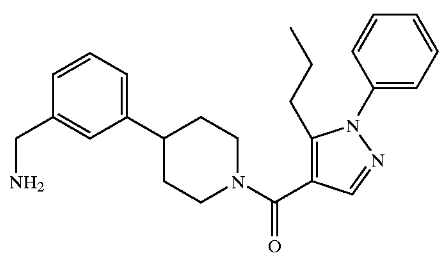 | 403.3 | >95% |
| 336 | 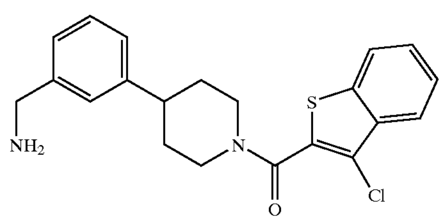 | 385.2, 387.2 | >95% |
| 337 | 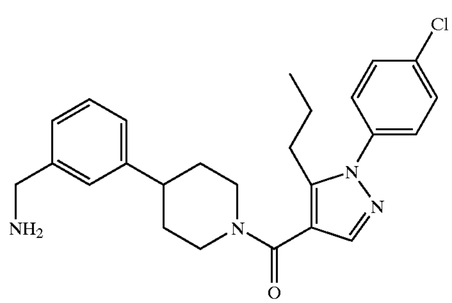 | 437.3, 439.3 | >95% |

TABLE 6-continued
| EG | Structure | M/Z | MS area % |
|---|---|---|---|
| 338 | 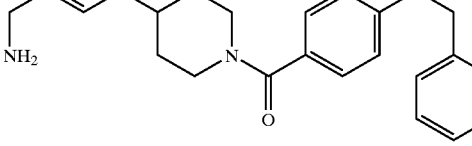 | 401.3 | >95% |
| 339 | 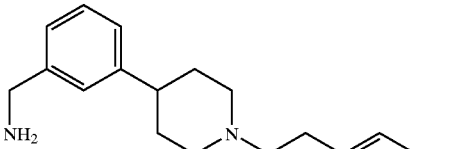 | 352.3 | >95% |
| 340 | 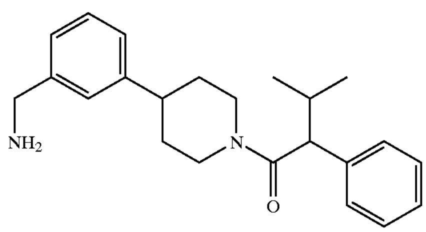 | 351.3 | >95% |
| 341 | 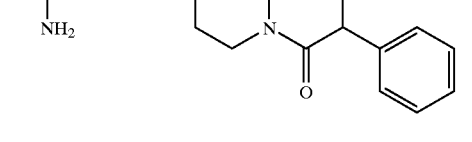 | 349.3 | >95% |
| 342 | 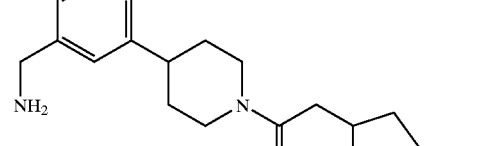 | 341.2 | >95% |
| 343 | 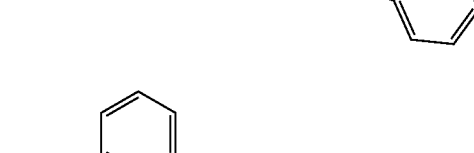 | 357.2 | >95% |

EXAMPLE 344
[4-(3-Aminomethyl-phenyl)-piperidin-1-yl]-[1,1';4',1"] terphenyl-3-yl-methanone hydrochloride A. {4-[3-N,N-Di-(tert-butoxycarbonyl)aminomethyl)-phenyl]-piperidin-1-yl}-(3-bromo-phenyl)-methanone By proceeding in a similar manner to the method described in EXAMPLE 105B, but using 3-bromobenzoic acid in place of 5-tert-butoxycarbonylamino-nicotinic acid, there was prepared {4-[3-(tert-butoxycarbonyl)aminomethyl)-phenyl]-piperidin-1-yl}-(3-bromo-phenyl)-methanone as a colorless oil. MS (CI) m/z 573 (M+H).

B. {4-[3-N,N-Di-(tert-butoxycarbonyl)aminomethyl)-phenyl]-piperidin-1-yl}-[1,1';4',1"]terphenyl-3-yl-methanone By proceeding in a similar manner to the method described in EXAMPLE 17D, but using 4-biphenylboronic acid in place of 1-(5-phenylethyl-pyridine-3-carbonyl)-4-(pinacolatoboronyl)-1,2,3,6-tetrahydro-pyridine and {4-[3-N,N-di-(tert-butoxycarbonyl)aminomethyl)-phenyl]-piperidin-1-yl}-(3-bromo-phenyl)-methanone in place of N-(tert-butoxycarbonyl)-3-bromo-4-fluoro-benzylamine, there was prepared {4-[3-N,N-di-(tert-butoxycarbonyl)aminomethyl)-phenyl-piperidin-1-yl}-[1,1';4',1"]terphenyl-3-yl-methanone as a yellow oil. MS (CI) m/z 647 (M+H).

C. [4-(3-Aminomethyl-phenyl)-piperidin-1-yl]-[1,1';4',1"] terphenyl-3-yl-methanone hydrochloride By proceeding in a similar manner to the method described in EXAMPLE 105D, but using {4-[3-N,N-di-(tert-butoxycarbonyl)aminomethyl)-phenyl]-piperidin-1-yl}-[1,1';4',1"]terphenyl-3-yl-methanone, there was prepared [4-(3-aminomethyl-phenyl)-piperidin-1-yl]-[1,1';4', 1"]terphenyl-3-yl-methanone hydrochloride as a cream-colored solid. MS (CI) m/z 447 (M+H).

EXAMPLE 345
3-[1-(6-Chloroquinoline-3-carbonyl)-piperidin-4-yl]-benzylamine di-hydrochloride A. Ethyl 6-chloroquinoline-3-carboxylate Ethyl 4,6-Dichloroquinoline-3-carboxylate [prepared as described in C. C. Price and R. M. Roberts *J. Amer. Chem. Soc.* 68, 1204 (1964); C. J. Ohnmacht, Jr. *J. Med. Chem.* 14, 17 (1971)](2.0 g, 7.4 mmol) was added portionwise to a solution of sodium borohydride (1.2 g, 31 mmol) in 15 ml of methoxyethanol at about 0° C. The reaction mixture was warmed to room temperature over 3 hours then diluted with ethyl acetate. After standard aqueous workup (dil HCl; saturated NaHCO$_3$) the organic layer was dried (NaSO$_4$) and concentrated to a residue. The residue was exposed to air oxidation (about 14 days) and extracted repeatedly with boiling heptane. The heptane was removed in vacuo to yield ethyl 6-chloroquinoline-3-carboxylate as a beige solid. $^1$H NMR [(CDCl$_3$), 300 MHz]: δ 9.38 (bs, 1H), 8.68 (s, 1H), 8.05 (d, 1H), 7.83 (s, 2H), 7.69 (d, 1H), 4.40 (q, 2H), 1.39 (t, 3H). MS(EI): 236(M$^+$+H).

B. 6-Chloroquinoline-3-carboxylic acid

Ethyl 6-chloroquinoline-3-carboxylate (0.19 g, 0.81 mmol) was saponified by treatment with dioxane (10 ml) and 10% aqueous sodium hydroxide (10 ml) at reflux for 3 hours. The dioxane was removed under vacuo; the aqueous solution remaining was acidified with HCl. The precipitated product was collected and washed with water to isolate 6-chloroquinoline-3-carboxylic acid as an off-white solid (0.14 g, 0.67 mmol). $^1$H NMR [(CD$_3$OD), 300 MHz]: δ 9.35 (s, 1H), 8.95 (s, 1H), 8.17 (s, 1H), 8.1 (d, 2H), 7.87 (d, 1H).

C. N,N-bis-(tert-butoxycarbonyl)-3-[1-(6-chloroquinoline-3-carbonyl)-piperidin-4-yl]benzylamine By proceeding in a similar manner to the method described in EXAMPLE 1C, but using 6-chloroquinoline-3-carboxylic acid in place of 5-phenylethynyl-pyridine-3-carboxylic acid, crude title compound was prepared. The crude product was purified by flash chromatography (25–50% ethyl acetate/Heptane) to yield the title compound as a white amorphous solid. $^1$H NMR[(CDCl$_3$), 300 MHz]: δ 8.98 (bs, 1H), 8.20 (s, M1), 8.05 (d, 1H), 7.88 (s, 1H), 7.72 (d, 1H), 7.08–7.31 (m, 4H), 4.93 (br m, 1H), 4.78 (s, 2H), 3.90 (br m, 1H), 3.27 (br m, 1H), 3.95 (br m, 1H), 2.82 (m, 1H), 1.6–2.1 (br m, 4H), 1.47 (s, 18H).

D. 3-[1-(6-Chloroquinoline-3-carbonyl)-piperidin-4-yl]-benzylamine

N,N-bis-(tert-butoxycarbonyl)-3-[1-(6-Chloroquinoline-3-carbonyl)-piperidin-4-yl]benzylamine (0.055 g, 0.095 mmol) was treated with a solution of 15% trifluoroacetic acid in methylene chloride (5 ml) at 0° C. The reaction was warmed to ambient temperature over 2.5 hr and the solvents were removed in vacuo. The residue was triturated with ether to yield the title compound (0.033 g, 0.087 mmol) as an amorphous solid. $^1$H NMR[(CD$_3$)$_2$SO, 500 MHz]: δ 8.95 (s, 1H), 8.44 (s, 1H), 8.20 (s, 1H), 8.07 (d, 1H), 7.84 (d, 2H), 7.23–7.40 (m, 4H), 4.67 (m, 1H), 7.34 (m, 3H), 4.75 (br m, 1H), 4.05 (m, 2H), 3.75 (br m, 1H), 3.30 (br m, 1H), 2.80–3.00 (br m, 2H), 1.90 (br m, 1H), 1.6–1.8 (br m, 3H). MS(EI): 380(M$^+$+H).

EXAMPLE 346
1-[4-(3-Aminomethyl-phenyl)-piperidin-1-yl]-1-(3-benzylamino-phenyl)-methanone dihydrochloride A. [3-(4-{3-[N,N-Bis-(tert-butoxycarbonyl)amino-methyl]-phenyl}-piperidine-1-carbonyl)-phenyl]-carbamic acid tert-butyl ester By proceeding in a similar manner to the method described in EXAMPLE 105B, but using 3-(Boc-amino) benzoic acid in place of 5-tert-butoxycarbonylamino-nicotinic acid, there was prepared [3-(4-{3-[N,N-bis-(tert-butoxycarbonyl)amino-methyl]-phenyl}-piperidine-1-carbonyl)-phenyl]-carbamic acid tert-butyl ester as a white solid. $^1$H NMR (300 MHz, CDCl3): δ 7.40–7.50 (m, 2H), 7.22–7.37 (m, 2H), 7.04–7.15 (m, 4H), 4.75–4.90 (br m, 1H), 4.76 (s, 2H), 3.80–3.96 (br m, 1H), 3.00–3.25 (br m, 1H), 2.68–2.95 (m, 2H), 1.40–2.05 (m partially obscured, 4H), 1.52 (s, 9H), 1.45 (s, 18H). MS (CI): m/z 610 (M+H).

B. Benzyl-[3-(4-{3-[N,N-Bis-(tert-butoxycarbonyl)amino-methyl]-phenyl}-piperidine-1-carbonyl)-phenyl]-carbamic acid tert-butyl ester By proceeding in a similar manner to the method described in EXAMPLE 105C, but using benzyl bromide in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared benzyl-[3-(4-{3-[N,N-Bis-(tert-butoxycarbonyl)amino-methyl]-phenyl}-piperidine-1-carbonyl)-phenyl]-carbamic acid tert-butyl ester as a white solid. $^1$H NMR (300 MHz, CDCl$_3$): δ 7.03–7.34 (m, 13H), 4.75–4.90 (m partially obscured, 1H), 4.84 (br s, 2H), 4.77 (s, 2H), 3.69–3.85 (br m, 1H), 2.90–3.10 (br m, 1H), 2.65–2.90 (m, 2H), 1.40–2.00 (m partially obscured, 4H), 1.45 (s, 18H), 1.41 (s, 9H). MS (CI): m/z 700 (M+H).

C. 1-[4-(3-Aminomethyl-phenyl)-piperidin-1-yl]-1-(3-benzylamino-phenyl)-methanone dihydrochloride By proceeding in a similar manner to the method described in EXAMPLE 105D, but using prepared benzyl-[3-(4-{3-[N,N-Bis-(tert-butoxycarbonyl)amino-methyl]-phenyl}-piperidine-1-carbonyl)-phenyl]-carbamic acid tert-butyl ester, there was prepared 1-[4-(3-aminomethyl-phenyl)-piperidin-1-yl]-1-(3-benzylamino-phenyl)-methanone dihydrochloride as a white solid. $^1$H NMR [300 MHz, (CD$_3$)$_2$SO]: δ 8.26 (br s, 3H), 7.20–7.55 (m, 9H), 7.11

(tr, 1H), 6.66 (d, 1H), 6.57 (m, 2H), 4.40–4.70 (br m, 1H), 4.30 (s, 2H), 4.15 (m, 1H), 4.01 (q, 2H), 2.90–3.15 (br m, 1H), 2.65–2.90 (br m, 2H), 1.35–1.95 (br m, 4H). MS (ESI): m/z 400 (M+H).

EXAMPLE 347

1-{4-(3-Aminomethyl-phenyl)-piperidin-1-yl]-1-{3-[(naphthalen-2-ylmethyl)-amino]-phenyl}-methanone dihydrochloride A. [3-(4-{3-[N,N-Bis-(tert-butoxycarbonyl)amino-methyl]-phenyl}-piperidine-1-carbonyl)-phenyl]-naphthalen-2-ylmethyl-carbamic acid tert-butyl ester By proceeding in a similar manner to the method described in EXAMPLE 105C, but using 2-(bromomethyl) naphthalene in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared [3-(4-{3-[N,N-bis-(tert-butoxycarbonyl)amino-methyl]-phenyl}-piperidine-1-carbonyl)-phenyl]-naphthalen-2-ylmethyl-carbamic acid tert-butyl ester as a white solid. $^1$H NMR (300 MHz, CDCl$_3$): δ 7.61–7.80 (m, 4H), 7.38–7.45 (m, 3H), 6.99–7.34 (m, 8H), 5.00 (br s, 2H), 4.70–4.90 (m partially obscured, 1H), 4.76 (s, 2H), 3.55–3.75 (br m, 1H), 2.70–2.95 (br m, 2H), 2.55–2.70 (m, 1H), 1.40–1.95 (m partially obscured, 4H), 1.45 (s, 18H), 1.42 (s, 9H). MS (ESI): m/z 650 (M+H).

B. 1-{4-(3-Aminomethyl-phenyl)-piperidin-1-yl]-1-{3-[(naphthalen-2-ylmethyl)-amino]-phenyl}-methanone dihydrochloride By proceeding in a similar manner to the method described in EXAMPLE 105D, but using [3-(4-{3-[N,N-Bis-(tert-butoxycarbonyl)amino-methyl]-phenyl}-piperidine-1-carbonyl)-phenyl]-naphthalen-2-ylmethyl-carbamic acid tert-butyl ester, there was prepared 1-{4-(3-aminomethyl-phenyl)-piperidin-1-yl]-1-{3-[(naphthalen-2-ylmethyl)-amino]-phenyl}-methanone dihydrochloride as a white solid. $^1$H NMR [300 MHz, (CD$_3$)$_2$SO]: δ 8.22 (br s, 3H), 7.81–7.88 (m, 4H), 7.11–7.54 (m, 8H), 6.69 (d, 1H), 6.59 (s, 1H), 6.54 (d, 1H), 4.45–4.65 (m partially obscured, 1H), 4.47 (s, 2H), 4.01 (q, 2H), 3.60–3.80 (m partially obscured, 1H), 2.85–3.05 (br m, 1H), 2.65–2.85 (br m, 2H), 1.30–1.95 (br m, 4H). MS (ESI): m/z 450 (M+H).

EXAMPLE 348

3-[(3-{1-[4-(3-Aminomethyl-phenyl)-piperidin-1-yl]-methanoyl}-phenylamino)-methyl]-benzonitrile dihydrochloride A. [3-(4-{3-[N,N-Bis-(tert-butoxycarbonyl)amino-methyl]-phenyl}-piperidine-1-carbonyl)-phenyl]-(3-cyano-benzyl)-carbamic acid tert-butyl ester By proceeding in a similar manner to the method described in EXAMPLE 105C, but using α-bromo-m-tolunitrile in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared [3-(4-{3-[N,N-bis-(tert-butoxycarbonyl)amino-methyl]-phenyl}-piperidine-1-carbonyl)-phenyl]-(3-cyano-benzyl)-carbamic acid tert-butyl ester as a white solid. $^1$H NMR (300 MHz, CDCl$_3$): δ 7.06–7.55 (m, 12H), 4.70–4.90 (m partially obscured, 1H), 4.86 (s, 2H), 4.77 (s, 2H), 3.70–3.90 (br m, 1H), 2.95–3.20 (br m, 1H), 2.65–2.95 (br m, 2H), 1.40–2.00 (m partially obscured, 4H), 1.45 (s, 18H), 1.41 (s, 9H). MS (CI): m/z 725 (M+H).

B. 3-[(3-{1-[4-(3-Aminomethyl-phenyl)-piperidin-1-yl]-methanoyl}-phenylamino)-methyl]-benzonitrile dihydrochloride By proceeding in a similar manner to the method described in EXAMPLE 105D, but [3-(4-{3-[N,N-bis-(tert-butoxycarbonyl)amino-methyl]-phenyl}-piperidine-1-carbonyl)-phenyl]-(3-cyano-benzyl)-carbamic acid tert-butyl ester, there was prepared 3-[(3-{1-[4-(3-aminomethyl-phenyl)-piperidin-1-yl]-methanoyl}-phenylamino)-methyl]-benzonitrile dihydrochloride as a white solid. $^1$H NMR [300 MHz, (CD$_3$)$_2$SO]: δ 8.18 (br s, 3H), 7.75 (s, 1H), 7.65 (m, 2H), 7.49 (tr, 1H), 7.21–7.35 (m, 4H), 7.08 (tr, 1H), 6.61 (d, 1H), 6.52 (m, 2H), 4.40–4.70 (br m, 1H), 4.33 (s, 2H), 3.98 (q, 2H), 3.50–3.70 (m partially obscured, 1H), 2.85–3.10 (br m, 1H), 2.65–2.85 (br m, 2H), 1.30–1.90 (br m, 4H). MS (ESI): m/z 425 (M+H).

EXAMPLE 349

1-[4-(3-Aminomethyl-phenyl)-piperidin-1-yl]-1-[3-(4-bromo-benzylamino)-phenyl]-methanone dihydrochloride A. (4-Bromo-benzyl)-[3-(4-{3-[N,N-bis-(tert-butoxycarbonyl)amino-methyl]-phenyl}-piperidine-1-carbonyl)-phenyl]-carbamic acid tert-butyl ester By proceeding in a similar manner to the method described in EXAMPLE 105C, but using 4-bromobenzyl bromide in place of 4-bromo-2-fluorobenzyl bromide and using [3-(4-{3-[N,N-bis-(tert-butoxycarbonyl)amino-methyl]-phenyl}-piperidine-1-carbonyl)-phenyl]-carbamic acid tert-butyl ester, there was prepared (4-bromo-benzyl)-[3-(4-{3-[N,N-bis-(tert-butoxycarbonyl)amino-methyl]-phenyl}-piperidine-1-carbonyl)-phenyl]-carbamic acid tert-butyl ester as a clear oil. $^1$H NMR (300 MHz, CDCl$_3$): δ 7.41 (d, 2H), 7.06–7.38 (m, 8H), 7.10 (d, 2H), 4.70–4.90 (br m, partially obscured, 1H), 4.78 (s, 2H), 4.77 (s, 2H), 4.25–4.45 (br m, 1H), 3.70–3.85 (br m, 1H), 2.90–3.15 (br m, 1H), 2.65–2.90 (br m, 2H), 1.40–2.00 (m partially obscured, 4H), 1.45 (s, 18H), 1.41 (s, 9H). MS (CI): m/z 778 (M+H).

B. 1-[4-(3-Aminomethyl-phenyl)-piperidin-1-yl]-1-[3-(4-bromo-benzylamino)-phenyl]-methanone dihydrochloride By proceeding in a similar manner to the method described in EXAMPLE 105D, but using (4-bromo-benzyl)-[3-(4-{3-[N,N-bis-(tert-butoxycarbonyl)amino-methyl]-phenyl}-piperidine-1-carbonyl)-phenyl]-carbamic acid tert-butyl ester, there was prepared 1-[4-(3-aminomethyl-phenyl)-piperidin-1-yl]-1-[3-(4-bromo-benzylamino)-phenyl]-methanone dihydrochloride as a white solid. $^1$H NMR [300 MHz, (CD$_3$)$_2$SO]: δ 8.28 (br s, 3H), 7.25–7.66 (m, 8H), 7.11 (tr, 1H), 6.64 (d, 1H), 6.55 (m, 2H), 4.45–4.70 (br m, 1H), 4.28 (s, 2H), 4.15 (m, 1H), 4.01 (q, 2H), 2.90–3.15 (br m, 1H), 2.65–2.90 (br m, 2H), 1.30–1.95 (br m, 4H). MS (ESI): m/z 480 (M+H).

EXAMPLE 350

[4-(3-Aminomethyl-phenyl)-piperidin-1-yl]-[1',1';4',1"] terphenyl-3-yl-methanone hydrochloride A. {4-[3-N,N-Di-(tert-butoxycarbonyl)aminomethyl)-phenyl]-piperidin-1-yl}-(3-bromo-phenyl)-methanone By proceeding in a similar manner to the method described in EXAMPLE 105B, but using 3-bromobenzoic acid in place of 5-tert-butoxycarbonylamino-nicotinic acid, there was prepared {4-[3-N,N-di-(tert-butoxycarbonyl) aminomethyl)-phenyl]-piperidin-1-yl}-(3-bromo-phenyl)-methanone as a colorless oil. $^1$H NMR (300 MHz, CDCl$_3$): δ 7.55 (m, 2H), 7.24–7.37 (m, 2H), 7.08–7.16 (m, 4H), 4.75–4.92 (br m, 1H), 4.77 (s, 2H), 3.75–3.90 (br m, 1H), 3.00–3.25 (br m, 1H), 2.70–3.00 (br m, 2H), 1.50–2.00 (m partially obscured, 4H) 1.45 (s, 18H). MS (CI): m/z 573 (M+H).

B. {4-[3-N,N-Di-(tert-butoxycarbonyl)aminomethyl)-phenyl]-piperidin-1-yl}-[1',1';4',1"]terphenyl-3-yl-methanone By proceeding in a similar manner to the method described in EXAMPLE 17D, but using 4-biphenylboronic acid in place of 1-(5-phenylethyl-pyridine-3-carbonyl)-4-(pinacolatoboronyl)-1,2,3,6-tetrahydro-pyridine and {4-[3-N,N-di-(tert-butoxycarbonyl)aminomethyl)-phenyl]-piperidin-1-yl}-(3-bromo-phenyl)-methanone in place of N-(tert-butoxycarbonyl)-3-bromo-4-fluoro-benzylamine, there was prepared {4-[3-N,N-di-(tert-butoxycarbonyl)aminomethyl)-phenyl]-piperidin-1-yl}-[1',1';4',1"]terphenyl-3-yl-methanone as a yellow oil. $^1$H NMR (300 MHz, CDCl$_3$): δ 67.61–7.71 (m, 8H), 7.34–7.53 (m, 6H), 7.14 (m, 3H), 4.80–5.00 (m, 1H), 4.77 (s, 2H), 3.85–4.05 (br m, 1H), 3.00–3.25 (br m, 1H), 2.70–3.00 (br m, 2H), 1.50–2.05 (m, 4H), 1.44 (s, 18H). MS (CI): m/z 647 (M+H).

C. [4-(3-Aminomethyl-phenyl)-piperidin-1-yl]-[1',1';4',1"]terphenyl-3-yl-methanone hydrochloride By proceeding in a similar manner to the method described in EXAMPLE 105D, but using {4-[3-N,N-di-(tert-butoxycarbonyl)aminomethyl)-phenyl]-piperidin-1-yl}-[1',1';4',1"]terphenyl-3-yl-methanone, there was prepared [4-(3-aminomethyl-phenyl)-piperidin-1-yl]-[1',1';4', 1"]terphenyl-3-yl-methanone hydrochloride as a cream-colored solid. $^1$H NMR [300 MHz, (CD$_3$)$_2$SO]: δ 8.24 (br s, 3H), 7.73–7.84 (m, 8H), 7.29–7.61 (m, 9H), 4.55–4.80 (br m, 1H), 4.01 (q, 2H), 3.65–3.85 (br m, 1H), 2.75–3.05 (br m, 2H), 1.50–2.00 (br m, 4H). MS (CI): m/z 447 (M+H).

EXAMPLE 351
4-(3-Aminomethyl-phenyl)-piperidine-1-carboxylic acid (3,4-dichloro-phenyl)-amide trifluoroacetate 3,4-Dichlorophenyl isocyanate (60 mg, 0.319 mmol) was added to a stirring solution of 4-[3-(N,N-di-tert-butoxycarbonyl)aminomethyl)phenyl]piperidine (100 mg, 0.256 mmol) in DCM (5 mL) at room temperature. After 16 hours the reaction was quenched with water (5 mL) and separated, and extracted the aqueous phase with DCM (5 mL). The combined organics were dried over anhydrous sodium sulfate, and concentrated to dryness. The residue was purified by dry flash column chromatography on silica with 50:50, dichloromethane:ethyl acetate. 4-[3-(N,N-di-tert-butoxycarbonylaminomethyl)phenyl]-piperidine-1-carboxylic acid (3,4-dichloro-phenyl)-amide was isolated as a colorless oil, which was dissolved in dichloromethane (25 mL), cooled at 0° C., and treated with trifluoroacetic acid (3 mL). The reaction mixture was stirred at room temperature under nitrogen for 2 hours, and concentrated to dryness in vacuo. The residue was dissolved in 20% acetonitrile/water [containing 0.1% trifluoroacetic acid](9 mL) and purified by preparative reverse-phase HPLC (C-18, 10 micron reverse-phase column), eluting with 10% to 100% acetonitrile/water (containing 0.1% trifluoroacetic acid). The product fractions were combined and the acetonitrile removed in vacuo. The aqueous residue was frozen and lyophilized to give the title compound as an amorphous white solid (68 mg, 53%). $^1$H NMR [(CD$_3$)$_2$SO]: δ 8.82 (s, H, NH); 7.88 (s, H); 7.84 (br s, 3H, NH$_3^+$); 7.46 (s, H); 7.37–7.22 (m, 5H); 4.24 (br d, 2H); 3.99 (s, 2H); 2.89 (br t, 2H); 2.83–2.70 (m, H); 1.82–1.71 (m, 2H); 1.60–1.44 (m, 2H). MS(Ion spray): 378 and 380 (M$^+$+1).

EXAMPLE 352
4-(3-Aminomethyl-phenyl)-piperidine-1-carboxylic acid 2,3-dimethoxybenzylamide-trifluoroacetate (3-Piperidin-4-yl-benzyl) carbamate Wang resin (EXAMPLE 122D) (60 μmol) was suspended in dichloromethane (2 mL) and added diisopropylethylamine (0.66 mmol) followed by phosgene (0.6 mmol of a 20% solution in toluene). The reaction mixture was shaken for 5 minutes before washing the resin with toluene (×8). The resin was suspended in DMF (2 mL) and to this was added a solution of 2,3-dimethoxybenzylamine (0.6 mmol) in DMF (1.5 mL) and the reaction mixture shaken for 5 minutes before washing the resin with DMF (×3). The resin was then suspended in dichloromethane (2 mL) and treated with TFA (0.5 mL). The reaction mixture was shaken for 5 minutes, before the resin was filtered off and the filtrate concentrated to dryness to give the title compound (48 μmol) as a pale yellow solid. MS (EI) 383 (M$^+$).

By proceeding in a similar manner to the method described in EXAMPLES 351 AND 352, the following compounds set forth in Table 7 were prepared, as the trifluoroacetate salts:

TABLE 7

| EG | Structure | M/Z | MS area % |
|---|---|---|---|
| 353 | 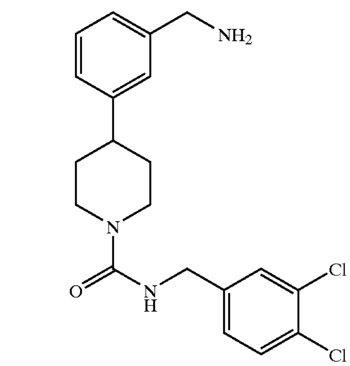 | 391 | >95% |
| 354 | 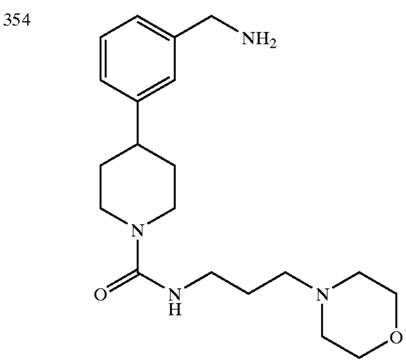 | 360 | >95% |
| 355 | 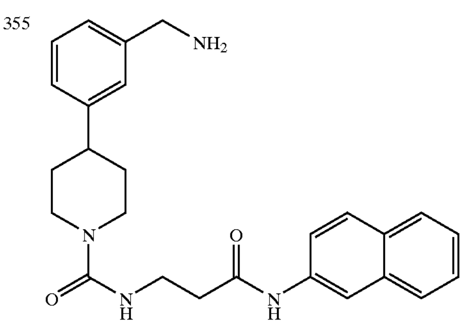 | 430 | >95% |

TABLE 7-continued

| EG | Structure | M/Z | MS area % |
|---|---|---|---|
| 356 | 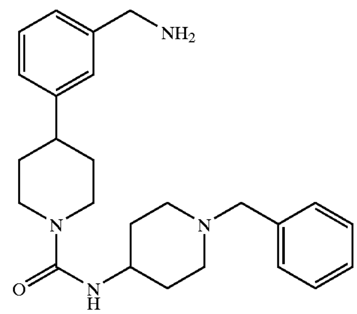 | 406 | >95% |
| 357 | 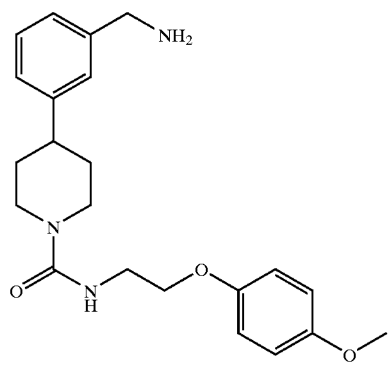 | 383 | >95% |
| 358 | 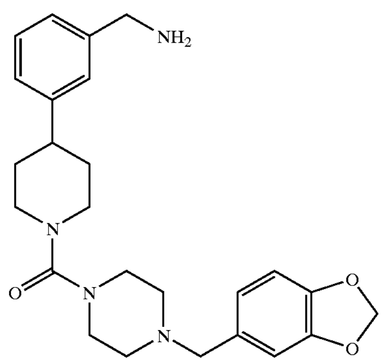 | 436 | >95% |
| 359 | 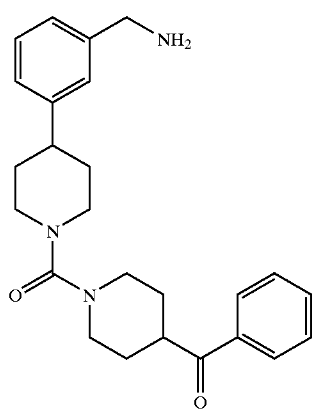 | 405 | >95% |
| 360 | | 419 | >95% |
| 361 | | 435 | >95% |
| 362 | | 423 | >95% |

TABLE 7-continued

| EG | Structure | M/Z | MS area % |
|---|---|---|---|
| 363 | (3-aminomethylphenyl)-piperidine linked via carbonyl to piperidine-piperidine | 384 | >95% |
| 364 | (3-aminomethylphenyl)-piperidine linked via carbonyl to piperazine-pyrimidine | 380 | >95% |
| 365 | (3-aminomethylphenyl)-piperidine linked via carbonyl to N-methyl-N-benzylamine | 337 | >95% |

In vitro Test Procedure

Since all the actions of tryptase, as described in the background section, are dependent on its catalytic activity, then compounds that inhibit its catalytic activity will potentially inhibit the actions of tryptase. Inhibition of this catalytic activity may be measured by the in vitro enzyme assay and the cellular assay.

Tryptase inhibition activity is confirmed using either isolated human lung tryptase or recombinant human β tryptase expressed in yeast cells. Essentially equivalent results are obtained using isolated native enzyme or the expressed enzyme. The assay procedure employs a 96 well microplate (Costar 3590) using L-pyroglutamyl-L-prolyl-L-arginine-para-nitroanilide (S2366: Quadratech) as substrate (essentially as described by McEuen et. al. Biochem Pharm, 1996, 52, pages 331–340). Assays are performed at room temperature using 0.5 mM substrate ($2 \times K_m$) and the microplate is read on a microplate reader (Beckman Biomek Plate reader) at 405 nm wavelength. The inhibition constant (Ki) for particular compounds of the present invention is set forth in Table 8. It was determined using the procedure set forth herein.

Materials and Methods for Tryptase Primary Screen (Chromogenic Assay)

Assay Buffer 50 mM Tris (pH 8.2), 100 mM NaCl, 0.05% Tween 20, 50 ug/ml heparin.

Substrate

S2366 (Stock solutions of 2.5 mM).

Enzyme

Purified recombinant beta Tryptase Stocks of 310 ug/ml.
Protocol (Single Point Determination)
  Add 60 ul of diluted substrate (final concentration of 500 uM in assay buffer) to each well
  Add compound in duplicates, final concentration of 20 uM, volume 20 ul
  Add enzyme at a final concentration of 50 ng/ml in a volume of 20 ul
  Total volume for each well is 100 ul
  Agitate briefly to mix and incubate at room temp in the dark for 30 minutes
  Read absorbencies at 405 nM
  Each plate has the following controls
  Totals: 60 ul of substrate, 20 ul of buffer (with 0.2% final concentration of DMSO), 20 ul of enzyme
  Non-specific: 60 ul of substrate, 40 ul of buffer (with 0.2% DMSO)
  Totals: 60 ul of substrate, 20 ul of buffer (No DMSO), 20 ul of enzyme
  Non-specific: 60 ul of substrate, 40 ul of buffer (No DMSO)
Protocol ($IC_{50}$ and Ki Determination)

The protocol is essentially the same as above except that the compound is added in duplicates at the following final concentrations: 0.01, 0.03, 0.1, 0.3, 1, 3, 10 uM (All dilutions carried out manually). For every assay, whether single point or IC50 determination, a standard compound is used to derive $IC_{50}$ for comparison. From the IC 50 value, the Ki can be calculated using the following formula: $Ki = IC_{50}/(1+[Substrate]/Km)$.

Using this procedure, Ki values with respect to tryptase for particular compounds of the present invention are set forth in Table 8 below:

TABLE 8

| EXAMPLE # | NAME | Tryptase Ki (nM) |
|---|---|---|
| 13 | [4-(3-Aminomethyl-phenyl)-piperidin-1-yl]-(5-phenethyl-thiophen-2-yl)-methanone hydrochloride | 50 |
| 15 | [4-(3-Aminomethyl-phenyl)-piperidin-1-yl]-(3-phenoxymethyl-phenyl)-methanone hydrochloride) | 1,070 |

TABLE 8-continued

| EXAMPLE # | NAME | Tryptase Ki (nM) |
|---|---|---|
| 18 | [4-(5-Aminomethyl-2-methyl-phenyl)-piperidin-1-yl]-(5-phenethyl-pyridin-3-yl)-methanone di-hydrochloride) | 69 |
| 19 | 4-(3-Aminomethyl-phenyl)-piperidin-1-yl]-[3-(5-phenyl-1,3,4-oxadiazol-2-yl)-phenyl]-methanone hydrochloride) | 180 |
| 35 | 4-(3-Aminomethyl-phenyl)-1-(5-phenethyl-pyridine-3-carbonyl)-piperidine-4-carbonitrile | 93 |
| 36 | [4-(3-Aminomethylphenyl)piperidin-1-yl]-(3,4-dichloro-phenyl)-methanone trifluoroacetate | 31 |
| 48 | 1-[4-(3-Aminomethyl-phenyl)-piperidin-1-yl]-1-(4-chloro-phenyl)-methanone trifluoroacetate | 390 |
| 49 | 1-[4-(3-Aminomethyl-phenyl)-piperidin-1-yl]-1-{3-[5-(2-chloro-phenyl)-[1,3,4]oxadiazol-2-yl]-phenyl}-methanone trifluoroacetate | 390 |
| 70 | 1-[4-(3-Aminomethyl-phenyl)-piperidin-1-yl]-1-(4,5,6,7-tetrahydro-benzo[c]thiophen-1-yl)-methanone-trifluoroacetate. | 290 |
| 83 | 1-[4-(3-Aminomethyl-phenyl)-piperidin-1-yl]-1-[3-(4-fluoro-phenylethynyl)-phenyl]-methanone trifluoroacetate | 870 |
| 92 | 1-[4-(3-Aminomethyl-phenyl)-piperidin-1-yl]-1-(5-chloro-thieno[3,2-b]thiophen-2-yl)-methanone trifluoroacetate | 190 |
| 97 | [4-(3-Aminomethylphenyl)-piperidin-1-yl]-(4-phenylethyl-phenyl)-methanone hydrochloride | 450 |
| 98 | [4-(3-Aminomethylphenyl)-piperidin-1-yl]-{3-[2-(2-hydroxyphenyl)-ethyl]-phenyl)-methanone hydrochloride | 180 |
| 100 | [4-(5-Aminomethyl-thiophen-2-yl)-piperidin-1-yl]-(5-phenylethyl-pyridin-3-yl)-methanone di-hydrochloride | 490 |
| 13 | [4-(3-Aminomethyl-phenyl)-piperidin-1-yl]-(5-phenethyl-thiophen-2-yl)-methanone hydrochloride | 50 |
| 15 | [4-(3-Aminomethyl-phenyl)-piperidin-1-yl]-(3-phenoxymethyl-phenyl)-methanone hydrochloride) | 1,070 |
| 18 | [4-(5-Aminomethyl-2-methyl-phenyl)-piperidin-1-yl]-(5-phenethyl-pyridin-3-yl)-methanone di-hydrochloride) | 69 |
| 35 | 4-(3-Aminomethyl-phenyl)-1-(5-phenethyl-pyridine-3-carbonyl)-piperidine-4-carbonitrile | 93 |
| 48 | 1-[4-(3-Aminomethyl-phenyl)-piperidin-1-yl]-1-(4-chloro-phenyl)-methanone trifluoroacetate | 390 |
| 49 | 1-[4-(3-Aminomethyl-phenyl)-piperidin-1-yl]-1-{3-[5-(2-chloro-phenyl)-[1,3,4]oxadiazol-2-yl]-phenyl}-methanone trifluoroacetate | 390 |
| 70 | 1-[4-(3-Aminomethyl-phenyl)-piperidin-1-yl]-1-(4,5,6,7-tetrahydro-benzo[c]thiophen-1-yl)-methanone-trifluoroacetate. | 290 |
| 83 | 1-[4-(3-Aminomethyl-phenyl)-piperidin-1-yl]-1-[3-(4-fluoro-phenylethynyl)-phenyl]-methanone trifluoroacetate | 870 |
| 92 | 1-[4-(3-Aminomethyl-phenyl)-piperidin-1-yl]-1-(5-chloro-thieno[3,2-b]thiophen-2-yl)-methanone trifluoroacetate | 190 |
| 97 | [4-(3-Aminomethylphenyl)-piperidin-1-yl]-(4-phenylethyl-phenyl)-methanone hydrochloride | 450 |
| 98 | [4-(3-Aminomethylphenyl)-piperidin-1-yl]-{3-[2-(2-hydroxyphenyl)-ethyl]-phenyl)-methanone hydrochloride | 180 |
| 100 | [4-(5-Aminomethyl-thiophen-2-yl)-piperidin-1-yl]-(5-phenylethyl-pyridin-3-yl)-methanone di-hydrochloride | 490 |

This data clearly shows that compounds of the present invention exhibit tryptase inhibition activity. Consequently, compounds of the present invention readily have applications in pharmaceutical compositions for treating a wide variety of tryptase related conditions, and naturally, in methods for treating such conditions in patients.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A compound of formula (I):

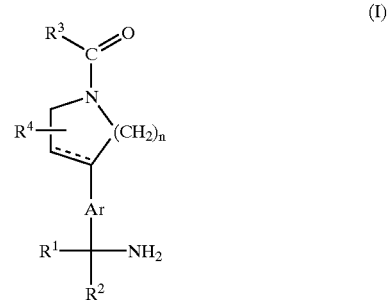

such that Ar is an aryl or a heteroaryl, and the

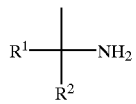

group is beta to the

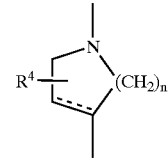

on the aryl,
wherein,

----- is a single or a double bond;
$R^1$ and $R^2$ are each independently hydrogen or lower alkyl;
$R^3$ is aryl, arylalkenyl, cycloalkenyl, cycloalkyl, heteroaryl, heteroarylalkenyl, heterocycloalkenyl, a carbon linked heterocycloalkyl or alkyl optionally substituted by one or more groups selected from hydroxy, alkoxy, alkyloxycarbonylamino, cycloalkyl, heterocycloalkyl, $R^6$, $-OR^6$, $-S(O)_m R^6$ or $-C(=O)-R^6$;
$R^4$ is hydrogen, acyl, alkoxy, alkyloxycarbonyl, carboxy, cyano, halo, hydroxy, $-C(=O)-NY^1Y^2$ or alkyl optionally substituted with alkoxy, alkylcarbonylamino, alkylsulfonylamino, hydroxy, $-S(O)_m$-alkyl or $-NY^1Y^2$;
$R^6$ is aryl or heteroaryl;
$Y^1$ and $Y^2$ are independently hydrogen, alkenyl, alkyl, aryl, arylalkyl, cycloalkyl, heteroaryl, heteroarylalkyl or heterocycloalkyl; or the group —NY$^1$Y$^2$ may form a cyclic amine;

m is zero or an integer 1 to 2; and n is 2; or an N-oxide of said compound, a prodrug of said compound, a pharmaceutically acceptable salt of said compound, a solvate of said compound or a hydrate of said compound.

2. The compound of claim 1, wherein R$^1$ or R$^2$ is hydrogen, or R$^1$ and R$^2$ are hydrogen, and R$^3$ is an aryl or a heteroaryl.

3. The compound of claim 2, wherein said R$^3$ is a phenyl or a naphthyl.

4. The compound of claim 2, wherein said R$^3$ aryl is aryl substituted with at least one substituent.

5. The compound of claim 4, wherein said substituent is selected from the group consisting of a halo atom, an alkyl substituted by aryl, an alkyl substituted by aryloxy, an alkyl substituted by aroyl, an alkyl substituted by heteroaryl, an arylalkynyl, a heteroarylalkynyl, an aryl, a heteroaryl, an arylalkenyl and an arylalkyloxy.

6. The compound of claim 5, wherein said aryl or heteroaryl of said substituent is further substituted by at least one aryl group substituent.

7. The compound of claim 2, wherein said heteroaryl is a pyridyl, a quinolinyl, a thienyl, a furanyl, or an indolyl.

8. The compound of claim 7, wherein said heteroaryl is substituted with at least one substituent.

9. The compound of claim 8, wherein said substituent is an alkyl, an alkyl substituted by an aryl, an alkyl substituted by an aryloxy, an alkyl substituted by an aroyl, an alkyl substituted heteroaryl, an arylalkynyl, a heteroarylalkynyl, a heteroaryl, an arylalkenyl or an arylalkyoxy.

10. The compound of claim 9, wherein said aryl of said substituent is further substituted by at least one aryl substituent.

11. The compound of claim 1, wherein R$^4$ is hydrogen or a cyano group.

12. The compound of claim 1, wherein R$^5$ is a hydrogen, a lower alkyl, or a halo.

13. The compound of claim 1, wherein:

Ar comprises a phenyl group;

R$^1$ and R$^2$ are both hydrogen;

R$^3$ is an aryl, a naphthyl, or a heteroaryl;

R$^4$ is hydrogen or a cyano; and

----- is a single bond.

14. The compound of claim 13, wherein R$^3$ as aryl or naphthyl is substituted with at least one substituent selected from the group consisting a halo atom, an alkyl substituted by aryl, an alkyl substituted by aryloxy, an alkyl substituted by aroyl, an alkyl substituted by aryloxy, an alkyl substituted aroyl, an alkyl substituted by a heteroaryl, an arylalkynyl, a heteroarylalkynyl, an aryl, a heteroaryl, an arylalkenyl, and an arylalkyloxy.

15. The compound of claim 14, wherein said aryl or said heteroaryl of said substituent is further substituted by at least one aryl substituent.

16. The compound of claim 13, wherein R$^3$ as heteroaryl is substituted by at least one substituent selected from the group consisting of a pyridyl, a quinolinyl, a thienyl, a furanyl, and an indolyl.

17. The compound of claim 16, wherein said substituent of said heteroaryl is further substituted by at least one moiety selected from the group consisting of an alkyl substituted by an aryl, an alkyl substituted by an aryloxy, an alkyl substituted by an aroyl, an alkyl substituted heteroaryl, an arylalkynyl, a heteroarylalkynyl, a heteroaryl, an arylalkenyl, or an arylalkyloxy.

18. The compound of claim 17, wherein an aryl of said moiety is further substituted by at least one aryl substituent.

19. A compound of formula (Ia):

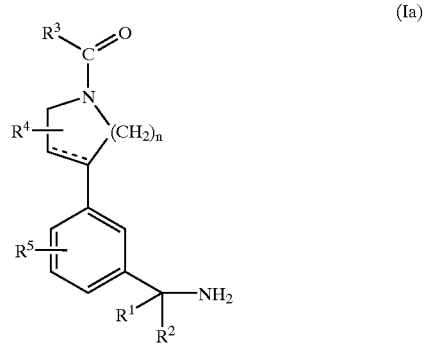

(Ia)

wherein,

----- is a single or double bond;

R$^1$ and R$^2$ are each independently hydrogen or lower alkyl;

R$^3$ is aryl, arylalkenyl, cycloalkenyl, cycloalkyl, heteroaryl, heteroarylalkenyl, heterocycloalkenyl, a carbon linked heterocycloalkyl or alkyl optionally substituted by one or more groups selected from hydroxy, alkoxy, alkyloxycarbonylamino, cycloalkyl, heterocycloalkyl, R$^6$, —OR$^6$, —S(O)$_m$R$^6$ or —C(=O)—R$^6$;

R$^4$ is hydrogen, acyl, alkoxy, alkyloxycarbonyl, carboxy, cyano, halo, hydroxy, —C(=O)—NY$^1$Y$^2$ or alkyl optionally substituted with alkoxy, alkylcarbonylamino, alkylsulfonylamino, hydroxy, —S(O)$_m$-alkyl or —NY$^1$Y$^2$;

R$^5$ is hydrogen, acyl, alkoxy, alkyloxycarbonyl, aryl, carboxy, cyano, halo, heteroaryl, heteroaryloxy, heterocycloalkyl, heterocycloalkyloxy, heterocycloalkylalkyloxy, heteroarylalkyloxy, hydroxy, trifluoromethyl, —C(=O)—NY$^1$Y$^2$, —NY$^1$Y$^2$, —Z$^1$—C$_{2-6}$alkylene-R$^7$ or alkyl optionally substituted with alkoxy, alkylcarbonylamino, alkylsulfonylamino, aryl, heteroaryl, heterocycloalkyl, hydroxy, ureido, —C(=O)—NY$^1$Y$^2$, —SO$_2$—NY$^1$Y$^2$, —S(O)$_m$-alkyl or —NY$^1$Y$^2$, and, R$^6$ is aryl or heteroaryl;

R$^7$ is hydroxy, alkoxy, ureido, —C(=O)—NY$^1$Y$^2$, —SO$_2$—NY$^1$T$^2$, —S(O)$_m$-alkyl or —NY$^1$Y$^2$, R$^8$ is hydrogen or lower alkyl;

Y$^1$ and Y$^2$ are independently hydrogen, alkenyl, alkyl, aryl, arylalkyl, cycloalkyl, heteroaryl, heteroarylalkyl or heterocycloalkyl; or the group —NY$^1$Y$^2$ may form a cyclic amine;

Z$^1$ is O, S(O)$_m$ or NR$^8$;

m is zero or an integer 1 or 2; and n is 2; or an N-oxide of said compound, a prodrug of said compound, a pharmaceutically acceptable salt of said compound, a solvate of said compound, an N-oxide of said solvate of said compound, or a prodrug of said solvate of said compound.

20. The compound of claim 19, wherein $R^3$ is a phenyl or a naphthyl.

21. The compound of claim 20, wherein said aryl is substituted by at least one substituent selected from the group consisting of a halo atom, an alkyl substituted by an aryl, an alkyl substituted by a heteroaryl.

22. The compound of claim 21, wherein said aryl or heteroaryl of said substituent is further substituted by at least one aryl group substituent.

23. The compound of claim 19, wherein $R^3$ is phenyl$C_{1-3}$alkylpyridyl, phenyl$C_{1-3}$alkylthienyl or indolyl.

24. The compound of claim 23, wherein the phenyl$C_{1-3}$alkylpyridyl is 5-phenylethyl-pyrid-3-yl, the phenyl$C_{1-3}$alkylthienyl is and the indolyl is indol-6-yl.

25. The compound of claim 19, wherein $R^3$ is a heteroaryl selected from the group consisting of a pyridyl, a quinolinyl, a thienyl, a furanyl, and an indolyl.

26. The compound of claim 25, wherein said heteroaryl is substituted by at least one substituent selected from the group consisting of an alkyl substituted by an aryl, or an alkyl substituted by a heteroaryl.

27. The compound of claim 26, wherein said aryl and said heteroaryl of said substituent are further substituted by at least one aryl group substituent.

28. The compound of claim 27, wherein $R^3$ is phenyl$C_{1-3}$alkylpyridyl, phenyl$C_{1-3}$alkylthienyl or indolyl.

29. The compound of claim 28, wherein the phenyl$C_{1-3}$alkylpyridyl is 5-phenylethyl-pyrid-3-yl, the phenyl$C_{1-3}$alkylthienyl is 5-phenylethyl-thien-2-yl and the indolyl is indol-6-yl.

30. The compound of claim 19, wherein $R^4$ is a hydrogen or a cyano.

31. The compound of claim 19, wherein $R^5$ is a hydrogen, a lower alkyl or a halo.

32. The compound of claim 31, wherein $R^5$ methyl or a fluoro.

33. The compound of claim 31, wherein $R^5$ is attached to the phenyl ring of formula (Ia) in the position para to the $CH_2NH_2$ group.

34. The compound of claim 19, wherein:
$R^3$ is a phenyl, a naphthyl, a heteroaryl selected from the group consisting a pyridyl, a quinolinyl, a thienyl, a furanyl, and an indolyl, a phenyl substituted by at least one substituent, a naphthyl substituted by at least one substituent, or a heteroaryl selected from the group consisting a pyridyl, a quinolinyl, a thienyl, a furanyl, and an indolyl, that is substituted by at least one substituent,
wherein said substituent is selected from the group consisting of a halo atom, an alkyl substituted by aryl, and alkyl substituted heteroaryl, wherein the aryl or heteroaryl groups are further substituted by one or more aryl group substituents;
$R^4$ comprises hydrogen or a cyano; and
$R^5$ comprises hydrogen, a lower alkyl or a halo.

35. The compound of claim 34, wherein:
$R^3$ is phenyl$C_{1-3}$alkylpyridyl, phenyl$C_{1-3}$alkylthienyl or indolyl;
$R^4$ is a hydrogen or a cyano; and
$R^5$ is a methyl or a fluoro, and is attached to the phenyl ring of formula (Ia) in the position para to the $CR^1R^2NH_2$ group.

36. The compound of claim 35, wherein the phenyl$C_{1-3}$alkylpyridyl is 5-phenylethyl-pyrid-3-yl, the phenyl$C_{1-3}$alkylthienyl is 5-phenylethyl-thien-2-yl and the indolyl is indol-6-yl.

37. A compound of claim 19, having formula (Ib):

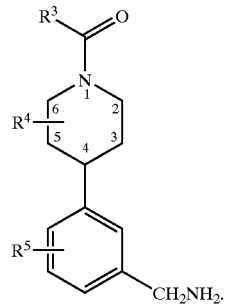

(Ib)

38. The compound of claim 37, wherein $R^3$ is a phenyl or a naphthyl.

39. The compound of claim 38, wherein said aryl is substituted by at least one substituent selected from the group consisting of a halo atom, an alkyl substituted by an aryl, and an alkyl substituted by a heteroaryl.

40. The compound of claim 39, wherein said aryl or heteroaryl of said substituent is further substituted by at least one aryl group substituent.

41. The compound of claim 37, wherein $R^3$ is a pyridyl, a quinolinyl, a thienyl, a furanyl, or an indolyl.

42. The compound of claim 40, wherein said heteroaryl is substituted by at least one substituent selected from the group consisting of an alkyl substituted by an aryl, and an alkyl substituted by a heteroaryl.

43. The compound of claim 40, wherein said aryl and said heteroaryl of said substituent are further substituted by at least one aryl group substituent.

44. The compound of claim 37, wherein $R^3$ is phenyl$C_{1-3}$alkylpyridyl, phenyl$C_{1-3}$alkylthienyl or indolyl.

45. The compound of claim 37, wherein $R^4$ is a hydrogen or a cyano.

46. The compound of claim 37, wherein $R^5$ is a hydrogen, a lower alkyl or a halo.

47. The compound of claim 46, wherein $R^5$ is a methyl or a fluoro.

48. The compound of claim 46, wherein $R^5$ is attached to the phenyl ring of formula (Ib) in the position para to the $CH_2NH_2$ group.

49. The compound of claim 37, wherein:
$R^3$ is a phenyl, a naphthyl, a heteroaryl selected from the group consisting a pyridyl, a quinolinyl, a thienyl, a furanyl, and an indolyl, a phenyl substituted by at least one substituent, a naphthyl substituted by at least one substituent, or a heteroaryl selected from the group consisting of a pyridyl, a quinolinyl, a thienyl, a furanyl, and an indolyl, that is substituted by at least one substituent,
wherein said substituent is selected from the group consisting of a halo atom, an alkyl substituted by aryl, and alkyl substituted heteroaryl, wherein the aryl or heteroaryl groups are further substituted by one or more aryl group substituents;
$R^4$ is hydrogen or a cyano; and
$R^5$ is hydrogen, a lower alkyl or a halo.

50. The compound of claim 49, wherein:
$R^3$ is phenyl$C_{1-3}$alkylpyridyl, phenyl$C_{1-3}$alkylthienyl or indolyl;
$R^4$ is a hydrogen or a cyano; and
$R^5$ is a methyl or a fluoro.

51. The compound of claim 1, wherein

----- is a single bond.

52. The compound of claim 1, selected from the group consisting of:

3-[1-(5-phenylethynyl-pyridine-3-carbonyl)-piperidin-4-yl]-benzylamine;

3-[1-(3-phenylethyl-benzoyl)-piperidin-4-yl]-benzylamine;

3-{1-[3-(4-hydroxyphenyl)ethyl-benzoyl]-piperidin-4-yl}-benzylamine;

3-{1-[3-(6-amino-pyridin-3-yl)ethyl-benzoyl]-piperidin-4-yl}-benzylamine;

3-[1-(5-phenylethyl-thiophene-2-carbonyl)-piperidin-4-yl]-benzylamine;

4-fluoro-3-[1-(5-phenylethyl-pyridine-3-carbonyl)-piperidin-4-yl]-benzylamine;

4-methyl-3-[1-(5-phenylethyl-pyridine-3-carbonyl)-piperidin-4-yl]-benzylamine;

3-[1-(indole-6-carbonyl)-piperidin-4-yl]-benzylamine;

4-(3-aminomethyl-phenyl)-1-(5-phenethyl-pyridine-3-carbonyl)-piperidine-4-carbonitrile;

[4-(3-aminomethylphenyl)piperidin-1-yl]-(3,4-dichlorophenyl)methanone;

1-{1-[4-(3-Aminomethyl-phenyl)-piperidin-1-yl]-methanoyl}-3-methylsulfanyl-6,7-dihydro-5H-benzo[c]thiophen-4-one trifluoroacetate;

1-[4-(3-Aminomethyl-phenyl)-piperidin-1-yl]-1-(3-methylsulfanyl-6,7-dihydro-benzo[c]thiophen-1-yl)-methanone trifluoroacetate;

1-{1-[4-(3-Aminomethyl-phenyl)-piperidin-1-yl]-methanoyl}-3-ethylsulfanyl-6,6-dimethyl-6,7-dihydro-5H-benzo[c]thiophen-4-one trifluoroacetate;

1-{1-[4-(3-Aminomethyl-phenyl)-piperidin-1-yl]-methanoyl}-3-propylsulfanyl-6,7-dihydro-5H-benzo[c]thiophen-4-one trifluoroacetate;

1-{1-[4-(3-Aminomethyl-phenyl)-piperidin-1-yl]-methanoyl}-3-isopropylsulfanyl-6,7-dihydro-5H-benzo[c]thiophen-4-one trifluoroacetate;

1-[4-(3-Aminomethyl-phenyl)-piperidin-1-yl]-1-benzo[b]thiophen-2-yl-methanone-trifluoroacetate;

1-[4-(3-Aminomethyl-phenyl)-4-hydroxy-piperidin-1-yl]-1-(5-phenethyl-pyridin-3-yl)-methanone-ditrifluoroacetate;

1-[4-(3-Aminomethyl-phenyl)-piperidin-1-yl]-1-(1-methyl-1H-indol-3-yl)-methanone-trifluoroacetate;

1-[4-(3-Aminomethyl-phenyl)-piperidin-1-yl]-1-[3-(2-fluoro-phenylethynyl)-phenyl]-methanone trifluoroacetate;

1-[4-(3-Aminomethyl-phenyl)-piperidin-1-yl]-1-{3-[2-(2-fluoro-phenyl)-ethyl]-phenyl}-methanone trifluoroacetate;

1-[4-(3-Aminomethyl-phenyl)-piperidin-1-yl]-1-{3-[2-(6-amino-pyridin-3-yl)-ethyl]-phenyl}-methanone trifluoroacetate;

1-[4-(3-Aminomethyl-phenyl)-piperidin-1-yl]-1-(6-chloro-thieno[3,2-b]thiophen-2-yl)-methanone trifluoroacetate;

(3R,4S) and (3S,4R)-4-(3-Aminomethyl-phenyl)-1-(5-phenethyl-pyridine-3-carbonyl)-piperidine-3-carboxylic acid ethyl ester dihydrochloride;

3-[1-(5-Phenylethynyl-furan-2-carbonyl)-piperidin-4-yl]-benzylamine trifluoroacetate;

4-(3-Aminomethyl-phenyl)-piperidine-1-carboxylic acid (3,4-dichloro-phenyl)-amide trifluoroacetate;

1-[4-(3-Aminomethyl-phenyl)-piperidin-1-yl]-1-(2,3-dihydro-benzofuran-5-yl)-methanone;

1-[4-(3-Aminomethyl-phenyl)-piperidin-1-yl]-1-(5,6-dichloro-pyridin-3-yl)-methanone;

1-[4-(3-Aminomethyl-phenyl)-piperidin-1-yl]-1-(3-bromo-4-fluoro-phenyl)-methanone;

(E)-1-[4-(3-Aminomethyl-phenyl)-piperidin-1-yl]-3-(2-nitro-phenyl)-propenone;

1-[4-(3-Aminomethyl-phenyl)-piperidin-1-yl]-1-(3-bromo-5-iodo-phenyl)-methanone; and (E)-1-[4-(3-Aminomethyl-phenyl)-piperidin-1-yl]-3-phenyl-propenone.

53. A pharmaceutical composition comprising a therapeutically effective amount of a compound of claim 1 and a pharmaceutically acceptable carrier thereof.

54. The pharmaceutical composition of claim 53, wherein said compound is selected from the group consisting of:

3-[1-(5-phenylethynyl-pyridine-3-carbonyl)-piperidin-4-yl]-benzylamine;

3-[1-(3-phenylethyl-benzoyl)-piperidin-4-yl]-benzylamine;

3-{1-[3-(4-hydroxyphenyl)ethyl-benzoyl]-piperidin-4-yl}-benzylamine;

3-{1-[3-(6-amino-pyridin-3-yl)ethyl-benzoyl]-piperidin-4-yl}-benzylamine;

3-[1-(5-phenylethyl-thiophene-2-carbonyl)-piperidin-4-yl]-benzylamine;

4-fluoro-3-[1-(5-phenylethyl-pyridine-3-carbonyl)-piperidin-4-yl]-benzylamine;

4-methyl-3-[1-(5-phenylethyl-pyridine-3-carbonyl)-piperidin-4-yl]-benzylamine;

3-[1-(indole-6-carbonyl)-piperidin-4-yl]-benzylamine;

4-(3-aminomethyl-phenyl)-1-(5-phenethyl-pyridine-3-carbonyl)-piperidine-4-carbonitrile;

[4-(3-aminomethylphenyl)piperidin-1-yl]-(3,4-dichlorophenyl)methanone;

1-{1-[4-(3-Aminomethyl-phenyl)-piperidin-1-yl]-methanoyl}-3-methylsulfanyl-6,7-dihydro-5H-benzo[c]thiophen-4-one trifluoroacetate;

1-[4-(3-Aminomethyl-phenyl)-piperidin-1-yl]-1-(3-methylsulfanyl-6,7-dihydro-benzo[c]thiophen-1-yl)-methanone trifluoroacetate;

1-{1-[4-(3-Aminomethyl-phenyl)-piperidin-1-yl]-methanoyl}-3-ethylsulfanyl-6,6-dimethyl-6,7-dihydro-5H-benzo[c]thiophen-4-one trifluoroacetate;

1-{1-[4-(3-Aminomethyl-phenyl)-piperidin-1-yl]-methanoyl}-3-propylsulfanyl-6,7-dihydro-5H-benzo[c]thiophen-4-one trifluoroacetate;

1-{1-[4-(3-Aminomethyl-phenyl)-piperidin-1-yl]-methanoyl}-3-isopropylsulfanyl-6,7-dihydro-5H-benzo[c]thiophen-4-one trifluoroacetate;

1-[4-(3-Aminomethyl-phenyl)-piperidin-1-yl]-1-benzo[b]thiophen-2-yl-methanone-trifluoroacetate;

1-[4-(3-Aminomethyl-phenyl)-4-hydroxy-piperidin-1-yl]-1-(5-phenethyl-pyridin-3-yl)-methanone-ditrifluoroacetate;

1-[4-(3-Aminomethyl-phenyl)-piperidin-1-yl]-1-(1-methyl-1H-indol-3-yl)-methanone-trifluoroacetate;

1-[4-(3-Aminomethyl-phenyl)-piperidin-1-yl]-1-[3-(2-fluoro-phenylethynyl)-phenyl]-methanone trifluoroacetate;

1-[4-(3-Aminomethyl-phenyl)-piperidin-1-yl]-1-{3-[2-(2-fluoro-phenyl)-ethyl]-phenyl}-methanone trifluoroacetate;

1-[4-(3-Aminomethyl-phenyl)-piperidin-1-yl]-1-{3-[2-(6-amino-pyridin-3-yl)-ethyl]-phenyl}-methanone tritrifluoroacetate;

1-[4-(3-Aminomethyl-phenyl)-piperidin-1-yl]-1-(6-chloro-thieno[3,2-b]thiophen-2-yl)-methanone trifluoroacetate;

(3R,4S) and (3S,4R)-4-(3-Aminomethyl-phenyl)-1-(5-phenethyl-pyridine-3-carbonyl)-piperdine-3-carboxylic acid ethyl ester dihydrochloride;

3-[1-(5-Phenylethynyl-furan-2-carbonyl)-piperidin-4-yl]-benzylamine trifluoroacetate;

4-(3-Aminomethyl-phenyl)-piperidine-1-carboxylic acid (3,4-dichloro-phenyl)-amide trifluoroacetate;

1-[4-(3-Aminomethyl-phenyl)-piperidin-1-yl]-1-(2,3-dihydro-benzofuran-5-yl)-methanone;

1-[4-(3-Aminomethyl-phenyl)-piperidin-1-yl]-1-(5,6-dichloro-pyridin-3-yl)-methanone;

1-[4-(3-Aminomethyl-phenyl)-piperidin-1-yl]-1-(3-bromo-4-fluoro-phenyl)-methanone;

(E)-1-[4-(3-Aminomethyl-phenyl)-piperidin-1-yl]-3-(2-nitro-phenyl)-propenone;

1-[4-(3-Aminomethyl-phenyl)-piperidin-1-yl]-1-(3-bromo-5-iodo-phenyl)-methanone;

(E)-1-[4-(3-Aminomethyl-phenyl)-piperidin-1-yl]-3-phenyl-propenone; and

1-[4-(3-Aminomethyl-phenyl)-piperidin-1-yl]-3-cyclohexyl-propan-1-one.

55. A pharmaceutical composition comprising a therapeutically effective amount of a compound of claim 19 and a pharmaceutically acceptable carrier thereof.

56. A pharmaceutical composition comprising a therapeutically effective amount of a compound of claim 37 and a pharmaceutically acceptable carrier thereof.

57. A method for treating asthma in a patient comprising administering to the patient a therapeutically effective amount of a compound of claim 1.

58. A method for treating asthma in a patient comprising administering to the patient a therapeutically effective amount of a compound of claim 19.

59. A method for treating asthma in a patient comprising administering to the patient a therapeutically effective amount of a compound of claim 37.

* * * * *